United States Patent
Alemparte-Gallardo et al.

(10) Patent No.: US 11,072,591 B2
(45) Date of Patent: Jul. 27, 2021

(54) TETRAZOLE COMPOUNDS AND THEIR USE IN THE TREATMENT OF TUBERCULOSIS

(71) Applicant: GLAXOSMITHKLINE INTELLECTUAL PROPERTY DEVELOPMENT LIMITED, Brentford (GB)

(72) Inventors: Carlos Alemparte-Gallardo, Tres Cantos (ES); Lourdes Encinas, Tres Cantos (ES); Jorge Esquivias Provencio, Tres Cantos (ES)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 16/639,163

(22) PCT Filed: Aug. 16, 2018

(86) PCT No.: PCT/EP2018/072205
§ 371 (c)(1),
(2) Date: Feb. 14, 2020

(87) PCT Pub. No.: WO2019/034729
PCT Pub. Date: Feb. 21, 2019

(65) Prior Publication Data
US 2020/0231555 A1    Jul. 23, 2020

(30) Foreign Application Priority Data

Aug. 17, 2017 (EP) .................................... 17382574

(51) Int. Cl.
| | |
|---|---|
| C07D 257/04 | (2006.01) |
| C07D 403/06 | (2006.01) |
| C07D 401/06 | (2006.01) |
| C07D 405/06 | (2006.01) |
| C07D 249/06 | (2006.01) |
| A61P 31/06 | (2006.01) |
| A61K 45/06 | (2006.01) |

(52) U.S. Cl.
CPC ............ *C07D 257/04* (2013.01); *A61P 31/06* (2018.01); *C07D 249/06* (2013.01); *C07D 401/06* (2013.01); *C07D 403/06* (2013.01); *C07D 405/06* (2013.01); *A61K 45/06* (2013.01)

(58) Field of Classification Search
CPC .. C07D 257/04; C07D 249/06; C07D 401/06; C07D 403/06; C07D 405/06; A61P 31/06; A61K 45/06

USPC .................................................... 514/252.05
See application file for complete search history.

(56) References Cited

U.S. PATENT DOCUMENTS

2003/0078434 A1    4/2003 Kurihara et al.

FOREIGN PATENT DOCUMENTS

| WO | WO 2008/124703 A2 | 10/2008 |
|---|---|---|
| WO | WO 2017/066964 A1 | 4/2017 |

OTHER PUBLICATIONS

Rangappa, et al. "Triazole: A Promising Antitubercular Agent". Chemical Biology & Drug Design, 86(4): 410-423 (Oct. 1, 2015).
Menendez, et al. "Synthesis and Biological Activities of Triazole Derivatives as Inhibitors of InhA and Antituberculosis Agents". European Journal of Medicinal Chemistry, 46(11): 5524-5531 (Sep. 10, 2011).
Tripathi, et al. "Application of Huisgen (3+2) Cycloaddition Reaction: Synthesis of 1-(2,3-dihydrobenzofuran-2-yl-methyl[1,2,3]-triazoles and Their Antitubercular Evaluations". European Journal of Medicinal Chemistry, 45(1): 142-148 (Jan. 1, 2010).
Mohite, et al. "In Vitro Evaluation of Tetrazoles as a Novel Class of Antimycobacterium Tuberculosis Agents". Advanced Pharmaceutical Bulletin, pp. 31-36 (Jan. 1, 2012). DOI 10.5681/apb.2012.005.
Menendez, et al., "Synthesis and biological activities of triazole derivatives as inhibitors of InhA and antituberculosis agents", European Journal of Medicinal Chemistry; 2011; 46(11); pp. 5524-5531.
Waisser, K., et al., "New groups of potential antituberculotics: 5-alkylthio-1-aryltetrazoles", Collection of Czechoslovak Chemical Communications, Institute of Organic Chemistry and Biochemistry; 1996; 61(5); pp. 791-798.
Wellington, S., et al., "A small molecule allosteric inhibitor of Mycobacterium tuberculosis tryptophan synthase", Nature Chemical Biology, Nature America, Springer Nature; 2017, vol. 13., pp. 943-950.

*Primary Examiner* — Kristin A Vajda
(74) *Attorney, Agent, or Firm* — Robert H. Brink; Nicole Ginanni; Edward R. Gimmi

(57) ABSTRACT

The invention relates to a compound of Formula (I) or a pharmaceutically acceptable salt thereof and their use in therapy, for example in the treatment of mycobacterial infections or in the treatment of diseases caused by *Mycobacterium*, such as tuberculosis.

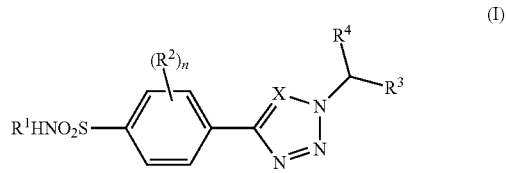

27 Claims, No Drawings

TETRAZOLE COMPOUNDS AND THEIR USE IN THE TREATMENT OF TUBERCULOSIS

This application is a § 371 of International Application No. PCT/EP2018/072205, filed 16 Aug. 2018, which claims the priority of EP 17382574.6, filed 17 Aug. 2017.

FIELD OF THE INVENTION

The invention relates to compounds, compositions containing them, and their use in therapy, for example in the treatment of mycobacterial infections or in the treatment of diseases caused by a *Mycobacterium*, such as tuberculosis (also known as TB).

BACKGROUND TO THE INVENTION

Nearly ten million people are infected with tuberculosis (TB) each year, causing an estimated 1.4 million deaths each year, and an additional 0.4 million deaths from TB disease among people living with human immunodeficiency virus (HIV) according to a report published by The World Health Organisation in 2016. Despite available treatments for tuberculosis, the global disease burden remains a major problem owing to *Mycobacterium tuberculosis*, the causative bacterial agent for TB, becoming resistant to many of the treatments.

In an attempt to prevent resistance to currently available drugs and future approved drugs increasing, TB is treated using combination therapies of three or more drugs. In addition, the treatment of TB often requires therapy using multiple drugs. The standard treatment currently used for drug-susceptible TB is a combination of isoniazid, rifampicin, pyrazinamide and ethambutol, which patients are required to take for two months, followed by isoniazid and rifampicin, only, for a further four months.

Multidrug-resistant TB (MDR-TB) is defined as resistance to at least isoniazid and rifampicin, the two most powerful first-line anti-TB medicines, and extensively drug-resistant TB (XDR-TB) is a form of MDR-TB that is also resistant to at least one fluoroquinolone and any of the second-line anti-TB injectable agents (i.e. amikacin, kanamycin or capreomycin), the two most important classes of medicines in the MDR-TB regimen. For the treatment of M(X)DR TB, it is necessary to administer a regimen of four or more second-line drugs.

The prevalence of TB infection throughout history, is largely due to the ability of *Mycobacterium tuberculosis* to persist in the host for long periods of time and cause disease even in the face of a highly orchestrated host immune response (Flynn, J. L. & Chan, J. (2001) Annu. Rev. Immunol. 19, 93-129). This unusual ability suggests that mycobacteria may use unique pathogenic mechanisms.

Target identification efforts indicates Tryptophan Synthase inhibition as a possible target for the treatment of TB. Tryptophan Synthase (TS) is a pyridoxal 50-phosphate-dependent α2β2 complex catalysing the last two steps of tryptophan biosynthesis in bacteria, plants and fungi.

The physiological reaction of TS is the conversion of indole-3-glycerol phosphate (IGP) and L-serine to L-tryptophan and D-glyceraldehyde-3-phosphate (G3P). *Mycobacterium tuberculosis* can synthesise its own tryptophan so that, unlike some other intracellular pathogens, it is able to survive the intracellular tryptophan starvation brought on by interferon γ [Zhang et al., Cell 2013, 155, 1296-1308]. Additionally, tryptophan biosynthesis is absent in mammals suggesting the potential for selective inhibition.

Owing to the ever growing emergence of multi-drug resistant strains of *Mycobacterium tuberculosis* and continued high incidence of TB, there exists an urgent need to provide further drug compounds for the treatment of TB, preferably having a new mode of action.

SUMMARY OF THE INVENTION

In a first aspect of the invention, there is provided a compound of Formula (I) or a pharmaceutically acceptable salt thereof:

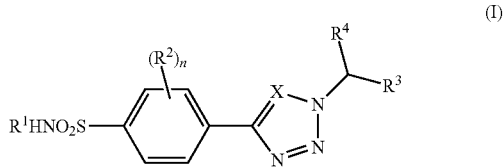

(I)

wherein
X is CH or N;
n is 0, 1 or 2;
$R^1$ is methyl, ethyl, cyanomethyl, C-linked acetamido, methyl acetate, 2-hydroxyethyl, 2-hydroxy-1-propyl, 1,3-dihydroxy-2-propyl or 1,2-dihydroxy-3-propyl;
$R^2$ is independently selected from halo, amino, hydroxymethyl, $C_{1-2}$ alkyl optionally substituted by up to three fluoro or $C_{1-2}$ alkoxy optionally substituted by up to three fluoro;
$R^3$ is phenyl, pyridyl, pyrimidinyl, pyrazinyl or pyridazinyl wherein each of these groups may be optionally substituted by one or two substituents selected from halo, cyano, $C_{1-2}$ alkyl optionally substituted by up to three fluoro and $C_{1-2}$ alkoxy optionally substituted by up to three fluoro, wherein the substituents may be the same or different; or
$R^3$ is cyclohexyl which may be optionally substituted by one or two fluoro or chloro wherein each substituent may be attached to the same carbon atom and each substituent may be the same or different; or
$R^3$ is tetrahydropyran; and
$R^4$ is H or methyl.

In a second aspect of the invention, there is provided a compound of Formula (I) or a pharmaceutically acceptable salt thereof, for use in therapy.

In a third aspect of the invention, there is provided a compound of Formula (I) or a pharmaceutically acceptable salt thereof, for use in the treatment of tuberculosis.

In a fourth aspect of the invention, there is provided a compound of Formula (I) or a pharmaceutically acceptable salt thereof, for use in the treatment of a mycobacterial infection or for use in the treatment of a disease caused by infection with a *Mycobacterium*.

In a fifth aspect of the invention, there is provided a method for the treatment of a mycobacterial infection in a mammal in need thereof, comprising administering to said mammal a therapeutically effective amount of a compound of Formula (I) or a pharmaceutically acceptable salt thereof.

In a sixth aspect of the invention, there is provided a method for the treatment of a disease caused by infection with a *Mycobacterium* in a mammal in need thereof, comprising administering to said mammal a therapeutically effective amount of a compound of Formula (I) or a pharmaceutically acceptable salt thereof.

In a seventh aspect of the invention, there is provided use of a compound of Formula (I) or a pharmaceutically acceptable salt thereof, in the manufacture of a medicament for use in the treatment of a mycobacterial infection or a disease caused by infection with a *Mycobacterium*.

In an eighth aspect of the invention, there is provided a pharmaceutical composition comprising (a) a compound of Formula (I) or a pharmaceutically acceptable salt thereof; and (b) a pharmaceutically acceptable excipient.

In a ninth aspect of the invention, there is provided a combination of (a) a compound of Formula (I) or a pharmaceutically acceptable salt thereof; and (b) at least one other anti-mycobacterial agent.

DETAILED DESCRIPTION OF THE INVENTION

As described above, in one aspect of the invention, there is provided a compound of Formula (I) or a pharmaceutically acceptable salt thereof:

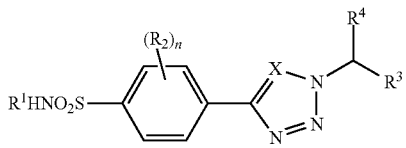

(I)

wherein
X is CH or N;
n is 0, 1 or 2;
$R^1$ is methyl, ethyl, cyanomethyl, C-linked acetamido, methyl acetate, 2-hydroxyethyl, 2-hydroxy-1-propyl, 1,3-dihydroxy-2-propyl or 1,2-dihydroxy-3-propyl;
$R^2$ is independently selected from halo, amino, hydroxymethyl, $C_{1-2}$ alkyl optionally substituted by up to three fluoro or $C_{1-2}$ alkoxy optionally substituted by up to three fluoro; and
$R^3$ is phenyl, pyridyl, pyrimidinyl, pyrazinyl or pyridazinyl wherein each of these groups may be optionally substituted by one or two substituents selected from halo, cyano, $C_{1-2}$ alkyl optionally substituted by up to three fluoro and $C_{1-2}$ alkoxy optionally substituted by up to three fluoro, wherein the substituents may be the same or different; or
$R^3$ is cyclohexyl which may be optionally substituted by one or two fluoro or chloro wherein each substituent may be attached to the same carbon atom and each substituent may be the same or different; or
$R^3$ is tetrahydropyran.

In one embodiment, the invention relates to a compound of Formula (I), as defined above.

In one embodiment, X is N.

In one embodiment, $R^4$ is H. When $R^4$ is H, Formula (I) may be defined according to Formula (Ia):

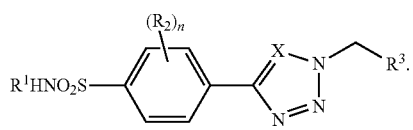

(Ia)

In one embodiment, when $R^4$ is methyl, it is (S)-methyl.

In one embodiment, n is 0 or 1. In a particular embodiment, n is 0.

As defined above, $R^1$ is methyl, ethyl, cyanomethyl, C-linked acetamido, methyl acetate, 2-hydroxyethyl, 2-hydroxy-1-propyl, 1,3-dihydroxy-2-propyl or 1,2-dihydroxy-3-propyl. In other words, $R^1$ is selected from one of the following groups, which correspond to those listed:

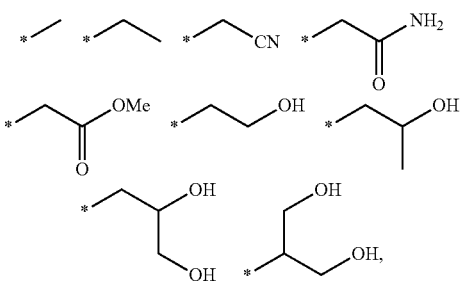

wherein * represents the point of attachment.

In one embodiment, $R^1$ is methyl, ethyl, cyanomethyl, C-linked acetamido, methyl acetate, 2-hydroxyethyl, (R)-2-hydroxy-1-propyl, (S)-2-hydroxy-1-propyl, 1,3-dihydroxy-2-propyl or 1,2-dihydroxy-3-propyl.

In one particular embodiment, $R^1$ is methyl, cyanomethyl, C-linked acetamido, 2-hydroxyethyl, (R)-2-hydroxy-1-propyl or (S)-2-hydroxy-1-propyl.

In one embodiment, $R^1$ is (R)-2-hydroxy-1-propyl, 2-hydroxyethyl, cyanomethyl or C-linked acetamido.

In one embodiment, $R^1$ is 2-hydroxyethyl, cyanomethyl or C-linked acetamido.

In one embodiment, $R^1$ is 2-hydroxyethyl or C-linked acetamido.

In one embodiment, $R^1$ is 2-hydroxyethyl.

As defined above, $R^2$ is independently selected from halo, amino, hydroxymethyl, $C_{1-2}$ alkyl optionally substituted by up to three fluoro or $C_{1-2}$ alkoxy optionally substituted by up to three fluoro.

In one embodiment, when n is 1 or 2, $R^2$ is halo, methoxy or methyl. In particular, $R^2$ is halo or methoxy. In one embodiment, when $R^2$ is halo, it is fluoro or chloro. In a particular embodiment, $R^2$ is chloro or fluoro.

In one embodiment, when n is 2, $R^2$ is halo, which is preferably fluoro.

In one embodiment, $R^2$ is attached to one of the carbon atoms of the phenyl ring which is adjacent to —$SO_2NHR^1$. In other words, $R^2$ is attached ortho relative to —$SO_2NHR^1$. In an alternative embodiment, $R^2$ is attached meta relative to —$SO_2NHR^1$.

As defined above, $R^3$ is phenyl, pyridyl, pyrimidinyl, pyrazinyl or pyridazinyl wherein each of these groups may be optionally substituted by one or two substituents selected from halo, cyano, $C_{1-2}$ alkyl optionally substituted by up to three fluoro and $C_{1-2}$ alkoxy optionally substituted by up to three fluoro, wherein the substituents may be the same or different In one embodiment, $R^3$ is phenyl, pyridyl or pyrimidinyl, wherein each of these groups may be optionally substituted by one or two substituents selected from halo, cyano, $C_{1-2}$ alkyl optionally substituted by up to three fluoro, $C_{1-2}$ alkoxy optionally substituted by up to three fluoro, wherein the substituents may be the same or different; or $R^3$ is cyclohexyl which may be optionally substituted by one or two fluoro or chloro wherein each substituent may be attached to the same carbon atom and each substituent may be the same or different; or $R^3$ is tetrahydropyran.

In one embodiment, $R^3$ is phenyl, pyridyl, pyrazinyl or pyrimidinyl, wherein each of these groups may be optionally substituted by one substituent selected from halo, cyano, $C_{1-2}$ alkyl optionally substituted by up to three fluoro and $C_{1-2}$ alkoxy optionally substituted by up to three fluoro.

In one particular embodiment, $R^3$ is phenyl or pyridyl, wherein each of these groups may be optionally substituted by one or two substituents selected from halo, cyano, $C_{1-2}$ alkyl optionally substituted by up to three fluoro and $C_{1-2}$ alkoxy optionally substituted by up to three fluoro, wherein the substituents may be the same or different.

In one embodiment, $R^3$ is phenyl or pyridyl, wherein each of these groups may be optionally substituted by one substituent selected from halo, cyano, $C_{1-2}$ alkyl optionally substituted by up to three fluoro and $C_{1-2}$ alkoxy optionally substituted by up to three fluoro.

In one embodiment, $R^3$ is phenyl optionally substituted by one substituent selected from fluoro, methoxy, ethoxy, cyano, ethyl, —$CHF_2$, —$OCF_3$ and —$CF_3$.

In one embodiment, $R^3$ is phenyl optionally substituted by one substituent selected from fluoro, methoxy, cyano, ethyl and —$CHF_2$.

In another embodiment, $R^3$ is pyridyl optionally substituted by one substituent selected from fluoro, chloro, methyl, methoxy and cyano.

In one embodiment, $R^3$ is phenyl, pyridyl, pyrimidinyl, pyrazinyl or pyridazinyl wherein each of these groups may be optionally substituted by one or two substituents selected from fluoro, chloro, cyano, methyl, ethyl difluoromethyl (—$CHF_2$), trifluoromethyl, methoxy, ethoxy and trifluoromethoxy (—$OCF_3$)

In one embodiment, $R^3$ is phenyl, pyridyl or pyrimidinyl, wherein each of these groups may be optionally substituted by one or two substituents selected from fluoro, chloro, cyano, methyl, ethyl difluoromethyl (—$CHF_2$), trifluoromethyl, methoxy and trifluoromethoxy (—$OCF_3$).

In one embodiment, when $R^3$ is pyridyl, it is 2-pyridyl, 3-pyridyl or 4-pyridyl, particularly 2-pyridyl optionally substituted by any one of the groups defined above.

In one embodiment, when $R^3$ is cyclohexyl, it is substituted with two fluorine atoms, which are attached to the same carbon atom. In a particular embodiment, the two fluorine atoms are attached at the 4-position, such that $R^3$ is, for example, 4,4-difluorocyclohexyl.

In one embodiment, $R^3$ is pyridyl optionally substituted by one substituent selected from fluoro and chloro. In a particular embodiment, $R^3$ is 2-pyridyl optionally substituted by fluoro. In one embodiment, $R^3$ is 2-pyridyl substituted by fluoro.

In one embodiment, when $R^3$ is tetrahydropyran, it may be one of the following:

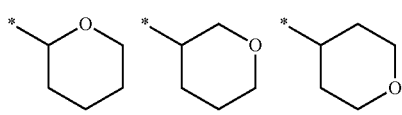

wherein * represents the point of attachment.

In one embodiment, when $R^3$ is tetrahydropyran, it is:

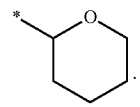

In one embodiment, when $R^3$ is tetrahydropyran, it is directed to a particular enantiomer, i.e. the (R)- or the (S)-enantiomer. Examples include the following:

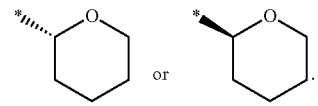 [SMILES: *[C@H]1CCCCO1 ; *[C@@H]1CCCCO1]

In one embodiment, when $R^1$ is 2-hydroxyethyl:
$R^3$ is phenyl optionally substituted by one substituent selected from fluoro, ethyl, methoxy, ethoxy, cyano, trifluoromethyl, —$OCF_3$ and —$CHF_2$;
$R^3$ is pyridyl optionally substituted by one or two substituents selected from fluoro, chloro, cyano, methyl and methoxy, wherein the substituents may be the same or different; pyrimidinyl optionally substituted by one methyl group;
$R^3$ is unsubstituted pyridazinyl;
$R^3$ is pyrazinyl optionally substituted by one substituent selected from methyl and methoxy;
$R^3$ is cyclohexyl which may be optionally substituted by one or two fluoro wherein each substituent may be attached to the same carbon atom; or
$R^3$ is tetrahydropyran.

In one embodiment, when $R^1$ is 2-hydroxyethyl, $R^3$ is phenyl optionally substituted by one substituent selected from fluoro, ethyl, methoxy, ethoxy, cyano, trifluoromethyl, —$OCF_3$ and —$CHF_2$; pyridyl optionally substituted by one or two substituents selected from fluoro, chloro, cyano, methyl and methoxy, wherein the substituents may be the same or different; pyrimidinyl optionally substituted by one methyl group; unsubstituted pyridazinyl; or pyrazinyl optionally substituted by one substituent selected from methyl and methoxy.

In one embodiment, when $R^1$ is 2-hydroxyethyl, $R^3$ is phenyl optionally substituted by one substituent selected from fluoro, ethyl, methoxy, ethoxy, cyano, trifluoromethyl, —$OCF_3$ and —$CHF_2$; pyridyl optionally substituted by one or two substituents selected from fluoro, chloro, cyano, methyl and methoxy, wherein the substituents may be the same or different; pyrimidinyl optionally substituted by one methyl group; or unsubstituted pyridazinyl.

In one embodiment, X is N; n is 0; $R^1$ is 2-hydroxyethyl; and $R^3$ is pyridyl optionally substituted by fluoro or chloro, preferably fluoro.

In one embodiment, the compound of Formula (I) is selected from the list consisting of:
(4-(2-(4-fluorobenzyl)-2H-tetrazol-5-yl)-N-(2-hydroxyethyl)benzenesulfonamide);
N-(2-hydroxyethyl)-4-(2-(pyrimidin-4-ylmethyl)-2H-tetrazol-5-yl)benzenesulfonamide;
4-(2-(4-fluorobenzyl)-2H-tetrazol-5-yl)-N-methylbenzenesulfonamide;
N-methyl-4-(2-(pyridin-4-ylmethyl)-2H-tetrazol-5-yl)benzenesulfonamide;
N-ethyl-4-(2-(pyridin-4-ylmethyl)-2H-tetrazol-5-yl)benzenesulfonamide;

N-(2-hydroxyethyl)-4-(2-(4-methoxybenzyl)-2H-tetrazol-5-yl)benzenesulfonamide;

N-(2-hydroxyethyl)-4-(2-((tetrahydro-2H-pyran-2-yl)methyl)-2H-tetrazol-5-yl)benzenesulfonamide;

4-(2-(4-chlorobenzyl)-2H-tetrazol-5-yl)-N-(2-hydroxyethyl)benzenesulfonamide;

4-(2-(4-cyanobenzyl)-2H-tetrazol-5-yl)-N-(2-hydroxyethyl)benzenesulfonamide;

4-(2-(4-(difluoromethyl)benzyl)-2H-tetrazol-5-yl)-N-(2-hydroxyethyl)benzenesulfonamide;

4-(2-((4,4-difluorocyclohexyl)methyl)-2H-tetrazol-5-yl)-N-(2-hydroxyethyl)benzenesulfonamide;

(R)—N-(2-hydroxypropyl)-4-(2-(pyridin-4-ylmethyl)-2H-tetrazol-5-yl)benzenesulfonamide (R)-4-(2-((4,4-difluorocyclohexyl)methyl)-2H-tetrazol-5-yl)-N-(2-hydroxypropyl)benzenesulfonamide;

(S)-4-(2-(4-fluorobenzyl)-2H-tetrazol-5-yl)-N-(2-hydroxypropyl)benzenesulfonamide;

N-(1,3-dihydroxypropan-2-yl)-4-(2-(4-fluorobenzyl)-2H-tetrazol-5-yl)benzenesulfonamide;

N-(1,3-dihydroxypropan-2-yl)-4-(2-(pyridin-4-ylmethyl)-2H-tetrazol-5-yl)benzenesulfonamide;

N-(2,3-dihydroxypropyl)-4-(2-(4-fluorobenzyl)-2H-tetrazol-5-yl)benzenesulfonamide;

4-(2-((5-chloropyridin-2-yl)methyl)-2H-tetrazol-5-yl)-N-(2-hydroxyethyl)benzenesulfonamide;

4-(2-(4-ethylbenzyl)-2H-tetrazol-5-yl)-N-(2-hydroxyethyl)benzenesulfonamide;

4-(2-((5-cyanopyridin-2-yl)methyl)-2H-tetrazol-5-yl)-N-(2-hydroxyethyl)benzenesulfonamide;

4-(2-((3,5-difluoropyridin-2-yl)methyl)-2H-tetrazol-5-yl)-N-(2-hydroxyethyl)benzenesulfonamide;

N-(2-hydroxyethyl)-4-(2-((6-methylpyridin-2-yl)methyl)-2H-tetrazol-5-yl)benzenesulfonamide;

N-(2-hydroxyethyl)-4-(2-((2-methylpyrimidin-4-yl)methyl)-2H-tetrazol-5-yl)benzenesulfonamide;

(R)-4-(2-(4-fluorobenzyl)-2H-tetrazol-5-yl)-N-(2-hydroxypropyl)benzenesulfonamide;

(R)-4-(2-((5-fluoropyridin-2-yl)methyl)-2H-tetrazol-5-yl)-N-(2-hydroxypropyl)benzenesulfonamide;

(R)—N-(2-hydroxypropyl)-4-(2-((5-methoxypyridin-2-yl)methyl)-2H-tetrazol-5-yl)benzenesulfonamide;

(R)—N-(2-hydroxypropyl)-4-(2-((5-methylpyridin-2-yl)methyl)-2H-tetrazol-5-yl)benzenesulfonamide;

(R)—N-(2-hydroxypropyl)-4-(2-(4-methoxybenzyl)-2H-tetrazol-5-yl)benzenesulfonamide;

4-(2-((5-fluoropyridin-2-yl)methyl)-2H-tetrazol-5-yl)-N-(2-hydroxyethyl)benzenesulfonamide;

4-(2-(3-fluoro-4-methoxybenzyl)-2H-tetrazol-5-yl)-N-(2-hydroxyethyl)benzenesulfonamide;

N-(2-hydroxyethyl)-4-(2-((5-methoxypyridin-2-yl)methyl)-2H-tetrazol-5-yl)benzenesulfonamide;

(N-(2-hydroxyethyl)-4-(2-((5-methylpyridin-2-yl)methyl)-2H-tetrazol-5-yl)benzenesulfonamide);

N-(2-hydroxyethyl)-4-(2-(pyridin-4-ylmethyl)-2H-tetrazol-5-yl)benzenesulfonamide;

N-(2-hydroxyethyl)-4-(2-((2-methylpyridin-4-yl)methyl)-2H-tetrazol-5-yl)benzenesulfonamide;

2-(4-(2-(4-methoxybenzyl)-2H-tetrazol-5-yl)phenylsulfonamido)acetamide;

2-(4-(2-(4-methylbenzyl)-2H-tetrazol-5-yl)phenylsulfonamido)acetamide;

2-(4-(2-(3,4-difluorobenzyl)-2H-tetrazol-5-yl)phenylsulfonamido)acetamide;

2-(4-(2-((5-fluoropyridin-2-yl)methyl)-2H-tetrazol-5-yl)phenylsulfonamido)acetamide;

2-(4-(2-((4,4-difluorocyclohexyl)methyl)-2H-tetrazol-5-yl)phenylsulfonamido)acetamide;

2-(4-(2-((5-methylpyridin-2-yl)methyl)-2H-tetrazol-5-yl)phenylsulfonamido)acetamide;

2-(4-(2-((5-chloropyridin-2-yl)methyl)-2H-tetrazol-5-yl)phenylsulfonamido)acetamide;

2-(4-(2-((2-methylpyridin-4-yl)methyl)-2H-tetrazol-5-yl)phenylsulfonamido)acetamide;

Methyl 2-(4-(2-(4-fluorobenzyl)-2H-tetrazol-5-yl)phenylsulfonamido)acetate;

Methyl 2-(4-(2-(pyridin-4-ylmethyl)-2H-tetrazol-5-yl)phenylsulfonamido)acetate;

2-(4-(2-(4-fluorobenzyl)-2H-tetrazol-5-yl)phenylsulfonamido)acetamide;

2-(4-(2-(pyridin-4-ylmethyl)-2H-tetrazol-5-yl)phenylsulfonamido)acet-amide;

(4-(2-(4-fluorobenzyl)-2H-tetrazol-5-yl)-N-(2-hydroxyethyl)-2-methoxybenzenesulfonamide);

(N-(2-hydroxyethyl)-2-methoxy-4-(2-(pyridin-4-ylmethyl)-2H-tetrazol-5-yl)benzenesulfonamide);

(4-(2-(4-cyanobenzyl)-2H-tetrazol-5-yl)-N-(2-hydroxyethyl)-2-methoxybenzenesulfonamide);

(4-(2-((5-fluoropyridin-2-yl)methyl)-2H-tetrazol-5-yl)-N-(2-hydroxyethyl)-2-methoxybenzenesulfonamide);

(2-methoxy-N-methyl-4-(2-(pyridin-4-ylmethyl)-2H-tetrazol-5-yl)benzenesulfonamide);

(N-(cyanomethyl)-4-(2-(4-fluorobenzyl)-2H-tetrazol-5-yl)benzenesulfonamide);

2-(4-(2-(4-fluorobenzyl)-2H-tetrazol-5-yl)-2-methoxyphenylsulfonamido)acetamide;

2-(4-(2-(4-cyanobenzyl)-2H-tetrazol-5-yl)-2-methoxyphenylsulfonamido)acetamide;

2-(2-methoxy-4-(2-(pyridin-4-ylmethyl)-2H-tetrazol-5-yl)phenylsulfonamido)acetamide;

(N-(cyanomethyl)-4-(2-(pyridin-4-ylmethyl)-2H-tetrazol-5-yl)benzenesulfonamide);

(N-(cyanomethyl)-4-(2-((5-fluoropyridin-2-yl)methyl)-2H-tetrazol-5-yl)benzenesulfonamide);

(N-(cyanomethyl)-4-(2-(pyrimidin-4-ylmethyl)-2H-tetrazol-5-yl)benzenesulfonamide;

(N-(cyanomethyl)-2-methoxy-4-(2-(pyridin-4-ylmethyl)-2H-tetrazol-5-yl)benzenesulfonamide);

(N-(cyanomethyl)-4-(1-(pyridin-4-ylmethyl)-1H-1,2,3-triazol-4-yl)benzenesulfonamide);

(N-(cyanomethyl)-4-(1-((5-fluoropyridin-2-yl)methyl)-1H-1,2,3-triazol-4-yl)benzenesulfonamide);

(4-(1-((5-fluoropyridin-2-yl)methyl)-1H-1,2,3-triazol-4-yl)-N-(2-hydroxyethyl)benzene sulfonamide);

(N-(2-hydroxyethyl)-4-(1-(4-methoxybenzyl)-1H-1,2,3-triazol-4-yl)benzenesulfonamide);

(4-(1-(4-fluorobenzyl)-1H-1,2,3-triazol-4-yl)-N-(2-hydroxyethyl)benzenesulfonamide);

(N-(2-hydroxyethyl)-4-(1-(pyridin-4-ylmethyl)-1H-1,2,3-triazol-4-yl)benzenesulfonamide);

(4-(1-(4-cyanobenzyl)-1H-1,2,3-triazol-4-yl)-N-(2-hydroxyethyl)benzenesulfonamide);

(N-(2-hydroxyethyl)-4-(1-((5-methylpyridin-2-yl)methyl)-1H-1,2,3-triazol-4-yl)benzenesulfonamide);

(2-(4-(1-(4-fluorobenzyl)-1H-1,2,3-triazol-4-yl)phenylsulfonamido)acetamide);

(2-(4-(1-((4,4-difluorocyclohexyl)methyl)-1H-1,2,3-triazol-4-yl)phenylsulfonamido)acetamide;

(R)-4-(1-(4-fluorobenzyl)-1H-1,2,3-triazol-4-yl)-N-(2-hydroxypropyl)benzenesulfonamide;

4-(2-((5-fluoropyridin-2-yl)methyl)-2H-tetrazol-5-yl)-N-(2-hydroxyethyl)-2-methylbenzenesulfonamide;

N-(2-hydroxyethyl)-2-methyl-4-(2-((tetrahydro-2H-pyran-2-yl)methyl)-2H-tetrazol-5-yl)benzenesulfonamide;
4-(2-((5-fluoropyridin-2-yl)methyl)-2H-tetrazol-5-yl)-N-(2-hydroxyethyl)-3-methylbenzenesulfonamide;
N-(2-hydroxyethyl)-3-methyl-4-(2-((tetrahydro-2H-pyran-2-yl)methyl)-2H-tetrazol-5-yl)benzenesulfonamide;
2-fluoro-4-(2-((5-fluoropyridin-2-yl)methyl)-2H-tetrazol-5-yl)-N-(2-hydroxyethyl)benzenesulfonamide;
2-fluoro-N-(2-hydroxyethyl)-4-(2-((tetrahydro-2H-pyran-2-yl)methyl)-2H-tetrazol-5-yl)benzenesulfonamide;
2-fluoro-4-(2-(4-fluorobenzyl)-2H-tetrazol-5-yl)-N-(2-hydroxyethyl)benzenesulfonamide;
2-fluoro-N-(2-hydroxyethyl)-4-(2-((tetrahydro-2H-pyran-4-yl)methyl)-2H-tetrazol-5-yl)benzenesulfonamide;
4-(2-(cyclohexylmethyl)-2H-tetrazol-5-yl)-2-fluoro-N-(2-hydroxyethyl)benzenesulfonamide;
2-chloro-4-(2-((5-fluoropyridin-2-yl)methyl)-2H-tetrazol-5-yl)-N-(2-hydroxyethyl)benzenesulfonamide;
3-chloro-4-(2-((5-fluoropyridin-2-yl)methyl)-2H-tetrazol-5-yl)-N-(2-hydroxyethyl)benzenesulfonamide;
2-(2-chloro-4-(2-(4-fluorobenzyl)-2H-tetrazol-5-yl)phenylsulfonamido)acetamide;
3-fluoro-4-(2-((5-fluoropyridin-2-yl)methyl)-2H-tetrazol-5-yl)-N-(2-hydroxyethyl)benzenesulfonamide;
3-fluoro-N-(2-hydroxyethyl)-4-(2-((tetrahydro-2H-pyran-2-yl)methyl)-2H-tetrazol-5-yl)benzenesulfonamide;
2,3-difluoro-4-(2-((5-fluoropyridin-2-yl)methyl)-2H-tetrazol-5-yl)-N-(2-hydroxyethyl)benzenesulfonamide;
2,3-difluoro-N-(2-hydroxyethyl)-4-(2-((tetrahydro-2H-pyran-2-yl)methyl)-2H-tetrazol-5-yl)benzenesulfonamide;
2,6-difluoro-4-(2-((5-fluoropyridin-2-yl)methyl)-2H-tetrazol-5-yl)-N-(2-hydroxyethyl)benzenesulfonamide;
(R)-2,6-difluoro-N-(2-hydroxyethyl)-4-(2-((tetrahydro-2H-pyran-2-yl)methyl)-2H-tetrazol-5-yl)benzenesulfonamide
N-(cyanomethyl)-4-(2-((tetrahydro-2H-pyran-4-yl)methyl)-2H-tetrazol-5-yl)benzenesulfonamide;
N-(cyanomethyl)-4-(2-(pyrazin-2-ylmethyl)-2H-tetrazol-5-yl)benzenesulfonamide;
N-(cyanomethyl)-4-(2-((5-methylpyrazin-2-yl)methyl)-2H-tetrazol-5-yl)benzenesulfonamide;
N-(cyanomethyl)-4-(2-((5-methoxypyrazin-2-yl)methyl)-2H-tetrazol-5-yl)benzenesulfonamide;
N-(cyanomethyl)-4-(2-((6-methoxypyridin-3-yl)methyl)-2H-tetrazol-5-yl)benzenesulfonamide;
N-(cyanomethyl)-4-(2-((tetrahydro-2H-pyran-2-yl)methyl)-2H-tetrazol-5-yl)benzenesulfonamide;
2-((4-(2-((4,4-difluorocyclohexyl)methyl)-2H-tetrazol-5-yl)-2-methoxyphenyl)sulfonamido)acetamide;
2-((4-(2-((tetrahydro-2H-pyran-2-yl)methyl)-2H-tetrazol-5-yl)phenyl)sulfonamido)acetamide;
N-(2-hydroxyethyl)-4-(2-(4-(trifluoromethoxy)benzyl)-2H-tetrazol-5-yl)benzenesulfonamide;
N-(2-hydroxyethyl)-4-(2-(4-(trifluoromethyl)benzyl)-2H-tetrazol-5-yl)benzenesulfonamide;
4-(2-(4-ethoxybenzyl)-2H-tetrazol-5-yl)-N-(2-hydroxyethyl)benzenesulfonamide;
4-(2-(cyclohexylmethyl)-2H-tetrazol-5-yl)-N-(2-hydroxyethyl)benzenesulfonamide;
N-(2-hydroxyethyl)-4-(2-((6-methylpyridin-3-yl)methyl)-2H-tetrazol-5-yl)benzenesulfonamide;
N-(2-hydroxyethyl)-4-(2-(pyridin-3-ylmethyl)-2H-tetrazol-5-yl)benzenesulfonamide;
(N-(2-hydroxyethyl)-4-(2-((5-methoxypyridin-2-yl)methyl)-2H-tetrazol-5-yl)benzenesulfonamide);
N-(2-hydroxyethyl)-4-(2-((tetrahydro-2H-pyran-3-yl)methyl)-2H-tetrazol-5-yl)benzenesulfonamide;
N-(2-hydroxyethyl)-4-(2-((tetrahydro-2H-pyran-4-yl)methyl)-2H-tetrazol-5-yl)benzenesulfonamide;
N-(2-hydroxyethyl)-4-(2-(pyridazin-4-ylmethyl)-2H-tetrazol-5-yl)benzenesulfonamide;
N-(2-hydroxyethyl)-4-(2-(pyridazin-3-ylmethyl)-2H-tetrazol-5-yl)benzenesulfonamide;
4-(2-(4-cyanobenzyl)-2H-tetrazol-5-yl)-N-methylbenzenesulfonamide;
N-(2-hydroxyethyl)-2-methoxy-4-(2-((5-methoxypyridin-2-yl)methyl)-2H-tetrazol-5-yl)benzenesulfonamide;
2-fluoro-4-(2-((5-fluoropyridin-2-yl)methyl)-2H-tetrazol-5-yl)-N-(2-hydroxyethyl)-5-methylbenzenesulfonamide;
(4-(2-(1-(5-fluoropyridin-2-yl)ethyl)-2H-tetrazol-5-yl)-N-(2-hydroxyethyl)benzenesulfonamide;
4-(2-(1-(5-fluoropyridin-2-yl)ethyl)-2H-tetrazol-5-yl)-N-(2-hydroxyethyl)benzenesulfonamide;
4-(1-(1-(4-fluorophenyl)ethyl)-1H-1,2,3-triazol-4-yl)-N-(2-hydroxyethyl)benzenesulfonamide;
2-(4-(2-(1-(4-fluorophenyl)ethyl)-2H-tetrazol-5-yl)phenylsulfonamido)acetamide; and
2-(4-(2-(1-(4-fluorophenyl)ethyl)-2H-tetrazol-5-yl)-2-methoxyphenylsulfonamido)acetamide.

In particular, the compound of Formula (I) is 4-(2-((5-fluoropyridin-2-yl)methyl)-2H-tetrazol-5-yl)-N-(2-hydroxyethyl)benzenesulfonamide.

It will further be appreciated that a compound of Formula (I) may exist in different tautomeric forms. All possible tautomers are contemplated to be within the scope of the present invention.

The compounds of Formula (I) or pharmaceutically acceptable salt thereof may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest. In one aspect of the invention, a compound of Formula (I) or pharmaceutically acceptable salt thereof is crystalline.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

Terms and Definitions

The term "$C_{1-2}$ alkyl optionally substituted by up to three fluoro" as used herein refers to methyl or ethyl each of which may be substituted by up to three fluorine atoms. Thus, non-limiting examples of groups bearing fluorine atoms included within this definition are —$CF_3$, —$CHF_2$, —$CH_2F$ and —$CH_2CF_3$.

The term "$C_{1-2}$ alkoxy optionally substituted by up to three fluoro" as used herein refers to methoxy (i.e. $OCH_3$) or ethoxy (i.e. $OCH_2CH_3$) each of which may be substituted by up to three fluorine atoms. Thus, non-limiting examples of such groups bearing fluorine atoms included within this definition are —$OCF_3$, —$OCHF_2$, —$OCH_2F$ and —$OCH_2CF_3$.

The term "halo" as used herein refers to a halogen selected from F, Cl and Br, preferably F and Cl.

The term "amino" as used herein refers to —$NH_2$.

The term "hydroxymethyl" as used herein refers to a methyl group wherein one of the hydrogen atoms has been exchanged for an OH group, i.e. an hydroxyl group.

The term "cyanomethyl" as used herein refers to a methyl group wherein one of the hydrogen atoms has been exchanged for a —CN group, i.e. a cyano group.

The term "cyano" as used herein refers to a —CN group.

The term "compounds of the invention" as used herein means a compound of Formula (I) or a pharmaceutically acceptable salt thereof. The term "a compound of the invention" means any one of the compounds of the invention as defined above.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, and this phrase also encompasses a mixture of a compound of Formula (I) and a pharmaceutically acceptable salt of a compound of Formula (I).

It is to be understood that references herein to a compound of Formula (I) or a pharmaceutically acceptable salt thereof includes a compound of Formula (I) as a free base or as a pharmaceutically acceptable salt thereof. Thus, in one embodiment, the invention is directed to a compound of Formula (I). In another embodiment, the invention is directed to a pharmaceutically acceptable salt of a compound of Formula (I).

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley—VCH/VHCA, 2011 (see http://www.wiley.com/WileyCDA/WileyTitle/productCd-3906390519.html).

Where the compound functionality allows, suitable pharmaceutically acceptable salts of the compound of Formula (I) can be formed, which include acid or base addition salts. Acid addition salts may be formed by reaction with the appropriate acid, optionally in a suitable solvent such as an organic solvent, to give the salt which can be isolated by crystallisation and filtration. Base addition salts may be formed by reaction with the appropriate base, optionally in a suitable solvent such as an organic solvent, to give the salt which can be isolated by crystallisation and filtration.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolidine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

An appropriate "therapeutically effective amount" will depend upon a number of factors including, for example, the age and weight of the subject, the precise condition requiring treatment and its severity, the nature of the formulation, and the route of administration, and will ultimately be at the discretion of the attendant physician.

It will be appreciated by those skilled in the art that references herein to treatment refer to the treatment of established conditions, including e.g. a mycobacterial infection or a disease resulting from a mycobacterial infection, such as tuberculosis. However, compounds of Formula (I) or pharmaceutically acceptable salts thereof may, depending on the condition, also be useful in the prevention of a mycobacterial infection or disease resulting from a mycobacterial infection, such as tuberculosis. Thus, in one embodiment, there is provided the treatment or prevention of a disease. In another embodiment there is provided the treatment of a disease. In a further embodiment there is provided the prevention of a disease.

The compounds of Formula (I) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in Formula (I), or in any chemical structure illustrated herein, is not specified, the structure is intended to encompass any stereoisomer and all mixtures thereof. Thus, compounds of Formula (I) containing one or more chiral centres may be used as racemic modifications including racemic mixtures and racemates, enantiomerically-enriched mixtures, or as enantiomerically-pure individual stereoisomers.

Compound Preparation

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention can be prepared according to the experimental procedures disclosed in the Examples section.

The general procedures used to synthesise the compounds of Formula (I) are described in reaction Schemes 1 to 4 below and illustrated in the examples.

Preparation of Compounds of Formula (I)

Compounds of Formula (Ia) which are tetrazole compounds of Formula (I) wherein X=N and $R^2$ is as defined in claim 1 (i.e. n is 1 or 2), in particular F or Cl, or OMe when adjacent to sulfonyl chloride or wherein $R^2$ is not present (i.e. n is 0) may be prepared according to the following general procedure as schematically shown in Scheme 1.

at a suitable temperature, for example 100° C. to 120° C., to produce 5-substituted 1H-tetrazoles 2.

Alternatively, a compound of Formula 2 may be obtained by reaction of sulfonyl chloride 3, wherein 3 is dissolved in a suitable solvent, for example, tetrahydrofuran followed by addition of an alkylamine having the formula $R_1NH_2$.

Compound 2 is then dissolved in a suitable solvent, for example, DMF, acetonitrile or acetone and an alkylating agent having the formula $R_3CH_2Y$ (wherein Y is a leaving group such as mesylate or halide, for example chlorine or bromine) is added in the presence of an inorganic base, for example potassium carbonate or an organic base, for example N,N-diisopropylethylamine or TEA at a suitable temperature, for example, rt to 90° C.

When $R^4$ is methyl, conditions substantially in accordance with conditions 2 set out in Scheme 1 are used for the coupling step.

Compounds of Formula Ia were obtained after purification.

Compounds of Formula Ib and Id which are tetrazole compounds (X=N) of Formula (I) wherein $R_2$ is other than to H (i.e. n is 1 or 2) may be prepared according to the following general procedures as schematically shown in Schemes 2a and 2c.

Scheme 1

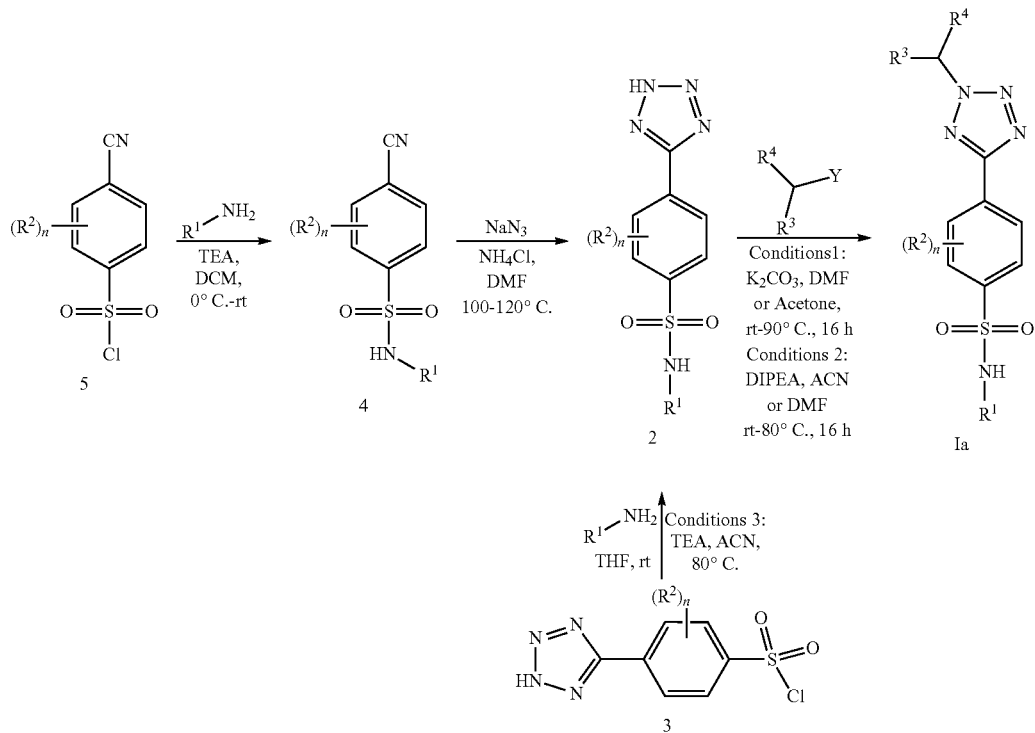

Preparation of compounds of Formula (I) wherein $R^1$ is methyl, ethyl, C-linked acetamido, methyl acetate, 2-hydroxyethyl, 2-hydroxy-1-propyl, 1,3-dihydroxy-2-propyl or 1,2-dihydroxy-3-propyl; and $R^2$ is as defined in claim 1

Sulfonyl chloride 5 is dissolved in a suitable solvent, for example dichloromethane, and an alkylamine having the formula $R_1NH_2$ in the presence of TEA is added to produce compounds of Formula 4. The reaction is carried out at a suitable temperature, for example, from 0° C. to ambient temperature. A cycloaddition reaction of a nitrile of Formula 4 with sodium azide and ammonium chloride is carried out Compounds of Formula Ib which are tetrazole compounds (X=N) of Formula (I) wherein $R^1$ is 2-hydroxyethyl and $R^2$ is other than H (for example, as defined in claim 1 when n is 1 or 2, more particularly methoxy, fluoro or methyl) may be prepared according to the following general procedure as schematically shown in Scheme 2a.

Scheme 2a

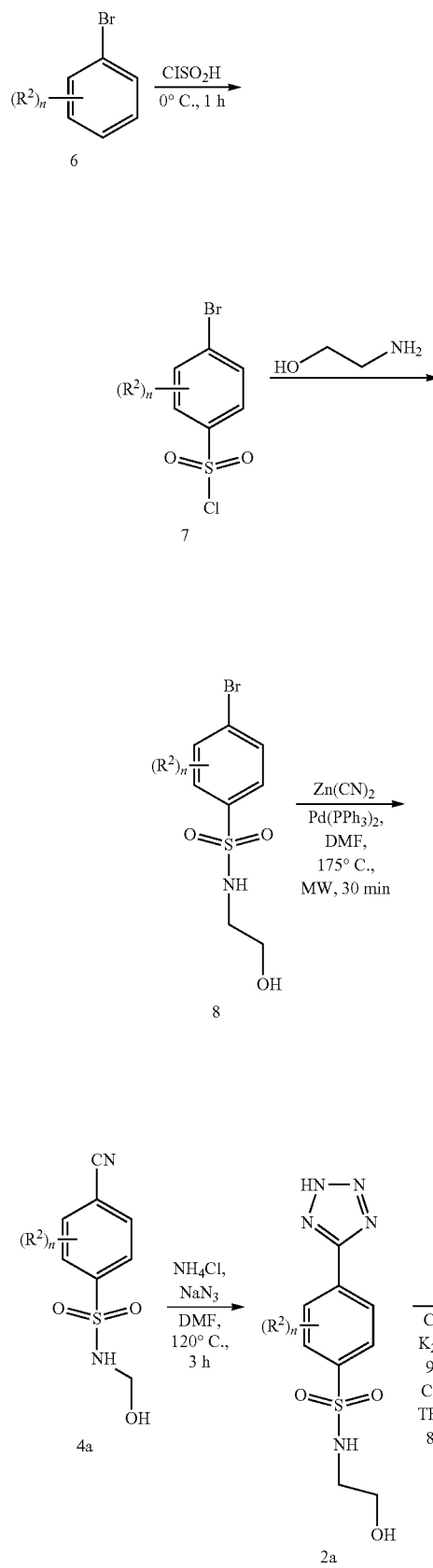

Compound 6 is reacted with chlorosulfonic acid at a suitable temperature, for example, about 0° C. for about 1 to 3 hours. The corresponding sulfonyl chloride 7 is then dissolved in a suitable solvent, for example dichloromethane, and reacted with an alkylamine having formula CH$_2$(OH)CH$_2$(NH$_2$) in the presence of TEA to produce compounds of Formula 8. Palladium-catalyzed cyanation reaction of aryl halide 8 with Zn(CN)$_2$ under microwave irradiation at a suitable temperature, for example, 175° C. for about 0.5 h affords nitrile compound 4a. Cycloaddition of nitrile 4a with sodium azide and ammonium chloride at a suitable temperature, for example 120° C., provides 5-substituted 1H-tetrazole 2a. Compound 2a is dissolved in a suitable solvent, for example, DMF or ACN and reacted with an alkylating agent having formula R$_3$CH$_2$Y (wherein Y is a leaving group such as mesylate or a halide, for example chlorine or bromine) in the presence of an inorganic base, for example, potassium carbonate or an organic base, for example TEA at a temperature ranging between 80 and 90° C.

Compounds of Formula Ib are obtained after purification.

Compounds of Formula Ic which are tetrazole compounds (X=N) of Formula (I) wherein R$^1$ is C-linked acetamido and wherein R$^2$ is as defined in claim 1 (in particular OMe, F or Cl) and when n is 1 or wherein R$^2$ is not present, i.e. n is 0, may be prepared according to the following general procedure as schematically shown in Scheme 2b.

Scheme 2b

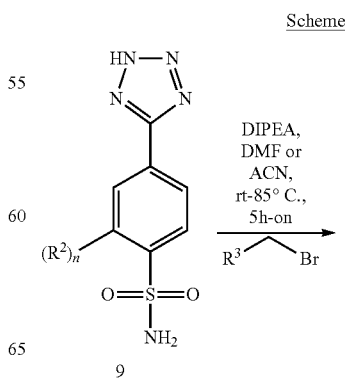

17

-continued

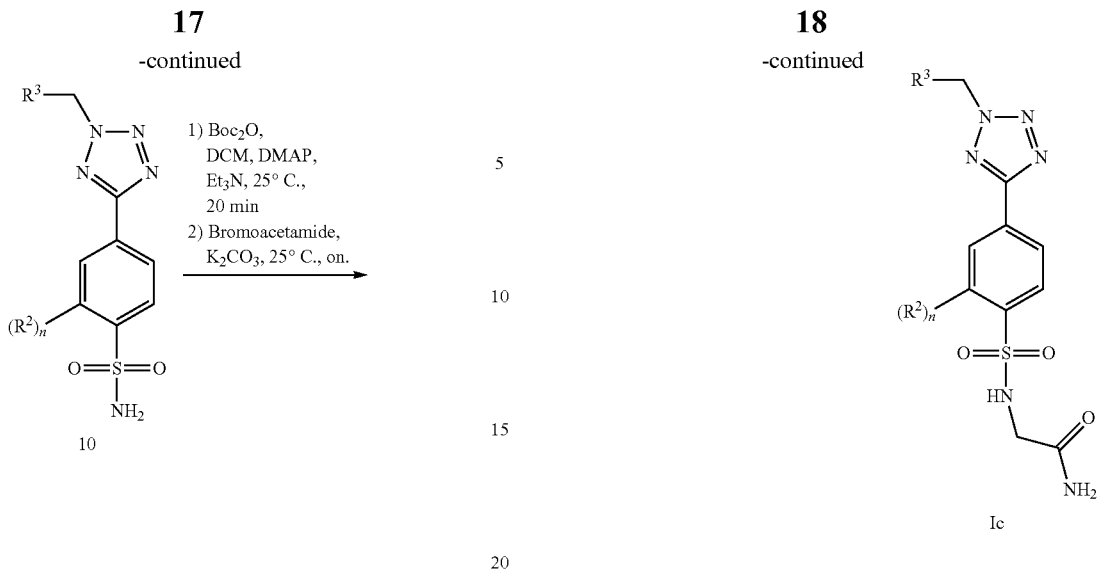

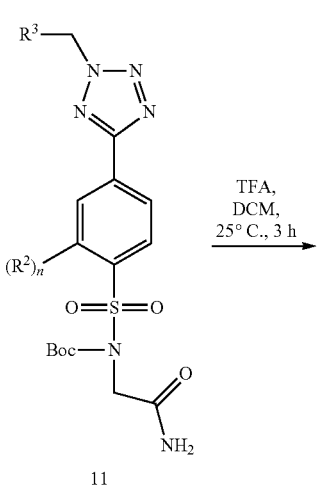

18

-continued

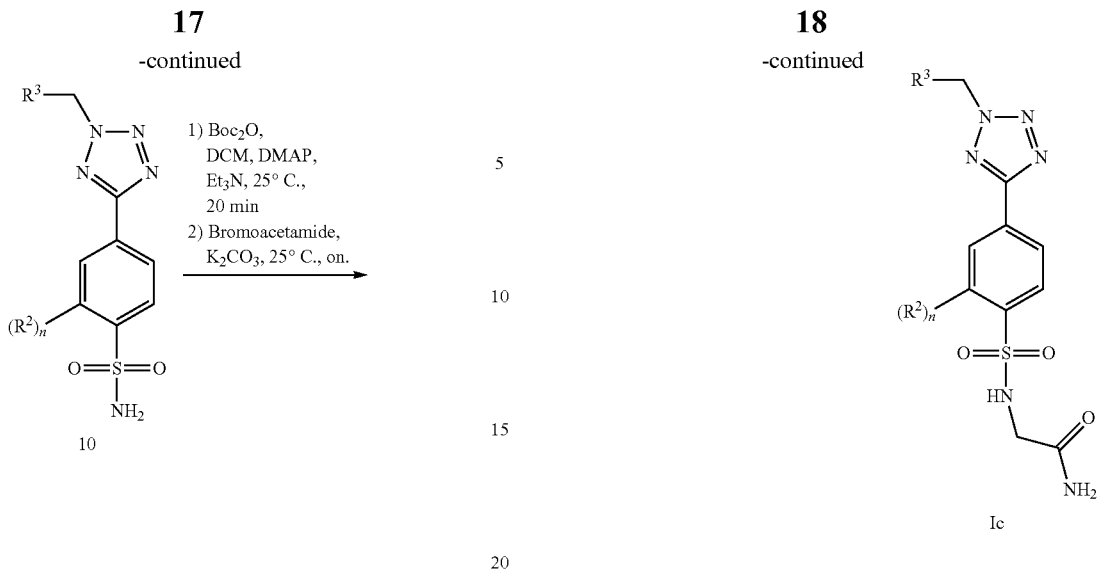

Compound 9 is dissolved in a suitable solvent, for example, DMF and reacted with an alkylating agent having formula $R_3CH_2Br$ in the presence of an organic base, for example DIPEA at a temperature ranging between ambient temperature to 80° C. The monoprotection of compound 10 with $(Boc)_2O$, triethylamine and a catalytic amount of 4-dimethylaminopyridine in dichloromethane, followed by N-alkylation using 2-bromoacetamide and potassium carbonate affords sulfonamide 11. Removal of the Boc protecting group from compound 11 e.g. using trifluoroacetic acid in dichloromethane at ambient temperature provides compounds Ic.

Compounds of Formula Ic are obtained after purification.

Compounds of Formula Id which are tetrazole compounds of Formula (I) wherein $R^1$ is cyanomethyl may be prepared according to the following general procedure as schematically shown in Scheme 2c.

Scheme 2c

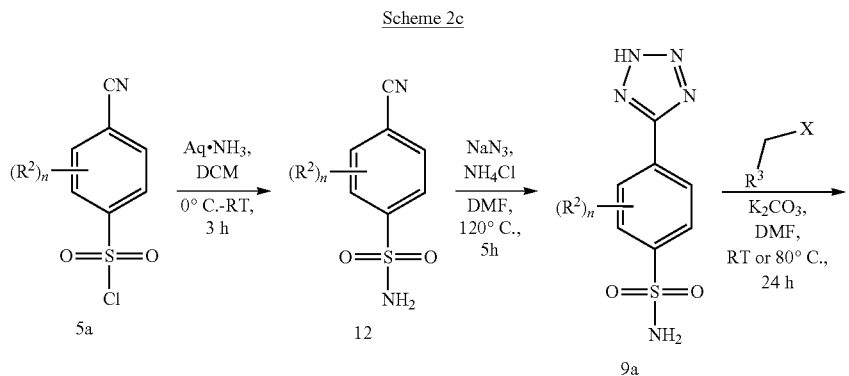

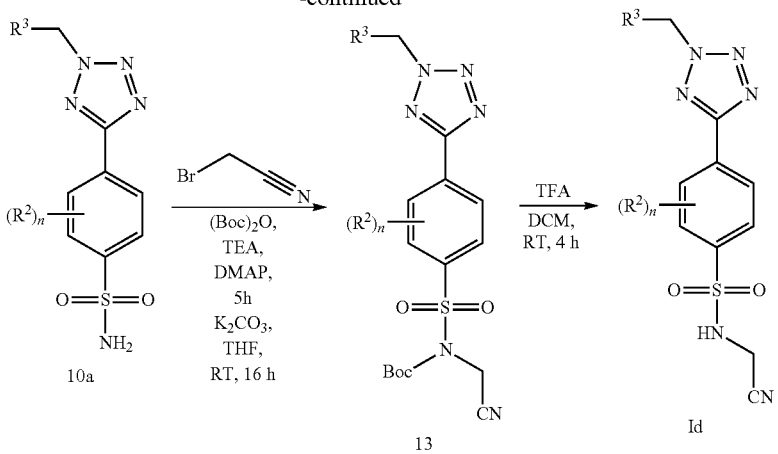

$R^3$ = Ph-F

Aryl sulfonyl chloride 5a is dissolved in aqueous ammonia and a suitable solvent, for example, dichloromethane at a suitable temperature, for example, from 0° C. to ambient temperature to produce primary sulfonamides 12. A cycloaddition reaction of the nitrile of Formula 12 with sodium azide and ammonium chloride is carried out at a suitable temperature, for example 120° C., to form 5-substituted 1H-tetrazoles 9a. Compound 9a is dissolved in a suitable solvent, for example, DMF and reacted with an alkylating agent having formula $R_3CH_2Y$ (wherein Y is a leaving group such as mesylate or a halide, for example chlorine or bromine) in the presence of an inorganic base, for example, potassium carbonate at a temperature ranging between ambient temperature to 80° C. The monoprotection of compound 10a with $(Boc)_2O$, triethylamine and a catalytic amount of 4-dimethylaminopyridine, followed by N-alkylation using alkylbromide and potassium carbonate, affords Boc-protected sulfonamide 13. Removal of the Boc protecting group e.g. using trifluoroacetic acid in dichloromethane at ambient temperature provides compounds of Formula Id. The products Id are obtained after purification.

Alternatively, sulfonamide 10a, benzotriazole and formaldehyde in ethanol/water are stirred at ambient temperature for about 48 h, wherein the benzotriazole-formaldehyde adduct is dissolved in DMSO and treated with KCN for 24 h to provide compound Id (when n is 0).

Compounds of Formula Ie which are triazole compounds (X=CH) of Formula (I) wherein $R^1$ and $R^2$ are as defined in claim 1, but not including $R^1$ is cyanomethyl, may be prepared according to the following general procedure as schematically shown in Scheme 3.

Scheme 3

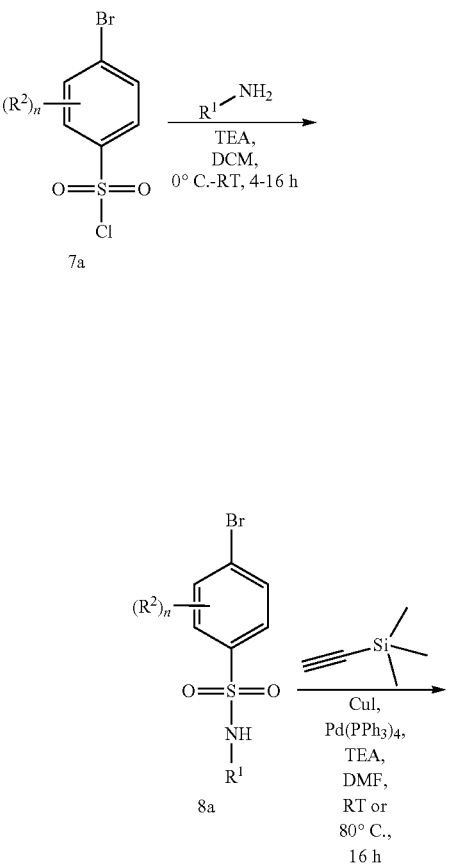

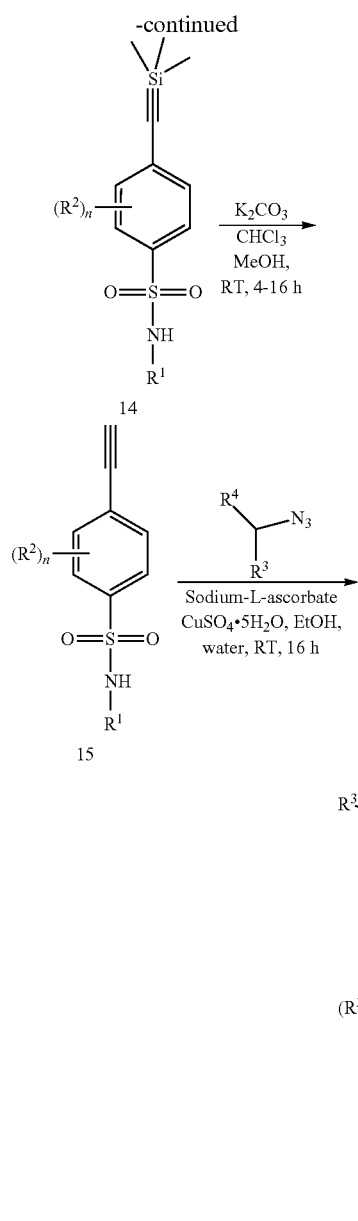

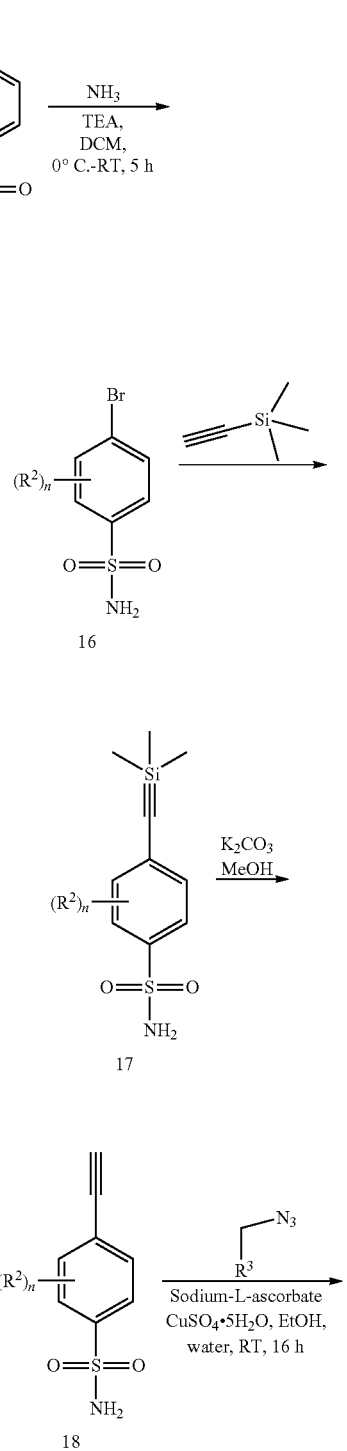

sulfate pentahydrate is reduced by sodium ascorbate in a mixture of ethanol and water at ambient temperature. Compounds of Formula Ie are obtained after purification.

Compounds of Formula (If) which are triazole compounds (X=CH) of Formula (I) wherein $R_1$ is cyanomethyl may be prepared according to the following general procedure as schematically shown in Scheme 4.

Scheme 4

Aryl sulfonyl chloride 7a is dissolved in a suitable solvent, for example dichloromethane, and reacted with an alkylamine having formula $R_1NH_2$ in the presence of TEA at a suitable temperature, for example, from 0° C. to ambient temperature to produce compounds of Formula 8a. An aryl bromide of Formula 9a is coupled in a Sonogashira type reaction with (trimethylsilyl)acetylene using a suitable catalyst system, for example tetrakis(triphenylphosphine)palladium(0) and cuprous(I)iodide, in a suitable solvent, for example DMF, in the presence of a base, for example triethylamine, at a temperature ranging between ambient temperature to 80° C., to give a compound of Formula 14. Deprotection of 14 to give a compound of 15 can be achieved with a base, for example potassium carbonate, in a suitable solvent, for example chloroform/methanol, at ambient temperature. 1,4-Disubstituted 1,2,3-triazoles of Formula Ie are obtained by a copper(I) catalyzed 1,3-dipolar cycloaddition reaction between appropriate aromatic azides and terminal acetylenes of Formula 15 wherein Cu(II)

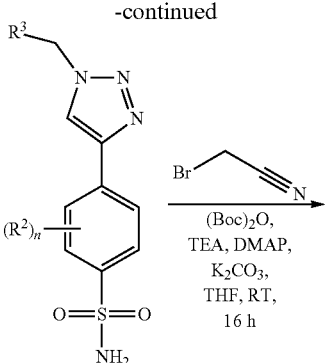

19

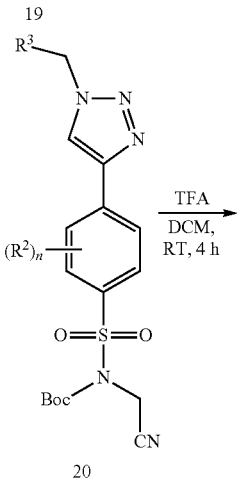

20

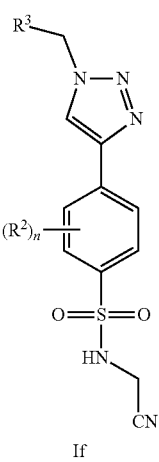

If

Aryl sulfonyl chloride 7a is dissolved in a suitable solvent, for example dichloromethane, and reacted with ammonia in the presence of TEA at a suitable temperature, for example, from 0° C. to ambient temperature to produce compounds of Formula 16. An aryl bromide of Formula 16 is coupled in a Sonogashira type reaction with (trimethylsilyl)acetylene using a suitable catalyst system, for example tetrakis(triphenylphosphine)palladium(0) and cuprous(I)iodide, in a suitable solvent, for example DMF, in the presence of a base, for example triethylamine, at 27° C., to give a compound of Formula 17. Deprotection of a compound of Formula 17 to give a compound of Formula 18, can be achieved with a base, for example potassium carbonate, in a suitable solvent, for example chloroform/methanol, at room temperature. 1,4-Disubstituted 1,2,3-triazoles of Formula 19 are obtained by a copper(I) catalyzed 1,3-dipolar cycload- dition reaction between appropriate aromatic azides and terminal acetylenes of Formula 18 wherein Cu(II) sulfate pentahydrate is reduced by sodium ascorbate in a mixture of ethanol and water at ambient temperature. The monoprotection of 19 with (Boc)$_2$O, triethylamine and a catalytic amount of 4-dimethylaminopyridine, followed by N-alkylation using alkylbromide and potassium carbonate, that affords the sulfonamide 20. Removal of the Boc protecting group e.g. using trifluoroacetic acid in dichloromethane at ambient temperature provides compounds If. Compounds of Formula If are obtained after purification.

Methods of Use

In one aspect, the invention relates to a compound of Formula (I), or a pharmaceutically acceptable salt thereof, for use in therapy.

In one aspect, the invention relates to a compound of Formula (I), or a pharmaceutically acceptable salt thereof, for use in the treatment of a mycobacterial infection. A mycobacterial infection is one caused by infection with a *Mycobacterium*.

The *Mycobacterium* may be a member of one of the following groups of *Mycobacterium*: *Mycobacterium tuberculosis* complex (MTC), *Mycobacterium avium* complex (MAC), *Mycobacterium gordonae* clade, *Mycobacterium kansasii* clade, *Mycobacterium chelonae* clade, *Mycobacterium fortuitum* clade, *Mycobacterium parafortuitum* clade or *Mycobacterium vaccae* clade. The *Mycobacterium* may also be *Mycobacterium ulcerans* or *Mycobacterium leprae*.

In one embodiment, the *Mycobacterium* is a member of the *Mycobacterium tuberculosis* complex (MTC).

Members of *Mycobacterium tuberculosis* complex (MTC) include *Mycobacterium tuberculosis*, *Mycobacterium africanum*, *Mycobacterium bovis*, *Mycobacterium bovis* BCG, *Mycobacterium canetti*, *Mycobacterium caprae*, *Mycobacterium microti* and *Mycobacterium pinnipedii*. These mycobacteria are causative agents of human and animal tuberculosis. *Mycobacterium tuberculosis* is the major cause of human tuberculosis.

In one embodiment, the infection is a *Mycobacterium tuberculosis* infection. In other words, the mycobacterial infection is caused by infection with *Mycobacterium tuberculosis*.

In one embodiment, the *Mycobacterium tuberculosis* is multidrug-resistant.

Members of *Mycobacterium avium* complex (MAC) include *Mycobacterium avium*, *Mycobacterium avium paratuberculosis*, *Mycobacterium avium silaticum*, *Mycobacterium avium hominissuis*, *Mycobacterium columbiense* and *Mycobacterium indicus pranii*.

Members of *Mycobacterium gordonae* clade include *Mycobacterium asiaticum* and *Mycobacterium gordonae*.

Members of *Mycobacterium kansasii* clade include *Mycobacterium gastri* and *Mycobacterium kansasii*.

Members of *Mycobacterium chelonae* clade include *Mycobacterium abscessus*, *Mycobacterium bolletii* and *Mycobacterium chelonae*.

Members of *Mycobacterium fortuitum* clade include *Mycobacterium boenickei*, *Mycobacterium brisbanense*, *Mycobacterium cosmeticum*, *Mycobacterium fortuitum*, *Mycobacterium fortuitum* subspecies *acetamidolyticum*, *Mycobacterium houstonense*, *Mycobacterium mageritense*, *Mycobacterium neworleansense*, *Mycobacterium peregrinum*, *Mycobacterium porcinum*, *Mycobacterium senegalense* and *Mycobacterium septicum*.

Members of *Mycobacterium parafortuitum* clade include *Mycobacterium austroafricanum*, *Mycobacterium diern-*

*hoferi, Mycobacterium frederiksbergense, Mycobacterium hodleri, Mycobacterium neoaurum* and *Mycobacterium parafortuitum*.

Therefore, the mycobacterial infection may be caused by infection with a *Mycobacterium* selected from the following: *Mycobacterium tuberculosis, Mycobacterium africanum, Mycobacterium bovis, Mycobacterium bovis* BCG, *Mycobacterium canetti, Mycobacterium caprae, Mycobacterium microti, Mycobacterium pinnipedii, Mycobacterium avium, Mycobacterium avium paratuberculosis, Mycobacterium avium silaticum, Mycobacterium avium hominissuis, Mycobacterium columbiense, Mycobacterium indicus pranii, Mycobacterium asiaticum, Mycobacterium gordonae, Mycobacterium gastri, Mycobacterium kansasii, Mycobacterium abscessus, Mycobacterium bolletii, Mycobacterium chelonae,* include *Mycobacterium boenickei, Mycobacterium brisbanense, Mycobacterium cosmeticum, Mycobacterium fortuitum, Mycobacterium fortuitum* subspecies *acetamidolyticum, Mycobacterium houstonense, Mycobacterium mageritense, Mycobacterium neworleansense, Mycobacterium peregrinum, Mycobacterium porcinum, Mycobacterium senegalense, Mycobacterium septicum, Mycobacterium austroafricanum, Mycobacterium diernhoferi, Mycobacterium frederiksbergense, Mycobacterium hodleri, Mycobacterium neoaurum, Mycobacterium parafortuitum, Mycobacterium ulcerans* and *Mycobacterium leprae*.

In another aspect, the invention relates to a compound of Formula (I), or a pharmaceutically acceptable salt thereof, for use in the treatment of a disease caused by infection with a *Mycobacterium*, where the *Mycobacterium* is selected from those hereinbefore described.

Diseases caused by infection with a *Mycobacterium* include, but are not limited to, tuberculosis (e.g. from *Mycobacterium tuberculosis*), leprosy (e.g. from *Mycobacterium leprae*), Johne's disease (e.g. from *Mycobacterium avium* subspecies *paratuberculosis*), Buruli or Bairnsdale ulcer (e.g. from *Mycobacterium ulceran*), Crohn's disease (e.g. from *Mycobacterium avium* subspecies *paratuberculosis*), pulmonary disease or pulmonary infection, pneumonia, bursa, synovial, tendon sheaths, localized abscess, lymphadenitis, skin and soft tissue infections, Lady Windermere syndrome (e.g. from *Mycobacterium avium* complex (MAC)), MAC lung disease, disseminated *Mycobacterium avium* complex (DMAC), disseminated *Mycobacterium avium* intraceullulare complex (DMAIC), hot-tub lung (e.g. from *Mycobacterium avium* complex), MAC mastitis, MAC pyomyositis, or granuloma disease.

In one embodiment, the disease is tuberculosis. Thus, one aspect of the invention relates to a compound of Formula (I), or a pharmaceutically acceptable salt thereof, for use in the treatment of tuberculosis.

In another aspect, the invention relates to a method of treatment of a mycobacterial infection in a mammal in need thereof, said treatment comprising administering to said mammal a therapeutically effective amount of a compound of Formula (I), or pharmaceutically acceptable salt thereof. As described herein, a mycobacterial infection is one caused by infection with a *Mycobacterium*. The *Mycobacterium* is as hereinbefore described.

In one embodiment, the invention relates to a method of treatment of a *Mycobacterium tuberculosis* infection.

In another aspect, the invention relates to a method of treatment of a disease caused by infection with a *Mycobacterium* in a mammal in need thereof, said treatment comprising administering to said mammal a therapeutically effective amount of a compound of Formula (I), or a pharmaceutically acceptable salt thereof.

In one embodiment, the disease is tuberculosis. Therefore, also described herein is a method of treatment of tuberculosis in a mammal in need thereof, said treatment comprising administering to said mammal a therapeutically effective amount of a compound of Formula (I), or a pharmaceutically acceptable salt thereof.

In one embodiment, the mammal is a human.

In another aspect, the invention relates to use of a compound of Formula (I), or a pharmaceutically acceptable salt thereof, in the manufacture of a medicament for use in the treatment of a mycobacterial infection or in the treatment of a disease caused by infection with a *Mycobacterium*.

Also described herein is the use of a compound of Formula (I), or a pharmaceutically acceptable salt thereof, in the manufacture of a medicament for use in the treatment of tuberculosis.

In an embodiment, the treatment of tuberculosis may be directed to the treatment of multidrug-resistant tuberculosis, extensively drug-resistant, or drug-sensitive tuberculosis. In addition, the treatment may be directed to pulmonary and/or extra-pulmonary tuberculosis. The treatment may also be directed to the treatment of latent TB.

In an embodiment, the compound of Formula (I) for use in the above described methods and treatments is 4-(2-((5-fluoropyridin-2-yl)methyl)-2H-tetrazol-5-yl)-N-(2-hydroxyethyl)benzenesulfonamide having the following structure:

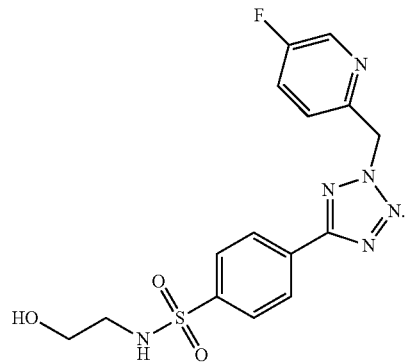 [SMILES: O=S(=O)(NCCO)c1ccc(-c2nnn(Cc3ccc(F)cn3)n2)cc1]

Pharmaceutical Compositions

The compounds of Formula (I) or pharmaceutically acceptable salts thereof will normally, but not necessarily, be formulated into pharmaceutical compositions prior to administration to a patient. Accordingly, in another aspect there is provided a pharmaceutical composition comprising a compound of Formula (I), or a pharmaceutically acceptable salt thereof, and a pharmaceutically acceptable excipient.

Pharmaceutical compositions may be administered by any appropriate route, for example by the oral (including buccal or sublingual), inhaled, intranasal, topical (including buccal, sublingual or transdermal), parenteral (including subcutaneous, intramuscular, intravenous or intradermal) route. In particular, pharmaceutical compositions are administered via an oral route of administration.

Suitable pharmaceutically acceptable excipients include the following types of excipients: carriers, diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants and buffering agents.

Suitable methods for formulating compounds of the invention will be familiar to those skilled in the art, which are described in Remington: The Science and Practice of Pharmacy, 21$^{st}$ Edition 2006.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

When a compound of Formula (I) or pharmaceutically acceptable salt thereof is used in the treatment of tuberculosis, they may be employed alone or in combination with a further therapeutic agent, such as a further anti-mycobacterial agent, in particular a further anti-tuberculosis agent and/or antiviral agent, including antiretroviral agents.

For example, the present invention relates to a combination of (a) a compound of Formula (I) or a pharmaceutically acceptable salt thereof, and (b) a further anti-tuberculosis agent. In an embodiment, the combination comprises two, three, four, five, six or seven additional anti-tuberculosis agents. For example, in the treatment of multidrug-resistant tuberculosis, it is common that combinations of four or more drugs are administered to patients. For example, in the treatment of drug-sensitive tuberculosis, it is common that combinations of three or four drugs are administered to patients.

The further anti-tuberculosis agent is an agent in development, approved or recommended for the treatment of tuberculosis and may be selected from isoniazid, rifampin, pyrazinamide, ethambutol, moxifloxacin, rifapentine, clofazimine, ethionamide, prothionamide, isoxyl, thiacetazone, a diarylquinoline such as bedaquiline (TMC207) or TBAJ-587, nitroimidazo-oxazine PA-824 (pretomanid), delamanid (OPC-67683), an oxazolidinone such as linezolid, tedizolid, radezolid, sutezolid (PNU-100480), posizolid (AZD-5847) or TBI-223, EMB analogue SQ109, OPC-167832, GSK3036656A (also known as GSK070), GSK2556286, GSK3211830, a benzothiazinone such as BTZ043 or PBTZ169, an azaindole such as TBA-7371, a dinitrobenzamide, or a beta-lactam such as sanfetrinem, meropenem, faropenem, ertapenem, tebipenem or beta-lactam combinations such as AUGMENTIN (amoxicillin-clavulanate).

In one embodiment, the further anti-tuberculosis agent is an agent in development, approved or recommended for the treatment of tuberculosis and may be selected from isoniazid, rifampin, pyrazinamide, ethambutol, moxifloxacin, rifapentine, clofazimine, ethionamide, prothionamide, isoxyl, thiacetazone, bedaquiline (TMC207), nitroimidazo-oxazine PA-824, delamanid (OPC-67683), an oxazolidinone such as linezolid, tedizolid, radezolid, sutezolid (PNU-100480), or posizolid (AZD-5847), EMB analogue SQ109, OPC-167832, GSK3036656 (also known as GSK070), GSK2556286, GSK3211830, and a benzothiazinone or a dinitrobenzamide.

A combination according to the present invention may further comprise an antiviral agent, including an antiretroviral agents.

Such antiretroviral agents may be selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

The combinations may conveniently be presented for use in the form of a pharmaceutical composition or formulation. Therefore, also contemplated herein is a pharmaceutical composition comprising (a) a compound of Formula (I) or a pharmaceutically acceptable salt thereof, as herein described, together with (b) a further anti-tuberculosis agent and (c) optionally an antiviral agent including antiretroviral agents, and (d) one or more pharmaceutically acceptable excipients, as herein described.

A compound of Formula (I) or a pharmaceutically acceptable salt thereof and further therapeutic agent may be administered together or separately and, when administered separately, this may occur separately or sequentially in any order (by the same or by different routes of administration). The amount of a compound of the invention or pharmaceutically acceptable salt thereof and the further therapeutically active agent(s) and the relative timings of administration will be selected in order to achieve the desired combined therapeutic effect.

EXAMPLES

The invention will now be illustrated by way of the following non-limiting examples. While particular embodiments of the invention are described below a skilled person will appreciate that various changes and modifications can be made. References to preparations carried out in a similar manner to, or by the general method of, other preparations, may encompass variations in routine parameters such as time, temperature, workup conditions, minor changes in reagents amounts, etc.

In certain of the following Intermediates and Examples, starting materials are identified by reference to other Intermediate or Example numbers. This does not signify that the actual material from any particular Intermediate or Example was necessarily used in a subsequent step exemplified herein, but is used as a short-hand means of denoting the relevant compound name.

Abbreviations

The following list provides definitions of certain abbreviations and symbols as used herein. It will be appreciated that the list is not exhaustive, but the meaning of those abbreviations and symbols not herein below defined will be readily apparent to those skilled in the art. In describing the invention, chemical elements are identified in accordance with the Periodic Table of the Elements.

| | |
|---|---|
| ACN/MeCN | Acetonitrile |
| anh | anhydrous |

| | |
|---|---|
| Boc | N-tert-butoxycarbonyl |
| (Boc)$_2$O | di-tert-butyl dicarbonate |
| CDCl3 | Deuterated chloroform |
| conc. | Concentration |
| DCM | Dichloromethane |
| DIPEA | Diisopropylethylamine |
| DMAP | 4-Dimethylaminopyridine |
| DMF | N,N-Dimethylformamide |
| DMSO | Dimethylsulfoxide |
| DMSO-d$_6$ | Deuterated dimethylsulfoxide |
| ee | enantiomeic excess |
| Et$_2$O | Diethyl ether |
| EtOAc | Ethyl acetate |
| g | grams |
| h | hours |
| HATU | N-[(Dimethylamino)]-1H-1,2,3-triazolo-[4,5-b]pyridin-1-ylmethylene]-N-methylmethanaminium hexafluorophosphate N-oxide |
| HCl | Hydrochloric acid |
| HPLC | High Performance Liquid Chromatography |
| Hz | Hertz |
| L | Litres |
| LCMS | Liquid Chromatography/Mass Spectrometry |
| M | Molar |
| Mesylate | Methanesulfonate |
| MeOH | Methanol |
| OMs | Methanesulfonate |
| MsCl | Mesyl chloride, methanesulfonyl chloride |
| min | Minutes |
| mL | Millilitre |
| mmol | Millimole |
| μM | Micromolar |
| MS | Mass spectrum |
| MW | Microwave |
| N | Normal concentration |
| NMR | Nuclear Magnetic Resonance spectroscopy |
| PBr$_3$ | Phosphorus tribromide |
| pet. ether | Petroleum ether |
| prep. | preparative |
| rt/RT | room temperature |
| Sat | saturated |
| SFC | Supercritical fluid chromatography |
| TFA | Trifluoroacetic acid |
| TEA | Triethylamine |
| THF | Tetrahydrofuran |
| THP | Tetrahydropyranyl |
| TLC | Thin layer chromatography |
| UPLC | Ultra Performance Liquid Chromatography |
| Ph$_3$P | triphenylphosphine |

Analytical Equipment $^1$H NMR spectra were recorded a Varian 400 MHz or Bruker Ultrashield DPX 400 MHz instruments.

Chemical shifts are expressed in parts per million (ppm, δ units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

All temperatures are reported in degrees centigrade.

MS and liquid chromatography: MS were recorded on Waters UPLC with PDA detector—Single quad & Triple Quad with mass analysis range up to M/Z=2000 or HPLC Agilent 1100 with Quadrupole 6120 (Agilent) system.

HPLC/UPLC data were recorded on Waters Alliance machine with PDA detector or 2695 and Waters H-Class with PDA detector or HPLC semi-preparative Agilent 1200

INTERMEDIATES

Synthesis of R3-Y Intermediates

Y is a leaving group such as mesylate or a halide, for example chlorine or bromine.

The alcohol function of Formula 22 was converted to the corresponding bromide 21 by the treatment of phosphorus tribromide (PBr$_3$) in dichloromethane or with triphenylphosphine (Ph$_3$P) and carbon tetrabromide (CBr$_4$) in dichloromethane at 0 to 28° C.

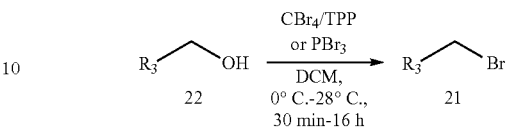

Intermediate 1: 4-(bromomethyl)pyrimidine

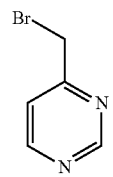

To a stirred solution of pyrimidin-4-ylmethanol (500 mg, 4.5454 mmol, commercial source: Manchestar) in dichloromethane (15 mL), carbon tetrabromide (2.26 g, 6.8181 mmol) and triphenyl phosphine (1.786 g, 6.8181 mmol) were added at 0° C. The reaction mixture was stirred at 26° C. for 2 h. Upon completion, the reaction mixture was concentrated under reduced pressure at 35° C. and the crude compound was purified by column chromatography (silica gel 100-200 mesh), eluted with 13% ethyl acetate in petroleum ether. The pure fractions were collected and concentrated under reduced pressure to afford 4-(bromomethyl)pyrimidine (270 mg, 34%) as a red liquid that was characterized by $^1$H-NMR. This crude was used without any purification in the next reaction. $^1$H NMR (400 MHz, CDCl$_3$) δ 9.19 (d, J=1.4 Hz, 1H), 8.76 (d, J=5.2 Hz, 1H), 7.49 (dd, J=5.2, 1.4 Hz, 1H), 4.45 (s, 2H).

Intermediate 2: 2-(bromomethyl)-5-methylpyridine

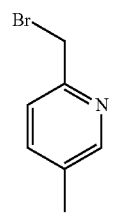

To a solution of (5-methylpyridin-2-yl)methanol (150 mg, 0.0012 mol, commercial source: Combi-Blocks) in dichloromethane (1.5 mL), triphenyl phosphine (629 mg, 0.0024 mol) was added at 28° C. The reaction mixture was stirred for 15 min at 0° C., followed by the addition of carbon tetrabromide (397 mg, 0.0012 mol). The reaction mixture was stirred at 28° C. for 3 h. On completion, the reaction mixture was concentrated under reduced pressure to afford 2-(bromomethyl)-5-methylpyridine (350 mg, crude) as a pale yellow gummy solid MS m/z (M, M+2)=186.1, 188.1. The compound was used for next step without any further purification.

Intermediate 3:
4-(bromomethyl)-1,1-difluorocyclohexane

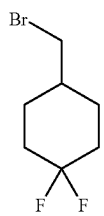

To a solution of (4,4-difluorocyclohexyl)methanol (1 g, 0.0066 mol, commercial source: J&W Pharma) in dichloromethane (5 mL), triphenyl phosphine (3.4 g, 0.0133 mol) was added at 26° C., followed by the addition of a solution of carbon tetrabromide (2.1 g, 0.0066 mol) in dichloromethane (5 mL) slowly in dropwise at 0° C. The reaction mixture was stirred at 26° C. for 16 h. On completion, the reaction mixture was concentrated under reduced pressure at 26° C. The crude was stirred with n-pentane (100 mL) at 26° C. for 10 min. The n-pentane layer was decanted and concentrated under reduced pressure to afford 4-(bromomethyl)-1,1-difluorocyclohexane (1.7 g) as a colorless liquid that was characterized by H-NMR. This crude was used without any purification in the next reaction. $^1$H NMR (400 MHz, CDCl$_3$) δ 3.31 (d, J=6.4 Hz, 2H), 2.21-2.06 (m, 2H), 2.00-1.90 (m, 2H), 1.83-1.63 (m, 3H), 1.47-1.32 (m, 2H).

Intermediate 4:
2-(bromomethyl)-5-methoxypyridine Hydrobromide

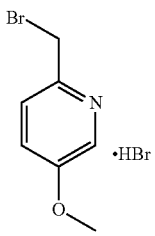

To a solution of (5-methoxypyridin-2-yl)methanol (200 mg, 0.00143 mol, commercial source: Combi-Blocks) in dichloromethane (2 mL), phosphorus tribromide (0.4 mL) was added at 0° C. The reaction mixture was stirred at 28° C. for 2 h. On completion, the reaction mixture was concentrated under reduced pressure to afford 2-(bromomethyl)-5-methoxypyridine hydrobromide (300 mg) as a brown solid. MS m/z [M+H]$^+$ & [M+2H]$^+$=202.00 and 204.0. The compound was used for the next step without any further purification.
(M, M+2)=202.00, 204.0

Intermediate 5: 2-(bromomethyl)-5-fluoropyridine Hydrobromide

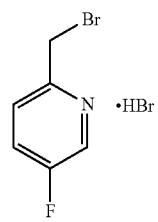

To a stirred solution of (5-fluoropyridin-2-yl)methanol (600 mg, 4.7244 mmol, commercial source: Combi-Blocks) in dichloromethane (15 mL), phosphorus tribromide (1.5 mL) was added at 0° C. The reaction mixture was allowed to stir at 26° C. for 3 h. On completion, the reaction mixture was concentrated under reduced pressure to afford 2-(bromomethyl)-5-fluoropyridine hydrobromide (1.7 g) as a yellow solid. $^1$H NMR (400 MHz, DMSO-d$_6$) δ 8.76-8.62 (m, 1H), 8.12-7.94 (m, 1H), 7.76-7.64 (m, 1H), 4.66 (s, 2H). MS m/z [M+H]$^+$=190.09. The compound was used for next step without any further purification.

Reaction Scheme for the Synthesis of Intermediate 8

Esterification of compound 23 with methyl iodide (MeI) and potassium carbonate (K$_2$CO$_3$) in DMF at 26° C. affords ester 24, that is reduced with sodium borohydride (NaBH$_4$) in methanol at a temperature ranging between 0 and 26° C. to provide the corresponding alcohol 22.

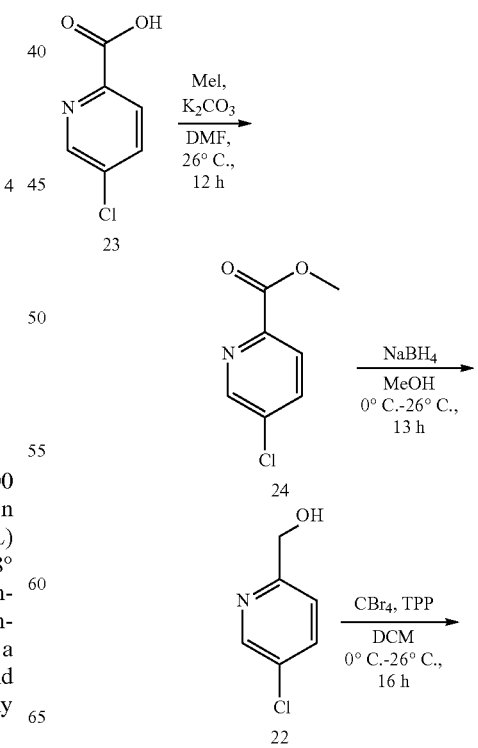

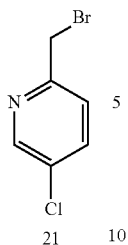

21

Intermediate 6: methyl 5-chloropicolinate

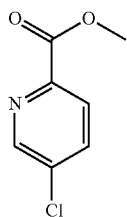

6

To a solution of 5-chloropicolinic acid (1 g, 6.34 mmol, commercial source: Combi-Blocks) in N,N-dimethylformamide (10 mL), potassium carbonate (1.75 g, 12.6 mmol) was added followed by methyl iodide (0.8 mL, 12.6 mmol) at 26° C. The reaction mixture was stirred for 12 h at the same temperature. On completion, the reaction mixture was quenched with ice cold water (100 mL) and extracted with ethyl acetate (200 mL). The organic layer was washed with water (2×100 mL) and brine solution (100 mL). The organic layer was dried over anhydrous Na$_2$SO$_4$, filtered and the filtrate was concentrated under reduced pressure to afford methyl 5-chloropicolinate (1.2 g) as a brown liquid. $^1$H NMR (400 MHz, DMSO-d$_6$) δ 8.77 (dd, J=2.4, 0.7 Hz, 1H), 8.14 (dd, J=8.4, 2.4 Hz, 1H), 8.07 (dd, J=8.4, 0.7 Hz, 1H), 3.89 (s, 3H). MS m/z [M+H]$^+$=172.25. The compound was used for next step without any further purification.

Intermediate 7: (5-chloropyridin-2-yl)methanol

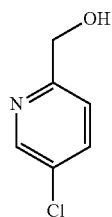

7

To a solution of methyl 5-chloropicolinate (1.2 g, 0.007 mol, Intermediate 6) in methanol (12 mL), sodium borohydride (0.53 g, 0.014 mol) was added portionwise at 0° C. The reaction mixture was stirred at 26° C. for 13 h. On completion, the reaction mixture was cooled to 0° C. and quenched with ice water (5 mL). The reaction mixture was stirred for 30 min at 26° C. and extracted with ethyl acetate (4×20 mL). The organic layer was washed with water (2×20 mL), dried over anhydrous Na$_2$SO$_4$, filtered and the filtrate was concentrated under reduced pressure to afford (5-chloropyridin-2-yl)methanol (500 mg, 48.5%) as an off white solid. $^1$H NMR (400 MHz, CDCl$_3$) δ 8.53 (d, J=2.3 Hz, 1H), 7.67 (dd, J=8.3, 2.4 Hz, 1H), 7.26-7.21 (m, 1H), 4.75 (s, 2H), 3.26 (s, 1H). MS m/z [M+H]$^+$=144.1.

Intermediate 8: 2-(bromomethyl)-5-chloropyridine

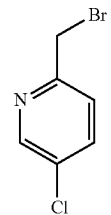

8

To a solution of (5-chloropyridin-2-yl)methanol (500 mg, 0.003 mol, Intermediate 7) in dichloromethane (4 mL), triphenylphosphine (1.57 g, 0.006 mol) was added at 26° C., followed by the addition of a solution of carbon tetrabromide (1.15 g, 0.003 mol) in dichloromethane (1 mL) at 0° C. The reaction mixture was stirred at 26° C. for 16 h. On completion, the reaction mixture was concentrated under reduced pressure. The crude was purified by column chromatography (silica gel 100-200 mesh), eluted with 5% ethyl acetate in pet ether. The pure fractions were collected and concentrated under reduced pressure to afford 2-(bromomethyl)-5-chloropyridine (200 mg, 30%) as a pale yellow liquid. $^1$H NMR (400 MHz, CDCl$_3$) δ 8.53 (d, J=2.5 Hz, 1H), 7.67 (dd, J=8.3, 2.5 Hz, 1H), 7.40 (d, J=8.3 Hz, 1H), 4.52 (s, 2H). MS m/z [M]=206.9.

General Scheme for Synthesis of Chloride Intermediates 9, 10 and 11

The alcohol function of Formula 22 is converted to the corresponding chlorides 25 using thionyl chloride in dichloromethane at 0 to 28° C.

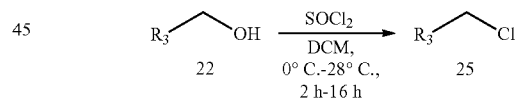

Intermediate 9: 2-(chloromethyl)-5-fluoropyridine

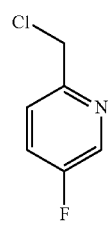

9

To a solution of (5-fluoropyridin-2-yl)methanol (10 g, 0.0787 mol, commercial source: Combi-Blocks) in dichloromethane (200 mL), thionyl chloride (18.72 g, 0.1574 mol, commercial source: Avra) was slowly added at 0° C. The reaction mixture was allowed to 28° C. and stirred for 2 h. On completion, the reaction mixture was cooled to 0° C., quenched with saturated ammonium chloride solution (200 mL) and extracted with dichloromethane (5×100 mL). The organic layer was dried over Na$_2$SO$_4$, filtered and the filtrate was concentrated under reduced pressure to afford 2-(chloromethyl)-5-fluoropyridine (7 g, 47%) as a yellow liquid that was characterized by H-NMR. This crude was used without any purification in the next reaction. $^1$H NMR (400 MHz, CDCl$_3$) δ 8.43 (d, J=2.8 Hz, 1H), 7.53-7.40 (m, 2H), 4.67 (s, 2H).

Intermediate 9': 2-(chloromethyl)-5-fluoropyridine Hydrochloride

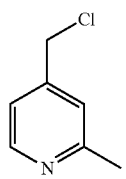

Thionyl chloride (0.419 mL, 5.74 mmol, commercial source: Aldrich) was added dropwise to a stirred solution of (5-fluoropyridin-2-yl)methanol (0.289 mL, 2.87 mmol, commercial source: Combi-Blocks) in Dichloromethane (5.74 mL) under nitrogen at rt. The mixture was stirred at rt for 16 h. The mixture was concentrated under reduced pressure to yield 2-(chloromethyl)-5-fluoropyridine hydrochloride (395 mg, 2.170 mmol, 76%) that was used in the next step without further purification. $^1$H NMR (400 MHz, DMSO-d$_6$) δ 11.68 (br s, 1H), 8.55 (d, J=3.0 Hz, 1H), 7.77 (dt, J=8.7, 3.0 Hz, 1H), 7.63 (dd, J=8.6, 4.5 Hz, 1H), 4.78 (s, 2H). MS m/z [M+H]$^+$=146.10.

Intermediate 10: 4-(chloromethyl)-2-methylpyridine

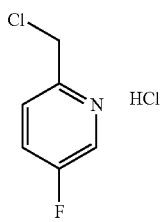

To a solution of (2-methylpyridin-4-yl)methanol (500 mg, 4.06 mmol, commercial source: Combi-Blocks) in dichloromethane (20 mL), thionyl chloride (0.45 mL, 1.5 mmol) was added at 0° C. The reaction mixture was allowed to 27° C. and stirred for 16 h. On completion, the reaction mixture was concentrated under reduced pressure. The residue was neutralized (pH 7) with saturated sodium bicarbonate solution (10 mL) and extracted with ethyl acetate (2×50 mL). The organic layer was dried over Na$_2$SO$_4$, filtered and the filtrate was evaporated under reduced pressure to afford 4-(chloromethyl)-2-methylpyridine (400 mg) as an off-white solid. $^1$H NMR (400 MHz, CDCl$_3$) δ 8.49 (d, J=5.1 Hz, 1H), 7.18 (s, 1H), 7.11 (dd, J=5.2, 1.6 Hz, 1H), 4.50 (s, 2H), 2.57 (s, 3H). MS m/z [M+H]$^+$=142.0.

Intermediate 11: 2-(chloromethyl)-5-methylpyridine

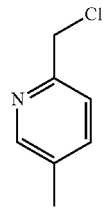

To a solution of (5-methylpyridin-2-yl)methanol (500 mg, 4.06 mmol, commercial source: Pharma Blocks) in dichloromethane (20 mL), thionyl chloride (0.45 mL, 6.09 mmol) was added at 0° C. The reaction mixture was stirred at 27° C. for 16 h. On completion, the reaction mixture was diluted with water (10 mL) and neutralized with saturated sodium bicarbonate solution (20 mL) and extracted with ethyl acetate (2×50 mL). The organic layer was dried over anhydrous Na$_2$SO$_4$, filtered and the filtrate was concentrated under reduced pressure to afford 2-(chloromethyl)-5-methylpyridine (400 mg, 69%) as an off white solid. $^1$H NMR (400 MHz, CDCl$_3$) δ 8.41 (s, 1H), 7.52 (d, J=7.5 Hz, 1H), 7.36 (d, J=7.9 Hz, 1H), 4.65 (s, 2H), 2.35 (s, 3H). MS m/z [M+H]$^+$=142.03.

General Scheme for Synthesis of Intermediates 12, 13, 14 and 15

The aromatic alcohol 23 of formula R$_3$CH$_2$OH is transformed to its corresponding mesylate 26 using methanesulfonyl chloride and triethylamine in dichloromethane (DCM) at temperature of 0° C.

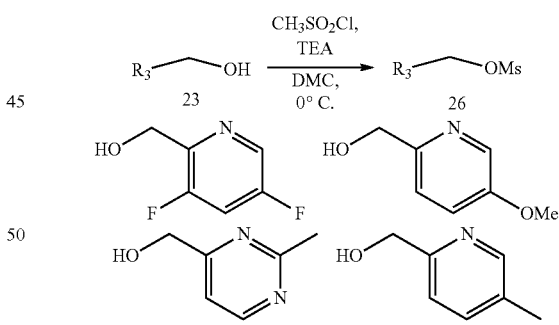

Intermediate 12: (3,5-difluoropyridin-2-yl)methyl Methanesulfonate

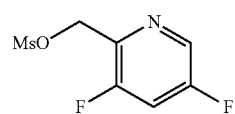

In an ice bath, a flask was charged with Dichloromethane (1 mL), (3,5-difluoropyridin-2-yl)methanol (200 mg, 1.378 mmol, commercial source: Rennothech-China, triethylamine (229 μL, 1.654 mmol) and finally methanesulfonyl chloride (118 μL, 1.516 mmol) that was added dropwise. The crude was left in the same conditions during 1.5 h. Upon completion, the mixture was partitioned between water and DCM and extracted with DCM (2×). Organic layers were dried over MgSO$_4$ (anh.) and filtered. Solvent was evaporated under vacuo conditions, obtaining (3,5-difluoropyridin-2-yl)methyl methanesulfonate (205 mg, 0.918 mmol, 66.6%) that was characterized by $^1$H NMR. This crude was used without any purification in the next reaction. $^1$H NMR (400 MHz, CDCl$_3$) δ 8.40 (d, J=2.5 Hz, 1H), 7.32-7.27 (m, 1H), 5.40 (d, J=2.0 Hz, 2H), 3.11 (s, 3H).

Intermediate 13: (2-methylpyrimidin-4-yl)methyl Methanesulfonate

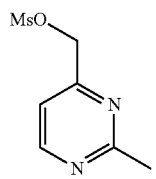

13

In an ice bath, a flask was charged with Dichloromethane (1 mL), (2-methylpyrimidin-4-yl)methanol (200 mg, 1.611 mmol, commercial source: Chembridge-USA), triethylamine (268 μL, 1.933 mmol) and finally methanesulfonyl chloride (138 μL, 1.772 mmol) that was added dropwise. The crude was left in the same conditions during 1.5 h. Upon completion, the mixture of reaction was partitioned between water and DCM and extracted with DCM (2×). Organic layers were dried over MgSO$_4$ (anh.) and filtered. Solvent was evaporated under vacuo conditions, obtaining (2-methylpyrimidin-4-yl)methyl methanesulfonate (245 mg, 1.212 mmol, 75%) that was characterized by $^1$H NMR and LCMS. This crude was used without any purification in the next reaction. $^1$H NMR (400 MHz, CDCl$_3$) δ 8.71 (d, J=5.1 Hz, 1H), 7.31 (d, J=5.1 Hz, 1H), 5.25 (s, 2H), 2.74 (s, 3H). MS m/z [M+H]$^+$=203.21

Intermediate 14: (5-methoxypyridin-2-yl)methyl Methanesulfonate

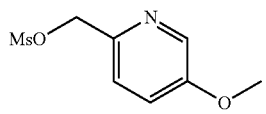

14

In an ice bath, a flask was charged with Dichloromethane (1 mL), (5-methoxypyridin-2-yl)methanol (200 mg, 1.437 mmol, commercial source: ARK PHARM-USA AK), triethylamine (239 μL, 1.725 mmol) and finally methanesulfonyl chloride (123 μL, 1.581 mmol) that was added dropwise. The crude was left in the same conditions during 1.5 h. Upon completion, the mixture of reaction was partitioned between water and DCM and extracted with DCM (2×). Organic layers were dried over MgSO$_4$ (anh.) and filtered. Solvent was evaporated under vacuo conditions, obtaining (5-methoxypyridin-2-yl)methyl methanesulfonate (312 mg, 1.437 mmol) that was characterized by LCMS. This crude was used without any purification in the next reaction. MS m/z [M+H]$^+$=218.10

Intermediate 15: (5-methylpyridin-2-yl)methyl Methanesulfonate

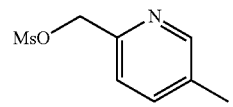

15

In an ice bath, a flask was charged with Dichloromethane (1 mL), triethylamine (270 μL, 1.949 mmol), (5-methylpyridin-2-yl)methanol (211 μL, 1.624 mmol, commercial source: AstaTech) and finally methanesulfonyl chloride (139 μL, 1.786 mmol) that was added dropwise. The crude was left in the same conditions during 1.5 h. Upon completion, the mixture of reaction was partitioned between water and DCM and extracted with DCM (2×). Organic layers were dried over MgSO$_4$ (anh.) and filtered. Solvent was evaporated under vacuo conditions, obtaining (5-methylpyridin-2-yl)methyl methanesulfonate (327 mg, 1.624 mmol) that was characterized by LCMS. This crude was used without any purification in the next reaction. MS m/z [M+H]$^+$=202.10

Intermediate 16: 4-cyano-N-(2-hydroxyethyl)benzenesulfonamide

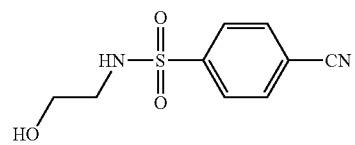

16

To a solution of 4-cyanobenzene-1-sulfonyl chloride (50 g, 0.2487 mol, commercial source: Combi-Blocks), 2-aminoethanol (18.2 g, 0.2985 mol, commercial source: Combi-Blocks) in tetrahydrofuran (500 mL) was added triethylamine (64 mL, 0.4974 mol, commercial source: Alfa) at 0° C. The temperature was raised to 28° C., and the reaction mixture was stirred for 2 h at the same temperature. Upon completion, the reaction mixture was dissolved in ethyl acetate (1000 mL) and washed with water (3×300 mL). The combined organic layers were dried over anhydrous Na$_2$SO$_4$, filtered and the filtrate was evaporated under reduced pressure. The crude was purified by column chromatography (silicagel 100-200 mesh), eluted with 40% ethyl acetate in hexane. The pure fractions were collected and concentrated under reduced pressure to afford 4-cyano-N-(2-hydroxyethyl)benzenesulfonamide (30 g, 53%) as a pale yellow solid. $^1$H NMR (400 MHz, DMSO-d$_6$) δ 8.07 (d, J=8.3 Hz, 2H), 7.94 (d, J=8.3 Hz, 2H), 7.93 (s, 1H), 4.69 (t, J=5.6 Hz, 1H), 3.39-3.32 (m, 2H), 2.86-2.79 (d, J=5.0 Hz, 2H). MS m/z [M−H]$^-$=225.26.

Intermediate 17: N-(2-hydroxyethyl)-4-(2H-tetrazol-5-yl)benzenesulfonamide

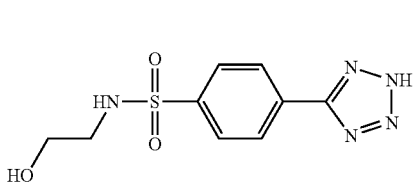

To a solution of 4-cyano-N-(2-hydroxyethyl)benzenesulfonamide (10 g, 0.0442 mol, Intermediate 16) in N,N-dimethylformamide (1000 mL), sodium azide (28.7 g, 0.442 mol) and ammonium chloride (23.6 g, 0.442 mol) were added at 28° C. The reaction mixture was heated to 100° C. and stirred for 3 h at the same temperature. Upon completion, the reaction mixture was cooled to 0° C., quenched with 1N HCl (500 mL) and stirred for 2 h at 0° C. The precipitated solid was filtered and dried under vacuum to afford N-(2-hydroxyethyl)-4-(2H-tetrazol-5-yl)benzenesulfonamide (6 g, 49%) as an off-white solid. $^1$H NMR (400 MHz, DMSO-$d_6$) δ 8.87 (br s, 1H), 8.37-8.28 (m, 2H), 8.02-7.97 (m, 2H), 7.88-7.82 (m, 1H), 3.38 (t, J=6.2 Hz, 2H), 2.90-2.80 (m, 2H). MS m/z [M+H]$^+$=270.1.

Intermediate 17': N-(2-hydroxyethyl)-4-(2H-tetrazol-5-yl)benzenesulfonamide

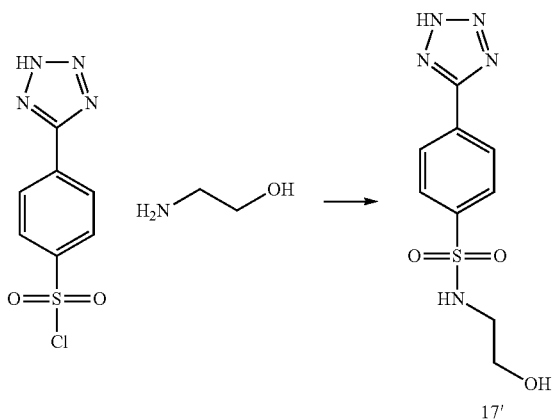

4-(2H-tetrazol-5-yl)benzenesulfonyl chloride (2.5 g, 10.22 mmol, commercial source: Achemblock-USA) dissolved in Tetrahydrofuran (25.5 mL) was added dropwise to a stirred solution of 2-aminoethanol (1.248 g, 20.44 mmol, commercial source: Aldrich) in Tetrahydrofuran (25.5 mL) at 0° C. under nitrogen. The mixture was stirred at rt for 16 h. The reaction mixture was quenched with 1N HCl and extracted with DCM. The organic layer was dried over Na$_2$SO$_4$ and concentrated under reduced pressure to give N-(2-hydroxyethyl)-4-(1H-tetrazol-5-yl)benzenesulfonamide (2 g, 7.43 mmol, 72.7%) that was used in the next step without further purification. $^1$H NMR (400 MHz, DMSO-$d_6$) δ 8.26-8.20 (m, 2H), 8.02-7.97 (m, 2H), 7.80 (t, J=5.8 Hz, 1H), 4.63 (br s, 1H), 3.37 (t, J=6.2 Hz, 2H), 2.84 (q, J=6.1 Hz, 2H). MS m/z [M+H]$^+$=270.18

Intermediate 18: (R)—N-(2-hydroxypropyl)-4-(2H-tetrazol-5-yl)benzenesulfonamide

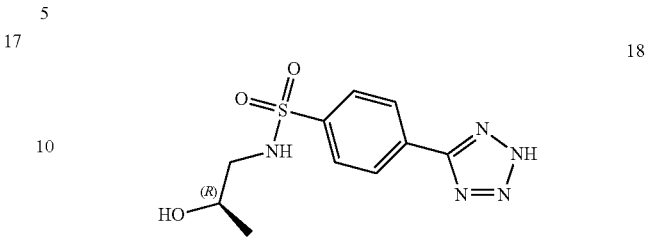

4-(2H-tetrazol-5-yl)benzenesulfonyl chloride (802 mg, 3.28 mmol, commercial source: Achemblock-USA) dissolved in Tetrahydrofuran (0.7 mL) was added dropwise to a stirred solution of (R)-1-aminopropan-2-ol (516 μL, 6.56 mmol, commercial source: Aldrich) in Tetrahydrofuran (0.7 mL) at rt under nitrogen. The mixture was stirred at rt overnight. Upon completion, 5N HCl was added (7 mL) to the reaction mixture and extracted with 20 mL DCM/MeOH (10%) (×4). The combined organic layers were dried over anhydrous Na$_2$SO$_4$ and concentrated under reduced pressure to yield a white solid, (R)—N-(2-hydroxypropyl)-4-(2H-tetrazol-5-yl)benzenesulfonamide (553 mg, 1.952 mmol, 59.5%) that was used in the next step without further purification. $^1$H NMR (400 MHz, DMSO-$d_6$) δ 8.24 (d, J=8.6 Hz, 2H), 8.01 (d, J=8.6 Hz, 2H), 7.79 (t, J=6.2 Hz, 1H), 3.62-3.57 (m, 1H), 2.76-2.66 (m, 2H), 1.00 (d, J=6.1 Hz, 3H). MS m/z [M+H]$^+$=284.17

Intermediate 18': (S)—N-(2-hydroxypropyl)-4-(2H-tetrazol-5-yl)benzenesulfonamide

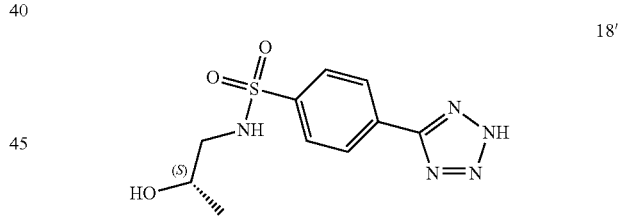

4-(2H-tetrazol-5-yl)benzenesulfonyl chloride (150 mg, 0.613 mmol, commercial source: Achemblock-USA) dissolved in Tetrahydrofuran (1.2 mL) was added dropwise to a stirred solution of (S)-1-aminopropan-2-ol (62.8 μL, 0.797 mmol, commercial source: Aldrich) in Tetrahydrofuran (1.2 mL) at rt under nitrogen. The mixture was stirred at rt for 1.5 h. On completion of the reaction, 2N HCl was added to the reaction mixture and extracted with DCM/MeOH (10%). The combined organic layers were dried over anhydrous Na$_2$SO$_4$ and concentrated under reduced pressure to yield a white solid, (S)—N-(2-hydroxypropyl)-4-(2H-tetrazol-5-yl) benzenesulfonamide (110 mg, 0.388 mmol, 63%) that was used in the next step without further purification. $^1$H NMR (400 MHz, DMSO-$d_6$) δ 8.24 (d, J=8.6 Hz, 2H), 8.01 (d, J=8.3 Hz, 2H), 7.77 (t, J=6.2 Hz, 1H), 3.64-3.56 (m, 1H), 2.76-2.64 (m, 2H), 1.00 (d, J=6.1 Hz, 3H). MS m/z [M+H]$^+$=284.2

Intermediate 19: N-(1,3-dihydroxypropan-2-yl)-4-(2H-tetrazol-5-yl)benzenesulfonamide

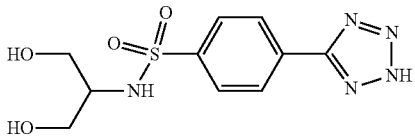

4-(2H-tetrazol-5-yl)benzenesulfonyl chloride (0.400 g, 1.635 mmol, commercial source: Achemblock-USA) dissolved in Tetrahydrofuran (5.5 mL) was added dropwise to a stirred solution of 2-aminopropane-1,3-diol (0.298 g, 3.27 mmol, commercial source: Aldrich) in Tetrahydrofuran (5.5 mL) at 0° C. under nitrogen. The mixture was stirred at rt for 16 h. The reaction mixture was quenched with 1N HCl and extracted with DCM. The organic layer was dried over $Na_2SO_4$ and concentrated under reduced pressure to give N-(1,3-dihydroxypropan-2-yl)-4-(2H-tetrazol-5-yl)benzenesulfonamide (0.268 g, 0.716 mmol, 43.8%). The product was used in the next step without further purification. $^1$H NMR (400 MHz, DMSO-$d_6$) δ 8.27-8.16 (m, 2H), 8.08-8.02 (m, 2H), 8.02-7.98 (m, 1H), 7.82-7.77 (m, 1H), 7.68 (d, J=7.8 Hz, 1H), 3.44-3.23 (m, 5H), 3.18-3.03 (m, 1H).

Intermediate 20: N-(2,3-dihydroxypropyl)-4-(2H-tetrazol-5-yl)benzenesulfonamide

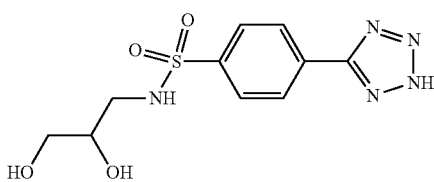

4-(2H-tetrazol-5-yl)benzenesulfonyl chloride (0.100 g, 0.409 mmol, commercial source: Achemblock-USA) dissolved in Tetrahydrofuran (1.6 mL) was added dropwise to a stirred solution of 3-aminopropane-1,2-diol (0.158 mL, 2.044 mmol, commercial source: Aldrich) in Tetrahydrofuran (1.6 mL) at 0° C. under nitrogen. The mixture was stirred at rt for 16 h. The reaction mixture was quenched with 1N HCl and extracted with DCM. The organic layer was dried over $Na_2SO_4$ and concentrated under reduced pressure to give N-(2,3-dihydroxypropyl)-4-(2H-tetrazol-5-yl)benzenesulfonamide (60 mg, 0.200 mmol, 49%). The product was used in the next step without further purification. MS m/z [M+H]$^+$=300.21

Intermediate 21: N-methyl-4-(2H-tetrazol-5-yl)benzenesulfonamide

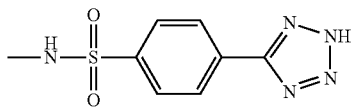

To a solution of 4-cyano-N-methylbenzenesulfonamide (500 mg, 2.551 mmol, commercial source: Combi-Blocks) in N,N-dimethylformamide (15 mL), sodium azide (1.65 g, 25.51 mmol) and ammonium chloride (1.36 g, 25.51 mmol) were added at 27° C. The reaction mixture was heated to 120° C. and stirred for 5 h. Upon completion, the reaction mixture was cooled to 27° C., quenched with 1N HCl (30 mL) and extracted with ethyl acetate (3×60 mL). The organic layer was dried over anhydrous $Na_2SO_4$, filtered and the filtrate was concentrated under reduced pressure to afford N-methyl-4-(2H-tetrazol-5-yl) benzenesulfonamide (800 mg, crude) as an off-white solid. $^1$H NMR (400 MHz, DMSO-$d_6$) δ 8.28-8.20 (m, 2H), 8.03-7.97 (m, 2H), 7.61 (q, J=4.8 Hz, 1H), 2.47 (d, J=5.0 Hz, 3H). MS m/z [M+H]$^+$= 240.08

Intermediate 22: 4-cyano-N-ethylbenzenesulfonamide

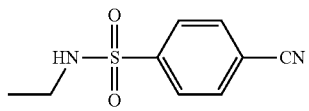

To a solution of 4-cyanobenzene-1-sulfonyl chloride (2 g, 9.92 mmol, commercial source: Aldrich) in dichloromethane (30 mL), ethylamine hydrochloride (890 mg, 10.91 mmol, commercial source: Avra) and triethylamine (2.5 g, 24.75 mmol) were added at 27° C. The reaction mixture was stirred at 27° C. for 1 h Upon completion, the reaction mixture was poured into water (100 mL) and extracted with dichloromethane (3×80 mL). The combined organic layer was dried over anhydrous $Na_2SO_4$, filtered and the filtrate was concentrated under reduced pressure. The crude was washed with mixture of dichloromethane (2 mL) and petroleum ether (20 mL) to afford 4-cyano-N-ethylbenzenesulfonamide (1.5 g, 69%) as a white solid. $^1$H NMR (400 MHz, CDCl$_3$) δ 8.03-7.95 (m, 2H), 7.87-7.76 (m, 2H), 4.43 (br s, 1H), 3.12-3.03 (m, 2H), 1.14 (t, J=7.2 Hz, 3H). MS m/z [M−H]$^-$=209.05

Intermediate 23: N-ethyl-4-(2H-tetrazol-5-yl)benzenesulfonamide

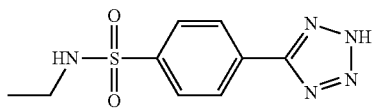

To a solution of 4-cyano-N-ethylbenzenesulfonamide (500 mg, 2.38 mmol, Intermediate 22) in N,N-dimethylformamide (10 mL), sodium azide (1.55 g, 23.809 mmol) and ammonium chloride (1.27 g, 23.809 mmol) were added at 27° C. The reaction mixture was heated to 120° C. and stirred for 5 h at the same temperature. Upon completion, the reaction mixture was cooled to 27° C., quenched with 1N HCl (60 mL) and extracted with ethyl acetate (3×50 mL). The organic layer was dried over anhydrous $Na_2SO_4$, filtered and the filtrate was concentrated under reduced pressure. The crude was washed with a mixture of dichloromethane (2 mL) and n-pentane (10 mL) to afford N-ethyl-4-(2H-tetrazol-5-yl)benzenesulfonamide (700 mg, 97%) as an off white solid. ¹H NMR (400 MHz, DMSO-d₆) δ 8.33-8.18 (m, 2H), 8.01 (d, J=8.5 Hz, 2H), 7.74 (t, J=5.7 Hz, 1H), 2.86-2.76 (m, 2H), 1.00 (t, J=7.2 Hz, 3H). MS m/z [M+H]⁺=254.10.

Intermediate 24: 2-(4-cyanophenylsulfonamido)acetamide

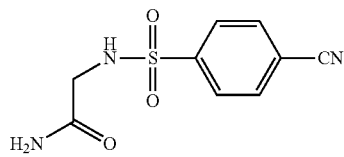

24

To a solution of 4-cyanobenzene-1-sulfonyl chloride (5 g, 0.0248 mol, commercial source: Combi-Blocks) in tetrahydrofuran (100 mL), triethylamine (5 g, 0.0496 mol) was added at 28° C., followed by the addition of 2-aminoacetamide (1.84 g, 0.0248 mol, commercial source: Combi-Blocks) at 0° C. The reaction mixture was allowed to 28° C. and stirred for 2 h at the same temperature. Upon completion, the reaction mixture was concentrated under reduced pressure. The residue was dissolved in ethyl acetate (100 mL) and washed with water (3×50 mL). The organic layer was dried over anhydrous Na₂SO₄, filtered and the filtrate was concentrated under reduced pressure to afford 2-(4-cyanophenylsulfonamido)acetamide (4 g, 67%) as a pale yellow solid. ¹H NMR (400 MHz, DMSO-d₆) δ 8.23 (s, 1H), 8.08 (d, J=8.5 Hz, 2H), 8.00-7.92 (m, 2H), 7.32 (s, 1H), 7.08 (s, 1H), 3.46 (s, 2H). MS m/z [M-H]⁻=238.2

Intermediate 25: 2-(4-(2H-tetrazol-5-yl)phenylsulfonamido)acetamide

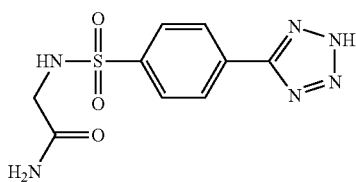

25

To a solution of 2-(4-cyanophenylsulfonamido)acetamide (4 g, 0.0167 mol, Intermediate 24) in N,N-dimethylformamide (40 mL), sodium azide (10.8 g, 0.1673 mol) and ammonium chloride (8.9 g, 0.1673 mol) were added at 28° C. The reaction mixture was heated to 100° C. and stirred for 3 h. Upon completion, the reaction mixture was cooled to 28° C. and quenched with 1N HCl (30 mL) slowly at 0° C. and stirred for 30 min. The precipitated solid was filtered and dried under vacuum to afford 2-(4-(2H-tetrazol-5-yl)phenylsulfonamido)acetamide (3 g, 51%) as a white solid. ¹H NMR (400 MHz, DMSO-d₆) δ 8.31-8.14 (m, 2H), 8.13-7.99 (m, 3H), 7.27 (s, 1H), 7.06 (s, 1H), 3.45 (d, J=6.1 Hz, 2H). MS m/z [M+H]⁺=283.15.

Intermediate 26: methyl 2-(4-cyanophenylsulfonamido)acetate

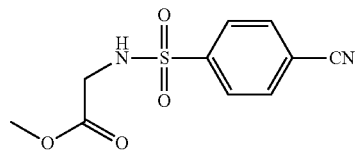

26

To a solution of methyl 2-aminoacetate hydrochloride (310 mg, 0.0024 mol, commercial source: Aldrich) in dichloromethane (5 mL), triethylamine (0.64 mL, 0.0048 mol) was added at 28° C. Followed by the addition of 4-cyanobenzene-1-sulfonyl chloride (500 mg, 0.0024 mol, commercial source: Combi-Blocks) in portionwise at 0° C. The reaction mixture was stirred at 28° C. for 16 h. Upon completion, the reaction mixture was concentrated under reduced pressure. The residue was dissolved in water (50 mL) and extracted with ethyl acetate (3×50 mL). The organic layer was dried over anhydrous Na₂SO₄, filtered and the filtrate was evaporated under reduced pressure to afford methyl 2-(4-cyanophenylsulfonamido)acetate (500 mg, 76%) as a yellow solid. ¹H NMR (400 MHz, DMSO-d₆) δ 8.53 (t, J=6.1 Hz, 1H), 8.07 (d, J=8.5 Hz, 2H), 7.99-7.89 (m, 2H), 3.80 (d, J=6.1 Hz, 2H), 3.52 (s, 3H). MS m/z [M-H]⁻=253.05

Intermediate 27: methyl 2-(4-(2H-tetrazol-5-yl)phenylsulfonamido)acetate

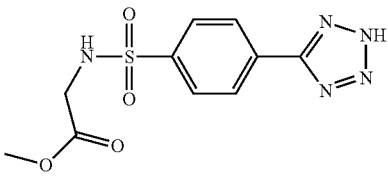

27

To a solution of methyl 2-(4-cyanophenylsulfonamido) acetate (500 mg, 0.0019 mol, Intermediate 26) in N,N-dimethylformamide (5 mL), sodium azide (1.2 g, 0.0196 mol) and ammonium chloride (1 g, 0.0196 mol) were added at 28° C. The reaction mixture was heated to 100° C. and stirred for 3 h at the same temperature. Upon completion, the reaction mixture was cooled to 0° C. and quenched with 1N HCl (2 mL) at 0° C. The precipitated solid compound was filtered and dried under vacuum to afford methyl 2-(4-(2H-tetrazol-5-yl)phenylsulfonamido)acetate (400 mg, 57%) as a white solid. ¹H NMR (400 MHz, DMSO-d₆) δ 8.40 (t, J=6.2 Hz, 1H), 8.26-8.19 (m, 2H), 8.00 (dd, J=8.7, 2.3 Hz, 2H), 3.79 (d, J=6.2 Hz, 2H), 3.52 (s, 3H). MS m/z [M-H]⁻=296.06

Intermediate 28: 2-(4-(2-(4-fluorobenzyl)-2H-tetrazol-5-yl)phenylsulfonamido)acetic Acid

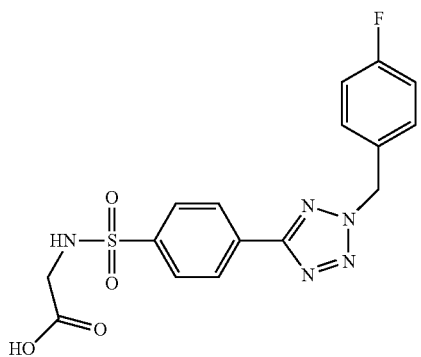

To a solution of 2-(4-(2-(4-fluorobenzyl)-2H-tetrazol-5-yl)phenylsulfonamido)acetate (380 mg, 0.0009 mol) in a mixture of tetrahydrofuran (3.8 mL) and methanol (3.8 mL), a solution of lithium hydroxide monohydrate (78 mg, 0.0013 mol) in water (1.9 mL) was added at 28° C. The reaction mixture was stirred for 3 h at the same temperature. Upon completion, the reaction mixture was concentrated under reduced pressure. The residue was diluted with water (30 mL) and acidified (pH 2) with 1N HCl (10 mL) at 0° C. The precipitated solid compound was filtered and dried under vacuum to afford 2-(4-(2-(4-fluorobenzyl)-2H-tetrazol-5-yl)phenylsulfonamido)acetic acid (220 mg, 59%) as a white solid. MS m/z [M+H]$^+$=392.14

Intermediate 29: 2-(4-(2-(pyridin-4-ylmethyl)-2H-tetrazol-5-yl)phenylsulfonamido)acetic Acid

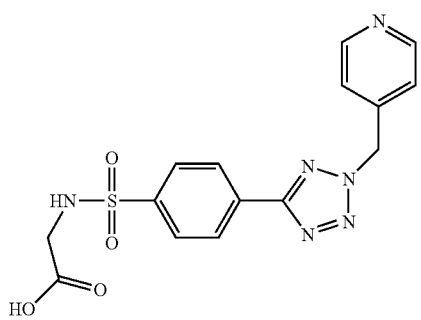

To a solution of 2-(4-(2-(pyridin-4-ylmethyl)-2H-tetrazol-5-yl)phenylsulfonamido)acetate (416 mg, 0.001 mol) in a mixture of tetrahydrofuran (4.1 mL) and methanol (4.1 mL) was added a solution of lithium hydroxide monohydrate (89 mg, 0.0021 mol) in water (2 mL) at 28° C. The reaction mixture was stirred at the same temperature for 2 h. Upon completion, the reaction mixture was concentrated under reduced pressure. The residue was diluted with water (20 mL) and neutralized (pH-7-8) with 1N HCl (5 mL). The precipitated solid compound was filtered and dried under vacuum to afford 2-(4-(2-(pyridin-4-ylmethyl)-2H-tetrazol-5-yl)phenylsulfonamido)acetic acid (245 mg, 65%) as a white solid. $^1$H NMR (400 MHz, DMSO-d$_6$) δ 12.84-12.56 (br s, 1H), 8.61 (d, J=5.7 Hz, 2H), 8.24 (d, J=8.3 Hz, 3H), 7.97 (d, J=8.5 Hz, 2H), 7.35 (d, J=5.9 Hz, 2H), 6.15 (s, 2H), 3.64 (d, J=5.0 Hz, 2H). MS m/z [M+H]$^+$=375.06

Intermediate 30: 4-bromo-2-methoxybenzene-1-sulfonyl Chloride

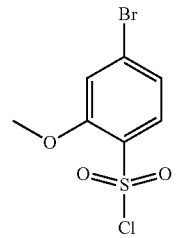

To the chlorosulfonic acid (54 mL, commercial source: Avra) was added 1-bromo-3-methoxybenzene (50 g, 0.568 mol, Commercial source: Avra) in dropwise maintaining the temperature of the reaction mixture at −5° C. The reaction mixture was stirred at 0° C. for 3 h. Upon completion, the reaction mixture was poured into ice (500 g) slowly and extracted with ethyl acetate (5×1 L). The organic layer was dried over anhydrous Na$_2$SO$_4$, filtered and the filtrate was evaporated under reduced pressure. The crude was purified by column chromatography (silica gel 100-200 mesh), eluted with 3% ethyl acetate in pet ether. The pure fractions were collected and concentrated under reduced pressure to afford 4-bromo-2-methoxybenzene-1-sulfonyl chloride (1.6 g, crude) as a white solid. $^1$H NMR (400 MHz, CDCl$_3$) δ 7.82 (d, J=8.3 Hz, 1H), 7.28 (d, J=2.2 Hz, 1H), 7.24-7.26 (m, 1H), 4.07 (s, 3H).

Intermediate 31: 4-bromo-N-(2-hydroxyethyl)-2-methoxybenzenesulfonamide

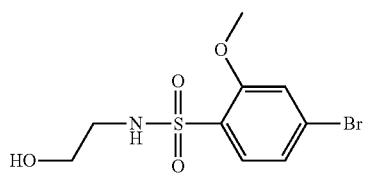

To a solution of 4-bromo-2-methoxybenzene-1-sulfonyl chloride (1.6 g, 0.00565 mol, Intermediate 30) in dichloromethane (20 mL), triethylamine (1.1 g, 0.0113 mol) was added at 28° C. and stirred for 10 min. Followed by the addition of 2-aminoethanol (413 mg, 0.0067 mol, commercial source: Alfa Aesar) at 28° C. and stirred for 2 h at the same temperature. Upon completion, the reaction mixture was concentrated under reduced pressure. The residue was washed with n-pentane (5×50 mL) and the solid compound was dried under vacuum to afford 4-bromo-N-(2-hydroxyethyl)-2-methoxybenzenesulfonamide (1.2 g, 55%) as an off-white solid. $^1$H NMR (400 MHz, DMSO-d$_6$) δ 7.65-7.60 (m, 1H), 7.44 (d, J=1.8 Hz, 1H), 7.30-7.26 (m, 1H), 7.24-7.17 (m, 1H), 4.67 (t, J=5.6 Hz, 1H), 3.92 (s, 3H), 3.35-3.30 (m, 2H), 2.86-2.76 (m, 2H). MS m/z [M+2H]$^+$=310.02.

Intermediate 32: 4-cyano-N-(2-hydroxyethyl)-2-methoxybenzenesulfonamide

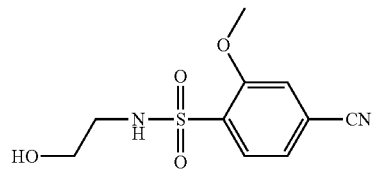

32

To an argon purged solution of 4-bromo-N-(2-hydroxyethyl)-2-methoxybenzenesulfonamide (1 g, 0.0032 mol, Intermediate 31) and zinc cyanide (2.4 g, 0.021 mol) in N,N-dimethylformamide (10 mL), tetrakis(triphenylphosphine)palladium(0) (1.8 g, 0.0016 mol) was added at 28° C. The reaction mixture was stirred at 175° C. for 30 min in the microwave. Upon completion, the reaction mixture was cooled to 28° C. and concentrated under reduced pressure. The crude was purified by column chromatography (silica gel 100-200 mesh), eluted with 60% ethyl acetate in pet ether. The pure fractions were collected and concentrated under reduced pressure to afford 4-cyano-N-(2-hydroxyethyl)-2-methoxybenzenesulfonamide (450 mg, 49%) as an off-white solid. $^1$H NMR (400 MHz, DMSO-$d_6$) δ 7.86 (d, J=8.1 Hz, 1H), 7.74 (d, J=1.3 Hz, 1H), 7.54 (dd, J=8, 1.4 Hz, 1H), 7.40 (t, J=5.8 Hz, 1H), 4.60 (t, J=5.6 Hz, 1H), 3.95 (s, 3H), 3.37-3.30 (m, 2H), 2.90-2.81 (m, 2H). MS m/z [M−H]$^-$= 255.14.

Intermediate 33: N-(2-hydroxyethyl)-2-methoxy-4-(2H-tetrazol-5-yl)benzenesulfonamide

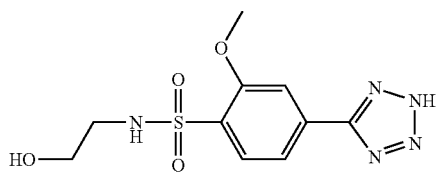

33

To a solution of 4-cyano-N-(2-hydroxyethyl)-2-methoxybenzenesulfonamide (450 mg, 0.00175 mol, Intermediate 32) in N,N-dimethylformamide (4.5 mL), sodium azide (1.1 g, 0.0175 mol) and ammonium chloride (0.93 g, 0.0175 mol) were added at 28° C. The reaction mixture was heated to 100° C. and stirred at the same temperature for 3 h. Upon completion, the reaction mixture was cooled to 0° C. and quenched with 1M HCl (30 mL) at 0° C. The reaction mixture was concentrated under reduced pressure. The crude was stirred with 15% methanol in dichloromethane (10 mL) for 1 h at 28° C. Filtered and the filtrate was evaporated under reduced pressure to afford N-(2-hydroxyethyl)-2-methoxy-4-(2H-tetrazol-5-yl) benzenesulfonamide (820 mg, crude) as an off-white solid. $^1$H NMR (400 MHz, DMSO-$d_6$) δ 8.04-7.89 (m, 2H), 7.40 (br s, 1H), 7.32-7.22 (m, 1H), 7.14 (br s, 1H), 4.02 (s, 3H), 3.45-3.37 (m, 2H), 2.91-2.82 (m, 2H). MS m/z [M+H]$^+$=300.19.

Reaction Scheme for the Synthesis of Intermediates 34, 35 and Example 51

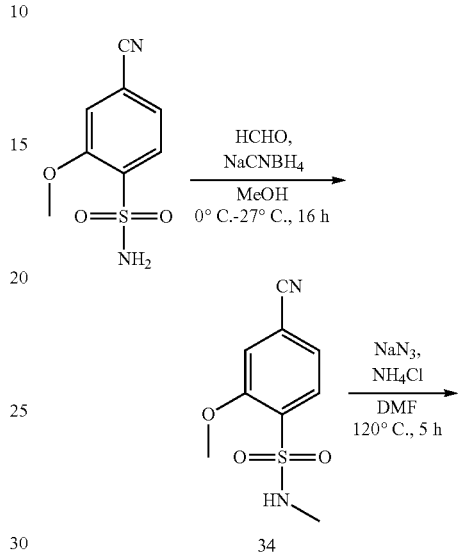

34

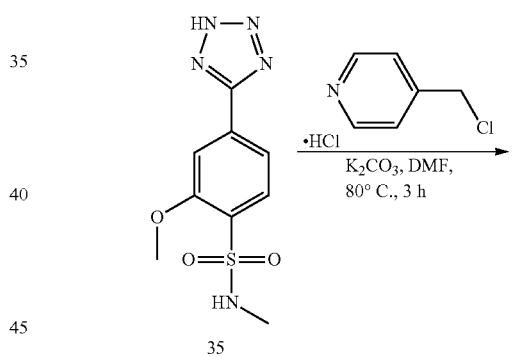

35

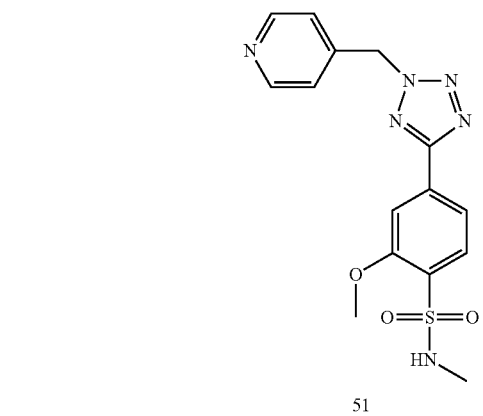

51

Intermediate 34: 4-cyano-2-methoxy-N-methylbenzenesulfonamide

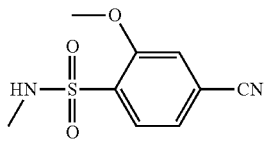

In a solution of 4-cyano-2-methoxybenzenesulfonamide (500 mg, 2.356 mmol, commercial source: Enamine) in methanol (15 mL), the pH was adjusted to 4 with 1N HCl (0.2 mL). Then, formaldehyde (30% aqueous solution) (2.5 mL, commercial source: Chemlabs) was added at 0° C. followed by the addition of sodium cyanoborohydride (296 mg, 4.71 mmol) at 0° C. The reaction mixture temperature was slowly raised to 27° C. and stirred for 16 h. Upon completion, the reaction mixture was concentrated under reduced pressure. The residue was basified with ammonia solution (30% aqueous) and extracted with ethyl acetate (3×50 mL). The organic layer was washed with brine (2×50 mL), dried over anhydrous $Na_2SO_4$, filtered and the filtrate was concentrated under reduced pressure. The crude was purified by column chromatography (silica gel 100-200 mesh), eluted with 50% ethyl acetate in petroleum ether. The pure fractions were collected and concentrated under reduced pressure to afford 4-cyano-2-methoxy-N-methyl-benzenesulfonamide (400 mg, 75%) as an off-white solid. $^1$H NMR (400 MHz, DMSO-$d_6$) δ 7.86 (d, J=8.1 Hz, 1H), 7.77 (d, J=1.1 Hz, 1H), 7.56 (dd, J=8.0, 1.2 Hz, 1H), 7.37 (m, 1H), 3.96 (s, 3H), 2.43 (d, J=5.0 Hz, 3H). MS m/z [M+H]$^+$=225.08.

Intermediate 35: 2-methoxy-N-methyl-4-(2H-tetrazol-5-yl)benzenesulfonamide

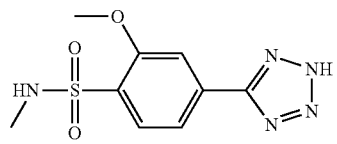

To a solution of 4-cyano-2-methoxy-N-methylbenzenesulfonamide (400 mg, 1.769 mmol, Intermediate 34) in N,N-dimethylformamide (10 mL) were added sodium azide (1.15 g, 17.69 mmol) and ammonium chloride (950 mg, 17.76 mmol) at 27° C. The reaction mixture was heated to 120° C. and stirred at the same temperature for 5 h. The progress of the reaction was monitored by TLC. On completion of the reaction, the reaction mixture was cooled to 27° C., quenched with 1N HCl (30 mL) and extracted with ethyl acetate (2×100 mL). The organic layer was dried over anhydrous $Na_2SO_4$, filtered and the filtrate was concentrated under reduced pressure. The residue was stirred with dichloromethane (10 mL) at 27° C. for 20 min. Filtered the solid and dried under vacuum to afford 2-methoxy-N-methyl-4-(2H-tetrazol-5-yl)benzenesulfonamide (300 mg, crude) as an off-white solid. $^1$H NMR (400 MHz, DMSO-$d_6$) δ 7.93 (d, J=7.9 Hz, 1H), 7.84 (d, J=1.3 Hz, 1H), 7.77 (d, J=7.9 Hz, 1H), 7.25 (m, 1H), 4.01 (s, 3H), 2.44 (d, J=5.0 Hz, 3H). MS m/z [M−H]$^-$=268.08.

Intermediate 36: 4-(2-(4-fluorobenzyl)-2H-tetrazol-5-yl)-2-methoxybenzenesulfonamide

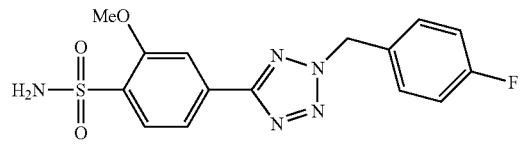

N-ethyl-N-isopropylpropan-2-amine (356 µL, 2.037 mmol) was added to a stirred solution of 2-methoxy-4-(2H-tetrazol-5-yl)benzenesulfonamide (260 mg, 1.019 mmol, Intermediate 51) and 1-(bromomethyl)-4-fluorobenzene (191 µL, 1.528 mmol, commercial source: Aldrich) in N,N-Dimethylformamide (DMF) (3395 µL) under nitrogen atmosphere. The solution was stirred at rt for 5 h. The reaction mixture was diluted with water and extracted with DCM twice. The organic layer was dried over anhydrous $Na_2SO_4$, filtered and the filtrate was concentrated under reduced pressure to obtain an oil that was washed with $CH_2Cl_2$ and a white solid was filtrated to yield 4-(2-(4-fluorobenzyl)-2H-tetrazol-5-yl)-2-methoxybenzenesulfonamide (243 mg, 65.7%). $^1$H NMR (400 MHz, DMSO-$d_6$) δ 7.90 (d, J=7.8 Hz, 1H), 7.78-7.69 (m, 2H), 7.56-7.46 (m, 2H), 7.31-7.19 (m, 4H), 6.04 (s, 2H), 4.01 (s, 3H). MS m/z [M+H]$^+$=419.19.

Intermediate 37: tert-butyl (2-amino-2-oxoethyl)((4-(2-(4-fluorobenzyl)-2H-tetrazol-5-yl)-2-methoxyphenyl)sulfonyl)carbamate

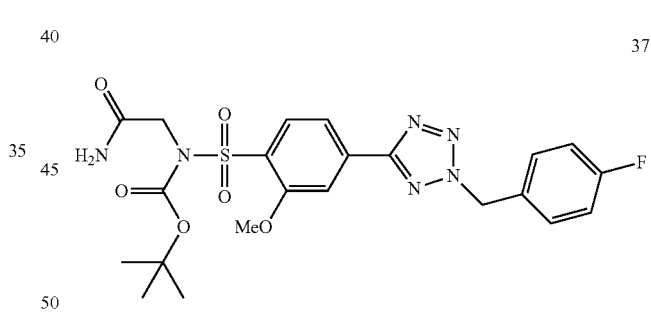

To a solution of 4-(2-(4-fluorobenzyl)-2H-tetrazol-5-yl)-2-methoxybenzenesulfonamide (240 mg, 0.660 mmol, Intermediate 36) in Tetrahydrofuran (2.7 mL), di-tert-butyl dicarbonate (0.455 mL, 1.981 mmol), Et$_3$N (0.110 mL, 0.793 mmol) and DMAP (40.3 mg, 0.330 mmol) were added. The resulting white solution was stirred at rt for 20 min. Almost immediately the reaction mixture turned white and thicker. Then, potassium carbonate (183 mg, 1.321 mmol) and 2-bromoacetamide (193 mg, 1.400 mmol) were added. Reaction mixture was stirred at rt. After 90 min the reaction mixture turned yellow and no thicker. The mixture was stirred at rt for 16 h. The reaction was quenched with sat. NaHCO$_3$ and was extracted with EtOAc (×2). The organic layer was washed with sat. NaCl, dried over Na$_2$SO$_4$ and filtered off. Solvent was evaporated under reduced pressure to obtain tert-butyl (2-amino-2-oxoethyl)((4-(2-(4-fluorobenzyl)-2H-tetrazol-5-yl)-2-methoxyphenyl)sulfonyl)carbamate (240 mg, 0.461 mmol, 69.8%). $^1$H NMR (400 MHz, DMSO-$d_6$) δ 8.06 (d, J=8.1 Hz, 1H), 7.89-7.74 (m, 2H), 7.57-7.49 (m, 2H), 7.46 (br s, 1H), 7.31-7.21 (m, 2H), 7.09 (br s, 1H), 6.05 (s, 2H), 4.32 (s, 2H), 4.01 (s, 3H), 1.18 (s, 9H). MS m/z [M+H]$^+$=521.25.

Intermediate 38: 4-(2-(4-cyanobenzyl)-2H-tetrazol-5-yl)-2-methoxybenzenesulfonamide

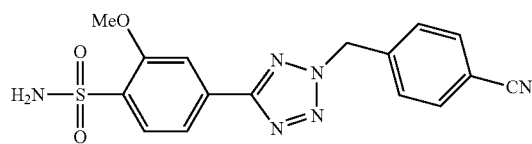

N-ethyl-N-isopropylpropan-2-amine (233 μL, 1.332 mmol) was added to a stirred solution of 2-methoxy-4-(2H-tetrazol-5-yl)benzenesulfonamide (170 mg, 0.666 mmol, Intermediate 51) and 4-(bromomethyl)benzonitrile (157 mg, 0.799 mmol, commercial source: Aldrich) in N,N-Dimethylformamide (DMF) (2220 μL) under nitrogen atmosphere. The solution was stirred at rt for 5 h. The reaction mixture was diluted with water and extracted with DCM twice. The organic layer was dried over anhydrous $Na_2SO_4$, filtered and the filtrate was concentrated under reduced pressure to obtain an oil that was washed with $CH_2Cl_2$ affording a white solid that was filtrated. The solid was triturated with MeOH to obtain a white solid, 4-(2-(4-cyanobenzyl)-2H-tetrazol-5-yl)-2-methoxybenzenesulfonamide (150 mg, 0.405 mmol, 60.8%). $^1$H NMR (400 MHz, DMSO-$d_6$) δ 7.94-7.86 (m, 3H), 7.80-7.70 (m, 2H), 7.59 (d, J=8.1 Hz, 2H), 7.24 (s, 2H), 6.19 (s, 2H), 4.01 (s, 3H). MS m/z [M+H]$^+$=371.10.

Intermediate 39: tert-butyl (2-amino-2-oxoethyl)((4-(2-(4-cyanobenzyl)-2H-tetrazol-5-yl)-2-methoxyphenyl)sulfonyl)carbamate

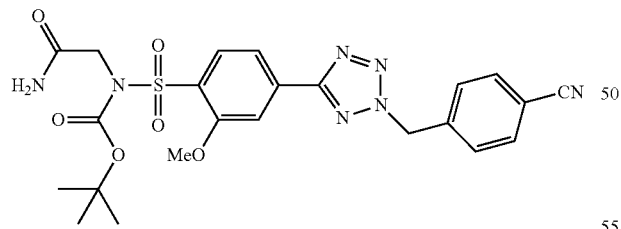

To a solution of 4-(2-(4-cyanobenzyl)-2H-tetrazol-5-yl)-2-methoxybenzenesulfonamide (150 mg, 0.405 mmol, Intermediate 38) in tetrahydrofuran (7 mL), di-tert-butyl dicarbonate (0.279 mL, 1.215 mmol), $Et_3N$ (0.068 mL, 0.486 mmol) and DMAP (24.74 mg, 0.202 mmol) were added. The resulting white solution was stirred at rt for 20 min. Almost immediately the reaction mixture turned white and thicker. Then, potassium potassium carbonate (112 mg, 0.810 mmol) and 2-bromoacetamide (118 mg, 0.859 mmol) were added. Reaction mixture was stirred at rt. After 90 min the reaction mixture turned yellow and no thicker. The mixture was stirred at rt for 16 h. The reaction was quenched with sat. $NaHCO_3$ and was extracted with EtOAc (×2). The organic layer was washed with sat. NaCl, dried over $Na_2SO_4$ and filtered off. Solvent was evaporated under reduced pressure to obtain tert-butyl (2-amino-2-oxoethyl)((4-(2-(4-cyanobenzyl)-2H-tetrazol-5-yl)-2-methoxyphenyl)sulfonyl)carbamate (240 mg, 0.364 mmol, 90%). The product was used in the next step without further purification and it was characterized in the next step.

Intermediate 40: 2-methoxy-4-(2-(pyridin-4-ylmethyl)-2H-tetrazol-5-yl)benzenesulfonamide

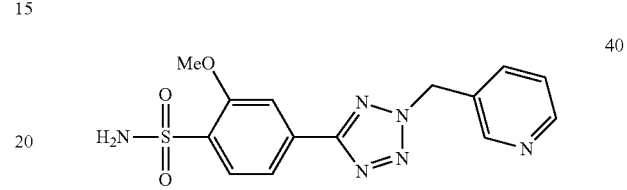

N-ethyl-N-isopropylpropan-2-amine (349 μL, 1.998 mmol) was added to a stirred solution of 2-methoxy-4-(2H-tetrazol-5-yl)benzenesulfonamide (170 mg, 0.666 mmol, Intermediate 51) and 4-(bromomethyl)pyridine hydrobromide (202 mg, 0.799 mmol, commercial source: Aldrich) in N,N-Dimethylformamide (DMF) (2220 μL) under nitrogen atmosphere. After 10 minutes the mixture turned black. The solution was stirred at rt for 3 h. The mixture was stirred at rt over the weekend. 4-(bromomethyl)pyridine hydrobromide (238 mg, 0.940 mmol, commercial source: Aldrich) and N-ethyl-N-isopropylpropan-2-amine (411 μL, 2.351 mmol) were added and the mixture was stirred at rt for 2 hours. There was some starting material, so the mixture was heated at 50° C. for 2 hours. The reaction mixture was diluted with water and extracted with DCM twice. The crude compound was purified by flash column chromatography (silica; EtOAc-cyclohexane from 0/100 to 100/0) for 25 min. The fractions were collected and concentrated in vacuo to obtain 2-methoxy-4-(2-(pyridin-4-ylmethyl)-2H-tetrazol-5-yl)benzenesulfonamide (150 mg, 0.433 mmol, 65%) as a white solid. $^1$H NMR (DMSO-$d_6$) δ 8.65-8.56 (m, 1H), 7.91 (d, J=8.6 Hz, 1H), 7.80-7.71 (m, 2H), 7.38-7.30 (m, 2H), 7.25 (s, 2H), 6.15 (s, 2H), 4.01 (s, 3H). MS m/z [M+H]$^+$=347.10.

Intermediate 41: tert-butyl (2-amino-2-oxoethyl)((2-methoxy-4-(2-(pyridin-4-ylmethyl)-2H-tetrazol-5-yl)phenyl)sulfonyl)carbamate

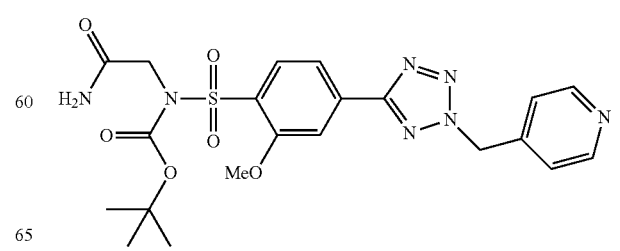

To a solution of 2-methoxy-4-(2-(pyridin-4-ylmethyl)-2H-tetrazol-5-yl)benzenesulfonamide (150 mg, 0.433 mmol, Intermediate 40) in anh. Tetrahydrofuran (10 mL), di-tert-butyl dicarbonate (0.298 mL, 1.299 mmol), Et₃N (0.072 mL, 0.520 mmol) and DMAP (26.5 mg, 0.217 mmol) were added. The resulting white solution was stirred at rt for 20 min. Almost immediately the reaction mixture turned white and thicker. Then, potassium carbonate (120 mg, 0.866 mmol) and 2-bromoacetamide (71.7 mg, 0.520 mmol) were added. Reaction mixture was stirred at rt. After 90 min the reaction mixture turned yellow and no thicker. The mixture was stirred at rt for 16 h. The reaction was quenched with sat. NaHCO₃ and was extracted with EtOAc (×2). The organic layer was washed with sat. NaCl, dried over Na₂SO₄ and filtered off. Solvent was evaporated under reduced pressure to obtain tert-butyl (2-amino-2-oxoethyl)((2-methoxy-4-(2-(pyridin-4-ylmethyl)-2H-tetrazol-5-yl)phenyl)sulfonyl)carbamate (35 mg, 0.070 mmol, 16%). MS m/z [M+H]⁺=504.20.

Intermediate 42: 4-cyanobenzenesulfonamide

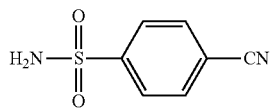

To a solution of 4-cyanobenzene-1-sulfonyl chloride (10 g, 49.59 mmol, commercial source: Combi-Blocks) in dichloromethane (100 mL), aqueous ammonia (25%) (50 mL) was added at 27° C. and stirred for 3 h at the same temperature. Upon completion, the reaction mixture was concentrated under reduced pressure. The obtained solid was stirred with 10% methanol in dichloromethane (150 mL) at 27° C. for 1 h. Filtered the solid compound and dried under vacuum to afford 4-cyanobenzenesulfonamide (8 g, crude) as an off-white solid. ¹H NMR (400 MHz, DMSO-d₆) δ 8.13-8.03 (m, 2H), 7.99-7.92 (m, 2H), 7.59-7.47 (br s, 2H). MS m/z [M−H]⁻=180.97.

Intermediate 43: 4-(2H-tetrazol-5-yl)benzenesulfonamide

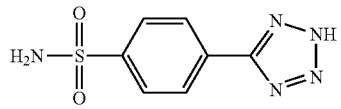

To a solution of 4-cyano benzenesulfonamide (3.8 g, 20.88 mmol, Intermediate 42 or commercial source: Combi-Blocks) in N,N-dimethylformamide (50 mL), sodium azide (13.57 g, 208.73 mmol) and ammonium chloride (11.17 g, 208.78 mmol) were added at 27° C. The reaction mixture was heated to 120° C. and was stirred at the same temperature for 5 h. Upon completion, the reaction mixture was cooled to 27° C., quenched with 1N HCl (150 mL) and extracted with ethyl acetate (3×100 mL). The organic layer was dried over anhydrous Na₂SO₄, filtered and the filtrate was concentrated under reduced pressure. The residue was stirred with dichloromethane (10 mL) at 27° C. for 30 min and filtered. The solid was dried under vacuum to afford 4-(2H-tetrazol-5-yl)benzenesulfonamide (3.2 g, 68%) as an off-white solid. ¹H NMR (400 MHz, DMSO-d₆) δ 8.23 (d, J=8.5 Hz, 2H), 8.04 (d, J=8.5 Hz, 2H), 7.53 (s, 2H). MS m/z [M−H]⁻=224.03.

Intermediate 44: 4-(2-(4-fluorobenzyl)-2H-tetrazol-5-yl)benzenesulfonamide

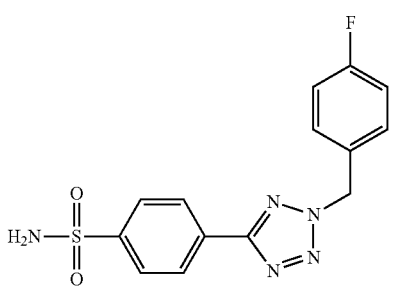

To a solution of 4-(2H-tetrazol-5-yl)benzenesulfonamide (1 g, 4.444 mmol, Intermediate 43 or commercial source: Butt-Park), potassium carbonate (1.23 g, 8.9 mmol) in N,N-dimethylformamide (20 mL), 4-Fluorobenzyl bromide (418 mg, 2.224 mmol, commercial source: Apollo Scientific) was added at 27° C. The resultant reaction mixture was stirred at 27° C. for 2 h. Upon completion, the reaction mixture was concentrated under reduced pressure. The crude was purified by column chromatography (silicagel 100-200 mesh), eluted with 60% ethyl acetate in petroleum ether. The pure fractions were collected and concentrated under reduced pressure to afford 4-(2-(4-fluorobenzyl)-2H-tetrazol-5-yl)benzenesulfonamide (400 mg, 27%) as an off-white solid. ¹H NMR (400 MHz, DMSO-d₆) δ 8.23 (d, J=8.5 Hz, 2H), 7.99 (d, J=8.5 Hz, 2H), 7.57-7.45 (m, 4H), 7.25 (s, 2H), 6.03 (s, 2H). MS m/z [M+H]⁺=333.92.

Intermediate 45: 4-(2-(pyridin-4-ylmethyl)-2H-tetrazol-5-yl)benzenesulfonamide

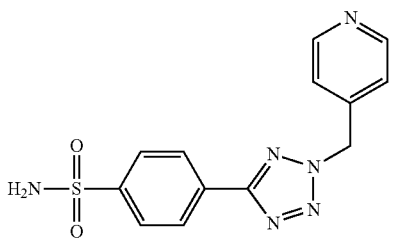

To a solution of 4-(2H-tetrazol-5-yl)benzenesulfonamide (1 g, 4.444 mmol, Intermediate 43 or commercial source: Butt-Park), potassium carbonate (1.23 g, 8.9 mmol) in N,N-dimethylformamide (20 mL), 4-(chloromethyl)pyridine hydrochloride (729 mg, 4.444 mmol, commercial source: Combi-Blocks) was added at 27° C. and stirred at the same temperature for 16 h. Upon completion, the reaction mixture was concentrated under reduced pressure. The crude was purified by column chromatography (silicagel 100-200 mesh), eluted with 10% methanol in dichloromethane. The pure fractions were collected and concentrated under reduced pressure to afford 4-(2-(pyridin-4-ylmethyl)-2H-tetrazol-5-yl)benzenesulfonamide (250 mg, 25%) as an off-white solid. $^1$H NMR (400 MHz, DMSO-$d_6$) δ 8.66-8.58 (m, 2H), 8.31-8.22 (m, 2H), 8.04-7.97 (m, 2H), 7.56-7.49 (m, 2H), 7.39-7.31 (m, 2H), 6.14 (s, 2H). MS m/z [M+H]$^+$= 317.2.

Intermediate 46: tert-butyl (cyanomethyl) ((4-(2-(pyridin-4-ylmethyl)-2H-tetrazol-5-yl) phenyl) sulfonyl) carbamate

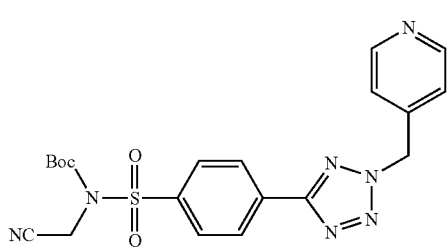

To a solution of 4-(2-(pyridin-4-ylmethyl)-2H-tetrazol-5-yl)benzenesulfonamide (250 mg, 0.79 mmol, Intermediate 45), 4-(Dimethylamino)pyridine (48.2 mg, 0.395 mmol) in tetrahydrofuran (10 mL), Boc-anhydride (0.7 mL, 3.16 mmol) and triethylamine (0.15 mL, 1.106 mmol) were added at 27° C. The reaction mixture was stirred at 27° C. for 3 h. Followed by the addition of potassium carbonate (218 mg, 1.58 mmol) and bromoacetonitrile (0.15 mL, 2.133 mmol) at 27° C. The resultant reaction mixture was stirred for 16 h at the same temperature. Upon completion, the reaction mixture was quenched with saturated sodium bicarbonate solution (100 mL) and extracted with ethyl acetate (2×100 mL). The organic layer was dried over anhydrous Na$_2$SO$_4$, filtered and the filtrate was concentrated under reduced pressure. The crude was purified by column chromatography (silica gel 100-200 mesh), eluted with 4% methanol in dichloromethane. The pure fractions were collected and concentrated under reduced pressure to afford tert-butyl (cyanomethyl) ((4-(2-(pyridin-4-ylmethyl)-2H-tetrazol-5-yl) phenyl) sulfonyl) carbamate (100 mg, crude) as an off white solid. $^1$H NMR (400 MHz, DMSO-$d_6$) δ 8.61 (d, J=5.9 Hz, 2H), 8.41-8.32 (m, 2H), 8.16 (d, J=8.3 Hz, 2H), 7.36 (d, J=5.9 Hz, 2H), 6.16 (s, 2H), 4.94 (s, 2H), 1.31 (s, 9H). MS m/z [M+H]$^+$=456.01.

Intermediate 47: 4-(2-((5-fluoropyridin-2-yl) methyl)-2H-tetrazol-5-yl)benzenesulfonamide

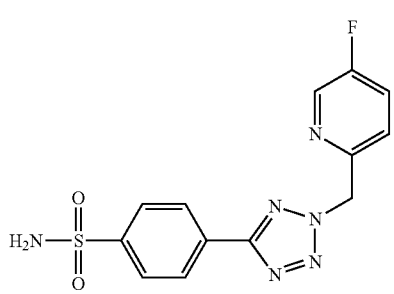

To a solution of 4-(2H-tetrazol-5-yl)benzenesulfonamide (1.3 g, 5.777 mmol, Intermediate 43 or commercial source: Butt-Park), and potassium carbonate (1.594 g, 11.555 mmol) in N,N-dimethylformamide (25 mL), 2-(bromomethyl)-5-fluoropyridine hydrobromide (1.565 g, 5.7777 mmol, intermediate 5) was added at 26° C. and stirred at same temperature for 24 h. Upon completion, the reaction mixture was concentrated under reduced pressure. The crude compound was purified by column chromatography (neutral alumina) using 6% methanol in dichloromethane. The pure fractions were collected and concentrated under reduced pressure to afford 4-(2-((5-fluoropyridin-2-yl)methyl)-2H-tetrazol-5-yl)benzenesulfonamide (1.3 g, 53%) as a white solid. $^1$H NMR (400 MHz, DMSO-$d_6$) δ 8.55 (d, J=2.8 Hz, 1H), 8.24 (d, J=8.3 Hz, 2H), 7.99 (d, J=8.3 Hz, 2H), 7.84 (dt, J=8.7, 3.1 Hz, 1H), 7.66 (dd, J=8.8, 4.4 Hz, 1H), 7.52 (s, 2H), 6.17 (s, 2H). MS m/z [M+H]$^+$=335.08.

Intermediate 48: tert-butyl(cyanomethyl)((4-(2-((5-fluoropyridin-2-yl)methyl)-2H-tetrazol-5-yl)phenyl) sulfonyl)carbamate

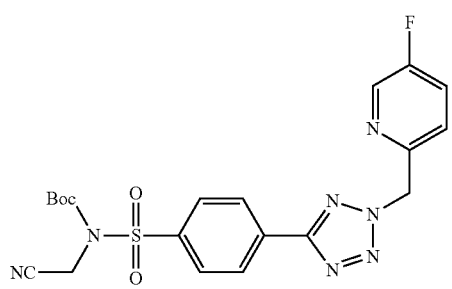

To a stirred solution of 4-(2-((5-fluoropyridin-2-yl)methyl)-2H-tetrazol-5-yl)benzenesulfonamide (600 mg, 1.796 mmol, Intermediate 47) in tetrahydrofuran (25 mL), a mixture of 4-(Dimethylamino)pyridine (110 mg, 0.898 mmol), Boc-anhydride (1.17 g, 5.389 mmol) and triethylamine (218 mg, 2.155 mmol) were added. The reaction mixture was stirred at 26° C. for 5 h. Followed by the addition of potassium carbonate (496 mg, 3.592 mmol) and bromoacetonitrile (539 mg, 4.491 mmol) at 26° C. The reaction mixture was stirred for 16 h at the same temperature. Upon completion, the reaction mixture was quenched with saturated sodium bicarbonate solution (60 mL) and extracted with ethyl acetate (3×60 mL). The combined organic layer was dried over anhydrous Na$_2$SO$_4$, filtered and the filtrate was concentrated under reduced pressure. The crude was purified by column chromatography (neutral alumina), and eluted with dichloromethane. The pure fractions were collected and concentrated under reduced pressure to afford tert-butyl(cyanomethyl)((4-(2-((5-fluoropyridin-2-yl)methyl)-2H-tetrazol-5-yl)phenyl)sulfonyl) carbamate (600 mg, 44%) as an off white solid. $^1$H NMR (400 MHz, DMSO-$d_6$) δ 8.54 (d, J=2.6 Hz, 1H), 8.41-8.25 (m, 2H), 8.21-8.09 (m, 2H), 7.84 (dt, J=8.7, 2.9 Hz, 1H), 7.73-7.61 (m, 1H), 6.28-6.08 (m, 2H), 4.94 (s, 2H), 1.30 (s, 9H). MS m/z [M+H]$^+$=474.40.

Intermediate 49: 4-(2-(pyrimidin-4-ylmethyl)-2H-tetrazol-5-yl)benzenesulfonamide

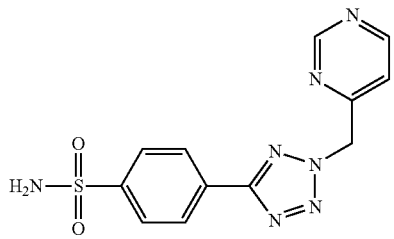

To a solution of 4-(2H-tetrazol-5-yl)benzenesulfonamide (350 mg, 1.5555 mmol Intermediate 43 or commercial source: Butt-Park) and potassium carbonate (429 mg, 3.111 mmol) in N,N-dimethylformamide (10 mL), 4-(bromomethyl)pyrimidine (269 mg, 1.5555 mmol, Intermediate 1) was added at 26° C. and stirred at the same temperature for 24 h. Upon completion, the reaction mixture was concentrated under reduced pressure. The crude compound was purified by column chromatography using 10% methanol in dichloromethane. The pure fractions were collected and concentrated under reduced pressure. The obtained compound was stirred with the mixture of dichloromethane (30 mL) and petroleum ether (100 mL) at 26° C. for 15 min. The precipitated solid compound was filtered and dried under vacuum to afford 4-(2-(pyrimidin-4-ylmethyl)-2H-tetrazol-5-yl)benzenesulfonamide (250 mg, 46%) as a red solid. $^1$H NMR (400 MHz, DMSO-$d_6$) δ 9.14 (s, 1H), 8.88 (d, J=5.3 Hz, 1H), 8.26 (d, J=8.4 Hz, 2H), 8.00 (d, J=8.3 Hz, 2H), 7.60 (s, 1H), 7.52 (s, 2H), 6.28 (s, 2H). MS m/z [M+H]$^+$=318.40.

Intermediate 50: tert-butyl(cyanomethyl)((4-(2-(pyrimidin-4-ylmethyl)-2H-tetrazol-5-yl)phenyl)sulfonyl)carbamate

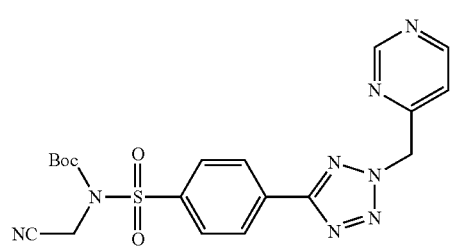

To a stirred solution of 4-(2-(pyrimidin-4-ylmethyl)-2H-tetrazol-5-yl)benzenesulfonamide (250 mg, 0.7886 mmol, Intermediate 49) in tetrahydrofuran (15 mL), a mixture of 4-(Dimethylamino)pyridine (48 mg, 0.394 mmol), Boc-anhydride (516 mg, 2.365 mmol) and triethylamine (96 mg, 0.946 mmol) were added at 26° C. The reaction mixture was stirred at 26° C. for 5 h. Followed by the addition of potassium carbonate (218 mg, 1.577 mmol) and bromoacetonitrile (236 mg, 1.9715 mmol) at 26° C. and the resultant reaction mixture was stirred for 16 h at the same temperature. Upon completion, the reaction mixture was quenched with saturated sodium bicarbonate solution (40 mL) and extracted with ethyl acetate (3×50 mL). The combined organic layer was dried over anhydrous Na$_2$SO$_4$, filtered and the filtrate was concentrated under reduced pressure. The crude was purified by column chromatography (neutral alumina) eluted in dichloromethane. The pure fractions were collected and concentrated under reduced pressure to afford tert-butyl(cyanomethyl)((4-(2-(pyrimidin-4-ylmethyl)-2H-tetrazol-5-yl)phenyl)sulfonyl)carbamate (250 mg, 52%) as brown gummy. $^1$H NMR (400 MHz, CDCl$_3$) δ 9.22 (d, J=1.2 Hz, 1H), 8.90-8.70 (m, 1H), 8.49-8.24 (m, 2H), 8.20-7.99 (m, 2H), 7.15 (dd, J=5.1, 1.2 Hz, 1H), 6.07-5.87 (m, 2H), 4.75 (s, 2H), 1.39 (s, 9H). MS m/z [M+H]$^+$=457.16

Intermediate 51: 2-methoxy-4-(2H-tetrazol-5-yl)benzenesulfonamide

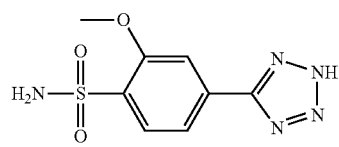

To a solution of 4-cyano-2-methoxybenzenesulfonamide (1 g, 4.712 mmol, commercial source: Enamine) in N,N-dimethylformamide (20 mL), sodium azide (3.06 g, 47.07 mmol) and ammonium chloride (2.52 g, 47.103 mmol) were added at 26° C. The reaction mixture was heated to 120° C. and was stirred for 4 h at the same temperature. Upon completion, the reaction mixture was cooled to 26° C., quenched with 1N HCl (40 mL) and extracted with ethyl acetate (2×50 mL). The organic layer was dried over anhydrous Na$_2$SO$_4$, filtered and the filtrate was concentrated under reduced pressure. The residue was stirred with mixture of dichloromethane (10 mL) and diethyl ether (10 mL) at 27° C. for 30 min. The precipitated solid compound was filtered and dried under vacuum to afford 2-methoxy-4-(2H-tetrazol-5-yl)benzenesulfonamide (890 mg, crude) as an off-white solid. $^1$H NMR (400 MHz, DMSO-$d_6$) δ 7.94 (d, J=8.2 Hz, 1H), 7.82 (d, J=1.5 Hz, 1H), 7.74 (dd, J=8.1, 1.5 Hz, 1H), 7.28 (s, 2H), 4.02 (s, 3H).

Intermediate 52: 2-methoxy-4-(2-(pyridin-4-ylmethyl)-2H-tetrazol-5-yl)benzenesulfonamide

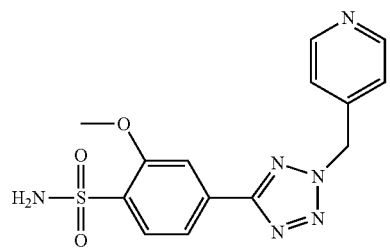

To a solution of 2-methoxy-4-(2H-tetrazol-5-yl)benzenesulfonamide (200 mg, 1.176 mmol, Intermediate 51) and potassium carbonate (325 mg, 2.352 mmol) in N,N-dimethylformamide (10 mL), 4-(chloromethyl)pyridine hydrochloride (193 mg, 1.177 mmol, commercial source: Combi-Blocks) was added at 26° C. The reaction mixture was heated to 80° C. and stirred at the same temperature for 2 h. Upon completion, the reaction mixture was concentrated under reduced pressure. The crude was purified by column chromatography (silicagel 100-200 mesh), eluted with 8% methanol in dichloromethane. The pure fractions were collected and concentrated under reduced pressure to afford 2-methoxy-4-(2-(pyridin-4-ylmethyl)-2H-tetrazol-5-yl)benzenesulfonamide (250 mg, crude) as a brown gum. ¹H NMR (400 MHz, DMSO-d₆) δ 8.65-8.58 (m, 2H), 7.90-7.85 (m, 1H), 7.85-7.69 (m, 2H), 7.40-7.28 (m, 2H), 7.22 (d, J=4.4 Hz, 2H), 6.14 (s, 2H), 3.95 (s, 3H). MS m/z [M+H]⁺= 347.15.

Intermediate 53: tert-butyl (cyanomethyl)((2-methoxy-4-(2-(pyridin-4-ylmethyl)-2H-tetrazol-5-yl)phenyl)sulfonyl)carbamate

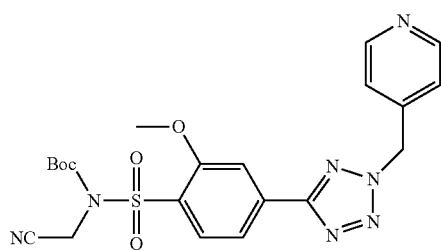

To a solution of 2-methoxy-4-(2-(pyridin-4-ylmethyl)-2H-tetrazol-5-yl)benzenesulfonamide (250 mg, 0.725 mmol, Intermediate 52) and 4-(Dimethylamino)pyridine (44 mg, 0.36 mmol) in tetrahydrofuran (10 mL), triethylamine (0.14 mL, 1.01 mmol) and Boc-anhydride (0.5 mL, 2.176 mmol) were added at 26° C. and stirred for 3 h. Followed by the addition of potassium carbonate (200 mg, 1.447 mmol) and bromoacetonitrile (0.14 mL, 2.009 mmol) at 26° C. The resultant reaction mixture was stirred for 16 h at the same temperature. Upon completion, the reaction mixture was concentrated under reduced pressure. The crude was purified by column chromatography (silicagel 100-200 mesh), eluted with 5% methanol in dichloromethane. The pure fractions were collected and concentrated under reduced pressure to afford tert-butyl (cyanomethyl)((2-methoxy-4-(2-(pyridin-4-ylmethyl)-2H-tetrazol-5-yl)phenyl)sulfonyl)carbamate (300 mg, crude) as a brown gum. ¹H NMR (400 MHz, DMSO-d₆) δ 8.72-8.43 (m, 2H), 8.08 (d, J=8.2 Hz, 1H), 7.95-7.77 (m, 2H), 7.50-7.21 (m, 2H), 6.16 (s, 2H), 4.85 (s, 2H), 4.07 (s, 3H), 1.24 (s, 9H). MS m/z [M+H]⁺=486.19.

General Scheme for the Synthesis of Azide Intermediates

The aromatic bromide 21 or alcohol 22 are transformed to its corresponding azide 27 using sodium azide

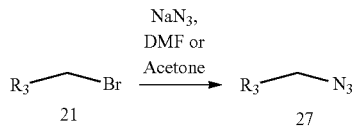

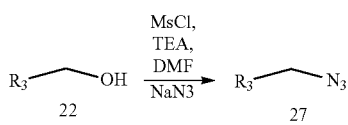

Intermediate 54: 1-(azidomethyl)-4-fluorobenzene

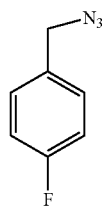

A solution of sodium azide (258 mg, 3.97 mmol) in water (8 mL) was added dropwise over 20 min to a solution of 1-(bromomethyl)-4-fluorobenzene (0.329 mL, 2.65 mmol, commercial source: Aldrich) in Acetone (20 mL) at 0° C. The reaction was allowed to warm up to 25° C. and stirred for 16 h. Acetone was removed under reduced pressure at 25° C., and the reaction mixture was extracted with hexane. Thereafter, the combined organic layers were put together and dried over Na₂SO₄, and the solvent was removed under reduced pressure to afford 1-(azidomethyl)-4-fluorobenzene (320 mg, 2.117 mmol, 80%) as a colorless oil. ¹H NMR (400 MHz, CDCl₃) δ 7.22-7.39 (m, 2H), 6.99-7.16 (m, 2H), 4.33 (s, 2H).

Intermediate 55: 4-(azidomethyl)pyridine

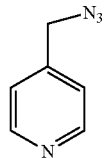

To a solution of pyridin-4-ylmethanol (1 g, 9.163 mmol, commercial source: AK Scientific), and triethylamine (1.3 mL, 9.337 mmol) in N,N-dimethylformamide (10 mL), mesyl chloride (0.7 mL, 9.043 mmol) was added at 0° C. The reaction mixture was allowed to 26° C. and stirred for 2 h. Followed by the addition of sodium azide (892 mg, 13.721 mmol) at 26° C. and stirred at the same temperature for 16 h. Upon completion, the reaction mixture was concentrated under reduced pressure. The crude was purified by column chromatography (silicagel 100-200 mesh), eluted with 50% ethyl acetate in pet ether. The pure fractions were collected and concentrated under reduced pressure to afford 4-(azidomethyl)pyridine (450 mg, 36%) as a yellow liquid. ¹H NMR (400 MHz, DMSO-d₆) δ 8.69-8.53 (m, 2H), 7.47-7.27 (m, 2H), 4.58 (s, 2H). MS m/z [M+H]⁺=135.16.

Intermediate 56: 4-(azidomethyl)benzonitrile

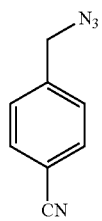

To a solution of 4-(bromomethyl)benzonitrile (500 mg, 2.55 mmol, commercial source: Alfa Aesar) in N,N-dimethylformamide (10 mL), sodium azide (175 mg, 2.692 mmol) was added at 26° C. The reaction mixture was stirred at the same temperature for 16 h. Upon completion, the reaction mixture was concentrated under reduced pressure. The crude was purified by column chromatography (silicagel 100-200 mesh), eluted with 10% ethyl acetate in petroleum ether. The pure fractions were collected and concentrated under reduced pressure to afford 4-(azidomethyl)benzonitrile (360 mg, 89%) as a yellow liquid. $^1$H NMR (400 MHz, DMSO-$d_6$) δ 7.91-7.81 (m, 2H), 7.58 (d, J=8.0 Hz, 2H), 4.61 (s, 2H). MS m/z [M]=157.9.

Intermediate 57: 2-(azidomethyl)-5-fluoropyridine

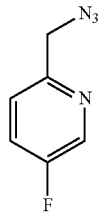

To a stirred solution of (5-fluoropyridin-2-yl)methanol (500 mg, 3.937 mmol, commercial source: Combi-Blocks) and triethylamine (398 mg, 3.937 mmol) in N,N-dimethylformamide (10 mL), mesyl chloride (451 mg, 3.937 mmol) was added at 27° C. The reaction mixture was stirred at 27° C. for 2 h. Followed by the addition of sodium azide (384 mg, 5.905 mmol) at 27° C. and the reaction mixture was stirred for 12 h at the same temperature. Upon completion, the reaction mixture was concentrated under reduced pressure. The crude compound was purified by column chromatography (silica gel 100-200 mesh) using 5% ethyl acetate in pet ether. The pure fractions were collected and concentrated under reduced pressure to afford 2-(azidomethyl)-5-fluoropyridine (150 mg, 25%) as a brown liquid. $^1$H NMR (400 MHz, CDCl$_3$) δ 8.46 (d, J=2.6 Hz, 1H), 7.47-7.40 (m, 1H), 7.39-7.33 (m, 1H), 4.48 (s, 2H). MS m/z [M+H]$^+$=153.12.

Intermediate 58: 2-(azidomethyl)-5-methylpyridine

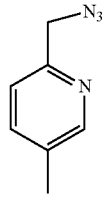

To a solution of (5-methylpyridin-2-yl)methanol (500 mg, 4.06 mmol, commercial source: Enamine) in N,N-dimethylformamide (10 mL), triethylamine (0.6 mL, 4.317 mmol) and mesyl chloride (0.3 mL, 3.876 mmol) were added at 0° C. The reaction mixture was allowed to 26° C. and stirred for 3 h. Followed by the addition of sodium azide (396 mg, 6.091 mmol) at 26° C. and the reaction mixture was stirred for 16 h at the same temperature. Upon completion, the reaction mixture was concentrated under reduced pressure. The crude was purified by column chromatography (silicagel 100-200 mesh), eluted with 40% ethyl acetate in pet ether. The pure fractions were collected and concentrated under reduced pressure to afford 2-(azidomethyl)-5-methylpyridine (300 mg, crude) as a yellow liquid. $^1$H NMR (400 MHz, DMSO-$d_6$) δ 8.43 (d, J=2.2 Hz, 1H), 7.65 (dd, J=8.0, 2.2 Hz, 1H), 7.33 (d, J=7.9 Hz, 1H), 4.45 (s, 2H), 2.30 (s, 3H). MS m/z [M+H]$^+$=149.06.

Intermediate 59: 4-(azidomethyl)-1,1-difluorocyclohexane

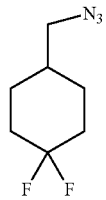

To a solution of 4-(bromomethyl)-1,1-difluorocyclohexane (600 mg, 0.0028 mol, Intermediate 3) in N,N-dimethylformamide (6 mL), sodium azide (549 mg, 0.0084 mol) was added at 26° C. The reaction mixture was heated to 100° C. and stirred for 16 h at the same temperature. Upon completion, the reaction mixture was used for the next step without any further purification. $^1$H NMR (400 MHz, CDCl$_3$) δ 3.18 (t, J=6.6 Hz, 2H), 2.17-1.98 (m, 2H), 1.85-1.57 (m, 5H), 1.37-1.20 (m, 2H).

Intermediate 60: 4-bromo-N-(2-hydroxyethyl)benzenesulfonamide

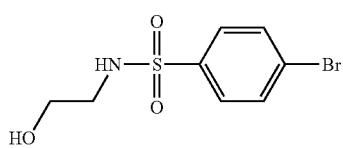

To a solution of 4-bromobenzene-1-sulfonyl chloride (5 g, 19.568 mmol, commercial source: Alfa Aesar) in dichloromethane (100 mL), triethylamine (8.15 mL, 58.941 mmol) and 2-aminoethanol (1.195 g, 19.59 mmol, commercial source: Avra) were added at 0° C. The reaction mixture temperature was raised to 26° C. and stirred for 3 h at the same temperature. Upon completion, the reaction mixture was concentrated under reduced pressure. The crude was purified by column chromatography (silicagel 100-200 mesh), eluted with 60% ethyl acetate in petroleum ether. The pure fractions were collected and concentrated under reduced pressure to afford 4-bromo-N-(2-hydroxyethyl)benzenesulfonamide (3.5 g, 64%) as an off-white solid. $^1$H NMR (400 MHz, DMSO-d$_6$) δ 7.88-7.77 (m, 2H), 7.72 (d, J=8.8 Hz, 3H), 4.66 (s, 1H), 3.36 (q, J=5.9 Hz, 2H), 2.80 (q, J=6.1 Hz, 2H). MS m/z [M+H]$^+$=279.92.

Intermediate 61: N-(2-hydroxyethyl)-4-((trimethylsilyl)ethynyl)benzenesulfonamide

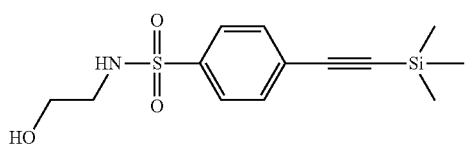

61

To a solution of 4-bromo-N-(2-hydroxyethyl)benzenesulfonamide (3 g, 10.714 mmol, Intermediate 60) in N,N-dimethylformamide (20 mL), triethylamine (4.3 g, 42.856 mmol) was added at 26° C. Reaction mixture was nitrogen purged for 10 min, trimethyl silyl acetylene (1.578 g, 16.071 mmol, commercial source: Avra) was added and again nitrogen purged for 15 min. Followed by the addition of copper(I)iodide (204 mg, 1.0714 mmol) and tetrakis(triphenylphosphine)palladium(0) (495 mg, 0.4285 mmol) at 26° C. The resultant reaction mixture was stirred at same temperature for 16 h in a sealed tube. Upon completion, the reaction mixture was poured into water (100 mL) and extracted with ethyl acetate (3×80 mL). The organic layer was dried over anhydrous Na$_2$SO$_4$, filtered and the filtrate was evaporated under reduced pressure. The crude was purified by column chromatography (silica gel 100-200 mesh), eluted with 30% ethyl acetate in petroleum ether. The pure fractions were collected and concentrated under reduced pressure to afford N-(2-hydroxyethyl)-4-((trimethylsilyl)ethynyl)benzenesulfonamide (1.3 g, 36%) as an off white solid. $^1$H NMR (400 MHz, CDCl$_3$) δ 7.80 (d, J=8.3 Hz, 2H), 7.59 (d, J=8.1 Hz, 2H), 4.86 (br s, 1H), 3.69 (q, J=5.0 Hz, 2H), 3.11 (d, J=4.8 Hz, 2H), 1.70 (t, J=4.8 Hz, 1H), 0.27 (s, 9H). MS m/z [M+H]$^+$=298.03.

Intermediate 62: 4-ethynyl-N-(2-hydroxyethyl)benzenesulfonamide

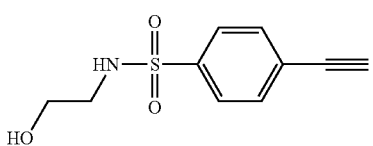

62

To a solution of N-(2-hydroxyethyl)-4-((trimethylsilyl)ethynyl)benzenesulfonamide (1.3 g, 4.377 mmol, Intermediate 61) in a mixture of chloroform (10 mL) and methanol (10 mL), potassium carbonate (302 mg, 2.188 mmol) was added at 26° C. and stirred for 5 h at the same temperature. Upon completion, the reaction mixture was evaporated under reduced pressure. The residue was diluted with 1N HCl (60 mL) and extracted with ethyl acetate (3×60 mL). The organic layer was dried over anhydrous Na$_2$SO$_4$, filtered and the filtrate was evaporated under reduced pressure to afford crude 4-ethynyl-N-(2-hydroxyethyl)benzenesulfonamide (800 mg, 70%). $^1$H NMR (400 MHz, DMSO-d$_6$) δ 7.85-7.78 (m, 2H), 7.73 (s, 1H), 7.71-7.65 (m, 2H), 4.48 (s, 1H), 3.35 (t, J=6.4 Hz, 3H), 2.79 (q, J=6.1 Hz, 2H). MS m/z [M−H]$^-$=224.26.

Intermediate 63: 2-(4-bromophenylsulfonamido)acetamide

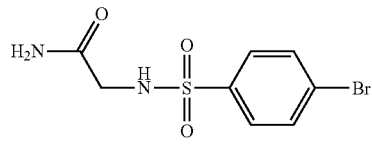

63

To a solution of 4-bromobenzene-1-sulfonyl chloride (10 g, 0.0394 mol, commercial source: Combi-Blocks) in tetrahydrofuran (150 mL), 2-aminoacetamide hydrochloride (5.1 g, 0.047 mol, commercial source: Alfa Aesar) was added at 28° C., followed by the slowly addition of triethylamine (15 mL, 0.118 mol) at 0° C. The reaction mixture was stirred at 28° C. for 2 h. Upon completion, the reaction mixture was diluted with ethyl acetate (500 mL) and washed with water (3×200 mL). The organic layer was dried over anhydrous Na$_2$SO$_4$, filtered and the filtrate was concentrated under reduced pressure to afford 2-(4-bromophenylsulfonamido) acetamide (8 g, 63%) as an off-white solid. $^1$H NMR (400 MHz, DMSO-d$_6$) δ 7.94 (br s, 1H), 7.86-7.63 (m, 4H), 7.24 (br s, 1H), 7.04 (br s, 1H), 3.38 (d, J=4.2 Hz, 2H). MS m/z [M−H]$^-$=291.02.

Intermediate 64: 2-(4-((trimethylsilyl)ethynyl)phenylsulfonamido)acetamide

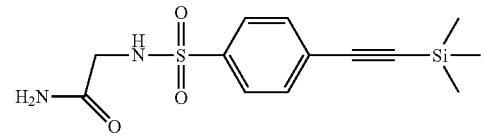

64

To an argon purged solution of 2-(4-bromophenylsulfonamido)acetamide (8 g, 0.0273 mol, Intermediate 63) and triethylamine (15.3 mL, 0.1092 mol) in N,N-dimethylformamide (40 mL), copper(I)iodide (519 mg, 0.0027 mol), ethynyltrimethylsilane (5.8 mL, 0.041 mol, commercial source: Avra) and tetrakis(triphenylphosphine)palladium(0) (1.26 g, 0.001 mol) were added at 28° C. The reaction mixture was stirred for 16 h at the same temperature. Upon completion, the reaction mixture was concentrated under reduced pressure. The crude was purified by column chromatography (silicagel 100-200 mesh), eluted with 80% ethyl acetate in pet ether. The pure fractions were collected and concentrated under reduced pressure to afford 2-(4-((trimethylsilyl)ethynyl)phenylsulfonamido)acetamide (4 g, 42%) as a brown solid. $^1$H NMR (400 MHz, DMSO-d$_6$) δ 7.95 (t, J=6.2 Hz, 1H), 7.87-7.70 (m, 2H), 7.63 (dd, J=8.5, 1.9 Hz, 2H), 7.25 (br s, 1H), 7.04 (br s, 1H), 3.45-3.34 (m, 2H), 0.25 (s, 9H). MS m/z [M−H]$^−$=309.17.

Intermediate 65: 2-(4-ethynyl phenylsulfonamido)acetamide

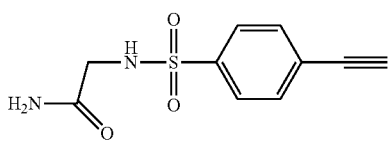

65

To a solution of 2-(4-((trimethylsilyl)ethynyl)phenylsulfonamido)acetamide (2 g, 0.0064 mol, Intermediate 64) in mixture of chloroform (10 mL) and methanol (10 mL), potassium carbonate (445 mg, 0.0032 mol) was added at 26° C. The reaction mixture was stirred for 16 h at the same temperature. Upon completion, the reaction mixture was concentrated under reduced pressure. The residue was dissolved in ethyl acetate (150 mL), washed with water (2×50 mL) and brine (2×30 mL). The organic layer was dried over anhydrous Na$_2$SO$_4$, filtered and the filtrate was evaporated under reduced pressure to afford 2-(4-ethynylphenylsulfonamido)acetamide (1.2 g, 68%) as a brown solid. $^1$H NMR (400 MHz, DMSO-d$_6$) δ 7.97 (s, 1H), 7.78 (d, J=8.5 Hz, 2H), 7.66 (d, J=8.5 Hz, 2H), 7.25 (s, 1H), 7.05 (s, 1H), 4.45 (s, 1H), 3.39 (s, 2H). MS m/z [M+H]$^+$=239.06.

Intermediate 66: (R)-4-bromo-N-(2-hydroxypropyl)benzenesulfonamide

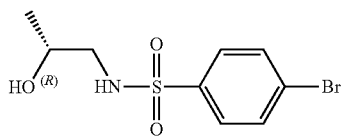

66

4-bromobenzenesulfonyl chloride (1023 mg, 4.00 mmol, commercial source: Aldrich) dissolved in tetrahydrofuran (1 mL) was added dropwise to a stirred solution of (R)-1-aminopropan-2-ol (601 mg, 8.01 mmol, commercial source: Aldrich) in Tetrahydrofuran (1 mL) at 0° C. under nitrogen. The mixture was stirred at rt for 16 h. The reaction mixture was quenched with 1N HCl and extracted with DCM. The organic layer was dried over Na$_2$SO$_4$ and concentrated under reduced pressure to give (R)-4-bromo-N-(2-hydroxypropyl)benzenesulfonamide (1.3 mg, 4.00 mmol, crude) as a crude solid that was used without further purification. $^1$H NMR (400 MHz, CDCl$_3$) δ 7.76-7.70 (m, 2H), 7.69-7.62 (m, 2H), 5.31 (brs, 1H), 3.96-3.84 (m, 1H), 3.10-3.02 (m, 1H), 2.84-2.74 (m, 1H), 1.17 (d, J=6.3 Hz, 3H).

Intermediate 67: (R)—N-(2-hydroxypropyl)-4-((trimethylsilyl)ethynyl)benzenesulfonamide

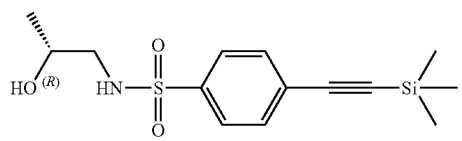

67

To a stirred solution of (R)-4-bromo-N-(2-hydroxypropyl)benzenesulfonamide (700 mg, 2.380 mmol, Intermediate 66) and ethynyltrimethylsilane (0.501 mL, 3.57 mmol) in Triethylamine (17 mL), copper(I) iodide (18.13 mg, 0.095 mmol) and Pd(PPh$_3$)$_4$ (41.2 mg, 0.036 mmol) were added. The mixture was heated to 80° C. for 16 h under N$_2$. The mixture was filtrated under celite and the solvent was evaporated to yield (R)—N-(2-hydroxypropyl)-4-((trimethylsilyl)ethynyl)benzenesulfonamide (726 mg, 2.331 mmol, crude) as an orange oil. MS m/z [M+H]$^+$=312.22.

Intermediate 68: (R)-4-ethynyl-N-(2-hydroxypropyl)benzenesulfonamide

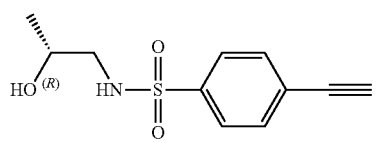

68

(R)—N-(2-hydroxypropyl)-4-((trimethylsilyl)ethynyl)benzenesulfonamide (726 mg, 2.331 mmol, Intermediate 67) was dissolved in Methanol (70 mL) and K$_2$CO$_3$ (1154 mg, 5.83 mmol) was added. The mixture was stirred at room temperature for 48 h. The mixture was concentrated, and partitioned between CH$_2$Cl$_2$ and H$_2$O. The organic layer was dried over MgSO$_4$, filtered and evaporated to dryness. The crude compound was purified by flash column chromatography (silica; EtOAc-cyclohexane from 0/100 to 50/50). The fractions were collected and concentrated in vacuo to yield (R)-4-ethynyl-N-(2-hydroxypropyl)benzenesulfonamide (260 mg, 1.087 mmol, 46.6%) as a yellow oil. $^1$H NMR (400 MHz, CDCl$_3$) δ 7.86-7.80 (m, 2H), 7.65-7.60 (m, 2H), 5.18-5.13 (m, 1H), 3.96-3.88 (m, 1H), 3.27 (s, 1H), 3.11-3.05 (m, 1H), 2.84-2.75 (m, 1H), 2.08 (d, J=4.5 Hz, 1H), 1.17 (d, J=6.3 Hz, 2H). MS m/z [M+H]$^+$=240.2.

Intermediate 69: 4-bromobenzenesulfonamide

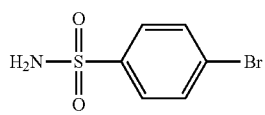

69

To a solution of 4-bromobenzene-1-sulfonyl chloride (5 g, 19.568 mmol, commercial source: Alfa Aesar) in dichloromethane (100 mL), ammonia solution (35% aqueous solution) (50 mL) was added at 27° C. and stirred for 4 h at 27° C. Upon completion, the reaction mixture was concentrated under reduced pressure. The crude was purified by column chromatography (silicagel 100-200 mesh), eluted with 60% ethyl acetate in petroleum ether. The pure fractions were collected and concentrated under reduced pressure to afford 4-bromobenzenesulfonamide (4 g, 86%) as an off-white solid. $^1$H NMR (400 MHz, DMSO-d$_6$) δ 7.83-7.71 (m, 4H), 7.45 (s, 2H). MS m/z [M−H]$^−$=233.93.

Intermediate 70:
4-((trimethylsilyl)ethynyl)benzenesulfonamide

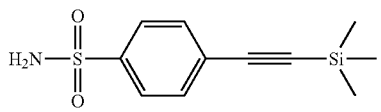

To a nitrogen purged solution of 4-bromobenzenesulfonamide (2 g, 8.475 mmol, Intermediate 69), triethylamine (4.71 mL, 33.851 mmol) and trimethylsilylacetylene (1.81 mL, 12.716 mmol) in N,N-dimethylformamide (10 mL), copper(I)iodide (161 mg, 0.845 mmol) and tetrakis (triphenyl phosphine)palladium(0) (392 mg, 0.339 mmol) were added at 27° C. and stirred at 27° C. for 16 h in a sealed tube. Upon completion, the reaction mixture was filtered through celite and the filtrate was evaporated under reduced pressure. The crude was purified by column chromatography (silicagel 100-200 mesh), eluted with 60% ethyl acetate in petroleum ether. The pure fractions were collected and concentrated under reduced pressure to afford 4-((trimethylsilyl)ethynyl)benzenesulfonamide (1.8 g, 85.7%) as an off-white solid. $^1$H NMR (400 MHz, DMSO-d$_6$) δ 7.80 (d, J=8.5 Hz, 2H), 7.65 (d, J=8.3 Hz, 2H), 7.46 (s, 2H), 0.25 (s, 9H). MS m/z [M−H]$^−$=252.00.

Intermediate 71: 4-ethynylbenzenesulfonamide

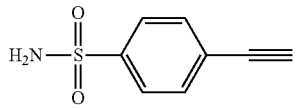

To a solution of 4-((trimethylsilyl)ethynyl)benzenesulfonamide (1.8 g, 7.115 mmol, Intermediate 70) in mixture of chloroform (10 mL) and methanol (10 mL), potassium carbonate (393 mg, 2.844 mmol) was added at 27° C. and stirred at 27° C. for 16 h. Upon completion, the reaction mixture was evaporated under reduced pressure. The residue was diluted with ethyl acetate (200 mL) and washed with 1N HCl (150 mL). The organic layer was dried over Na$_2$SO$_4$, filtered and the filtrate was evaporated under reduced pressure to afford 4-ethynylbenzenesulfonamide (1.4 g, crude) as a brown solid. $^1$H NMR (400 MHz, DMSO-d$_6$) δ 7.82 (d, J=8.3 Hz, 2H), 7.68 (d, J=8.3 Hz, 2H), 7.44 (s, 2H), 4.42 (s, 1H). MS m/z [M−H]$^−$=179.97.

Intermediate 72: 4-(1-(pyridin-4-ylmethyl)-1H-1,2,3-triazol-4-yl)benzenesulfonamide

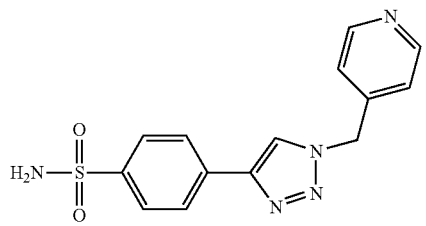

To a solution of 4-ethynylbenzenesulfonamide (800 mg, 4.419 mmol, Intermediate 71) and 4-(azidomethyl)pyridine (583 mg, 4.417 mmol, Intermediate 55) in a mixture of ethanol (10 mL) and water (10 mL), copper sulphate pentahydrate (110 mg, 0.442 mmol) and sodium-L-ascorbate (262 mg, 1.323 mmol) were added at 26° C. and stirred at 26° C. for 16 h. Upon completion, the reaction mixture was concentrated under reduced pressure. The crude was purified by column chromatography (silicagel 100-200 mesh), eluted with 10% methanol in dichloromethane. The pure fractions were collected and concentrated under reduced pressure to afford 4-(1-(pyridin-4-ylmethyl)-1H-1,2,3-triazol-4-yl)benzenesulfonamide (500 mg, crude) as a brown solid. $^1$H NMR (400 MHz, DMSO-d$_6$) δ 8.81 (s, 1H), 8.65-8.55 (m, 2H), 8.05 (d, J=8.4 Hz, 2H), 7.89 (d, J=8.4 Hz, 2H), 7.48-7.22 (m, 4H), 5.76 (d, J=6.7 Hz, 2H). MS m/z [M+H]$^+$=316.15.

Intermediate 73: tert-butyl (cyanomethyl)((4-(1-(pyridin-4-ylmethyl)-1H-1,2,3-triazol-4-yl)phenyl)sulfonyl)carbamate

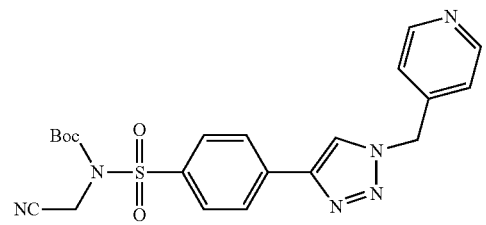

To a solution of 4-(1-(pyridin-4-ylmethyl)-1H-1,2,3-triazol-4-yl)benzenesulfonamide (500 mg, 1.587 mmol, Intermediate 72) and 4-(Dimethylamino)pyridine (97 mg, 0.794 mmol) in tetrahydrofuran (20 mL), triethylamine (0.3 mL, 2.158 mmol) and Di-tert-butyl dicarbonate (1.09 mL, 4.747 mmol) were added at 26° C. and stirred at 26° C. for 8 h followed by the addition of potassium carbonate (438.7 mg, 3.174 mmol) and bromoacetonitrile (0.3 mL, 4.31 mmol) at 26° C. The reaction mixture was stirred for 16 h at the same temperature. Upon completion, the reaction mixture was concentrated under reduced pressure. The crude was purified by column chromatography (silicagel 100-200 mesh), eluted with 10% methanol in dichloromethane. The pure fractions were collected and concentrated under reduced pressure to afford tert-butyl (cyanomethyl)((4-(1-(pyridin-4-ylmethyl)-1H-1,2,3-triazol-4-yl)phenyl)sulfonyl)carbamate (500 mg, crude) as a brown solid. $^1$H NMR (400 MHz, DMSO-d$_6$) δ

8.91 (s, 1H), 8.60 (br s, 2H), 8.17 (d, J=8.7 Hz, 2H), 8.04 (d, J=8.7 Hz, 2H), 7.29 (d, J=4.9 Hz, 2H), 5.78 (s, 2H), 4.92 (s, 2H), 1.31 (s, 9H). MS m/z [M+H]⁺=455.15.

Intermediate 74: 4-(1-((5-fluoropyridin-2-yl)methyl)-1H-1,2,3-triazol-4-yl)benzenesulfonamide

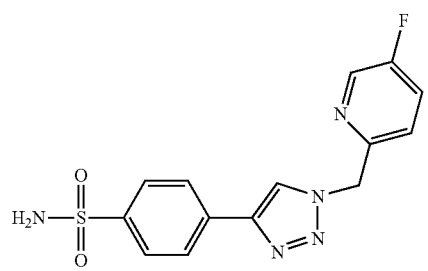

74

To a solution of 4-ethynylbenzenesulfonamide (4 g, 22.099 mmol, Intermediate 71) and 2-(azidomethyl)-5-fluoropyridine (3.36 g, 22.105 mmol, Intermediate 57) in a mixture of ethanol (50 mL) and water (50 mL), copper sulphate pentahydrate (550 mg, 2.209 mmol) and sodium-L-ascorbate (1.31 g, 6.616 mmol) were added at 27° C. and stirred for 16 h at 27° C. Upon completion, the reaction mixture was concentrated under reduced pressure. The crude was purified by column chromatography (silicagel 100-200 mesh), eluted with 4% methanol in dichloromethane. The pure fractions were collected and concentrated under reduced pressure to afford 4-(1-((5-fluoropyridin-2-yl)methyl)-1H-1,2,3-triazol-4-yl)benzenesulfonamide (4.6 g, 63%) as an off-white solid. ¹H NMR (400 MHz, DMSO-d₆) δ 8.77 (s, 1H), 8.59-8.54 (m, 1H), 8.05 (d, J=8.5 Hz, 2H), 7.88 (d, J=8.5 Hz, 2H), 7.84-7.76 (m, 1H), 7.58-7.49 (m, 1H), 7.36 (s, 2H), 5.79 (s, 2H). MS m/z [M+H]⁺=334.37.

Intermediate 75: tert-butyl (cyanomethyl)((4-(1-((5-fluoropyridin-2-yl)methyl)-1H-1,2,3-triazol-4-yl)phenyl)sulfonyl)carbamate

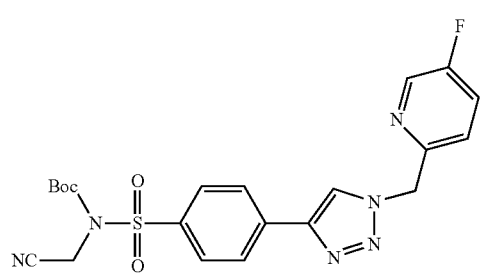

75

To a solution of 4-(1-((5-fluoropyridin-2-yl)methyl)-1H-1,2,3-triazol-4-yl)benzenesulfonamide (2.6 g, 7.808 mmol, Intermediate 74) and 4-(Dimethylamino)pyridine (477 mg, 3.904 mmol) in tetrahydrofuran (20 mL), di-tert-butyl dicarbonate (5.4 mL, 23.505 mmol) and triethylamine (1.6 mL, 16 mmol) were added at 27° C. The reaction mixture was stirred at 27° C. for 5 h followed by the addition of potassium carbonate (2.16 g, 15.629 mmol) and bromoacetonitrile (1.4 mL, 20.1 mmol) at 27° C. The reaction mixture was stirred for 16 h at the same temperature. Upon completion, the reaction mixture was concentrated under reduced pressure. The crude was purified by column chromatography (silicagel 100-200 mesh), eluted with 2% methanol in dichloromethane. The pure fractions were collected and concentrated under reduced pressure. The obtained compound was washed with diethyl ether (2×20 mL) and dried under vacuum to afford tert-butyl (cyanomethyl) ((4-(1-((5-fluoropyridin-2-yl) methyl)-1H-1,2,3-triazol-4-yl) phenyl) sulfonyl)carbamate (2 g, 54%) as an off-white solid. ¹H NMR (400 MHz, DMSO-d₆) δ 8.88 (s, 1H), 8.60-8.54 (m, 1H), 8.18 (d, J=8.5 Hz, 2H), 8.03 (d, J=8.5 Hz, 2H), 7.85-7.76 (m, 1H), 7.60-7.51 (m, 1H), 5.81 (s, 2H), 4.92 (s, 2H), 1.30 (s, 9H). MS m/z [M+H]⁺=473.22.

Intermediate 76: (4-bromo-2-methylbenzenesulfonyl Chloride)

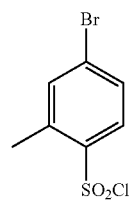

76

To a solution of 4-bromo-2-methylaniline (5.0 g, 26.874 mmol, commercial source: Sigma Aldrich) in acetic acid (12.5 mL) and conc. HCl (25 mL), an aqueous solution of NaNO₂ (2.78 g, 40.31 mmol, commercial source: Finar) was added slowly at 0° C. and stirred for 30 minutes. This reaction mixture was added to a prepared saturated solution of SO₂ in acetic acid (90 mL) and copper(II) chloride (1.8 g, 13.43 mmol, commercial source: Alfa Aesar) at 0° C. and stirred at room temperature for 16 h. Upon completion, the reaction mixture was diluted with water (100 mL) and extracted with ethyl acetate (3×100 mL). The organic layer was dried over anhydrous Na₂SO₄ and filtered. The filtrate was concentrated under reduced pressure to afford 4-bromo-2-methylbenzenesulfonyl chloride (5 g, crude) as a brown gum. ¹H NMR (400 MHz, CDCl₃) δ 7.94-7.91 (m, 1H), 7.61-7.59 (m, 1H), 7.54-7.51 (m, 1H), 2.78 (s, 3H). The compound was used without further purification.

Intermediate 77: 4-bromo-N-(2-hydroxyethyl)-2-methylbenzenesulfonamide

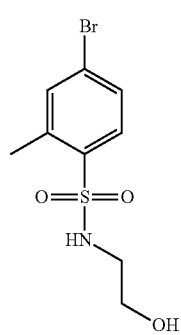

77

To a solution of 4-bromo-2-methylbenzenesulfonyl chloride (5 g, 18.55 mmol, Intermediate 76) in tetrahydrofuran (100 mL), triethylamine (7.2 mL, 51.94 mmol, commercial source: Finar) was added at 0° C., followed by 2-aminoethanol (1.35 g, 22.26 mmol, commercial source: Avra). The reaction mixture was allowed to reach 26° C. and stirred for 3 h at the same temperature. Upon completion, the reaction was diluted with ethyl acetate (150 mL) and water (50 mL). The aqueous layer was extracted with ethyl acetate (2×30 mL). The combined organic layers were dried over anhydrous $Na_2SO_4$, filtered and the filtrate was concentrated under reduced pressure. The crude was purified by column chromatography, eluted with 1.5% methanol in DCM. The pure fractions were concentrated under reduced pressure to afford 4-bromo-N-(2-hydroxyethyl)-2-methylbenzenesulfonamide (2.3 g, 40.8%) as an off-white solid. $^1$H NMR (400 MHz, DMSO-$d_6$) δ 7.76-7.72 (m, 2H), 7.67-7.65 (m, 1H), 7.60-7.58 (m, 1H), 4.65-4.61 (m, 1H), 3.35-3.31 (m, 2H), 2.85-2.79 (m, 2H), 2.6 (s, 3H). MS m/z [M+H]$^+$=296.09.

Intermediate 78: 4-cyano-N-(2-hydroxyethyl)-2-methylbenzenesulfonamide

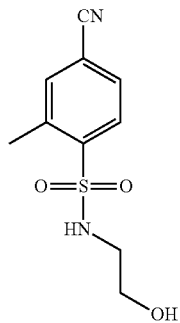

78

To a solution of 4-bromo-N-(2-hydroxyethyl)-2-methylbenzenesulfonamide (2.2 g, 7.748 mmol, Intermediate 77) in N,N-dimethylformamide (22 mL), $Zn(CN)_2$ (2.6 g, 22.43 mmol, commercial source: Sigma Aldrich) was added at 26° C. Reaction mixture was purged with nitrogen 10 min, tetrakis(triphenylphosphine)palladium(0) (0.863 g, 0.747 mmol, commercial source: Alfa Aesar) was added and again purged with nitrogen for 15 minutes at 26° C. The resultant reaction mixture was stirred at 120° C. for 40 minutes under microwave conditions. Upon completion, the reaction mixture was diluted with ethyl acetate (200 mL), filtered through a celite pad and evaporated under reduced pressure. The crude was purified by column chromatography, eluted with 35% ethyl acetate in petroleum ether. The pure fractions were concentrated under reduced pressure to afford 4-cyano-N-(2-hydroxyethyl)-2-methylbenzenesulfonamide (1.1 g, 42%) as a pale yellow solid. $^1$H NMR (400 MHz, DMSO-$d_6$) δ 7.95-7.91 (m, 3H), 7.84-7.79 (m, 1H), 4.65 (br s, 1H), 3.33-3.27 (m, 2H), 2.87-2.84 (m, 2H), 2.65 (s, 3H). MS m/z [M+H]$^+$=241.18.

Intermediate 79: N-(2-hydroxyethyl)-2-methyl-4-(2H-tetrazol-5-yl)benzenesulfonamide

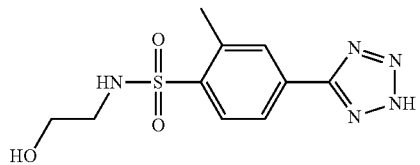

79

To a solution of 4-cyano-N-(2-hydroxyethyl)-2-methylbenzenesulfonamide (1.0 g, 4.16 mmol, Intermediate 78) in tetrahydrofuran (10 mL) and water (1 mL), sodium azide (1.02 g, 15.81 mmol) and zinc bromide (1.78 g, 7.90 mmol) were added at 26° C. The reaction mixture was heated to 85° C. and stirred for 16 h. Upon completion, the reaction mixture was cooled to 0° C., diluted with ice cold water (20 mL) and acidified with conc. HCl up to pH 2. The precipitated solid was filtered, washed with water and dried to afford N-(2-hydroxyethyl)-2-methyl-4-(2H-tetrazol-5-yl)benzenesulfonamide (600 mg) as an off-white solid. MS m/z [M+H]$^+$=284.17. The material was used in the next step without any further purification.

Intermediate 80: 4-bromo-3-methylbenzenesulfonyl Chloride

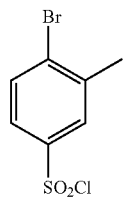

80

To a solution of 4-bromo-3-methylaniline (5.0 g, 26.87 mmol, commercial source: Combi-Blocks) in acetic acid (12.0 mL) and conc HCl (20 mL), an aqueous solution of $NaNO_2$ (2.78 g, 40.31 mmol, 20 mL water, commercial source: Avra) was added slowly at 0° C. and stirred for 30 minutes. This reaction mixture was added to a prepared saturated solution of $SO_2$ in acetic acid (50 mL) and copper (II) chloride (1.08 g, 8.06 mmol, commercial source: Combi-Blocks) at 10° C., and then stirred at 27° C. for 12 h. Upon completion, the reaction mixture was diluted with water (100 mL) and extracted with ethyl acetate (1 L). The combined organic solution was dried over anhydrous $Na_2SO_4$, filtered and the filtrate was concentrated under reduced pressure to afford 4-bromo-3-methylbenzenesulfonyl chloride (5 g, crude) as a brown gum. $^1$H NMR (400 MHz, $CDCl_3$) δ 7.92-7.88 (m, 1H), 7.80-7.77 (m, 1H), 7.73-7.69 (m, 1H), 2.53 (s, 3H).

Intermediate 81: 4-bromo-N-(2-hydroxyethyl)-3-methylbenzenesulfonamide

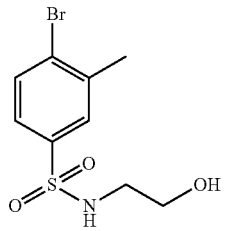

81

To a solution of 4-bromo-3-methylbenzenesulfonyl chloride (5 g, 18.65 mmol, Intermediate 80) in tetrahydrofuran (50 mL), triethylamine (5.2 mL, 37.3 mmol, commercial source: RCP) was added followed by 2-aminoethanol (1.13 g, 18.65 mmol, commercial source: RCP) at 0° C. The reaction mixture was allowed to reach 26° C. and stirred at the same temperature for 5 h. Upon completion, the reaction was diluted with ethyl acetate (2 L) and washed with water (1 L), brine solution (500 mL). The organic layer was dried over anhydrous $Na_2SO_4$, filtered and the filtrate was concentrated under reduced pressure to afford 4-bromo-N-(2-hydroxyethyl)-3-methylbenzenesulfonamide (5 g, 91%) as an off-white solid. $^1$H NMR (400 MHz, DMSO-d$_6$) δ 7.80-7.77 (m, 1H), 7.74-7.71 (m, 1H), 7.61-7.58 (m, 1H), 7.51-7.47 (m, 1H), 4.62 (t, J=5.6 Hz, 1H), 3.33 (q, J=6.0 Hz, 2H), 2.77 (q, J=6.1 Hz, 2H), 2.56 (s, 3H). MS m/z [M+H]$^+$= 294.08.

Intermediate 82: 4-cyano-N-(2-hydroxyethyl)-3-methylbenzenesulfonamide

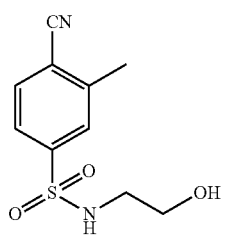

82

To a solution of 4-bromo-N-(2-hydroxyethyl)-3-methylbenzenesulfonamide (4 g, 13.68 mmol, Intermediate 81) in N,N-dimethylformamide (40 mL), $Zn(CN)_2$ (7.26 g, 41.08 mmol commercial source: Sigma Aldrich) was added at 26° C. The reaction mixture was nitrogen purged for 10 min, tetrakis(triphenylphosphine)palladium(0) (1.6 g, 1.36 mmol, commercial source: Alfa Aesar) was added and again nitrogen purged at 26° C. for 15 minutes. The resultant reaction mixture was stirred at 100° C. for 12 h. Upon completion, the reaction mixture was poured into water (1 L) and extracted with ethyl acetate (2×700 mL). The combined organic solution was dried over anhydrous $Na_2SO_4$, filtered and the filtrate was evaporated under reduced pressure. The crude was purified by Reveleris® flash chromatography system, eluted with 20% ethyl acetate in pet. ether. The pure fractions were concentrated under reduced pressure to afford 4-cyano-N-(2-hydroxyethyl)-3-methylbenzenesulfonamide (2.5 g, 76%) as a brown liquid. $^1$H NMR (400 MHz, DMSO-d6) δ 8.04-8.0 (m, 1H), 7.96 (s, 1H), 7.90-7.86 (m, 2H), 4.71-4.65 (m, 1H), 3.37 (q, J=6.0 Hz, 2H), 2.97 (t, J=6.1 Hz, 2H), 2.58 (s, 3H). MS m/z [M–H]$^-$=239.19.

Intermediate 83: N-(2-hydroxyethyl)-3-methyl-4-(2H-tetrazol-5-yl)benzenesulfonamide

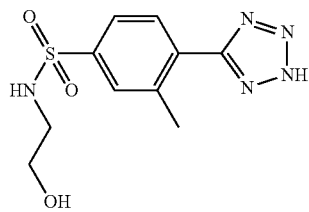

83

To a solution of 4-cyano-N-(2-hydroxyethyl)-3-methylbenzenesulfonamide (2.3 g, 9.58 mmol, Intermediate 82) in tetrahydrofuran (23 mL) and water (3 mL), sodium azide (2.36 g, 36.4 mmol, commercial source: Avra) and zinc bromide (4.09 g, 18.2 mmol, commercial source: Combi-Blocks) were added at 26° C. The reaction mixture was heated to 85° C. and stirred for 12 h. Upon completion, the reaction mixture was cooled to 0° C. and evaporated under reduced pressure. The crude was acidified with conc. HCl (30 mL) up to pH 2. The precipitated solid was filtered, washed with water and dried to afford N-(2-hydroxyethyl)-3-methyl-4-(2H-tetrazol-5-yl)benzenesulfonamide (1.5 g, crude) as an off-white solid. MS m/z [M–H]$^-$=282.18.

Intermediate 84: 4-bromo-2-fluorobenzene-1-sulfonyl Chloride

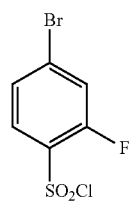

84

To a solution of 4-bromo-2-fluoroaniline (2.0 g, 10.58 mmol, commercial source: Combi-Blocks) in acetic acid (5 mL) and aq. HCl (8 mL), an aqueous solution of $NaNO_2$ (1.1 g, 15.87 mmol, commercial source: Avra) was added slowly at 0° C. and stirred for 45 minutes. This reaction mixture was added to a prepared saturated solution of $SO_2$ in acetic acid (20 mL) and copper(II) chloride (0.42 g, 3.17 mmol, commercial source: Combi-Blocks) at 0° C. and stirred at room temperature for 2 h. Upon completion, the reaction mixture was extracted with ethyl acetate (500 mL). The organic layer was dried over anhydrous $Na_2SO_4$, filtered and the filtrate was concentrated under reduced pressure to afford 4-bromo-2-fluorobenzene-1-sulfonyl chloride (2 g, crude) as a gum. $^1$H NMR (400 MHz, CDCl$_3$) 57.92-7.88 (m, 1H), 7.58-7.54 (m, 2H).

Intermediate 85: 4-bromo-2-fluoro-N-(2-hydroxyethyl)benzenesulfonamide

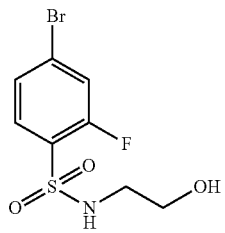

85

To a solution of 4-bromo-2-fluorobenzene-1-sulfonyl chloride (2 g, 7.35 mmol, Intermediate 84) in tetrahydrofuran (20 mL), triethylamine (2 mL, 14.7 mol, commercial source: RCP) was added followed by 2-aminoethanol (0.5 g, 7.35 mmol, commercial source: RCP) at 0° C. The reaction mixture was allowed to reach 26° C. and stirred at the same temperature for 5 h. Upon completion, the reaction was diluted with ethyl acetate (1 L). The organic layer was washed with water (500 mL), brine solution (200 mL), dried over anhydrous $Na_2SO_4$, filtered and the filtrate was concentrated under reduced pressure to afford 4-bromo-2-fluoro-N-(2-hydroxyethyl)benzenesulfonamide (2 g, 91%) as an off-white solid. $^1$H NMR (400 MHz, DMSO-$d_6$) δ 7.89-7.85 (m, 1H), 7.8-7.77 (m, 1H), 7.72-7.65 (m, 1H), 7.61-7.57 (m, 1H), 4.62 (t, J=5.6 Hz, 1H), 3.33 (q, J=6.0 Hz, 2H), 2.85 (q, J=6.1 Hz, 2H). MS m/z [M+2H]$^+$=298.04.

Intermediate 86: 4-cyano-2-fluoro-N-(2-hydroxyethyl)benzenesulfonamide

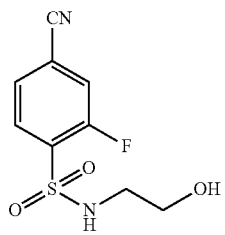

86

To a solution of 4-bromo-2-fluoro-N-(2-hydroxyethyl)benzenesulfonamide (2 g, 6.71 mmol, Intermediate 85) in N,N-dimethylformamide (20 mL), $Zn(CN)_2$ (3.56 g, 20.3 mmol, commercial source: Sigma Aldrich) was added at 26° C. The reaction mixture was nitrogen purged for 10 min, tetrakis(triphenylphosphine)palladium(0) (0.77 g, 0.67 mmol, commercial source: Alfa Aesar) was added and again nitrogen purged at 26° C. for 15 minutes. The resultant reaction mixture was stirred at 100° C. for 12 h. Upon completion, the reaction mixture was poured into water (500 mL) and extracted with ethyl acetate (2×500 mL). The organic layer was dried over anhydrous $Na_2SO_4$, filtered and the filtrate was evaporated under reduced pressure. The crude was purified by Reveleris® flash chromatography system, eluted with 15% ethyl acetate in petroleum ether. The pure fractions were concentrated under reduced pressure to afford 4-cyano-2-fluoro-N-(2-hydroxyethyl)benzenesulfonamide (1.1 g, 68%) as a brown liquid. $^1$H NMR (400 MHz, DMSO-$d_6$) δ 8.22 (s, 1H), 8.16-8.09 (m, 1H), 7.99-7.93 (m, 1H), 7.90-7.86 (m, 1H), 4.71-4.65 (m, 1H), 3.37 (q, J=6.0 Hz, 2H), 2.97 (t, J=6.1 Hz, 2H). MS m/z [M+H]$^+$=243.12

Intermediate 87: 2-fluoro-N-(2-hydroxyethyl)-4-(2H-tetrazol-5-yl)benzenesulfonamide

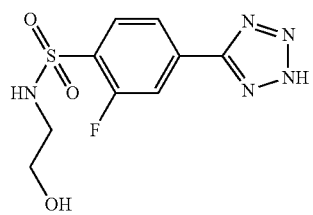

87

To a solution of 4-cyano-2-fluoro-N-(2-hydroxyethyl)benzenesulfonamide (1.0 g, 4.098 mmol, Intermediate 86) in tetrahydrofuran (10 mL) and water (1 mL), sodium azide (1.0 g, 15.57 mmol) and zinc bromide (1.75 g, 7.78 mmol) were added at 26° C. The reaction mixture was heated to 85° C. and stirred for 12 h. Upon completion, the reaction mixture was cooled to 0° C. and acidified with conc. HCl (30 mL) up to pH 2. The precipitated solid was filtered, washed with water and dried to afford 2-fluoro-N-(2-hydroxyethyl)-4-(2H-tetrazol-5-yl)benzenesulfonamide (1 g, 85%) as an off-white solid. $^1$H NMR (400 MHz, DMSO-$d_6$) δ 8.09-7.98 (m, 3H), 3.42-3.25 (m, J=6.4 Hz, 2H), 2.98 (q, J=6.1 Hz, 2H). MS m/z [M+H]$^+$=288.13

Intermediate 88: 4-(benzylthio)-3-chlorobenzonitrile

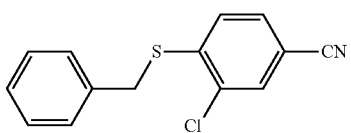

88

To a solution of 3,4-dichlorobenzonitrile (5 g, 29.25 mmol, commercial source: Alfa) in N,N-dimethylformamide (50 mL), potassium carbonate (9.7 g, 70.19 mmol) and phenylmethanethiol (4.35 g, 35.1 mmol, commercial source: Alfa) were added at 28° C. The resultant reaction mixture was stirred at 100° C. for 16 h. On completion of the reaction, the reaction mixture was cooled to 28° C. and diluted with ethyl acetate (200 mL). The organic layer was sequently washed with ice water (5×100 mL) and brine solution (50 mL). The organic layers were combined and dried over anhydrous $Na_2SO_4$, filtered and the filtrate was concentrated under reduced pressure to afford 4-(benzylthio)-3-chlorobenzonitrile (4 g, 28%, purity=53%). MS m/z [M−H]$^-$=258.42

Intermediate 89: 2-chloro-4-cyanobenzene-1-sulfonyl Chloride

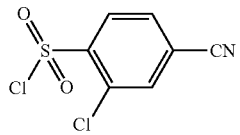

To a solution of 4-(benzylthio)-3-chlorobenzonitrile (4 g, 15.443 mmol, Intermediate 88) in acetic acid (6 mL), water (4 mL) and acetonitrile (160 mL), 1,3-dichloro-5,5-dimethylimidazolidine-2,4-dione (3.63 g, 18.531 mmol, commercial source: Aldrich) was added at 0° C. Reaction was stirred at 28° C. for 16 h. Upon completion, the reaction was concentrated under reduced pression to afford the crude that was diluted with ethyl acetate (200 mL) and water (50 mL). The organic layer was separated and washed with sat. NaHCO$_3$ solution (2×100 mL). The organic layer was washed with sat. NaCl (50 mL), dried over anhydrous Na$_2$SO$_4$ and filtered off. Solvent was evaporated under reduced pressure. The crude was purified by column chromatography (silicagel 100-200 mesh), eluted with 10% ethyl acetate in hexane. The pure fractions were collected and concentrated under reduced pressure to afford 2-chloro-4-cyanobenzene-1-sulfonyl chloride (1.6 g, 24%, purity 54%) as a brown solid.

Intermediate 90: 2-chloro-4-cyano-N-(2-hydroxyethyl)benzenesulfonamide

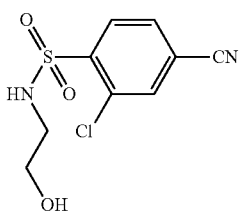

To a solution of 2-chloro-4-cyanobenzene-1-sulfonyl chloride (1.6 g, 6.81 mmol, Intermediate 89) in tetrahydrofuran (32 mL), triethylamine (2.3 mL, 17.026 mmol, commercial source: Finar) was added at 0° C., followed by 2-aminoethanol (0.49 g, 8.17 mmol, commercial source: Avra). The reaction mixture was allowed to reach 28° C. and stirred for 3 h at the same temperature. Upon completion, the reaction was diluted with ethyl acetate (100 mL) and water (50 mL). The organic layer was separated and dried over anhydrous Na$_2$SO$_4$, filtered and the filtrate was concentrated under reduced pressure. The crude was purified by column chromatography, eluted with 40% ethyl acetate in hexane. The pure fractions were concentrated under reduced pressure to afford 2-chloro-4-cyano-N-(2-hydroxyethyl)benzenesulfonamide (1 g, 53.3%) as an off-white solid. MS m/z [M+H]$^+$=261.05.

Intermediate 91: 2-chloro-N-(2-hydroxyethyl)-4-(2H-tetrazol-5-yl)benzenesulfonamide

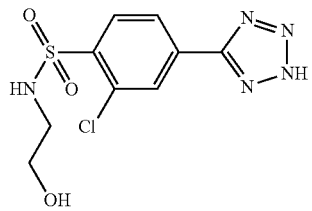

To a solution of 2-chloro-4-cyano-N-(2-hydroxyethyl) benzenesulfonamide (1.0 g, 3.8461 mmol, Intermediate 90) in tetrahydrofuran (10 mL) and water (1 mL), sodium azide (0.95 g, 14.615 mmol, commercial source: Avra) and zinc bromide (1.6 g, 7.307 mmol, commercial source: Alfa Aesar) were added at 28° C. The reaction mixture was heated to 100° C. and stirred for 16 h. Upon completion, the reaction mixture was cooled to 0° C. and quenched with ice water (20 mL). pH of the solution was adjusted by adding slowly, at 0° C., conc. HCl (35 mL) up to pH 2. Then, THF was removed under reduced pressure and the precipitated solid was filtered, washed with water and dried to afford 2-chloro-N-(2-hydroxyethyl)-4-(2H-tetrazol-5-yl)benzenesulfonamide (100 mg, 60%) as an off-white solid. MS m/z [M+H]$^+$=304.04

Intermediate 92: 4-(benzylthio)-2-chlorobenzonitrile

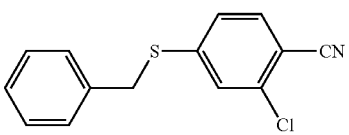

To a solution of 2-chloro-4-fluorobenzonitrile (5 g, 32.26 mmol, commercial source: Combi-Blocks) in N,N-dimethylformamide (50 mL), potassium carbonate (8.9 g, 64.52 mmol) and phenylmethanethiol (4.8 g, 38.71 mmol, commercial source: Alfa) were added at 28° C. The resultant reaction mixture was stirred at 100° C. for 16 h. On completion of the reaction, the reaction mixture was cooled to 28° C. and diluted with ethyl acetate (200 mL). The organic layer was sequently washed with ice water (5×100 mL) and brine solution (100 mL). The organic layers were combined and dried over anhydrous Na$_2$SO$_4$, filtered and the filtrate was concentrated under reduced pressure. The crude was purified by column chromatography (silicagel 100-200 mesh), eluted with 18% ethyl acetate in hexane to afford 4-(benzylthio)-2-chlorobenzonitrile (3.5 g, 41.7%). MS m/z [M+2H]$^+$=261.13

Intermediate 93: 3-chloro-4-cyanobenzene-1-sulfonyl Chloride

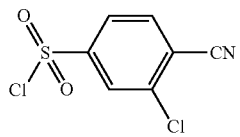

93

To a solution of 4-(benzylthio)-2-chlorobenzonitrile (3.5 g, 13.51 mmol, Intermediate 92) in acetonitrile (140 mL), acetic acid (5.25 mL), water (3.5 mL) and 1,3-dichloro-5,5-dimethylimidazolidine-2,4-dione (3.1 g, 16.21 mmol, commercial source: Aldrich) was added at 0° C. Reaction was stirred at 28° C. for 16 h. Upon completion, the reaction was concentrated under reduced pressure to afford the crude that was diluted with ethyl acetate (200 mL). The organic layer was separated and washed with sat. $NaHCO_3$ solution (3×50 mL). The organic layer was washed with sat. NaCl (50 mL), dried over anhydrous $Na_2SO_4$ and filtered off. Solvent was evaporated under reduced pressure. The crude was purified by column chromatography (silicagel 100-200 mesh), eluted with 10% ethyl acetate in hexane. The pure fractions were collected and concentrated under reduced pressure to afford 3-chloro-4-cyanobenzene-1-sulfonyl chloride (1.6 g, 42.5%) as a pale yellow solid.

Intermediate 94: 3-chloro-4-cyano-N-(2-hydroxyethyl)benzenesulfonamide

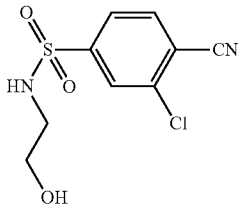

94

To a solution of 3-chloro-4-cyanobenzene-1-sulfonyl chloride (1.5 g, 6.38 mmol, Intermediate 93) in tetrahydrofuran (30 mL), triethylamine (1.8 mL, 12.77 mmol, commercial source: Finar) was added at 0° C., followed by 2-aminoethanol (0.38 g, 6.38 mmol, commercial source: Avra). The reaction mixture was allowed to reach 26° C. and stirred for 1 h at the same temperature. Upon completion, the reaction was concentrated under reduced pressure to afford the crude that was diluted with ethyl acetate (100 mL). The organic layer was sequently washed with water (2×50 mL) and brine solution (50 mL). The organic layers were combined and dried over anhydrous $Na_2SO_4$, filtered and the filtrate was concentrated under reduced pressure. The crude was purified by column chromatography (silicagel 100-200 mesh), eluted with 50% ethyl acetate in hexane to afford 3-chloro-4-cyano-N-(2-hydroxyethyl)benzenesulfonamide (1 g, 59.6%) as an off-white solid. MS m/z $[M-H]^-$=258.93.

Intermediate 95: 3-chloro-N-(2-hydroxyethyl)-4-(2H-tetrazol-5-yl)benzenesulfonamide

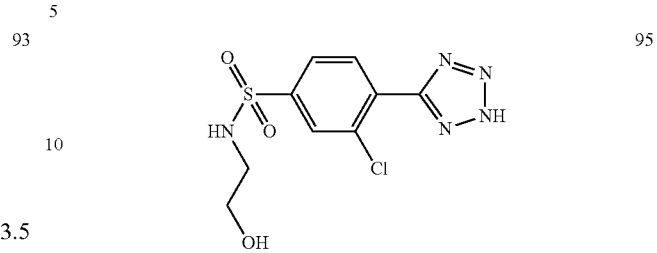

95

To a solution of 3-chloro-4-cyano-N-(2-hydroxyethyl)benzenesulfonamide (1.0 g, 3.846 mmol, Intermediate 94) in tetrahydrofuran (10 mL) and water (1 mL), sodium azide (0.95 g, 14.61 mmol) and zinc bromide (1.64 g, 7.31 mmol) were added at 28° C. The reaction mixture was heated to 85° C. and stirred for 16 h. Upon completion, the reaction mixture was cooled to 0° C. and acidified with conc. HCl (30 mL) up to pH 2. Then THF was evaporated under reduced pressure to afford 3-chloro-N-(2-hydroxyethyl)-4-(2H-tetrazol-5-yl)benzenesulfonamide (800 mg, 25%) as a white solid. The compound was used without further purification.

Intermediate 96: 2-chloro-4-cyanobenzenesulfonamide

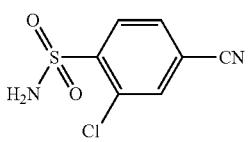

96

A stirred solution of 2-chloro-4-cyanobenzene-1-sulfonyl chloride (6.0 g, 25.416 mmol, Intermediate 89) in tetrahydrofuran (60 mL) was cooled to 0° C. and then ammonia gas was added over a period of 20 min. After purging, the reaction was stirred at 0° C. for 3 h. Upon completion, the reaction was concentrated under reduced pressure to afford the crude that was diluted with ethyl acetate (500 mL) and water (100 mL). Aqueous layer was extracted with ethyl acetate (3×30 mL). The organic layers were combined and washed with sat. NaCl solution (3×100 mL), dried over anhydrous $Na_2SO_4$ and filtered off. Solvent was evaporated under reduced pressure to afford 2-chloro-4-cyanobenzenesulfonamide (5 g, 88.9%) as an off white solid. MS m/z $[M-H]^-$=215.16.

Intermediate 97: 2-chloro-4-(2H-tetrazol-5-yl)benzenesulfonamide

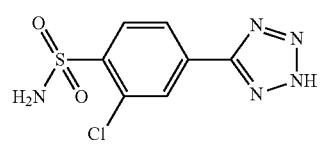

97

To a solution of 2-chloro-4-cyanobenzenesulfonamide (5.0 g, 23.08 mmol, Intermediate 96) in tetrahydrofuran (50 mL) and water (5 mL), sodium azide (5.7 g, 87.70 mmol) and zinc bromide (9.8 g, 43.85 mmol) were added at 26° C. The reaction mixture was heated to 85° C. and stirred for 16 h. Upon completion, the reaction mixture was cooled to 0° C. Then, it was quenched with cold water (50 mL) and acidified with conc. HCl (30 mL) up to pH 2. Then THF was evaporated under reduced pressure and obtained solid was filtered to afford 2-chloro-4-(2H-tetrazol-5-yl)benzenesulfonamide (5 g, 80.3%) as a white solid. The compound was used without further purification. MS m/z [M+H]$^+$=260.14.

Intermediate 98: 2-chloro-4-(2-(4-fluorobenzyl)-2H-tetrazol-5-yl)benzenesulfonamide

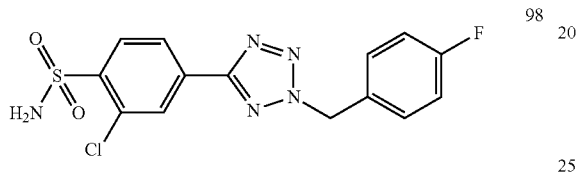

To a solution of 2-chloro-4-(2H-tetrazol-5-yl)benzenesulfonamide (5 g, 19.255 mmol, Intermediate 97) in acetonitrile (100 mL), N,N-diisopropylethylamine (6.7 mL, 38.51 mmol, commercial source: Finar) was added followed by the addition of 2-(bromomethyl)-5-fluoropyridine (0.169 g, 1.172 mmol, commercial source: Spectrochem) at 26° C. The reaction mixture was heated to 85° C. for 16 h. Upon completion, the reaction mixture was cooled to 26° C. and diluted with ethyl acetate (200 mL) and water (50 mL). It was stirred 15 minutes and then both layers were separated. The aqueous layer was extracted with ethyl acetate (3×50 mL). The combined organic layers were washed with brine solution (2×50 mL). The organic layer was dried over anhydrous Na$_2$SO$_4$ and filtered. The filtrate was evaporated under reduced pressure. The crude was purified by column chromatography (silicagel 100-200 mesh), eluted with 40% ethyl acetate in hexane. The pure fractions were collected and concentrated under reduced pressure to afford 2-chloro-4-(2-(4-fluorobenzyl)-2H-tetrazol-5-yl)benzenesulfonamide (4.2 g) as an off white solid, MS m/z [M+H]$^+$=368.15

Intermediate 99: tert-butyl (2-amino-2-oxoethyl)((2-chloro-4-(2-(4-fluorobenzyl)-2H-tetrazol-5-yl)phenyl)sulfonyl)carbamate

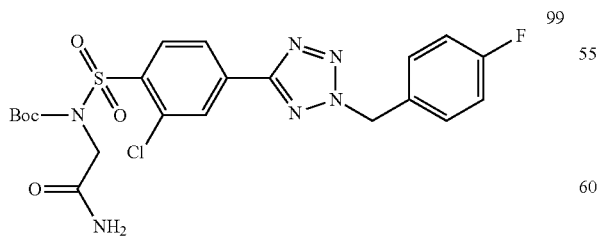

To a solution of 2-chloro-4-(2-(4-fluorobenzyl)-2H-tetrazol-5-yl)benzenesulfonamide (1 g, 2.719 mmol, Intermediate 98) in tetrahydrofuran (20 mL), 4-(Dimethylamino)pyridine (166 mg, 1.36 mmol) and triethylamine (0.57 mL, 4.08 mmol) were added followed by Boc-anhydride (1.78 g, 8.157 mmol) at 0° C. The reaction was stirred at 26° C. for 6 h. Then, potassium carbonate (0.75 g, 5.438 mmol) and bromoacetonitrile (0.56 g, 4.08 mmol) were added at 26° C. The resultant reaction mixture was stirred at 26° C. for 16 h. On completion of the reaction, the reaction mixture was quenched with ice cold water (50 mL) and extracted with ethyl acetate (3×50 mL). The organic layer was dried over anhydrous Na$_2$SO$_4$ and filtered. The filtrate was evaporated under reduced pressure. The crude was purified by column chromatography (silicagel 100-200 mesh), eluted with 50% ethyl acetate in hexane. The pure fractions were collected and concentrated under reduced pressure to afford tert-butyl (2-amino-2-oxoethyl)((2-chloro-4-(2-(4-fluorobenzyl)-2H-tetrazol-5-yl)phenyl)sulfonyl)carbamate (440 mg, 27%) as an off white solid, MS m/z [M+H]$^+$=525.40

Intermediate 100: 4-amino-2-fluorobenzonitrile

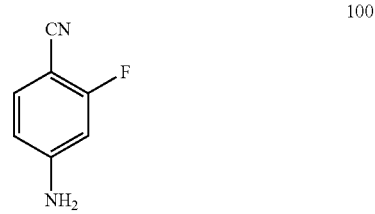

To a solution of 4-bromo-3-fluoroaniline (5.0 g, 26.46 mmol, commercial source: Matrix) in N,N-dimethylformamide (50 mL), Zn(CN)$_2$ (9.3 g, 79.38 mmol, commercial source: Sigma Aldrich) was added at 26° C. The reaction mixture was purged with nitrogen for 10 min, tetrakis(triphenylphosphine)palladium(0) (6.1 g, 5.29 mmol, commercial source: Alfa Aesar) was added and purged again with nitrogen for 10 minutes at 26° C. The resultant reaction mixture was stirred at 130° C. for 16 h. Upon completion, the reaction mixture was cooled to 26° C. and diluted with ethyl acetate (2×500 mL). The organic layer was washed with water (2×100 mL), dried over anhydrous Na$_2$SO$_4$, filtered and the filtrate was evaporated under reduced pressure. The crude was purified by column chromatography using silica (100-200 mesh), eluted with 15% ethyl acetate in petroleum ether. The pure fractions were concentrated under reduced pressure to afford 4-amino-2-fluorobenzonitrile (2.7 g, 72%) as an off white solid. $^1$H NMR (400 MHz, CDCl$_3$) δ 7.38-7.31 (m, 1H), 6.47-6.38 (m, 2H), 4.26 (br s, 2H). MS m/z [M+H]$^+$=137.06

Intermediate 101: 4-cyano-3-fluorobenzene-1-sulfonyl Chloride

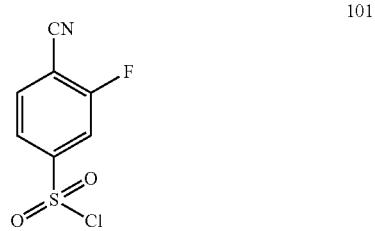 [SMILES: N#Cc1ccc(S(=O)(=O)Cl)cc1F]

To a solution of 4-amino-2-fluorobenzonitrile (2.0 g, 14.69 mmol, Intermediate 100) in acetic acid (5 mL) and conc. HCl (10 mL), an aqueous solution of NaNO$_2$ (1.52 g, 22.03 mmol, commercial source: Finar) was added slowly at 0° C. and stirred for 30 minutes. This reaction mixture was added to a prepared saturated solution of SO$_2$ in acetic acid (36 mL) and copper(II) chloride (0.987 g, 7.34 mmol, commercial source: Alfa Aesar) at −5° C., and stirred at room temperature for 16 h. Upon completion, the reaction mixture was diluted with water (100 mL) and extracted with ethyl acetate (3×100 mL). The combined organic layers were dried over anhydrous Na$_2$SO$_4$, filtered and the filtrate was concentrated under reduced pressure to afford 4-cyano-3-fluorobenzene-1-sulfonyl chloride (1.5 g, crude) as a brown solid. $^1$H NMR (400 MHz, CDCl$_3$) δ 8.01-7.91 (m, 1H), 7.63-7.56 (m, 1H), 7.39-7.31 (m, 1H)

Intermediate 102: 4-cyano-3-fluoro-N-(2-hydroxyethyl)benzenesulfonamide

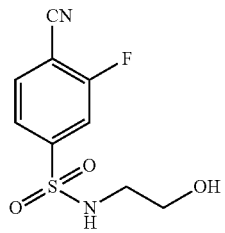

Triethylamine (2.3 mL, 17.07 mmol, commercial source: Finar) was added to a solution of 4-cyano-3-fluorobenzene-1-sulfonyl chloride (1.5 g, 6.83 mmol, Intermediate 101) in tetrahydrofuran (30 mL), followed by addition of 2-aminoethanol (500 mg, 8.14 mmol, commercial source: Avra) at 0° C. The reaction mixture was allowed to reach 26° C. and stirred for 3 h at the same temperature. Upon completion, the reaction was diluted with ethyl acetate (100 mL). The organic layer was washed with water (3×30 mL), dried over anhydrous Na$_2$SO$_4$, filtered and the filtrate was concentrated under reduced pressure. The crude was purified by column chromatography using silica (100-200 mesh), eluted with 2.5% methanol in dichloromethane. The pure fractions were concentrated under reduced pressure to afford 4-cyano-3-fluoro-N-(2-hydroxyethyl)benzenesulfonamide (700 mg, 42.8%) as an off-white solid. $^1$H NMR (400 MHz, DMSO-d$_6$) δ 8.21-8.16 (m, 1H), 8.03 (br s, 1H), 7.91-7.87 (m, 1H), 7.83-7.73 (m, 1H), 4.73-4.67 (m, 1H), 3.41-3.35 (m, 2H), 2.91-2.87 (m, 2H). MS m/z [M−H]$^-$=243.12

Intermediate 103: 3-fluoro-N-(2-hydroxyethyl)-4-(2H-tetrazol-5-yl)benzenesulfonamide

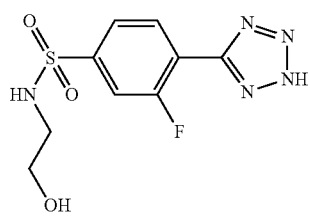

To a solution of 4-cyano-3-fluoro-N-(2-hydroxyethyl)benzenesulfonamide (700 mg, 2.86 mmol, Intermediate 102) in tetrahydrofuran (7 mL) and water (0.7 mL), sodium azide (708 mg, 10.89 mmol) and zinc bromide (1.22 g, 5.44 mmol, commercial source: Alfa Aesar) were added at 26° C. The reaction mixture was heated to 85° C. and stirred for 16 h. Upon completion, the reaction mixture was cooled to 0° C. and acidified with conc. HCl (40 ml) up to pH 2. The precipitated solid was filtered, washed with water and dried to afford 3-fluoro-N-(2-hydroxyethyl)-4-(2H-tetrazol-5-yl)benzenesulfonamide (500 mg, 58.9%) as a white solid. $^1$H NMR (400 MHz, DMSO-d$_6$) δ 8.32-8.25 (m, 1H), 7.94-7.90 (m, 1H), 7.88-7.82 (m, 2H), 4.65 (br s, 1H), 3.39 (t, J=6.1 Hz, 2H), 2.92-2.87 (m, 2H). MS m/z [M−H]$^-$=286.15

Intermediate 104: 4-bromo-2,3-difluorobenzenesulfonyl Chloride

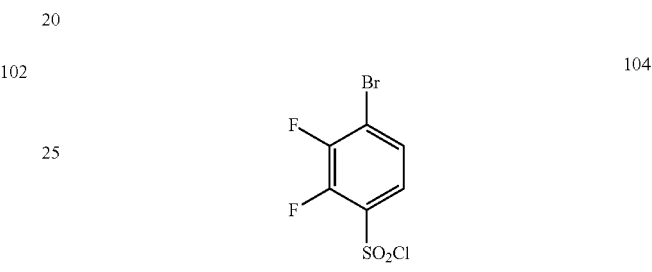

To a solution of 4-bromo-2,3-difluoroaniline (5.0 g, 24.16 mmol, commercial source: Combi-Blocks) in acetic acid (12.5 mL) and conc. HCl (25 mL), an aqueous solution of NaNO$_2$ (2.5 g, 36.24 mmol, commercial source: Avra) was added slowly at 0° C. and stirred for 30 minutes. This reaction mixture was added to a prepared saturated solution of SO$_2$ in acetic acid (90 mL) and copper(II) chloride (1.62 g, 12.08 mmol, commercial source: Alfa Aesar) at −5° C., and then stirred at room temperature for 16 h. Upon completion, the reaction mixture was diluted with water (200 mL) extracted with ethyl acetate (3×100 mL). The organic layer was dried over anhydrous Na$_2$SO$_4$, filtered and the filtrate was concentrated under reduced pressure to afford 4-bromo-2,3-difluorobenzenesulfonyl chloride (5 g, crude) as a gummy solid. $^1$H NMR (400 MHz, CDCl$_3$) δ 7.68-7.65 (m, 1H), 7.61-7.57 (m, 1H)

Intermediate 105: 4-bromo-2,3-difluoro-N-(2-hydroxyethyl)benzenesulfonamide

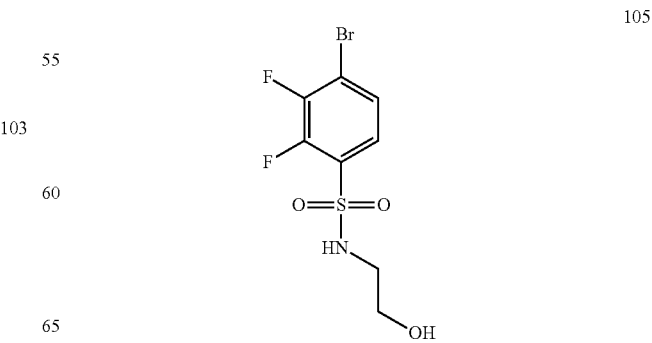

To a solution of 4-bromo-2,3-difluorobenzenesulfonyl chloride (5 g, 17.24 mmol, Intermediate 104) in tetrahydrofuran (100 mL), triethylamine (6.0 mL, 43.12 mmol, commercial source: Finar) was added, followed by the addition of 2-aminoethanol (1.65 g, 20.69 mmol, commercial source: Avra) at 0° C. The reaction mixture was allowed to reach 26° C. and it was stirred for 3 h at the same temperature. Upon completion, the reaction was diluted with ethyl acetate (200 mL) and washed with water (50 mL), brine solution (2×100 mL), dried over anhydrous Na$_2$SO$_4$, filtered and the filtrate was concentrated under reduced pressure. The crude was purified by column chromatography, eluted with 50% ethyl acetate in pet. ether. The pure fractions were concentrated under reduced pressure to afford 4-bromo-2,3-difluoro-N-(2-hydroxyethyl)benzenesulfonamide (2.8 g, 42%) as an off-white solid. $^1$H NMR (400 MHz, DMSO-d$_6$) δ 8.18-8.14 (m, 1H), 7.76-7.71 (m, 1H), 7.57-7.53 (m, 1H), 4.66-4.62 (m, 1H), 3.40-3.35 (m, 2H), 2.98-2.94 (m, 2H). MS m/z [M−H]$^-$=316.14

Intermediate 106: 4-cyano-2,3-difluoro-N-(2-hydroxyethyl)benzenesulfonamide

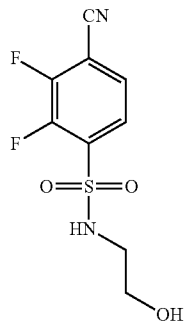

106

To a solution of 4-bromo-2,3-difluoro-N-(2-hydroxyethyl)benzenesulfonamide (2.8 g, 8.89 mmol, Intermediate 105) in N,N-dimethylformamide (28 mL), Zn(CN)$_2$ (3.9 g, 33.78 mmol, commercial source: Sigma Aldrich) was added at 26° C. The reaction mixture was purged with nitrogen for 10 min, tetrakis(triphenylphosphine)palladium(0) (2.0 g, 1.77 mmol, commercial source: Alfa Aesar) was added and purged again with nitrogen for 15 minutes at 26° C. The resultant reaction mixture was stirred at 150° C. in microwave reactor for 30 minutes. Upon completion, the reaction mixture was diluted with ethyl acetate (100 mL), filtered through a celite pad and evaporated under reduced pressure. The crude was purified by column chromatography, eluted with 50% ethyl acetate in pet. ether. The pure fractions were concentrated under reduced pressure to afford 4-cyano-2,3-difluoro-N-(2-hydroxyethyl)benzenesulfonamide (1.2 g, 41%) as a brown solid. $^1$H NMR (400 MHz, DMSO-d$_6$) δ 8.42-8.38 (m, 1H), 7.95-7.90 (m, 1H), 7.76-7.72 (m, 1H), 4.67-4.63 (m, 1H), 3.41-3.36 (m, 2H), 3.02-2.99 (m, 2H). MS m/z [M−H]$^-$=261.22

Intermediate 107: 2,3-difluoro-N-(2-hydroxyethyl)-4-(2H-tetrazol-5-yl)benzenesulfonamide

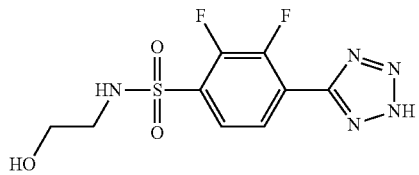

107

To a solution of 4-cyano-2,3-difluoro-N-(2-hydroxyethyl)benzenesulfonamide (1.2 g, 4.57 mmol, Intermediate 106) in tetrahydrofuran (12 mL) and water (1.2 mL), sodium azide (1.13 g, 17.40 mmol) and zinc bromide (1.95 g, 8.7 mmol) were added at 26° C. The reaction mixture was heated to 90° C. and stirred for 16 h. Upon completion, the reaction mixture was cooled to 0° C. and acidified with conc. HCl (10 mL) up to pH 2. The precipitated solid was filtered, washed with water and dried to afford 2,3-difluoro-N-(2-hydroxyethyl)-4-(2H-tetrazol-5-yl)benzenesulfonamide (700 mg, 46.8%) as a brown solid. $^1$H NMR (400 MHz, DMSO-d$_6$) δ 8.31-8.27 (m, 1H), 8.07-8.01 (m, 1H), 7.82-7.77 (m, 1H), 3.42-3.38 (m, 2H), 3.04-2.98 (m, 2H). MS m/z [M−H]$^-$=304.19

Intermediate 108: 4-bromo-2,6-difluorobenzene-1-sulfonyl Chloride

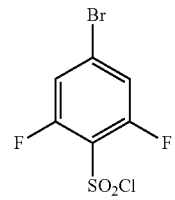

108

To a solution of 4-bromo-2,6-difluoroaniline (5.0 g, 24.03 mmol, commercial source: Combi-Blocks) in acetic acid (12 mL) and conc. HCl (25 mL), an aqueous solution of NaNO$_2$ (2.5 g, 36.05 mmol, commercial source: Avra) was added slowly at 0° C. and stirred for 45 minutes at −5° C. This reaction mixture was added to a prepared saturated solution of SO$_2$ in acetic acid (50 mL) and copper(II) chloride (0.96 g, 7.16 mmol, commercial source: Combi-Blocks) and stirred at room temperature for 2 h. Upon completion, the reaction mixture was extracted with ethyl acetate (1 L). The organic layer was washed with water (500 mL) and brine solution (100 mL), dried over anhydrous Na$_2$SO$_4$, filtered and the filtrate was concentrated under reduced pressure to afford 4-bromo-2,6-difluorobenzene-1-sulfonyl chloride (5 g, 71%) as a brown solid. $^1$H NMR (400 MHz, CDCl$_3$) δ 7.38-7.30 (m, 2H)

Intermediate 109: 4-bromo-2,6-difluoro-N-(2-hydroxyethyl)benzenesulfonamide

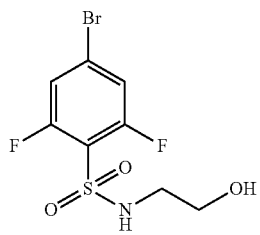

To a solution of 4-bromo-2,6-difluorobenzene-1-sulfonyl chloride (5 g, 17.24 mmol, Intermediate 108) in tetrahydrofuran (50 mL), triethylamine (4.8 mL, 34.38 mmol, commercial source: RCP) was added, followed by addition of 2-aminoethanol (1.05 g, 17.24 mmol, commercial source: RCP) at 0° C. The reaction mixture was allowed to reach 28° C. and stirred for 5 h at the same temperature. Upon completion, the reaction was diluted with ethyl acetate (700 mL). The organic layer was washed with water (500 mL) and brine solution (100 mL), dried over anhydrous $Na_2SO_4$, filtered and the filtrate was concentrated under reduced pressure. The crude was purified by Reveleris® flash chromatography system, eluted with 10-20% ethyl acetate in pet. ether. The pure fractions were concentrated under reduced pressure to afford 4-bromo-2,6-difluoro-N-(2-hydroxyethyl)benzenesulfonamide (3 g, 55%) as a brown solid. $^1$H NMR (400 MHz, DMSO-$d_6$) δ 8.31-8.27 (m, 1H), 7.73-7.68 (m, 2H), 4.71-4.66 (m, 1H), 3.41-3.38 (m, 2H), 3.03-2.97 (m, 2H). MS m/z [M−H]$^-$=314.13

Intermediate 110: 4-cyano-2,6-difluoro-N-(2-hydroxyethyl)benzenesulfonamide

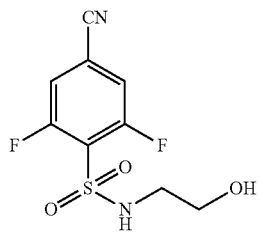

To a solution of 4-bromo-2,6-difluoro-N-(2-hydroxyethyl)benzenesulfonamide (3 g, 9.55 mmol, Intermediate 109) in N,N-dimethylformamide (30 mL), $Zn(CN)_2$ (5.0 g, 28.66 mmol, commercial source: Sigma Aldrich) was added at 26° C. The reaction mixture was purged with nitrogen for 10 min, tetrakis(triphenylphosphine)palladium(0) (1.1 g, 0.95 mmol, commercial source: Alfa Aesar) was added and purged again with nitrogen for 15 minutes at 26° C. The resultant reaction mixture was stirred at 80° C. for 18 h. Upon completion, the reaction mixture was poured into water (500 mL) and extracted with ethyl acetate (500 mL). The organic layer was washed with water (3×100 mL) and brine solution (50 mL). The organic layer was dried over anhydrous $Na_2SO_4$, filtered and the filtrate was evaporated under reduced pressure. The crude was purified by Reveleris® flash chromatography system, eluted with 20% ethyl acetate in pet. ether. The pure fractions were concentrated under reduced pressure to afford 4-cyano-2,6-difluoro-N-(2-hydroxyethyl)benzenesulfonamide (1.5 g, 60%) as a brown solid. $^1$H NMR (400 MHz, DMSO-$d_6$) δ 8.00-7.93 (m, 2H), 7.59-7.52 (m, 1H), 4.64 (t, J=5.4 Hz, 1H), 3.39 (q, J=5.9 Hz, 2H), 3.04 (q, J=6.1 Hz, 2H). MS m/z [M−H]$^-$=261.26

Intermediate 111: 2,6-difluoro-N-(2-hydroxyethyl)-4-(2H-tetrazol-5-yl)benzenesulfonamide

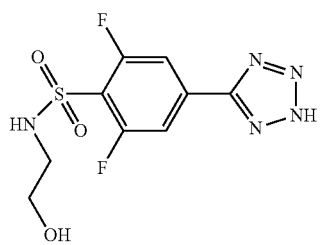

To a solution of 4-cyano-2,6-difluoro-N-(2-hydroxyethyl)benzenesulfonamide (1.5 g, 5.72 mmol, Intermediate 110) in tetrahydrofuran (15 mL) and water (1.5 mL), sodium azide (1.4 g, 21.73 mmol, commercial source: Avra) and zinc bromide (2.4 g, 10.86 mmol, commercial source: CombiBlocks) were added at 26° C. The reaction mixture was heated to 85° C. and stirred for 12 h. Upon completion, the reaction mixture was cooled to 0° C. and acidified with conc. HCl (30 mL) up to pH 2. The precipitated solid was filtered, washed with water and dried to afford 2,6-difluoro-N-(2-hydroxyethyl)-4-(2H-tetrazol-5-yl)benzenesulfonamide (1 g, crude) as an off-white solid. $^1$H NMR (400 MHz, DMSO-$d_6$) δ 7.75-7.67 (m, 2H), 7.41-7.35 (m, 1H), 4.75-4.68 (m, 1H), 3.43-3.38 (m, 2H), 3.06-2.98 (m, 2H). MS m/z [M−H]$^-$= 304.22

Intermediate 112: 4-(2-((tetrahydro-2H-pyran-4-yl)methyl)-2H-tetrazol-5-yl)benzenesulfonamide

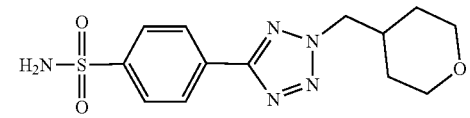

To a solution of 4-(2H-tetrazol-5-yl) benzene sulfonamide (1 g, 4.439 mmol, Intermediate 43) in N,N-dimethylformamide (20 mL), potassium carbonate (1.2 g, 8.69 mmol, commercial source: RCP) was added, followed by the addition of 4-(bromomethyl)tetrahydro-2H-pyran (874 mg, 4.88 mmol, commercial source: Sigma Aldrich) at 26° C. The reaction mixture was heated to 100° C. for 16 h. Upon completion, the reaction mixture was cooled to 26° C. and concentrated under reduced pressure. The crude was purified by column chromatography eluting with 3% methanol in DCM. The pure fractions were concentrated under reduced pressure to afford 4-(2-((tetrahydro-2H-pyran-4-yl)methyl)-2H-tetrazol-5-yl)benzenesulfonamide (500 mg) as an off-white solid. $^1$H NMR (400 MHz, DMSO-$d_6$) δ 8.30-8.19 (m, 2H), 8.04-7.93 (m, 2H), 7.48 (br s, 2H), 4.76-4.66 (m, 2H), 3.90-3.74 (m, 2H), 3.26-3.16 (m, 1H), 2.71-2.62 (m, 1H), 2.34-2.25 (m, 1H), 1.58-1.46 (m, 2H), 1.41-1.30 (m, 2H). MS m/z [M+H]⁺=324.18. The compound was used without further purification.

Intermediate 113: tert-butyl (cyanomethyl)((4-(2-((tetrahydro-2H-pyran-4-yl)methyl)-2H-tetrazol-5-yl)phenyl)sulfonyl)carbamate

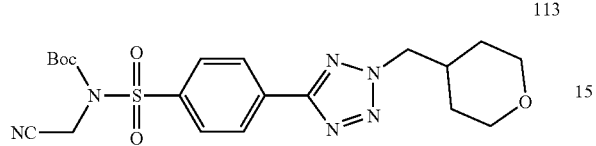

113

To a solution of 4-(2-((tetrahydro-2H-pyran-4-yl)methyl)-2H-tetrazol-5-yl)benzenesulfonamide (500 mg, 1.548 mmol, Intermediate 112) in tetrahydrofuran (20 mL), DMAP (94.4 mg, 0.773 mmol, commercial source: Avra), triethylamine (0.3 mL, 2.15 mmol, commercial source: RCP) were added, followed by the addition of Boc-anhydride (0.71 ml, 3.09 mmol, commercial source: Avra) and stirred at 26° C. for 5 h. Then potassium carbonate (426.9 mg, 3.08 mmol, commercial source: RCP) was added, followed by the addition of bromoacetonitrile (0.16 mL, 2.297 mmol, commercial source: Avra) and stirred at 26° C. for 16 h. Upon completion, the reaction mixture was concentrated under reduced pressure. The crude was purified by column chromatography eluting with 40% ethyl acetate in petroleum ether. The pure fractions were concentrated under reduced pressure to afford tert-butyl (cyanomethyl)((4-(2-((tetrahydro-2H-pyran-4-yl)methyl)-2H-tetrazol-5-yl)phenyl)sulfonyl)carbamate (400 mg) as an off-white solid. ¹H NMR (400 MHz, DMSO-d₆) δ 8.38-8.32 (m, 2H), 8.19-8.13 (m, 2H), 4.94 (s, 2H), 4.74-4.67 (m, 2H), 3.91-3.79 (m, 2H), 3.76-3.70 (m, 1H), 3.34-3.29 (m, 2H), 2.34-2.22 (m, 2H), 2.04-1.94 (m, 1H), 1.55-1.45 (m, 1H), 1.29-1.18 (m, 9H). MS m/z [M+H]⁺=463.30. The compound was used without further purification.

Intermediate 114: ethyl 2-(4-cyanophenylsulfonamido)acetate

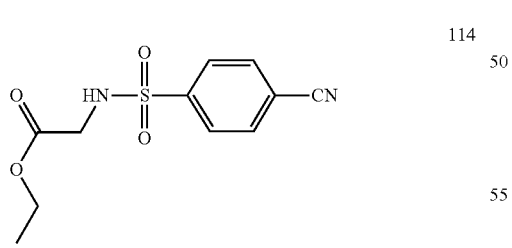

114

To a solution of ethyl 2-aminoacetate hydrochloride (8.27 g, 59.496 mmol, commercial source: Avra) in N,N-dimethylformamide (100 mL), triethylamine (13.8 mL, 99.208 mmol, commercial source: RCP) was added at 27° C., followed by the addition of 4-cyanobenzene-1-sulfonyl chloride (10 g, 49.6 mmol, commercial source: Combi-Blocks) at 0° C. The reaction mixture was slowly allowed to reach 27° C. and stirred for 5 h at the same temperature. Upon completion, the reaction was poured into ice water (2 L). The precipitated solid was filtered and dried under vacuum to afford ethyl 2-(4-cyanophenylsulfonamido)acetate (8 g, crude) as an off-white solid. ¹H NMR (400 MHz, DMSO-d₆) δ 8.51 (br s, 1H), 8.07 (d, J=8.3 Hz, 2H), 7.96 (d, J=8.6 Hz, 2H), 3.97 (q, J=7.0 Hz, 2H), 3.78 (s, 2H), 1.09 (t, J=7.1 Hz, 3H). MS m/z [M−H]⁻=267.07

Intermediate 115: ethyl 2-(4-(2H-tetrazol-5-yl)phenylsulfonamido)acetate

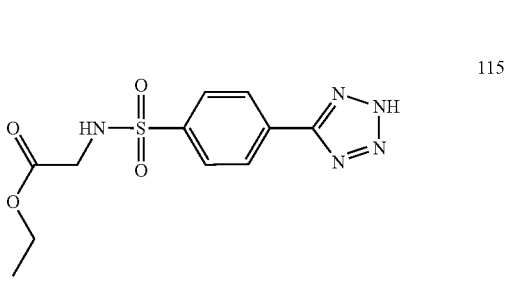 [SMILES: CCOC(=O)CNS(=O)(=O)c1ccc(-c2nn[nH]n2)cc1]

115

To a solution of ethyl 2-(4-cyanophenylsulfonamido)acetate (20 g, 74.546 mmol, Intermediate 114) in N,N-dimethylformamide (250 mL), sodium azide (48.5 g, 746.04 mmol, commercial source: Spectrochem) and ammonium chloride (39.9 g, 745.79 mmol, commercial source: Chemlabs) were added at 27° C. The reaction mixture was heated to 80° C. and stirred for 16 h at the same temperature. Upon completion, the reaction mixture was cooled to 0° C. and quenched with 1N HCl (800 mL). The precipitated solid was filtered and dried under vacuum to afford ethyl 2-(4-(2H-tetrazol-5-yl)phenylsulfonamido)acetate (15 g, crude) as an off-white solid. ¹H NMR (400 MHz, DMSO-d₆) δ 8.40 (t, J=6.0 Hz, 1H), 8.27 (d, J=8.3 Hz, 2H), 8.01 (d, J=8.3 Hz, 2H), 3.98 (q, J=7.0 Hz, 2H), 3.77 (d, J=6.1 Hz, 2H), 1.09 (t, J=7.0 Hz, 3H). MS m/z [M+H]⁺=312.04

Intermediate 116: 2-(chloromethyl)pyrazine

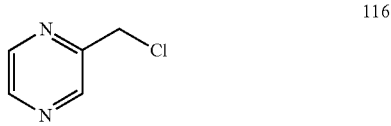

116

To a solution of pyrazin-2-ylmethanol (500 mg, 4.545 mmol, commercial source: Combi-Blocks) in dichloromethane (20 mL), thionyl chloride (0.4 mL, 5.514 mmol, commercial source: Avra) was added at 0° C. The reaction mixture was allowed to reach 26° C. and stirred for 16 h at the same temperature. Upon completion, the reaction mixture was concentrated under reduced pressure. The residue was neutralized with saturated sodium bicarbonate solution (20 mL) and extracted with ethyl acetate (3×20 mL). The organic layer dried over anhydrous Na₂SO₄, filtered and the filtrate was concentrated under reduced pressure to afford 2-(chloromethyl)pyrazine (400 mg, crude) as a brown liquid. ¹H NMR (400 MHz, CDCl₃) δ 8.76 (s, 1H), 8.59-8.54 (m, 2H), 4.70 (s, 2H). MS m/z [M+H]⁺=129.02. The compound was used without further purification.

Intermediate 117: ethyl 2-(4-(2-(pyrazin-2-ylmethyl)-2H-tetrazol-5-yl)phenylsulfonamido)acetate

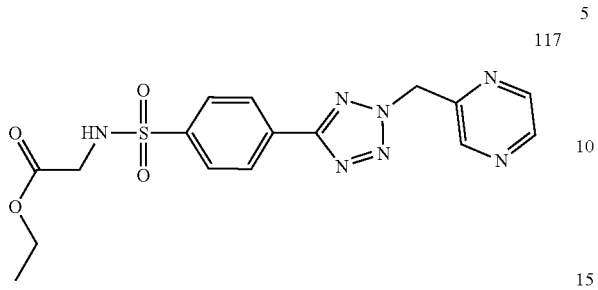

To a solution of ethyl 2-(4-(2H-tetrazol-5-yl)phenylsulfonamido)acetate (500 mg, 0.0016 mol, Intermediate 115), 2-(chloromethyl)pyrazine (204 mg, 0.0016 mol, Intermediate 116) in acetonitrile (5 mL), N,N-diisopropylethylamine (0.55 mL, 0.0032 mol, commercial source: Finar) was added at 26° C. The reaction mixture was heated to 90° C. and stirred for 8 h at the same temperature. Upon completion, the reaction mixture was cooled to 26° C., dissolved in ethyl acetate (100 mL) and washed with water (2×50 mL). The organic layer was dried over anhydrous Na$_2$SO$_4$, filtered and the filtrate was evaporated under reduced pressure to afford ethyl 2-(4-(2-(pyrazin-2-ylmethyl)-2H-tetrazol-5-yl)phenylsulfonamido)acetate (400 mg, crude) as an off white gummy solid. MS m/z [M+H]$^+$=403.21. The compound was used without further purification.

Intermediate 118: 2-(4-(2-(pyrazin-2-ylmethyl)-2H-tetrazol-5-yl)phenylsulfonamido)acetamide To a solution of ethyl 2-(4-(2-(pyrazin-2-ylmethyl)-2H-tetrazol-5-yl)phenylsulfonamido)acetate (400 mg, 0.0009 mol, Intermediate 117) in methanol (8 mL), methanolic ammonia solution (4M in MeOH) (4 mL, commercial source: HYCHEM) was added at 26° C. The reaction mixture was heated to 60° C. and stirred for 48 h at the same temperature in a sealed tube. Upon completion, the reaction mixture was cooled to 26° C. and concentrated under reduced pressure. The residue was dissolved in ethyl acetate (100 mL) and washed with water (2×50 mL). The organic layer was dried over anhydrous Na$_2$SO$_4$, filtered and the filtrate was evaporated under reduced pressure to afford 2-(4-(2-(pyrazin-2-ylmethyl)-2H-tetrazol-5-yl)phenylsulfonamido)acetamide (200 mg, 41%) as an off white solid. MS m/z [M+H]$^+$=375.05. The compound was used without further purification.

Intermediate 119: 2-(chloromethyl)-5-methylpyrazine

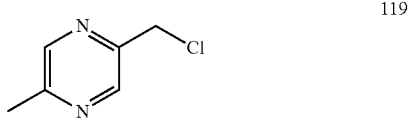

To a solution of (5-methylpyrazin-2-yl)methanol (500 mg, 4.028 mmol, commercial source: Combi-Blocks) in dichloromethane (20 mL), thionyl chloride (0.35 mL, 4.825 mmol, Commercial source: Avra) was added slowly at 0° C. The reaction mixture was allowed to reach 26° C. and stirred for 16 h at the same temperature. Upon completion, the reaction mixture was concentrated under reduced pressure. The residue was neutralized with saturated sodium bicarbonate solution (20 mL) and extracted with ethyl acetate (3×20 mL). The combined organic solution was dried over Na$_2$SO$_4$, filtered and the filtrate was concentrated under reduced pressure to afford 2-(chloromethyl)-5-methylpyrazine (500 mg, crude) as a brown liquid. $^1$H NMR (400 MHz, CDCl$_3$) δ 8.60 (s, 1H), 8.43 (s, 1H), 4.67 (s, 2H), 2.59 (s, 3H). MS m/z [M+H]$^+$=143.04

Intermediate 120: ethyl 2-(4-(2-((5-methylpyrazin-2-yl)methyl)-2H-tetrazol-5-yl)phenylsulfonamido)acetate

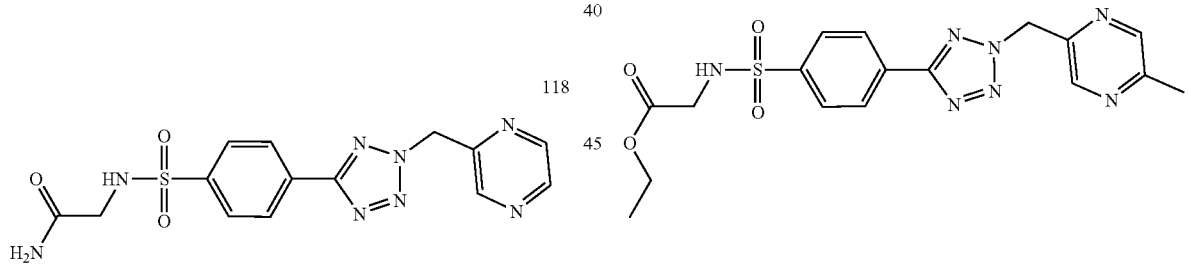

To a solution of ethyl 2-(4-(2H-tetrazol-5-yl)phenylsulfonamido)acetate (500 mg, 0.0016 mol, Intermediate 115), 2-(chloromethyl)-5-methylpyrazine (228 mg, 0.0016 mol, Intermediate 119) in acetonitrile (5 mL), N,N-diisopropylethylamine (0.55 mL, 0.0032 mol, commercial source: Finar) was added at 26° C. The reaction mixture was heated to 80° C. and stirred for 8 h at the same temperature. Upon completion, the reaction was cooled to 26° C., dissolved in ethyl acetate (100 mL) and washed with water (2×30 mL). The organic layer was dried over Na$_2$SO$_4$, filtered and the filtrate was concentrated under reduced pressure to afford ethyl 2-(4-(2-((5-methylpyrazin-2-yl)methyl)-2H-tetrazol-5-yl)phenylsulfonamido)acetate (400 mg, crude) as an off-white gummy solid. MS m/z [M+H]$^+$=418.23. The material was used in the next step without any further purification.

Intermediate 121: 2-(4-(2-((5-methylpyrazin-2-yl)methyl)-2H-tetrazol-5-yl)phenylsulfonamido)acetamide

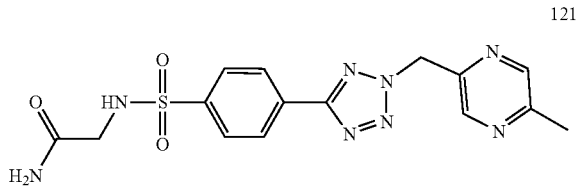 [SMILES: Cc1cnc(Cn2nnc(-c3ccc(S(=O)(=O)NCC(N)=O)cc3)n2)cn1]

121

To a solution of ethyl 2-(4-(2-((5-methylpyrazin-2-yl)methyl)-2H-tetrazol-5-yl)phenylsulfonamido)acetate (400 mg, 0.0009 mol, Intermediate 120) in methanol (8 mL), methanolic ammonia solution (4M in MeOH) (4 mL, commercial source: HYCHEM) was added at 26° C. The reaction mixture was heated to 60° C. and stirred for 48 h at the same temperature in a sealed tube. Upon completion, the reaction mixture was cooled to 26° C. and concentrated under reduced pressure. The residue was dissolved in ethyl acetate (100 mL) and washed with water (3×40 mL). The organic layer was dried over anhydrous $Na_2SO_4$, filtered and the filtrate was evaporated under reduced pressure to afford 2-(4-(2-((5-methylpyrazin-2-yl)methyl)-2H-tetrazol-5-yl)phenylsulfonamido)acetamide (220 mg, crude) as an off white solid. MS m/z $[M+H]^+$=389.17. The material was used in the next step without any further purification.

Intermediate 122: 2-(chloromethyl)-5-methoxypyrazine

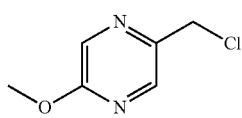

122

To a solution of (5-methoxypyrazin-2-yl) methanol (200 mg, 0.0014 mol, commercial source: Combi-Blocks) in dichloromethane (2 mL), thionyl chloride (509 mg, 0.0042 mol, commercial source: Avra) was added slowly at 0° C. The reaction mixture was allowed to reach 26° C. and stirred for 1 h at the same temperature. Upon completion of the reaction, the reaction mixture was poured into saturated sodium bicarbonate solution (50 mL) at 0° C. slowly and extracted with ethyl acetate (3×30 mL). The organic layer was dried over anhydrous $Na_2SO_4$, filtered and the filtrate was concentrated under reduced pressure to afford 2-(chloromethyl)-5-methoxypyrazine (250 mg, crude) as a pale yellow liquid. $^1$H NMR (400 MHz, CDCl$_3$) δ 8.22-8.18 (2H), 4.65 (s, 2H), 3.98 (s, 3H). MS m/z $[M+H]^+$=159.01

Intermediate 123: 2-(4-(2-((5-methoxypyrazin-2-yl)methyl)-2H-tetrazol-5-yl)phenylsulfonamido)acetamide

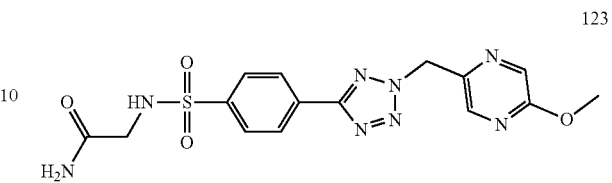

123

To a solution of 2-(4-(2H-tetrazol-5-yl)phenylsulfonamido)acetamide (400 mg, 0.0014 mol, Intermediate 25), 2-(chloromethyl)-5-methoxypyrazine (246 mg, 0.0015 mol, Intermediate 122) in acetonitrile (4 mL), N,N-diisopropylethylamine (0.48 mL, 0.0028 mol, commercial source: Finar) was added at 26° C. The reaction mixture was heated to 80° C. and stirred for 8 h at the same temperature. Upon completion, the reaction mixture was cooled to 26° C., dissolved in ethyl acetate (100 mL) and washed with water (2×50 mL). The organic layer was dried over anhydrous $Na_2SO_4$, filtered and the filtrate was evaporated under reduced pressure to afford 2-((4-(2-((5-methoxypyrazin-2-yl)methyl)-2H-tetrazol-5-yl)phenyl)sulfonamido)acetamide (250 mg, crude) as an off white solid. MS m/z $[M+H]^+$=405.12. Material was used in the next step without any further purification.

Intermediate 124: 4-(2-((6-methoxypyridin-3-yl)methyl)-2H-tetrazol-5-yl)benzenesulfonamide

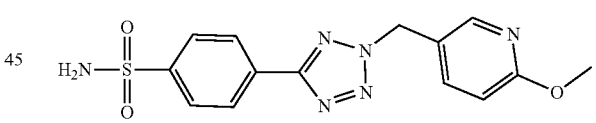

124

To a solution of 4-(2H-tetrazol-5-yl) benzene sulfonamide (500 mg, 2.22 mmol, Intermediate 43) in DMF (20 mL), potassium carbonate (613 mg, 4.44 mmol, commercial source: RCP) was added, followed by the addition of 5-(chloromethyl)-2-methoxypyridine (420 mg, 2.66 mmol, commercial source: Enamine) at 26° C. The reaction mixture was heated to 80° C. for 5 h. Upon completion, the reaction mixture was cooled to 26° C. and concentrated under reduced pressure. The crude was purified by column chromatography eluting with 3% methanol in DCM. The pure fractions were concentrated under reduced pressure to afford 4-(2-((6-methoxypyridin-3-yl)methyl)-2H-tetrazol-5-yl)benzenesulfonamide (2) (500 mg, crude). MS m/z $[M+H]^+$=347.19. The compound was used without further purification.

Intermediate 125: tert-butyl (cyanomethyl)((4-(2-((6-methoxypyridin-3-yl)methyl)-2H-tetrazol-5-yl)phenyl)sulfonyl)carbamate

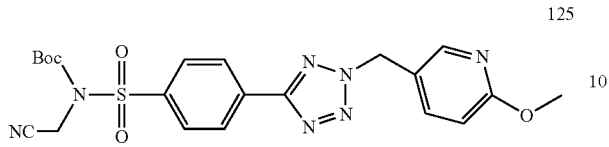

To a solution of 4-(2-((6-methoxypyridin-3-yl)methyl)-2H-tetrazol-5-yl)benzenesulfonamide (500 mg, 1.445 mmol, Intermediate 124) in THF (10 mL), DMAP (88 mg, 0.72 mmol, commercial source: Avra) and triethylamine (0.3 mL, 2.158 mmol, commercial source: RCP) were added followed by the addition of Boc-anhydride (0.7 mL, 3.047 mmol, commercial source: Avra) and stirred at 26° C. for 5 h. Then, potassium carbonate (400 mg, 2.89 mmol, commercial source: RCP) was added followed by the addition of bromoacetonitrile (0.15 mL, 2.15 mmol, commercial source: Avra) and stirred at 26° C. for 16 h. Upon completion, the reaction mixture was concentrated under reduced pressure. The crude was purified by column chromatography eluting with 30% ethyl acetate in petroleum ether. The pure fractions were concentrated under reduced pressure to afford tert-butyl (cyanomethyl)((4-(2-((6-methoxypyridin-3-yl)methyl)-2H-tetrazol-5-yl)phenyl)sulfonyl)carbamate (100 mg, crude) as a gum. MS m/z [M+H]$^+$=486.35. The compound was used without further purification.

Intermediate 126: 4-(2-((tetrahydro-2H-pyran-2-yl)methyl)-2H-tetrazol-5-yl)benzenesulfonamide

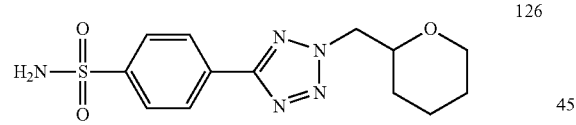

To a solution of 4-(2H-tetrazol-5-yl)benzenesulfonamide (2.0 g, 8.879 mmol, Intermediate 43) in DMF (50.0 mL), potassium carbonate (2.45 g, 17.754 mmol, commercial source: RCP) was added followed by the addition of 2-(bromomethyl)tetrahydro-2H-pyran (1.91 g, 10.667 mmol, Commercial source: Sigma Aldrich) at 26° C. The reaction mixture was heated to 80° C. for 16 h. Upon completion, the reaction mixture was cooled to 26° C. and evaporated under reduced pressure. The crude was purified by column chromatography (silicagel 100-200 mesh), eluted with 4% methanol in dichloromethane. The pure fractions were concentrated under reduced pressure to afford 4-(2-((tetrahydro-2H-pyran-2-yl)methyl)-2H-tetrazol-5-yl)benzenesulfonamide (1.0 g, 34.8%). 1H NMR (400 MHz, DMSO-d$_6$) δ 8.26-8.22 (m, 2H), 8.04-7.99 (m, 2H), 7.50 (br s, 2H) 4.80-4.76 (m, 2H), 3.95-3.89 (m, 1H), 3.83-3.77 (m, 1H), 1.87-1.79 (m, 1H), 1.75-1.68 (m, 1H), 1.57-1.50 (m, 1H) 1.48-1.43 (m, 2H) 1.39-1.24 (m, 2H). MS m/z [M+H]$^+$= 324.28.

Intermediate 127: tert-butyl (cyanomethyl)((4-(2-((tetrahydro-2H-pyran-2-yl)methyl)-2H-tetrazol-5-yl)phenyl)sulfonyl)carbamate

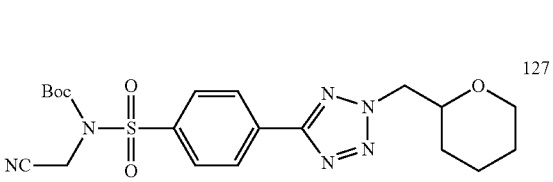 [SMILES: CC(C)(C)OC(=O)N(CC#N)S(=O)(=O)c1ccc(-c2nnn(CC3CCCCO3)n2)cc1]

To a solution of 4-(2-((tetrahydro-2H-pyran-2-yl)methyl)-2H-tetrazol-5-yl)benzenesulfonamide (1.0 g, 3.096 mmol, Intermediate 126) in THF (20 mL), DMAP (189 mg, 1.547 mmol, commercial source: Avra) and triethylamine (0.65 mL, 4.673 mmol, commercial source: RCP) were added followed by the addition of Boc-anhydride (1.42 mL, commercial source: Avra) and stirred at 26° C. for 6 h. Then, potassium carbonate (854 mg, 6.188 mmol, commercial source: RCP) was added followed by the addition of bromoacetonitrile (0.43 mL, 6.173 mmol, commercial source: Avra) and stirred at 26° C. for 16 h. Upon completion, the reaction mixture was concentrated under reduced pressure. The crude was purified by column chromatography eluting with 30% ethyl acetate in petroleum ether. The pure fractions were concentrated under reduced pressure to afford tert-butyl (cyanomethyl)((4-(2-((tetrahydro-2H-pyran-2-yl)methyl)-2H-tetrazol-5-yl)phenyl)sulfonyl)carbamate (1.0 g, crude) as a gum. The compound was used without further purification

Intermediate 128: 4-(2-((4,4-difluorocyclohexyl)methyl)-2H-tetrazol-5-yl)-2-methoxybenzenesulfonamide

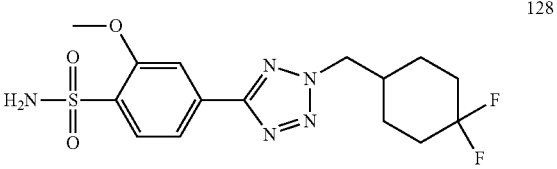 [SMILES: COc1cc(-c2nnn(CC3CCC(F)(F)CC3)n2)ccc1S(N)(=O)=O]

N,N-diisopropylethylamine (164 µL, 0.940 mmol, commercial source: Aldrich) was added to a stirred solution of 2-methoxy-4-(2H-tetrazol-5-yl)benzenesulfonamide (120 mg, 0.470 mmol, Intermediate 51') and 4-(bromomethyl)-1,1-difluorocyclohexane (70.8 µL, 0.470 mmol, commercial source: Combi-Blocks) in N,N-Dimethylformamide (DMF) (1.57 mL) under nitrogen atmosphere. The mixture was stirred at rt overnight and then at 70° C. for 24 h. 4-(bromomethyl)-1,1-difluorocyclohexane (14.17 µL, 0.094 mmol, commercial source: Combi-Blocks) and N,N-diisopropylethylamine (82 µL, 0.470 mmol) were added and the mixture was stirred at 70° C. for 6 h. Upon completion, the reaction mixture was diluted with water and extracted with dichloromethane (twice). The combined organic solution was dried over anhydrous Na$_2$SO$_4$, filtered and the filtrate was evaporated under reduced pressure to give 4-(2-((4,4-difluorocyclohexyl)methyl)-2H-tetrazol-5-yl)-2-methoxybenzenesulfonamide (177 mg, crude) that was used in the next step without further purification.

Intermediate 129: tert-butyl (2-amino-2-oxoethyl) ((4-(2-((4,4-difluorocyclohexyl)methyl)-2H-tetrazol-5-yl)-2-methoxyphenyl)sulfonyl)carbamate

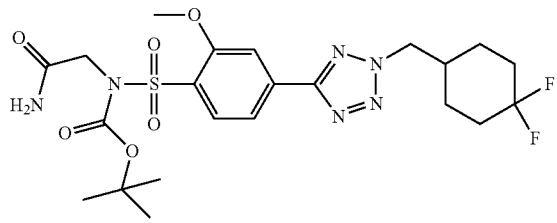

129

To a solution of 4-(2-((4,4-difluorocyclohexyl)methyl)-2H-tetrazol-5-yl)-2-methoxybenzenesulfonamide (174 mg, 0.305 mmol, Intermediate 128) in anh. Tetrahydrofuran (7 mL), di-tert-butyl dicarbonate (0.21 mL, 0.916 mmol), Et$_3$N (0.051 mL, 0.366 mmol) and DMAP (18.66 mg, 0.153 mmol) were added. The resulting solution was stirred at rt overnight. Potassium carbonate (84 mg, 0.611 mmol) and 2-bromoacetamide (89 mg, 0.647 mmol) were added. The reaction mixture was stirred at rt. After 6 h, more potassium carbonate (42.2 mg, 0.305 mmol) and 2-bromoacetamide (42.1 mg, 0.305 mmol) were added and the mixture was stirred overnight. Then, the reaction mixture was heated to 50° C. and stirred at that temperature over the weekend. Upon completion, the reaction mixture was quenched with sat. NaHCO$_3$ and was extracted with ethyl acetate (twice). The organic layer was washed with sat. NaCl, dried over Na$_2$SO$_4$ and filtered. The filtrate was concentrated under reduced pressure to obtain tert-butyl (2-amino-2-oxoethyl) ((4-(2-((4,4-difluorocyclohexyl)methyl)-2H-tetrazol-5-yl)-2-methoxyphenyl)sulfonyl)carbamate (210 mg, crude) that was used in the next step without further purification.

Intermediate 130: 4-ethoxybenzyl Methanesulfonate

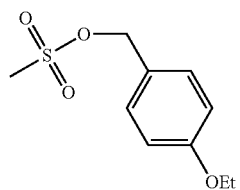

130

To a solution of (4-ethoxyphenyl)methanol (300 mg, 1.971 mmol, commercial source: Apollo SCI) and triethylamine (328 µL, 2.365 mmol) in Dichloromethane (15 mL) at 0° C., methanesulfonyl chloride (168 µL, 2.168 mmol) was added dropwise. The mixture was stirred at 0° C. for 3 h. Upon completion, the reaction mixture was diluted with water and DCM and extracted with DCM (2×20 ml). The combined organic layers were dried over anh. MgSO4 and filtered. The filtrate was concentrated under reduced pressure to obtain 4-ethoxybenzyl methanesulfonate (454 mg, 100%) This product was used without any purification in the next reaction.

Intermediate 131: 3-(chloromethyl)tetrahydro-2H-pyran

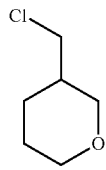

131

To a solution of (tetrahydro-2H-pyran-3-yl)methanol (1 g, 8.621 mmol, commercial source: Frapps) in Dichloromethane (20 mL), thionyl chloride (1 mL, 13.785 mmol, commercial source: Avra) was added slowly at 0° C. and then stir at 26° C. for 16 h. Upon completion, the reaction mixture was evaporated under reduced pressure, diluted with saturated NaHCO$_3$ solution (50 mL) and extracted with dichloromethane (3×50 mL). The combined organic solution was dried over anhydrous Na$_2$SO$_4$, filtered and the filtrate was concentrated under reduced pressure to afford 3-(chloromethyl)tetrahydro-2H-pyran (300 mg). $^1$H NMR (400 MHz, DMSO-d$_6$) δ 3.90-3.73 (m, 4H), 3.35-3.20 (m, 2H), 1.90-1.81 (m, 1H), 1.77-1.50 (m, 2H), 1.35-1.17 (m, 2H).

Intermediate 132: 4-(chloromethyl)pyridazine

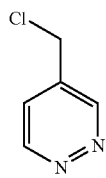

132

To a solution of 4-methylpyridazine (1 g, 10.625 mmol, commercial source: Combi-Blocks) in acetonitrile (10.0 mL), trichloroisocyanuric acid (1.2 g, 5.163 mmol, commercial source: Avra) was added at 26° C. The reaction mixture was stirred at 26° C. for 3 h. Upon completion, the reaction mixture was evaporated under reduced pressure. The crude was purified by column chromatography (silica-gel 100-200 mesh), eluted with 80% ethyl acetate in pet. Ether. The pure fractions were concentrated under reduced pressure to afford 4-(chloromethyl)pyridazine (400 mg, crude). $^1$H NMR (400 MHz, CDCl$_3$) δ 9.26-9.20 (m, 2H), 7.55-7.51 (m, 1H), 4.58 (s, 2H). MS m/z [M+H]$^+$=129.1

Intermediate 133: 3-(chloromethyl) pyridazine

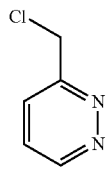

133

To a solution of 3-methylpyridazine (300 mg, 3.18 mmol, commercial source: Alfa Aesar) in Chloroform (10.0 mL), trichloroisocyanuric acid (360 mg, 1.549 mmol, commercial source: Avra) was added at 26° C. The reaction mixture was stirred at 26° C. for 3 h. Upon completion, the reaction mixture was evaporated under reduced pressure. The crude was purified by column chromatography (silicagel 100-200 mesh), eluted with 70% ethyl acetate in pet. ether. The pure fractions were concentrated under reduced pressure to afford 3-(chloromethyl)pyridazine (200 mg, crude). $^1$H NMR (400 MHz, DMSO-$d_6$) δ 9.18-9.14 (m, 1H), 7.75-7.70 (m, 1H), 7.58-7.51 (m, 1H), 4.91 (s, 2H). MS m/z [M+H]$^+$=129.20

Intermediate 134:
2-(chloromethyl)-5-methoxypyridine

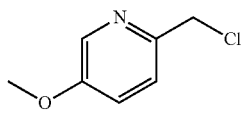

To a solution of (5-methoxypyridin-2-yl)methanol (300 mg, 0.0021 mol, commercial source: Combi-Blocks) in dichloromethane (3 mL), thionyl chloride (0.509 mL, 0.0064 mol, commercial source: Avra) was added slowly at 0° C. The reaction mixture was allowed to reach 26° C. and stirred for 1 h at the same temperature. Upon completion, the reaction mixture was poured into saturated sodium bicarbonate solution (100 mL) at 0° C. slowly and extracted with ethyl acetate (3×30 mL). The combined organic solution was dried over anhydrous Na$_2$SO$_4$, filtered and the filtrate was concentrated under reduced pressure to afford 2-(chloromethyl)-5-methoxypyrazine (280 mg, 82%) as a brown liquid. $^1$H NMR (400 MHz, CDCl$_3$) δ 8.29-8.26 (m, 1H), 7.40-7.36 (m, 1H), 7.23-7.20 (m, 1H), 4.65-4.63 (m, 2H), 3.87 (s, 3H). MS m/z [M+H]$^+$=158.06

Intermediate 135:
4-bromo-2-fluoro-5-methylbenzene-1-sulfonyl Chloride

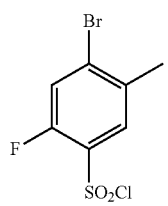

To 2-bromo-4-fluoro-1-methylbenzene (6.0 g, 31.9 mmol, commercial source: Combi-Blocks), Chlorosulfonic acid (6.5 g, 55 mmol, commercial source: Avra) was added dropwise at 0° C. This reaction mixture was stirred at rt for 5 h. Upon completion, the reaction mixture was quenched in ice-water (60 mL) and extracted with ethyl acetate (3×50 mL). The combined organic solution was washed with sat. NaHCO$_3$ (20 mL). The organic phase was dried over anhydrous Na$_2$SO$_4$, filtered and the filtrate was concentrated under reduced pressure to afford 4-bromo-2-fluoro-5-methylbenzene-1-sulfonyl chloride (7 g, crude). The compound was used without further purification.

Intermediate 136: 4-bromo-2-fluoro-N-(2-hydroxyethyl)-5-methylbenzenesulfonamide

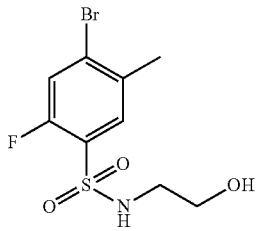

To a solution of 4-bromo-2-fluoro-5-methylbenzene-1-sulfonyl chloride (7 g, 24.34 mmol, Intermediate 135) in tetrahydrofuran (80 mL), 2-aminoethanol (1.487 g, 24.34 mmol, commercial source: Avra) was added followed by triethylamine (6.7 mL, 48.69 mmol, commercial source: Avra) at room temperature. The reaction mixture was stirred at room temperature for 5 h. Upon completion, the reaction was was poured into ice-cold water (250 mL) and then extracted with ethyl acetate (2×500 mL) and washed with sodium bicarbonate solution (200 mL). The organic layers were dried over anhydrous Na$_2$SO$_4$, filtered and the filtrate was concentrated under reduced pressure. The crude was purified by column chromatography, eluted with 50% ethyl acetate in pet. ether. The pure fractions were collected and concentrated under reduced pressure to afford 4-bromo-2-fluoro-N-(2-hydroxyethyl)-5-methylbenzenesulfonamide (5 g, 66.6%) as a brown coloured liquid.

Intermediate 137: 4-cyano-2-fluoro-N-(2-hydroxyethyl)-5-methylbenzenesulfonamide

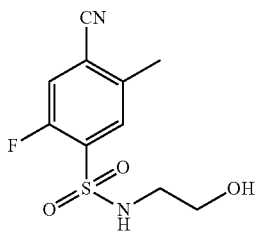

To a solution of 4-bromo-2-fluoro-N-(2-hydroxyethyl)-5-methylbenzenesulfonamide (4.5 g, 14.46 mmol, Intermediate 136) in N,N-dimethylformamide (45 mL), Zn(CN)$_2$ (7.68 g, 43.4 mmol commercial source: Avra) was added in a sealed tube at room temperature. The reaction mixture was nitrogen purged for 10 min, tetrakis(triphenylphosphine)palladium(0) (1.67 g, 1.44 mmol, commercial source: Alfa Aesar) was added and again nitrogen purged at 26° C. for 15 minutes. The resultant reaction mixture was stirred at 100° C. overnight. Upon completion, the reaction mixture was diluted with ethyl acetate (200 mL) and washed with ice-cold water (2×500 mL). The organic solution was dried over anhydrous Na$_2$SO$_4$, filtered and the filtrate was evaporated under reduced pressure. The crude was purified by column chromatography, eluted with 35% ethyl acetate in pet. ether. The pure fractions were collected and concentrated under reduced pressure to afford 4-cyano-2-fluoro-N-(2-hydroxyethyl)-5-methylbenzenesulfonamide (1.2 g, 32%, purity=78%) as a white coloured liquid. MS m/z [M−H]⁻= 257.1. The compound was used without further purification.

Intermediate 138: 2-fluoro-N-(2-hydroxyethyl)-5-methyl-4-(2H-tetrazol-5-yl)benzenesulfonamide

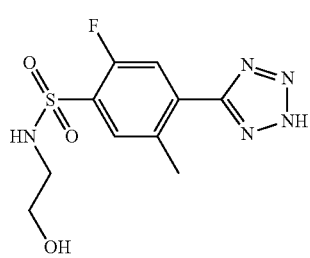

To a solution of 4-cyano-2-fluoro-N-(2-hydroxyethyl)-5-methylbenzenesulfonamide (1.5 g, 5.807 mmol, Intermediate 137) in tetrahydrofuran (10 mL) and water (1 mL), zinc bromide (2.48 g, 11.034 mmol, commercial source: Spectrochem) was added at room temperature, followed by addition of sodium azide (1.623 g, 24.973 mmol, commercial source: Avra) at 0° C. The reaction mixture was heated to 85° C. and stirred overnight. Upon completion, the reaction mixture was cooled to 0° C. and ice-cold water (100 mL) was added, then followed by the addition of conc. HCl (10 mL) until pH 2. Then THF was evaporated under reduced pressure and obtained solid that was filtered to afford 2-fluoro-N-(2-hydroxyethyl)-5-methyl-4-(2H-tetrazol-5-yl)benzenesulfonamide (1 g, crude) as a brown coloured liquid. MS m/z [M+H]⁺=302.1

Synthesis of (2-(1-bromoethyl)-5-fluoropyridine) Intermediate

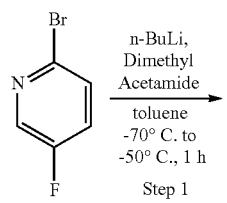

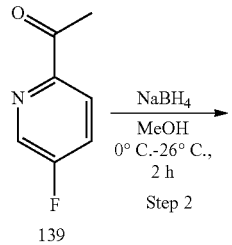

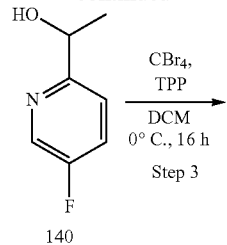

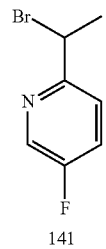

Intermediate 139: 1-(5-fluoropyridin-2-yl)ethanone

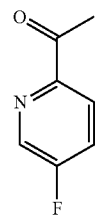

To a solution of 2-bromo-5-fluoropyridine (2 g, 0.0113 mol, commercial source: Combi-Blocks) in dry toluene (20 mL), n-butyl lithium (2.5 M in n-hexane) (4.5 ml, 0.0113 mmol, commercial source: Hychem) was added in dropwise at −70° C. and followed by the addition of N,N-dimethylacetamide (1.18 g, 0.0136 mmol, commercial source: Alfa) at −70° C. The reaction mixture was stirred at −50° C. for 1 h. Upon completion, the reaction mixture was quenched with methanol (20 mL) and stirred for 30 min at 5-10° C., followed by the addition of saturated ammonium chloride solution (50 mL), stirred for 40 min at 26° C. and extracted with ethyl acetate (3×70 mL). The organic layer was dried over anhydrous Na₂SO₄, filtered and the filtrate was concentrated under reduced pressure to afford 1-(5-fluoropyridin-2-yl)ethanone (1.8 g, 85%) as a pale yellow liquid. ¹H NMR (400 MHz, CDCl₃) δ 8.50 (d, J=2.6 Hz, 1H), 8.16-8.07 (m, 1H), 7.55-7.46 (m, 1H), 2.70 (s, 3H). MS m/z [M+H]⁺=140.16

Intermediate 140: 1-(5-fluoropyridin-2-yl)ethanol

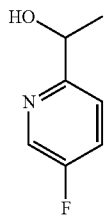

140

To a solution of 1-(5-fluoropyridin-2-yl)ethanone (1.8 g, 0.0129 mol, Intermediate 139) in methanol (18 mL), sodium borohydride (0.95 g, 0.0258 mol, commercial source: Aldrich) was added lot wise at 0° C. The reaction mixture was stirred at 26° C. for 2 h. Upon completion, the reaction was quenched with water (30 mL) at 0° C. and extracted with ethyl acetate (3×30 mL). The organic layer was dried over anhydrous $Na_2SO_4$, filtered and the filtrate was concentrated under reduced pressure to afford 1-(5-fluoropyridin-2-yl)ethanol (800 mg, 37%) as a pale brown liquid. $^1$H NMR (400 MHz, $CDCl_3$) δ 8.40 (d, J=2.9 Hz, 1H), 7.45-7.38 (m, 1H), 7.33-7.27 (m, 1H), 4.94-4.86 (m, 1H), 3.76-3.66 (m, 1H), 1.54 (s, 3H). MS m/z $[M+H]^+$=142.01

Intermediate 141: 2-(1-bromoethyl)-5-fluoropyridine

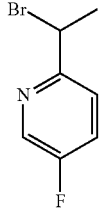

141

To a solution of 1-(5-fluoropyridin-2-yl)ethanol (700 mg, 0.0049 mol, Intermediate 140) in dichloromethane (3.5 mL), triphenyl phosphine (2.5 g, 0.0098 mol, commercial source: Aldrich) was added at 26° C. The reaction mixture was stirred for 15 min at the same temperature. Followed by the addition of a solution of carbon tetrabromide (1.6 g, 0.0049 mol, Commercial source: Avra) in dichloromethane (3.5 mL) dropwise at 0° C. The reaction mixture was stirred for 16 h. Upon completion, the reaction mixture was concentrated under reduced pressure. The crude was purified by column chromatography (silicagel 100-200 mesh), eluted with 10% ethyl acetate in pet ether. The pure fractions were collected and concentrated under reduced pressure to afford 2-(1-bromoethyl)-5-fluoropyridine (350 mg, 30%) as a pale yellow liquid. $^1$H NMR (400 MHz, $CDCl_3$) δ 8.42 (d, J=2.6 Hz, 1H), 7.50-7.44 (m, 1H), 7.43-7.36 (m, 1H), 5.24 (q, J=7.0 Hz, 1H), 2.07 (d, J=7.0 Hz, 3H). MS m/z $[M+H]^+$ & $[M+2H]^+$=204.10 & 206.11

Synthesis of 1-(1-bromoethyl)-4-fluorobenzene Intermediate

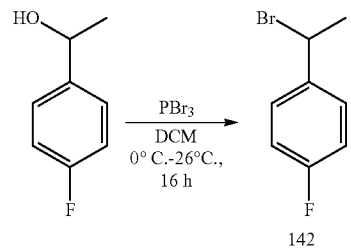

Intermediate 142: 1-(1-bromoethyl)-4-fluorobenzene

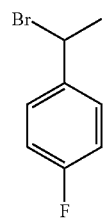

142

To a solution of 1-(4-fluorophenyl)ethanol (500 mg, 0.0036 mol, commercial source: Apollo) in dichloromethane (5 mL) at 0° C., $PBr_3$ (0.5 mL, commercial source: TCI) was slowly added and the mixture stirred at 26° C. for 16 h. Upon completion, the reaction mixture was concentrated under reduced pressure. $NaHCO_3$ solution (70 mL) was added and extracted with ethyl acetate (3×30 mL). The organic layers were combined and washed with brine (50 mL), dried over $Na_2SO_4$, filtered and concentrated to afford crude 1-(1-bromoethyl)-4-fluorobenzene (310 mg) as a brown liquid. It was used in the next step without further purification.

Synthesis of 1-(1-azidoethyl)-4-fluorobenzene Intermediate

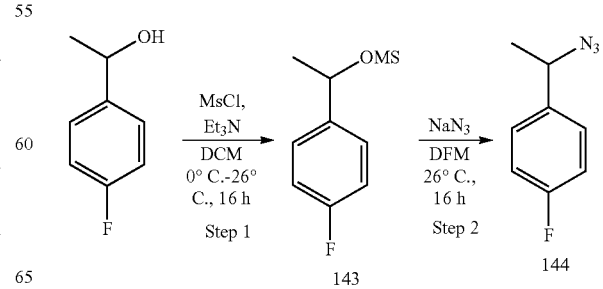

Intermediate 143: 1-(4-fluorophenyl)ethyl Methanesulfonate

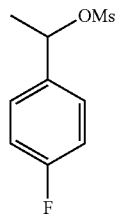

143

To a solution of 1-(4-fluorophenyl)ethanol (200 mg, 0.0014 mol, commercial source: Aochem) in dichloromethane (4 mL), triethylamine (0.4 mL, 0.0029 mol, commercial source: Finar) and mesyl chloride (0.16 mL, 0.0021 mol, commercial source: Avra) were added at 0° C. The reaction mixture was stirred at 26° C. for 16 h. Upon completion, dichloromethane (60 mL) and water (10 mL) were added. The organic layer was dried over anhydrous $Na_2SO_4$, filtered and the filtrate was concentrated under reduced pressure to afford crude 1-(4-fluorophenyl)ethyl methanesulfonate (300 mg) as a pale yellow liquid that was used in the next step without further purification.

Intermediate 144: 1-(1-azidoethyl)-4-fluorobenzene

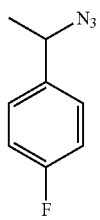

144

To a solution of 1-(4-fluorophenyl)ethyl methanesulfonate (220 mg, 0.0010 mol, Intermediate 143) in DMF (2.2 mL), sodium azide (196 mg, 0.0030 mol, commercial source: Avra) was added at 26° C. and stirred for 16 h. Upon completion, 1N HCl (10 mL) was added at 0° C. It was extracted with ethyl acetate, the organic layers combined, washed with cold water (3×20 mL), dried over $Na_2SO_4$, filtered and concentrated under reduced pressure affording crude 1-(1-azidoethyl)-4-fluorobenzene (290 mg) as a brown gummy liquid that was used in the next step without further purification.

Intermediate 145: ethyl 2-(4-(2-(1-(4-fluorophenyl)ethyl)-2H-tetrazol-5-yl)phenylsulfonamido)acetate

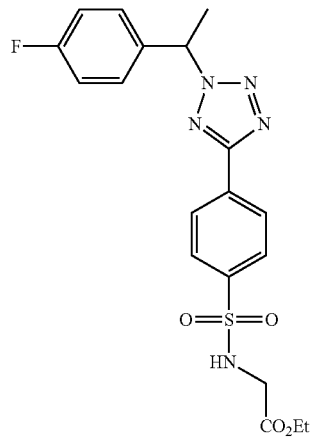

145

To a solution of ethyl 2-(4-(2H-tetrazol-5-yl)phenylsulfonamido)acetate (500 mg, 0.0016 mol, Intermediate 115) in acetonitrile (10 mL), N,N-diisopropylethylamine (0.7 mL, 0.0040 mol, commercial source: Finar) and 1-(1-bromoethyl)-4-fluorobenzene (389 mg, 0.0019 mol, Intermediate 142) was added at 26° C. and the mixture stirred at 85° C. for 16 h. Upon completion, it was cooled to 26° C. and dissolved in ethyl acetate (100 mL) and water (20 mL). The organic layer was separated, dried over $Na_2SO_4$, filtered and concentrated under reduced pressure. The crude was purified by column chromatography (silicagel 100-200 mesh), eluted with 1.5% methanol in dichloromethane. The pure fractions were collected and concentrated under reduced pressure to afford ethyl 2-(4-(2-(1-(4-fluorophenyl)ethyl)-2H-tetrazol-5-yl)phenylsulfonamido)acetate (300 mg, 41%) as an off white solid. MS m/z $[M+H]^+$=434.26.

Intermediate 146: 2-(4-(2-(1-(4-fluorophenyl)ethyl)-2H-tetrazol-5-yl)phenylsulfonamido)acetic Acid

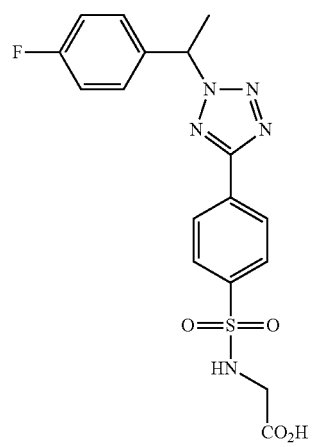

146

To a solution of ethyl 2-(4-(2-(1-(4-fluorophenyl)ethyl)-2H-tetrazol-5-yl)phenylsulfonamido)acetate (300 mg, 0.00069 mol, Intermediate 145) in THF (3 mL) and methanol (3 mL), LiOH.H$_2$O (58 mg, 0.0014 mol, commercial source: Fimar) was added at 26° C. and stirred for 2 h. Upon completion, it was concentrated under reduced pressure, dissolved in water and washed with ethyl acetate (2×20 mL). pH of the aqueous layer was acidified with 2N HCl (20 mL) at 0° C. A precipitate was formed that was filtered and dried under vacuum affording 2-(4-(2-(1-(4-fluorophenyl)ethyl)-2H-tetrazol-5-yl)phenylsulfonamido)acetic acid (140 mg, 50%) as a white solid. MS m/z [M+H]$^+$=405.05

Intermediate 147: 4-(2-(1-(4-fluorophenyl)ethyl)-2H-tetrazol-5-yl)-2-methoxybenzenesulfonamide

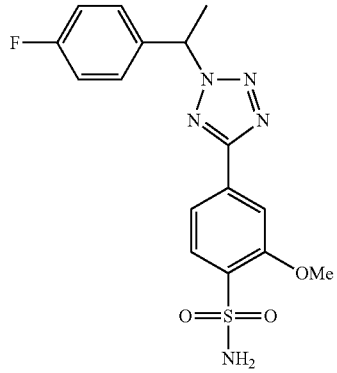

147

To a solution of ethyl 2-(4-(2H-tetrazol-5-yl)phenylsulfonamido)acetate (1.2 g, 0.0047 mol, Intermediate 51) and 1-(1-bromoethyl)-4-fluorobenzene (1.14 g, 0.0056 mol, Intermediate 142) in acetonitrile (24 mL), N,N-diisopropylethylamine (2.0 mL, 0.0118 mol, commercial source: Finar) was added at 26° C. and the mixture stirred at 85° C. for 16 h. Upon completion, it was cooled to 26° C. and dissolved in ethyl acetate (100 mL) and water (20 mL). The organic layer was separated, dried over Na$_2$SO$_4$, filtered and concentrated under reduced pressure. The crude was purified by column chromatography (silicagel 100-200 mesh), eluted with 1% methanol in dichloromethane. The pure fractions were collected and concentrated under reduced pressure to afford 4-(2-(1-(4-fluorophenyl)ethyl)-2H-tetrazol-5-yl)-2-methoxybenzenesulfonamide (500 mg, 27%) as an off white solid. MS m/z [M+H]$^+$=378.52

Intermediate 148: tert-butyl (2-amino-2-oxoethyl)((4-(2-(1-(4-fluorophenyl)ethyl)-2H-tetrazol-5-yl)-2-methoxyphenyl)sulfonyl)carbamate

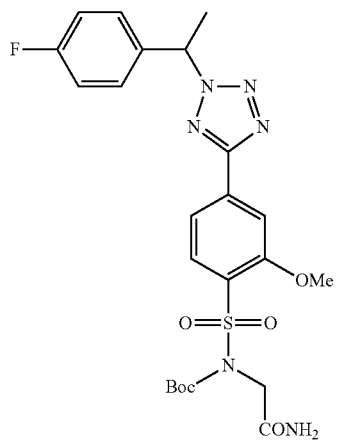

148

To a solution of 4-(2-(1-(4-fluorophenyl)ethyl)-2H-tetrazol-5-yl)-2-methoxybenzenesulfonamide (500 mg, 0.0013 mol, Intermediate 147) in THF (5 mL), N,N-dimethylaminopyridine (80 mg, 0.00066 mol, commercial source: Avra) and triethylamine (0.27 mL, 0.0020 mol, commercial source: Finar), followed by (Boc)$_2$O (868 mg, 0.0040 mol, commercial source: Avra) were added at 0° C. and the mixture stirred at 26° C. for 6 h. Then, K$_2$CO$_3$ (366 mg, 0.0027 mol, commercial source: Finar) and 2-bromoacetamide (270 mg, 0.0020 mol, commercial source: Alfa) were added and the mixture stirred at 26° C. for 16 h. Upon completion, ethyl acetate (100 mL) and water (40 mL) were added. The aqueous layer was extracted with ethyl acetate (2×30 mL). Combined organic layers were dried over Na$_2$SO$_4$, filtered and concentrated under reduced pressure. The crude was purified by column chromatography (silicagel 100-200 mesh), eluted with 0.5% methanol in dichloromethane. The pure fractions were collected and concentrated under reduced pressure affording tert-butyl (2-amino-2-oxoethyl)((4-(2-(1-(4-fluorophenyl)ethyl)-2H-tetrazol-5-yl)-2-methoxyphenyl)sulfonyl)carbamate (300 mg, 41%) as an off white solid. MS m/z [M-Boc+H]$^+$=435.18

Examples

Example 1: (4-(2-(4-fluorobenzyl)-2H-tetrazol-5-yl)-N-(2-hydroxyethyl)benzenesulfonamide)

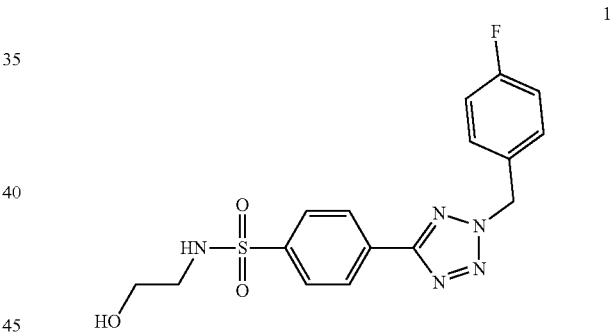

1

To a solution of N-(2-hydroxyethyl)-4-(2H-tetrazol-5-yl)benzenesulfonamide (1.3 g, 4.832 mmol, Intermediate 17), potassium carbonate (1.333 g, 9.665 mmol) in N,N-dimethylformamide (15 mL), 1-(bromomethyl)-4-fluorobenzene (1.826 g, 9.665 mmol, commercial source: Aldrich) was added at 26° C. The reaction mixture was stirred at the same temperature for 5 h. Reaction was monitored by TLC. On completion of the reaction, the reaction mixture was poured into ice water (200 mL) and the precipitated solid compound was filtered. The gummy solid was dissolved in 10% methanol in dichloromethane (50 mL) and concentrated under reduced pressure. The crude was purified by column chromatography (silica gel 100-200 mesh), eluted with 2% Methanol in dichloromethane. The pure fractions were collected and concentrated under reduced pressure to afford (370 mg, 20%) as an off-white solid. $^1$H NMR (400 MHz, DMSO-d$_6$) δ 8.26-8.21 (m, 2H), 7.98-7.93 (m, 2H), 7.76-7.71 (m, 1H), 7.54-7.47 (m, 2H), 7.27-7.20 (m, 2H), 6.02 (s, 2H), 4.65 (t, J=5.6 Hz, 1H), 3.40-3.33 (m, 2H), 2.86-2.79 (m, 2H). MS m/z [M+H]$^+$=378.26

Example 2: N-(2-hydroxyethyl)-4-(2-(pyrimidin-4-ylmethyl)-2H-tetrazol-5-yl)benzenesulfonamide

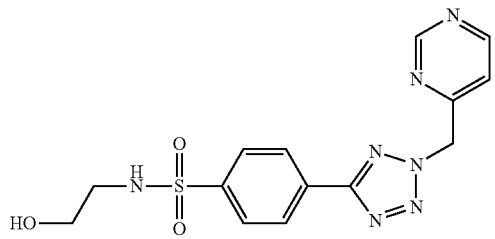

2

To a solution of N-(2-hydroxyethyl)-4-(2H-tetrazol-5-yl)benzenesulfonamide (100 mg, 0.371 mmol, Intermediate 17), potassium carbonate (103 mg, 0.746 mmol) in N,N-dimethylformamide (10 mL), 4-(bromomethyl)pyrimidine (64 mg, 0.37 mmol, Intermediate 1) was added at 26° C. The reaction mixture was stirred at 26° C. for 16 h. Reaction was monitored by TLC. On completion of the reaction, the reaction mixture was concentrated under reduced pressure. The crude was purified by column chromatography (silica gel 100-200 mesh), eluted with 5% methanol in dichloromethane. The pure fractions were collected and concentrated under reduced pressure. The obtained compound was further purified by prep-HPLC to afford N-(2-hydroxyethyl)-4-(2-(pyrimidin-4-ylmethyl)-2H-tetrazol-5-yl)benzenesulfonamide (22 mg, 16%) as an off-white solid. $^1$H NMR (400 MHz, DMSO-$d_6$) δ 9.13 (d, J=1.3 Hz, 1H), 8.87 (d, J=5.3 Hz, 1H), 8.27 (d, J=8.8 Hz, 2H), 7.97 (d, J=8.8 Hz, 2H), 7.56-7.62 (m, 1H), 6.27 (s, 2H), 4.67 (br s, 1H), 3.37 (t, J=6.4 Hz, 2H), 2.84 (t, J=6.3 Hz, 2H). MS m/z [M+H]$^+$=362.12.

Prep-HPLC Conditions:
Column: kromasil PHENYL (250×25) mm, 10µ
Mobile phase: A—10 mM ammonium bicarbonate (aq), B—acetonitrile
Method (time in min/% of B): A:B=68:32, ISOCRATIC.
Flow: 25 mL/min
Temperature: Ambient Example 3: 4-(2-(4-fluorobenzyl)-2H-tetrazol-5-yl)-N-methylbenzenesulfonamide

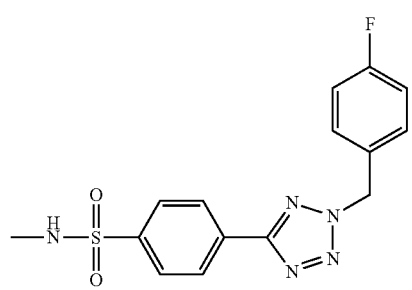

3

To a solution of N-methyl-4-(2H-tetrazol-5-yl)benzene sulfonamide (296 mg, 1.238 mmol, Intermediate 21), potassium carbonate (342 mg, 2.477 mmol) in N,N-dimethylformamide (8 mL), 1-(bromomethyl)-4-fluorobenzene (233 mg, 1.2385 mmol, commercial source: Combi-Blocks) was added at 27° C. The resultant reaction mixture was stirred at 27° C. for 2 h. The progress of the reaction was monitored by TLC. On completion of the reaction, the reaction mixture was poured into water (60 mL). The precipitated solid compound was filtered and dried under vacuum. The crude was purified by column chromatography (silica gel 100-200 mesh), eluted with 3% methanol in dichloromethane. The pure fractions were collected and concentrated under reduced pressure to afford 4-(2-(4-fluorobenzyl)-2H-tetrazol-5-yl)-N-methylbenzenesulfonamide (104 mg, 24%) as a white solid. $^1$H NMR (400 MHz, DMSO-$d_6$) δ 8.28-8.22 (m, 2H), 7.97-7.91 (m, 2H), 7.60-7.54 (m, 1H), 7.54-7.48 (m, 2H), 7.28-7.20 (m, 2H), 6.02 (s, 2H), 2.44 (d, J=4.6 Hz, 3H). MS m/z [M+H]$^+$=348.14

Example 4: N-methyl-4-(2-(pyridin-4-ylmethyl)-2H-tetrazol-5-yl)benzenesulfonamide

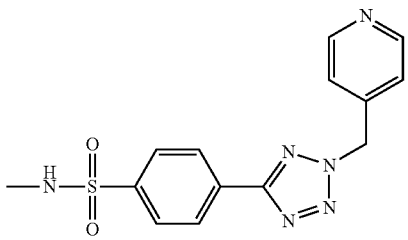

4

To a solution of N-methyl-4-(2H-tetrazol-5-yl)benzenesulfonamide (296 mg, 1.238 mmol, Intermediate 21), potassium carbonate (513 mg, 3.715 mmol) in N,N-dimethylformamide (8 mL), 4-(chloromethyl)pyridine hydrochloride (203 mg, 1.238 mmol, commercial source: Alfa Aesar) was added at 27° C. and the reaction mixture was stirred for 2 h. The resultant reaction mixture was heated to 80° C. and stirred for 2 h at the same temperature. The progress of the reaction was monitored by TLC. On completion of the reaction, the reaction mixture was concentrated under reduced pressure. The crude compound was purified by column chromatography (silica gel 100-200 mesh), eluted with 3% Methanol in dichloromethane. The pure fractions were collected and concentrated under reduced pressure to afford N-methyl-4-(2-(pyridin-4-ylmethyl)-2H-tetrazol-5-yl)benzenesulfonamide (40 mg, 9%) as an off-white solid. $^1$H NMR (400 MHz, DMSO-$d_6$) δ 8.60 (d, J=5.9 Hz, 2H), 8.27 (d, J=8.3 Hz, 2H), 7.95 (d, J=8.3 Hz, 2H), 7.61-7.55 (m, 1H), 7.34 (d, J=5.5 Hz, 2H), 6.13 (s, 2H), 2.44 (d, J=5.0 Hz, 3H). MS m/z [M+H]$^+$=331.12

Example 5: N-ethyl-4-(2-(pyridin-4-ylmethyl)-2H-tetrazol-5-yl)benzenesulfonamide

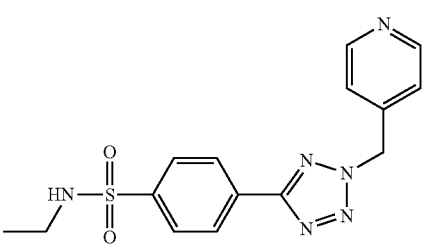

5

To a solution of N-ethyl-4-(2H-tetrazol-5-yl)benzenesulfonamide (350 mg, 1.383 mmol, Intermediate 23), potassium carbonate (573 mg, 4.150 mmol) in N,N-dimethylformamide (7 mL), 4-(chloromethyl)pyridine hydrochloride (227 mg, 1.383 mmol, commercial source: Alfa Aesar) was added at 27° C. The resultant reaction mixture was stirred at 27° C. for 24 h. The progress of the reaction was monitored by TLC. On completion of the reaction, the reaction mixture was concentrated under reduced pressure. The crude compound was purified by column chromatography (silica gel 100-200 mesh), eluted with 3% methanol in dichloromethane. The pure fractions were collected and concentrated under reduced pressure to afford N-ethyl-4-(2-(pyridin-4-ylmethyl)-2H-tetrazol-5-yl)benzenesulfonamide (60 mg, 12%) as an off white solid. $^1$H NMR (400 MHz, DMSO-d$_6$) δ 8.63-8.57 (m, 2H), 8.29-8.23 (m, 2H), 7.99-7.92 (m, 2H), 7.69 (t, J=5.7 Hz, 1H), 7.34 (d, J=5.9 Hz, 2H), 6.13 (s, 2H), 2.87-2.76 (m, 2H), 0.97 (t, J=7.2 Hz, 3H). MS m/z [M+H]$^+$=345.06

Example 6: N-(2-hydroxyethyl)-4-(2-(4-methoxybenzyl)-2H-tetrazol-5-yl)benzenesulfonamide

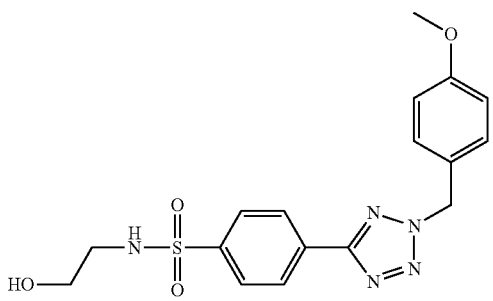

To a solution of N-(2-hydroxyethyl)-4-(2H-tetrazol-5-yl)benzenesulfonamide (100 mg, 0.0003 mol, Intermediate 17) in acetonitrile (1 mL), N,N-diisopropylethylamine (70 mg, 0.0006 mol) was added at 0° C. and stirred for 10 min at 0° C. Followed by the addition of 1-(bromomethyl)-4-methoxybenzene (89 mg, 0.0004 mol, commercial source: Alfa Aesar) at 0° C. Then the reaction mixture was stirred at 28° C. for 16 h. Reaction was monitored by TLC. On completion of the reaction, the reaction mixture was concentrated under reduced pressure. The crude was purified by column chromatography (silicagel 100-200 mesh), eluted with 1.5% methanol in dichloromethane. The pure fractions were collected and concentrated under reduced pressure to afford N-(2-hydroxyethyl)-4-(2-(4-methoxybenzyl)-2H-tetrazol-5-yl)benzenesulfonamide (64 mg, 54%) as a white solid. $^1$H NMR (400 MHz, DMSO-d$_6$) δ 8.26-8.19 (m, 2H), 7.98-7.93 (m, 2H), 7.73 (t, J=5.7 Hz, 1H), 7.42-7.36 (m, 2H), 6.98-6.93 (m, 2H), 5.93 (s, 2H), 4.65 (t, J=5.6 Hz, 1H), 3.74 (s, 3H), 3.39-3.33 (m, 2H), 2.86-2.79 (m, 2H). MS m/z [M+H]$^+$=390.13

General Procedure for Alkylation of Tetrazoles

N,N-Diisopropylethylamine (1-4 eq) was added dropwise to a stirred solution of N-(2-hydroxyethyl)-4-(2H-tetrazol-5-yl)benzenesulfonamide (1 eq) and the alkylating agent (1 or 2 eq) in N,N-Dimethylformamide (0.3 M) under nitrogen at rt. The mixture was stirred at rt for 1-16 h. Some reactions required heating at 50° C. and stirring for 16 h, additionally further heating to 70° C.-80° C. and stirred for a further 2 h or overnight. The mixture was concentrated under reduced pressure. The crude compound was purified. The desired fractions were collected and concentrated in vacuo to yield the products.

Example 7: N-(2-hydroxyethyl)-4-(2-((tetrahydro-2H-pyran-2-yl)methyl)-2H-tetrazol-5-yl)benzenesulfonamide

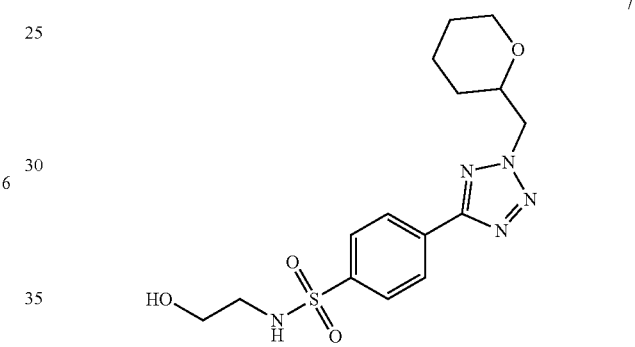

DIPEA (778 μl, 4.46 mmol) was added dropwise to a stirred solution of N-(2-hydroxyethyl)-4-(2H-tetrazol-5-yl)benzenesulfonamide (300 mg, 1.114 mmol, Intermediate 17') and 2-(bromomethyl)tetrahydro-2H-pyran (285 μl, 2.228 mmol, commercial source: Aldrich) in N,N-Dimethylformamide (DMF) (3714 μl) at rt under nitrogen. The mixture was stirred at rt for 3 days. As starting material remained, it was stirred at 70° C. overnight. The mixture was concentrated under reduced pressure. The crude compound was purified by flash column chromatography (silica; EtOAc-cyclohexane from 0/100 to 50/50). The desired fractions were collected and concentrated in vacuo to obtain the product as a racemic mixture N-(2-hydroxyethyl)-4-(2-((tetrahydro-2H-pyran-2-yl)methyl)-2H-tetrazol-5-yl)benzenesulfonamide (49 mg, 0.133 mmol, 28%). $^1$H NMR (400 MHz, Acetone-d$_6$) δ 7.84-7.78 (m, 2H), 7.56-7.50 (m, 2H), 7.33 (t, J=5.9 Hz, 1H), 4.37-4.32 (m, 2H), 4.25 (t, J=5.6 Hz, 1H), 3.50-3.44 (m, 1H), 3.38-3.32 (m, 1H), 2.94-2.90 (m, 2H), 2.86-2.80 (m, 1H), 2.41-2.37 (m, 2H), 1.40-1.25 (m, 2H), 1.12-0.85 (m, 4H). MS m/z [M−H]$^-$=366.2

Examples 8-17 were prepared by methods analogous to that described for Example 7 replacing the alkylating reagents and base conditions with those indicated in Table 1. The method used for purification is indicated as footnotes.

TABLE 1

| Ex. | Structure | Conditions | Alkylating agent & conditions | Yield & Physical data |
|---|---|---|---|---|
| 8 | 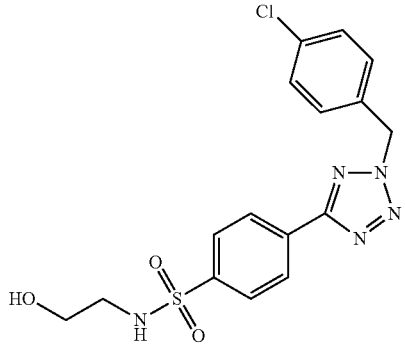<br>4-(2-(4-chlorobenzyl)-2H-tetrazol-5-yl)-N-(2-hydroxyethyl)benzenesulfonamide<br>(See footnote a) | DIPEA (1 eq, 78 μl, 0.446 mmol)/ Intermediate 17' | 4-Chlorobenzyl bromide (1 eq, 92 mg, 0.446 mmol, commercial source: Aldrich); stirred at rt for 16 h | Yield: 66%, white solid. $^1$H NMR (400 MHz, DMSO-$d_6$) δ 8.25-8.21 (m, 2H), 7.98-7.93 (m, 2H), 7.76 (br s, 1H), 7.50-7.43 (m, 4H), 6.04 (s, 2H), 4.67 (t, J = 5.6 Hz, 1H), 3.38-3.33 (m, 2H), 2.83-2.80 (m, 2H). MS m/z [M − H]$^-$ = 392.1 |
| 9 | 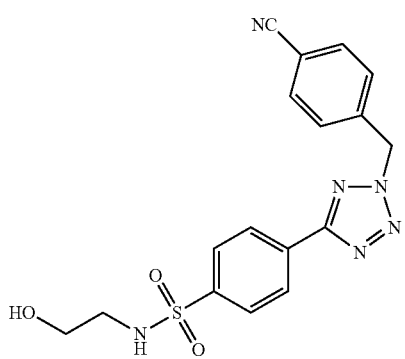<br>4-(2-(4-cyanobenzyl)-2H-tetrazol-5-yl)-N-(2-hydroxyethyl)benzenesulfonamide<br>(See footnote a) | DIPEA (1 eq, 55.1 μl, 0.316 mmol)/ Intermediate 17' | 4-(bromomethyl)benzonitrile (1 eq, 61.9 mg, 0.316 mmol) (commercial source: Aldrich); stirred at rt for 3 h | Yield: 73%. $^1$H NMR (400 MHz, DMSO-$d_6$) δ 8.26-8.22 (m, 2H), 7.99-7.93 (m, 2H), 7.91-7.86 (m, 2H), 7.76 (br s, 1H), 7.58 (d, J = 8.3 Hz, 2H), 6.17 (s, 2H), 4.67 (t, J = 5.6 Hz, 1H), 3.38-3.33 (m, 2H), 2.84-2.80 (m, 2H). MS m/z [M + H]$^+$ = 385.08 |
| 10 | 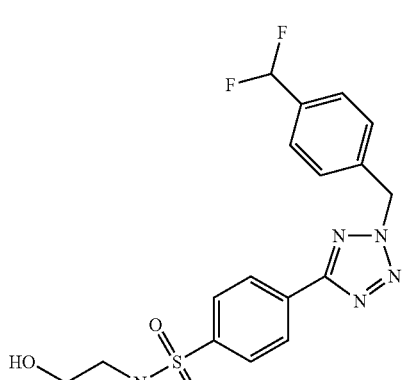<br>4-(2-(4-difluoromethyl)benzyl)-2H-tetrazol-5-yl)-N-(2-hydroxyethyl)benzenesulfonamide<br>(See footnote b) | DIPEA (1 eq, 78 μl, 0.446 mmol)/ Intermediate 17' | 4-(Difluoromethyl)benzyl bromide (1 eq, 99 mg, 0.446 mmol) (commercial source: Apollo UK); stirred at rt for 16 h | Yield: 21%, white solid. $^1$H NMR (400 MHz, DMSO-$d_6$) δ 8.25-8.23 (m, 2H), 7.96-7.94 (m, 2H), 7.77 (br s, 1H), 7.62-7.60 (m, 2H), 7.56-7.54 (m, 2H), 6.12 (s, 2H), 4.68 (t, J = 5.6 Hz, 1H), 3.38-3.32 (m, 2H), 2.84-2.79 (m, 2H). MS m/z [M − H]$^-$ = 408.2 |

TABLE 1-continued

| Ex. | Structure | Conditions | Alkylating agent & conditions | Yield & Physical data |
|---|---|---|---|---|
| 11 | 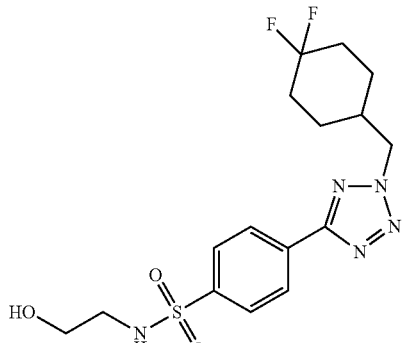<br>4-(2-((4,4-difluorocyclohexyl)methyl)-2H-tetrazol-5-yl)-N-(2-hydroxyethyl)benzenesulfonamide<br>(See footnote a) | DIPEA (1 eq, 97 μl, 0.557 mmol)/ Intermediate 17' | 4-(bromomethyl)-1,1-difluorocyclohexane (1 eq, 84 μl, 0.557 mmol, commercial source: Fluorochem); stirred at rt for 16 h, then at 50° C. for 72 h. | Yield: 52%, white solid. $^1$H NMR (400 MHz, DMSO-$d_6$) δ 8.27-8.22 (m, 2H), 8.00-7.94 (m, 2H), 7.81-7.74 (m, 1H), 4.74 (d, J = 7.1 Hz, 2H), 4.69 (t, J = 5.6 Hz, 1H), 3.39-3.33 (m, 2H), 2.85-2.80 (m, 2H), 2.27-2.12 (m, 1H), 2.07-1.95 (m, 2H), 1.92-1.63 (m, 4H), 1.40-1.28 (m, 2H). MS m/z [M − H]$^-$ = 400.01 |
| 12 | 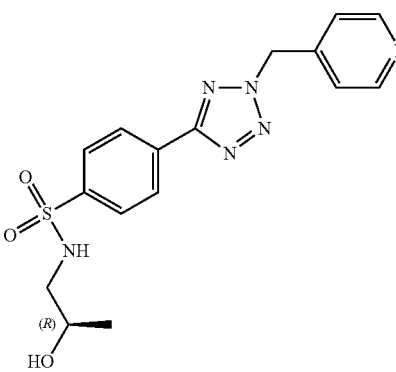<br>(R)-N-(2-hydroxypropyl)-4-(2-(pyridin-4-ylmethyl)-2H-tetrazol-5-yl)benzene-sulfonamide<br>(See footnote c) | DIPEA (4 eq, 518 μl, 2.96 mmol)/ Intermediate 18 | 4-(bromomethyl) pyridine hydrobromide (1 eq, 375 mg, 1.482 mmol, commercial source: Aldrich); stirred at rt for 16 h, then at 50° C. for 3 h | Yield: 66%, white solid. $^1$H NMR (400 MHz, DMSO-$d_6$) δ 8.62-8.56 (m, 2H), 8.28-8.23 (m, 2H), 7.99-7.93 (m, 2H), 7.74 (t, J = 6.1 Hz, 1H), 7.34 (d, J = 5.8 Hz, 2H), 6.14 (s, 2H), 4.68 (br s, 1H), 3.62-3.53 (m, 1H), 2.74-2.61 (m, 2H), 0.98 (d, J = 6.1 Hz, 3H). MS m/z [M + H]$^+$ = 375.3 |
| 13 | 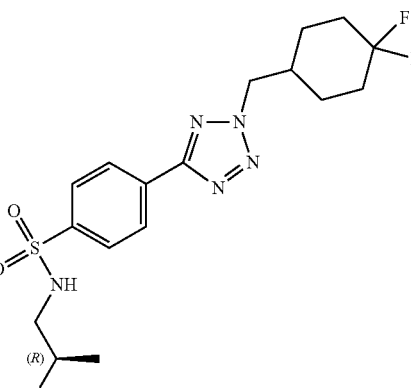<br>(R)-4-(2-((4,4-difluorocyclohexyl)methyl)-2H-tetrazol-5-yl)-N-(2-hydroxypropyl)benzene-sulfonamide<br>(See footnote d) | DIPEA (1.5 eq, 76 μl, 0.436 mmol)/ Intermediate 18 | 4-(bromomethyl)-1,1-difluoro-cyclohexane (1.5 eq, 65.9 μl, 0.436 mmol, commercial source: Fluorochem); stirred at rt for 16 h, then at 50° C. for 16 h and finally at 80° C. for other 2 h | Yield: 46%, white solid. $^1$H NMR (400 MHz, DMSO-$d_6$) δ 8.29-8.25 (m, 2H), 8.01-7.96 (m, 2H), 7.74 (br s, 1H), 4.75 (d, J = 7.1 Hz, 2H), 4.70 (d, J = 4.8 Hz, 1H), 3.63-3.57 (m, 1H), 2.76-2.65 (m, 2H), 2.25-2.14 (m, 1H), 2.10-1.97 (m, 2H), 1.92-1.65 (m, 4H), 1.42-1.20 (m, 2H), 1.00 (d, J = 6.3 Hz, 3H). MS m/z [M − H]$^-$ = 414.2 |

TABLE 1-continued

| Ex. | Structure | Conditions | Alkylating agent & conditions | Yield & Physical data |
|---|---|---|---|---|
| 14 | 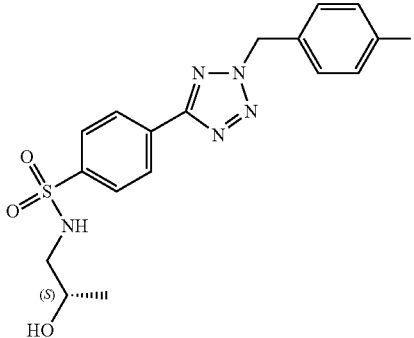<br>(S)-4-(2-(4-fluorobenzyl)-2H-tetrazol-5-yl)-N-(2-hydroxypropyl)benzenesulfonamide<br>(See footnote e) | DIPEA (1 eq, 67.8 μl, 0.388 mmol)/ Intermediate 18' | 4-Fluorobenzyl bromide (1 eq, 48.3 μl, 0.388 mmol, commercial source: Aldrich); stirred at rt for 4 h. | Yield: 39%, white solid. $^1$H NMR (400 MHz, DMSO-$d_6$) δ 8.25-8.20 (m, 2H), 7.98-7.92 (m, 2H), 7.73 (br s, 1H), 7.53-7.48 (m, 2H), 7.27-7.21 (m, 2H), 6.03 (s, 2H), 4.68 (d, J = 4.8 Hz, 1H), 3.63-3.53 (m, 1H), 2.74-2.61 (m, 2H), 0.97 (d, J = 6.3 Hz, 3H). MS m/z [M + H]$^+$ = 392.05 |
| 15 | 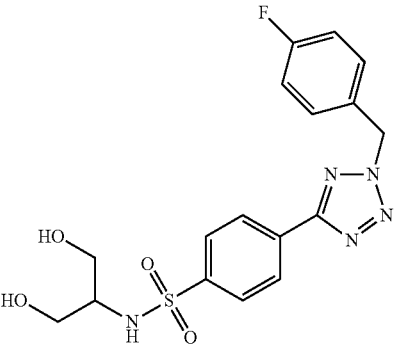<br>N-(1,3-dihydroxypropan-2-yl)-4-(2-(4-fluorobenzyl)-2H-tetrazol-5-yl)benzenesulfonamide<br>(See footnote d) | DIPEA (1 eq, 37.3 μl, 0.214 mmol)/ Intermediate 19 | 1-(bromo-methyl)-4-fluorobenzene (1 eq, 26.6 μl, 0.214 mmol, commercial source: Aldrich); stirred at rt for 3 h | Yield: 53%, white solid. $^1$H NMR (400 MHz, DMSO-$d_6$) δ 8.23-8.16 (m, 2H), 8.02-7.94 (m, 2H), 7.62 (d, J = 7.8 Hz, 1H), 7.54-7.48 (m, 2H), 7.28-7.21 (m, 2H), 6.02 (s, 2H), 4.54 (t, J = 5.6 Hz, 2H), 3.30-3.25 (m, 2H), 3.11-3.04 (m, 1H). MS m/z [M − H]$^-$ = 406.2 |
| 16 | 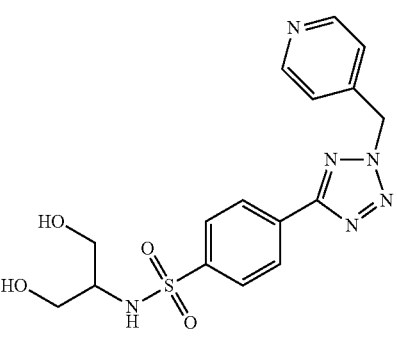<br>N-(1,3-dihydroxypropan-2-yl)-4-(2-(pyridin-4-ylmethyl)-2H-tetrazol-5-yl)benzenesulfonamide<br>(See footnote f) | DIPEA (2 eq, 65.4 μl, 0.374 mmol)/ Intermediate 19 | 4-(bromo-methyl)pyridine hydrobromide (1 eq, 47.3 mg, 0.187 mmol, commercial source: Aldrich); stirred at rt for 16 h, then at 50° C. for 20 h | Yield: 7%, white solid. $^1$H NMR (400 MHz, DMSO-$d_6$) δ 8.62-8.58 (m, 2H), 8.24-8.20 (m, 2H), 8.01-7.96 (m, 2H), 7.62 (br s, 1H), 7.35-7.32 (m, 2H), 6.13 (s, 2H), 4.54 (t, J = 5.6 Hz, 2H), 3.34-3.26 (m, 2H), 3.12-3.06 (m, 1H). MS m/z [M + H]$^+$ = 391.4 |

TABLE 1-continued

| Ex. | Structure | Conditions | Alkylating agent & conditions | Yield & Physical data |
|---|---|---|---|---|
| 17 | N-(2,3-dihydroxypropyl)-4-(2-(4-fluorobenzyl)-2H-tetrazol-5-yl)benzenesulfonamide (See footnote e) | DIPEA (1 eq, 35.0 μl, 0.200 mmol)/ Intermediate 20 | 4-Fluorobenzyl bromide (1 eq, 24.93 μl, 0.200 mmol, commercial source: Aldrich); stirred at rt for 1 h | Yield: 25%, white solid. $^1$H NMR (400 MHz, DMSO-$d_6$) δ 8.26-8.20 (m, 2H), 7.99-7.93 (m, 2H), 7.70-7.64 (m, 1H), 7.53-7.48 (m, 2H), 7.27-7.21 (m, 2H), 6.03 (s, 2H), 4.75 (d, J = 5.3 Hz, 1H), 4.54-4.48 (m, 1H), 3.47-3.40 (m, 1H), 3.28-3.18 (m, 2H), 2.93-2.86 (m, 1H), 2.68-2.58 (m, 1H). MS m/z [M + H]$^+$ = 408.09 | a) Residue was purified by flash chromatography with EtOAc in cyclohexane from 0/100 to 50/50 b) Residue was purified by HPLC preparative using X-Bridge column (30 × 150 mm) linear gradient 30-100% ACN/H$_2$O (10 mM NH$_4$HCO$_3$)

c) Residue was purified by flash chromatography EtOAc/EtOH (3:1)-cyclohexane from 0/100 to 50/50, followed by EtOAc-cyclohexane from 0/100 to 50/50 d) Residue was purified by flash chromatography EtOAc/EtOH (3:1)-cyclohexane from 0/100 to 50/50 e) The reaction mixture was quenched with 1N HCl and extracted with ethyl acetate. The organic layer was dried over Na$_2$SO$_4$ and concentrated under reduced pressure.

f) Residue was purified by flash chromatography EtOAc/EtOH (3:1)-cyclohexane from 0/100 to 50/50, then the product was triturated with ACN and finally was purified by HPLC preparative using X-Bridge column (30 × 150 mm) linear gradient 20-100% ACN/H$_2$O (10 mM NH$_4$HCO$_3$)

General Procedure for Alkylation of Tetrazoles

N,N-Diisopropylethylamine (1-4 eq) was added to a stirred solution of N-(2-hydroxyethyl)-4-(2H-tetrazol-5-yl)benzenesulfonamide (1 eq) in N,N-dimethylformamide (0.3 M). The alkylating agent (1 or 2 eq) was then added and the mixture was stirred at rt for at least 16 h. The mixture was concentrated under reduced pressure. The crude compound was purified primarily by flash column chromatography. The desired fractions were collected and concentrated in vacuo to yield the final products.

Example 18: 4-(2-((5-chloropyridin-2-yl)methyl)-2H-tetrazol-5-yl)-N-(2-hydroxyethyl)benzenesulfonamide

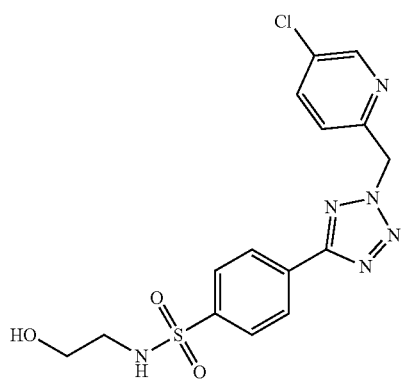

DIPEA (4, eq, 0.519 mL, 2.97 mmol) was added to a stirred solution of N-(2-hydroxyethyl)-4-(2H-tetrazol-5-yl)benzenesulfonamide (1 eq, 0.200 g, 0.743 mmol, Intermediate 17') in N,N-Dimethylformamide (DMF) (2.476 mL). Then 2-(bromomethyl)-5-chloropyridine (2 eq, 0.307 g, 1.485 mmol, commercial source: Biogene Organics) was added and the mixture was stirred at rt for 72 h. The mixture was concentrated under reduced pressure. The crude compound was purified by flash column chromatography (silica; EtOAc-cyclohexane from 0/100 to 100/0). The desired fractions were collected and concentrated in vacuo to obtain 4-(2-((5-chloropyridin-2-yl)methyl)-2H-tetrazol-5-yl)-N-(2-hydroxyethyl)benzenesulfonamide (205 mg, 70%) as a white solid. $^1$H NMR (400 MHz, CDCl$_3$) δ 8.58 (d, J=2.3 Hz, 1H), 8.26-8.21 (m, 2H), 8.02 (dd, J=8.3, 2.5 Hz, 1H), 7.98-7.91 (m, 2H), 7.77 (t, J=5.9 Hz, 1H), 7.58 (d, J=8.3 Hz, 1H), 6.18 (s, 2H), 4.68 (t, J=5.6 Hz, 1H), 3.35 (q, J=6.3 Hz, 2H), 2.82 (q, J=6.2 Hz, 2H). MS m/z [M−H]$^−$=393.05

Examples 19-28 were prepared by methods analogous to that described for Example 18 replacing the alkylating reagents and base conditions with those indicated in Table 2. When the method used for purification was different from that for Example 18, it is indicated.

TABLE 2

| Ex. | Structure | Conditions | Alkylating agent & conditions | Yield & Physical data |
|---|---|---|---|---|
| 19 | 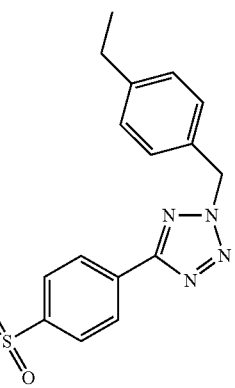<br>4-(2-(4-ethylbenzyl)-2H-tetrazol-5-yl)-N-(2-hydroxyethyl)benzenesulfonamide<br>(See footnote a) | DIPEA (2 eq, 259 μl, 1.485 mmol)/ Intermediate 17' | 1-(bromomethyl)-4-ethylbenzene (1 eq, 148 mg, 0.743 mmol, commercial source: Ukrorgsynthesis BBV); stirred at rt for 16 h | Yield: 70%, white solid. $^1$H NMR (400 MHz, DMSO-$d_6$) δ 8.26-8.20 (m, 2H), 7.98-7.92 (m, 2H), 7.79-7.72 (m, 1H), 7.36-7.31 (m, 2H), 7.27-7.21 (m, 2H), 5.97 (s, 2H), 4.67 (t, J = 5.6 Hz, 1H), 3.37-3.33 (m, 2H), 2.86-2.78 (m, 2H), 2.61-2.54 (m, 2H), 1.14 (t, J = 7.6 Hz, 3H). MS m/z [M − H]$^-$ = 386.1 |
| 20 | 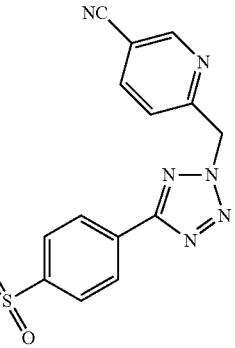<br>4-(2-((5-cyanopyridin-2-yl)methyl)-2H-tetrazol-5-yl)-N-(2-hydroxyethyl)benzenesulfonamide<br>(See footnotes b, c) | DIPEA (4 eq, 389 μl, 2.228 mmol)/ Intermediate 17' | 6-(bromomethyl)nicotinonitrile (2 eq, 220 mg, 1.114 mmol, commercial source: ARK PHARM-USA); stirred at rt overnight. | Yield: 35%. $^1$H NMR (400 MHz, DMSO-$d_6$) δ 8.96 (d, J = 1.3 Hz, 1H), 8.40 (dd, J = 8.1, 2.0 Hz, 1H), 8.28-8.21 (m, 2H), 8.00-7.92 (m, 2H), 7.78 (br s, 1H), 7.72 (d, J = 8.1 Hz, 1H), 6.32 (s, 2H), 4.69 (t, J = 5.4 Hz, 1H), 3.39-3.31 (m, 2H), 2.82 (t, J = 6.3 Hz, 2H). MS m/z [M − H]$^-$ = 384.2 |
| 21 | 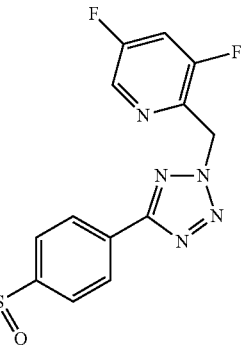<br>4-(2-((3,5-difluoropyridin-2-yl)methyl)-2H-tetrazol-5-yl)-N-(2-hydroxyethyl)benzenesulfonamide<br>(See footnote d) | DIPEA (2 eq, 259 μl, 1.485 mmol)/ Intermediate 17' | (3,5-difluoropyridin-2-yl)methyl methanesulfonate (1 eq, 182 mg, 0.817 mmol, Intermediate 12); stirred at rt for 16 h | Yield: 14%, white solid $^1$H NMR (400 MHz, DMSO-$d_6$) δ 8.49 (d, J = 2.5 Hz, 1H), 8.26-8.20 (m, 2H), 8.12-8.05 (m, 1H), 7.99-7.92 (m, 2H), 7.77 (t, J = 5.9 Hz, 1H), 6.24 (m, 2H), 4.69 (t, J = 5.6 Hz, 1H), 3.39-3.35 (m, 2H), 2.86-2.79 (m, 2H). MS m/z [M − H]$^-$ = 395.1 |

TABLE 2-continued

| Ex. | Structure | Conditions | Alkylating agent & conditions | Yield & Physical data |
|---|---|---|---|---|
| 22 | N-(2-hydroxyethyl)-4-(2-((6-methylpyridin-2-yl)methyl)-2H-tetrazol-5-yl)benzenesulfonamide (See footnotes b, e) | DIPEA (4 eq, 389 µl, 2.228 mmol)/ Intermediate 17' | 2-(bromomethyl)-6-methylpyridine (1.5 eq, 155 mg, 0.836 mmol, commercial source: Aldrich); stirred at rt for 3 days | Yield: 21%, white solid. $^1$H NMR (400 MHz, DMSO-d$_6$) δ 8.27-8.21 (m, 2H), 7.98-7.93 (m, 2H), 7.78-7.71 (m, 2H), 7.28-7.20 (m, 2H), 6.07 (s, 2H), 4.67 (t, J = 5.4 Hz, 1H), 3.39-3.32 (m, 2H), 2.82 (t, J = 6.2 Hz, 2H), 2.40 (s, 3H). MS m/z [M + H]$^+$ = 375.3 |
| 23 | N-(2-hydroxyethyl)-4-(2-((2-methylpyridin-4-yl)methyl)-2H-tetrazol-5-yl)benzenesulfonamide (See footnotes f, g) | DIPEA (2 eq, 259 µl, 1.485 mmol)/ Intermediate 17' | (2-methylpyrimidin-4-yl)methyl methanesulfonate (1 eq, 150 mg, 0.743 mmol, Intermediate 13); stirred at rt for 16 h | Yield: 12%. $^1$H NMR (400 MHz, DMSO-d$_6$) δ 8.73 (d, J = 5.3 Hz, 1H), 8.29-8.22 (m, 2H), 8.00-7.94 (m, 2H), 7.29 (d, J = 5.1 Hz, 1H), 6.18 (s, 2H), 4.68 (t, J = 5.6 Hz, 1H), 3.39-3.33 (m, 2H), 2.82 (t, J = 6.3 Hz, 2H), 2.54 (s, 3H). MS m/z [M − H]$^−$ = 374.1 |
| 24 | (R)-4-(2-(4-fluorobenzyl)-2H-tetrazol-5-yl)-N-(2-hydroxypropyl)benzenesulfonamide (See footnote a) | DIPEA (1 eq, 154 µl, 0.882 mmol)/ Intermediate 18 | 4-Fluorobenzyl bromide (1 eq, 110 µl, 0.882 mmol, commercial source: Aldrich); stirred at rt for 5 h | Yield: 43%, white solid. $^1$H NMR (400 MHz, DMSO-d$_6$) δ 8.26-8.19 (m, 2H), 7.99-7.92 (m, 2H), 7.73 (br s, 1H), 7.53-7.48 (m, 2H), 7.27-7.21 (m, 2H), 6.03 (s, 2H), 4.68 (d, J = 4.8 Hz, 1H), 3.62-3.53 (m, 1H), 2.74-2.60 (m, 2H), 0.97 (d, J = 6.1 Hz, 3H). MS m/z [M − H]$^−$ = 390.2 |

TABLE 2-continued

| Ex. | Structure | Conditions | Alkylating agent & conditions | Yield & Physical data |
|---|---|---|---|---|
| 25 | 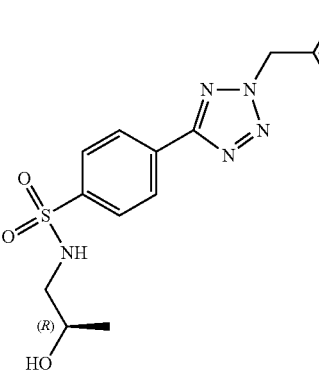<br>(R)-4-(2-((5-fluoropyridin-2-yl)methyl)-2H-tetrazol-5-yl)-N-(2-hydroxypropyl)benzenesulfonamide<br>(See footnote a) | and DIPEA (2 eq, 222 μl, 1.271 mmol)/ Intermediate 18 | 2-(chloromethyl)-5-fluoropyridine hydrochloride (1 eq, 116 mg, 0.635 mmol, Intermediate 9'); stirred at rt overnight | Yield: 19%, white solid. $^1$H NMR (400 MHz, DMSO-$d_6$) δ 8.53 (d, J = 3.0 Hz, 1H), 8.26-8.20 (m, 2H), 7.98-7.93 (m, 2H), 7.82 (dt, J = 8.7, 3.0 Hz, 1H), 7.73 (t, J = 5.7 Hz, 1H), 7.64 (dd, J = 8.7, 4.4 Hz, 1H), 6.16 (s, 2H), 4.68 (d, J = 4.8 Hz, 1H), 3.62-3.53 (m, 1H), 2.73-2.61 (m, 2H), 0.97 (d, J = 6.1 Hz, 3H). MS m/z [M − H]$^-$ = 391.1 |
| 26 | 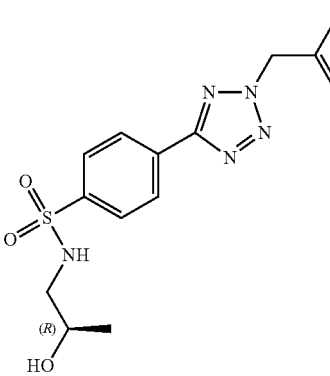<br>(R)-N-(2-hydroxypropyl)-4-(2-((5-methoxypyridin-2-yl)methyl)-2H-tetrazol-5-yl)benzenesulfonamide | DIPEA (1 eq, 117 μl, 0.671 mmol)/ Intermediate 18 | (5-methoxypyridin-2-yl)methyl methanesulfonate (1 eq, 146 mg, 0.671 mmol, Intermediate 14); stirred at rt overnight | Yield: 28%. $^1$H NMR (400 MHz, DMSO-$d_6$) δ 8.24-8.20 (m, 3H), 7.97-7.92 (m, 2H), 7.75-7.70 (m, 1H), 7.52-7.47 (m, 1H), 7.46-7.43 (m, 1H), 6.05 (s, 2H), 4.67 (d, J = 4.8 Hz, 1H), 3.81 (s, 3H), 3.62-3.53 (m, 1H), 2.74-2.61 (m, 2H), 0.97 (d, J = 6.3 Hz, 3H). MS m/z [M + H]$^+$ = 405.2 |
| 27 | 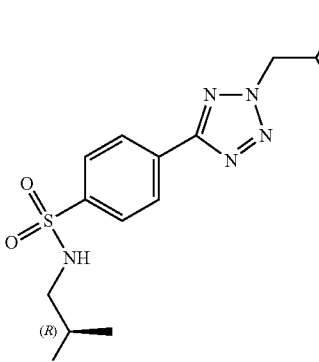<br>(R)-N-(2-hydroxypropyl)-4-(2-((5-methylpyridin-2-yl)methyl)-2H-tetrazol-5-yl)benzenesulfonamide | DIPEA (1 eq, 123 μl, 0.706 mmol)/ Intermediate 18 | (5-methylpyridin-2-yl)methyl methanesulfonate (1 eq, 142 mg, 0.706 mmol, Intermediate 15); stirred at rt overnight and then at 50° C. for 1 h. | Yield: 34%, white solid. $^1$H NMR (400 MHz, DMSO-$d_6$) δ 8.37-8.33 (m, 1H), 8.26-8.20 (m, 2H), 7.98-7.92 (m, 2H), 7.75-7.70 (m, 1H), 7.70-7.65 (m, 1H), 7.42-7.36 (m, 1H), 6.08 (s, 2H), 4.67 (d, J = 4.8 Hz, 1H), 3.62-3.53 (m, 1H), 2.75-2.60 (m, 2H), 2.28 (s, 3H), 0.97 (d, J = 6.1 Hz, 3H). MS m/z [M + H]$^+$ = 389.3 |

TABLE 2-continued

| Ex. | Structure | Conditions | Alkylating agent & conditions | Yield & Physical data |
|---|---|---|---|---|
| 28 | (R)-N-(2-hydroxypropyl)-4-(2-(4-methoxybenzyl)-2H-tetrazol-5-yl)benzenesulfonamide (See footnote a) | DIPEA (1 eq, 123 µl, 0.706 mmol)/ Intermediate 18 | 1-(bromomethyl)-4-methoxy-benzene (1 eq, 142 mg, 0.706 mmol, commercial source: ABChem-Canada); stirred at rt overnight | Yield: 24%, white solid. $^1$H NMR (400 MHz, DMSO-$d_6$) δ 8.22 (d, J = 8.3 Hz, 2H), 7.95 (d, J = 8.3 Hz, 2H), 7.73 (t, J = 6.1 Hz, 1H), 7.39 (d, J = 8.6 Hz, 2H), 6.95 (d, J = 8.8 Hz, 2H), 5.93 (s, 2H), 4.67 (d, J = 4.5 Hz, 1H), 3.73 (s, 3H), 3.62-3.53 (m, 1H), 2.74-2.61 (m, 2H), 0.97 (d, J = 6.3 Hz, 3H). MS m/z [M − H]$^−$ = 402.2 | a) Residue was purified by flash chromatography EtOAc-cyclohexane from 0/100 to 50/50
b) The reaction mixture was diluted with water and extracted with DCM twice. The organic layer was dried over anhydrous Na$_2$SO$_4$, filtered and the filtrate was concentrated under reduced pressure.
c) Residue was purified by flash chromatography EtOAc-cyclohexane from 0/100 to 100/0, then EtOAc/EtOH (3:1)-cyclohexane from 0/100 to 50/50. Finally, the residue was purified by HPLC preparative using X-Bridge column (19 × 150 mm) linear gradient 20-100% ACN/H$_2$O (10 mM NH$_4$HCO$_3$)
d) Residue was purified by flash chromatography EtOAc-cyclohexane from 0/100 to 50/50 (twice)
e) Residue was purified by flash chromatography EtOAc-cyclohexane from 0/100 to 30/70
f) Residue was purified by flash chromatography EtOAc-cyclohexane from 0/100 to 100/0
g) Residue was pruified by HPLC preparative X-Bridge column (19 × 50 mm) linear gradient 10-100% ACN/H$_2$O (100 mM NH$_4$HCO$_3$)

Example 29 (Prepared Via Intermediates 9' and 17'): 4-(2-((5-fluoropyridin-2-yl)methyl)-2H-tetrazol-5-yl)-N-(2-hydroxyethyl)benzenesulfonamide

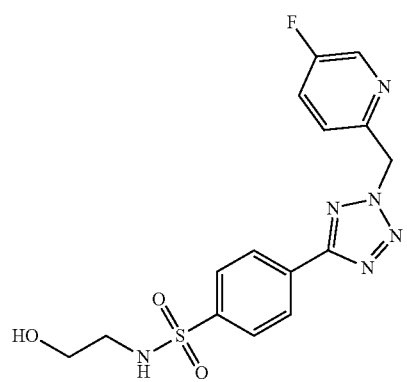

N,N-diisopropylethylamine (1.507 mL, 8.63 mmol, commercial source: Aldrich) was added to a stirred solution of N-(2-hydroxyethyl)-4-(2H-tetrazol-5-yl)benzenesulfonamide (0.581 g, 2.158 mmol, Intermediate 17') in N,N-Dimethylformamide (DMF) (7.19 mL). Then 2-(chloromethyl)-5-fluoropyridine hydrochloride (0.393 g, 2.158 mmol, Intermediate 9') was added and the mixture was stirred at rt for 16 h. The mixture was concentrated under reduced pressure. The crude compound was purified by flash column chromatography (silica gel; EtOAc-cyclohexane from 0/100 to 100/0). The desired fractions were collected and concentrated in vacuo. The yellow oil was precipitated with Et$_2$O and was filtered to obtain 4-(2-((5-fluoropyridin-2-yl)methyl)-2H-tetrazol-5-yl)-N-(2-hydroxyethyl)benzene-sulfonamide (178 mg, 0.447 mmol, 20.7%) as a white solid. $^1$H NMR (400 MHz, DMSO-$d_6$) δ 8.53 (d, J=2.8 Hz, 1H), 8.24 (d, J=8.6 Hz, 2H), 7.98-7.92 (m, 2H), 7.82 (dt, J=8.7, 2.9 Hz, 1H), 7.78-7.74 (m, 1H), 7.64 (dd, J=8.6, 4.5 Hz, 1H), 6.16 (s, 2H), 4.68 (t, J=5.6 Hz, 1H), 3.35 (q, J=6.2 Hz, 2H), 2.82 (q, J=5.6 Hz, 2H). MS m/z [M−H]$^−$=377.2

General Procedure for Alkylation of Tetrazoles

To a solution of N-(2-hydroxyethyl)-4-(2H-tetrazol-5-yl)benzenesulfonamide (1 eq) and the alkylating agent (1-1.6 eq) in acetonitrile, N,N-diisopropylethylamine (2-4 eq) was added at 28° C. The reaction mixture was heated to 80° C. and stirred for 16 h at the same temperature. The progress of the reaction was monitored by TLC. On completion of the reaction, the reaction mixture was cooled to 28° C., dissolved in ethyl acetate and washed with water (3×). The organic layer was dried over anhydrous Na$_2$SO$_4$, filtered and the filtrate was concentrated under reduced pressure. The crude compound was purified. The desired fractions were collected and concentrated in vacuo to yield the products.

Example 29 (Prepared Via Intermediates 9 and 17): 4-(2-((5-fluoropyridin-2-yl)methyl)-2H-tetrazol-5-yl)-N-(2-hydroxyethyl)benzenesulfonamide

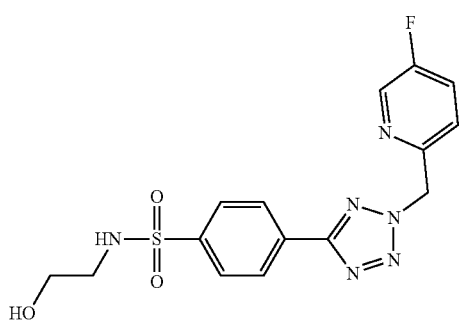

To a solution of N-(2-hydroxyethyl)-4-(2H-tetrazol-5-yl)benzenesulfonamide (6 g, 0.0223 mol, Intermediate 17), 2-(chloromethyl)-5-fluoropyridine (5 g, 0.0267 mol, Intermediate 9) in acetonitrile (90 mL), N,N-diisopropylethylamine (11 mL, 0.0669 mol) was added at 28° C. The reaction mixture was heated to 80° C. and stirred for 16 h at the same temperature. The progress of the reaction was monitored by TLC. On completion of the reaction, the reaction mixture was cooled to 28° C., dissolved in ethyl acetate (800 mL) and washed with water (3×200 mL). The organic layer was dried over anhydrous Na$_2$SO$_4$, filtered and the filtrate was concentrated under reduced pressure. The crude was purified by column chromatography (silicagel 100-200 mesh), eluted with 2% methanol in dichloromethane. The pure fractions were collected and concentrated under reduced pressure. The obtained solid compound was further purified by prep-HPLC to afford, after lyophilisation, 4-(2-((5-fluoropyridin-2-yl)methyl)-2H-tetrazol-5-yl)-N-(2-hydroxyethyl)benzenesulfonamide (2.88 g, 34%) as a white solid. $^1$H NMR (400 MHz, DMSO-d$_6$) δ 8.53 (d, J=3.1 Hz, 1H), 8.26-8.21 (m, 2H), 7.98-7.93 (m, 2H), 7.85-7.78 (m, 1H), 7.74 (br s, 1H), 7.63 (dd, J=8.6, 4.4 Hz, 1H), 6.16 (s, 2H), 4.65 (br s, 1H), 3.36 (t, J=6.2 Hz, 2H), 2.83 (t, J=6.2 Hz, 2H). MS m/z [M+H]$^+$=379.05.

Prep-HPLC Conditions:
Column: PURITAS C18 (250×30) mm, 10μ
Mobile phase: A—10 mM ammonium bicarbonate (aq), B—acetonitrile
Method (time in min/% of B): 0/30, 1/30, 10/70, 10.5/100, 13/100, 13.5/30
Flow: 30 mL/min
Temperature: ambient Examples 30-44 were prepared by methods analogous to that described for Example 29 replacing the alkylating reagents and base conditions with those indicated in Table 3. The method used for purification is indicated as footnotes.

TABLE 3

| Ex. | Structure | Conditions | Alkylating agent & conditions | Yield & Physical data |
|---|---|---|---|---|
| 30 | 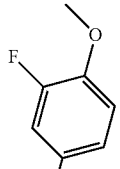<br>4-(2-(3-fluoro-4-methoxybenzyl)-2H-tetrazol-5-yl)-N-(2-hydroxyethyl)benzenesulfonamide<br>(See footnote a) | DIPEA (2 eq, 0.245 mL, 1.48 mmol)/ Intermediate 17 | 4-(bromomethyl)-2-fluoro-1-methoxybenzene (1.1 eq, 179 mg, 0.81 mmol, commercial source: Aldrich) | Yield: 16%, off-white solid. $^1$H NMR (400 MHz, DMSO-d$_6$) δ 8.26-8.21 (m, 2H), 7.98-7.92 (m, 2H), 7.73 (br s, 1H), 7.37-7.31 (m, 1H), 7.27-7.22 (m, 1H), 7.22-7.15 (m, 1H), 5.95 (s, 2H), 4.65 (t, J = 5.6 Hz, 1H), 3.82 (s, 3H), 3.36 (q, J = 6.2 Hz, 2H), 2.83 (t, J = 6.2 Hz, 2H). MS m/z [M − H]$^-$ = 406.11. |
| 31 | 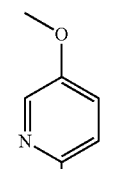<br>N-(2-hydroxyethyl)-4-(2-((5-methoxypyridin-2-yl)methyl)-2H-tetrazol-5-yl)benzenesulfonamide<br>(See footnote b) | DIPEA (3 eq, 0.39 mL, 0.0022 mol)/ Intermediate 17 | 2-(bromomethyl)-5-methoxypyridine hydrobromide (1.2 eq, 250 mg, 0.00089 mol, Intermediate 4) | Yield: 11%, white solid. $^1$H NMR (400 MHz, DMSO-d$_6$) δ 8.25-8.19 (m, 3H), 7.96-7.92 (m, 2H), 7.52-7.42 (m, 2H), 6.05 (s, 2H), 4.68 (br s, 1H), 3.82 (s, 3H), 3.38-3.32 (m, 2H), 2.82 (t, J = 6.4 Hz, 2H). MS m/z [M + H]$^+$ = 391.07. |

TABLE 3-continued

| Ex. | Structure | Conditions | Alkylating agent & conditions | Yield & Physical data |
|---|---|---|---|---|
| 32 | 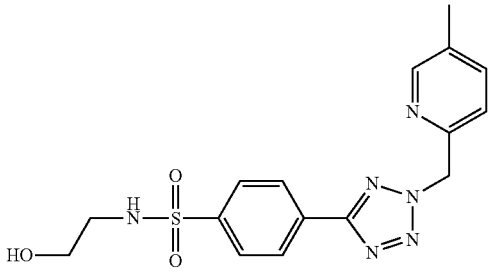<br>(N-(2-hydroxyethyl)-4-(2-((5-methylpyridin-2-yl)methyl)-2H-tetrazol-5-yl)benzenesulfonamide<br>(See footnotes c and d) | DIPEA (2.4 eq, 230 mg, 0.0017 mol)/ Intermediate 17 | 2-(bromomethyl)-5-methylpyridine (1.6 eq, 211 mg, 0.0011 mol, Intermediate 2); no work-up | Yield: 18.3%, white solid. $^1$H NMR (400 MHz, DMSO-$d_6$) δ 8.37-8.34 (m, 1H), 8.25-8.21 (m, 2H), 7.98-7.93 (m, 2H), 7.77-7.71 (m, 1H), 7.70-7.65 (m, 1H), 7.39 (d, J = 7.9 Hz, 1H), 6.08 (s, 2H), 4.65 (t, J = 5.6 Hz, 1H), 3.36 (q, J = 6.2 Hz, 2H), 2.83 (q, J = 6.1 Hz, 2H), 2.28 (s, 3H). MS m/z [M + H]$^+$ = 375.08. |
| 33 | 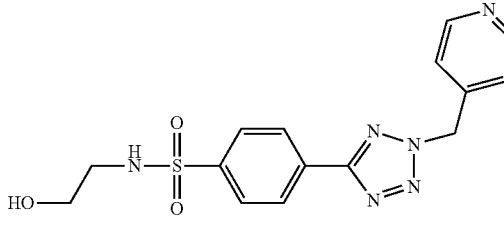<br>N-(2-hydroxyethyl)-4-(2-(pyridin-4-ylmethyl)-2H-tetrazol-5-yl)benzenesulfonamide<br>(See footnotes e and f) | DIPEA (4 eq, 15 mL, 0.088 mol)/ Intermediate 17 | 4-(chloromethyl) pyridine hydrochloride (1.5 eq, 5.4 g, 0.033 mol, commercial source: Combi-Blocks); heated to 80° C. and stirred for 48 h. No work-up | Yield: 26%, white solid. $^1$H NMR (400 MHz, DMSO-$d_6$) δ 8.62-8.59 (m, 2H), 8.30-8.24 (m, 2H), 8.00-7.95 (m, 2H), 7.76 (br s, 1H), 7.37-7.33 (m, 2H), 6.15 (s, 2H), 4.67 (br s, 1H), 3.41-3.34 (m, 2H), 2.84 (t, J = 6.4 Hz, 2H). MS m/z [M + H]$^+$ = 361.06 |
| 34 | 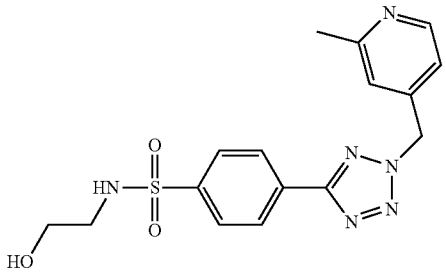<br>N-(2-hydroxyethyl)-4-(2-((2-methylpyridin-4-yl)methyl)-2H-tetrazol-5-yl)benzenesulfonamide<br>(See footnote g) | DIPEA (2 eq, 196 mg, 1.52 mmol)/ Intermediate 17 | 4-(chloromethyl)-2-methylpyridine (1.1 eq, 118 mg, 0.83 mmol, Intermediate 10) | Yield: 39%, off-white solid. $^1$H NMR (400 MHz, DMSO-$d_6$) δ 8.48-8.43 (m, 1H), 8.28-8.23 (m, 2H), 7.99-7.94 (m, 2H), 7.77-7.72 (m, 1H), 7.21-7.18 (m, 1H), 7.14-7.10 (m, 1H), 6.07 (s, 2H), 4.68-4.63 (m, 1H), 3.40-3.33 (m, 2H), 2.86-2.80 (m, 2H), 2.45 (s, 3H). MS m/z [M + H]$^+$ = 375.08 |

TABLE 3-continued

| Ex. | Structure | Conditions | Alkylating agent & conditions | Yield & Physical data |
|---|---|---|---|---|
| 35 | 2-(4-(2-(4-methoxybenzyl)-2H-tetrazol-5-yl)phenylsulfonamido)acetamide (See footnote h) | DIPEA (3 eq, 271 mg, 0.0021 mol)/ Intermediate 25 | 1-(bromomethyl)-4-methoxybenzene (1.2 eq, 170 mg, 0.00085 mol, commercial source: Alfa Aesar) | Yield: 28%, white solid. $^1$H NMR (400 MHz, DMSO-$d_6$) δ 8.23-8.17 (m, 2H), 8.02 (br s, 1H), 7.97-7.91 (m, 2H), 7.42-7.36 (m, 2H), 7.24 (br s, 1H), 7.03 (br s, 1H), 6.99-6.92 (m, 2H), 5.93 (s, 2H), 3.74 (s, 3H), 3.41 (s, 2H). MS m/z [M − H]$^−$ = 401.14 |
| 36 | 2-(4-(2-(4-methylbenzyl)-2H-tetrazol-5-yl)phenylsulfonamido)acetamide (See footnote i) | DIPEA (3 eq, 271 mg, 0.0021 mol)/ Intermediate 25 | 1-(bromomethyl)-4-methylbenzene (1.2 eq, 156 mg, 0.00085 mol, commercial source: Alfa Aesar). | Yield: 36%, white solid. $^1$H NMR (400 MHz, DMSO-$d_6$) δ 8.23-8.17 (m, 2H), 7.99 (br s, 1H), 7.97-7.91 (m, 2H), 7.35-7.28 (m, 2H), 7.26-7.17 (m, 3H), 7.02 (br s, 1H), 5.96 (s, 2H), 3.40 (s, 2H), 2.28 (s, 3H). MS m/z [M + H]$^+$ = 387.04. |
| 37 | 2-(4-(2-(3,4-difluorobenzyl)-2H-tetrazol-5-yl)phenylsulfonamido)acetamide (See footnote j) | DIPEA (2 eq, 0.23 mL, 1.4 mmol)/ Intermediate 25 | 4-(bromomethyl)-1,2-difluorobenzene (1.1 eq, 158 mg, 0.77 mmol, commercial source: Alfa Aesar) | Yield: 14%, off white solid. $^1$H NMR (400 MHz, DMSO-$d_6$) δ 8.26-8.21 (m, 2H), 8.01 (br s, 1H), 7.99-7.94 (m, 2H), 7.62-7.55 (m, 1H), 7.54-7.44 (m, 1H), 7.35-7.29 (m, 1H), 7.26 (br s, 1H), 7.05 (br s, 1H), 6.05 (s, 2H), 3.43 (s, 2H). MS m/z [M − H]$^−$ = 407.07 |

TABLE 3-continued

| Ex. | Structure | Conditions | Alkylating agent & conditions | Yield & Physical data |
|---|---|---|---|---|
| 38 | 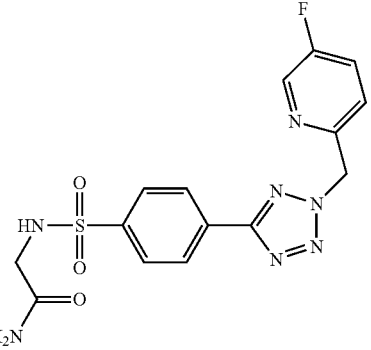<br>2-(4-(2-((5-fluoropyridin-2-yl)methyl)-2H-tetrazol-5-yl)phenylsulfonamido)acetamide<br>(See footnote h) | DIPEA (3 eq, 271 mg, 0.0021 mol)/ Intermediate 25 | 2-(chloromethyl)-5-fluoropyridine (1.2 eq, 123 mg, 0.00085 mol, Intermediate 9) | Yield: 26%, white solid. $^1$H NMR (400 MHz, DMSO-$d_6$) δ 8.53 (d, J = 2.8 Hz, 1H), 8.25-8.19 (m, 2H), 8.02-7.93 (m, 3H), 7.81 (dt, J = 8.7, 2.9 Hz, 1H), 7.64 (dd, J = 8.8, 4.4 Hz, 1H), 7.25 (br s, 1H), 7.054 (br s, 1H), 6.16 (s, 2H), 3.42 (s, 2H). MS m/z [M + H]$^+$ = 392.01. |
| 39 | 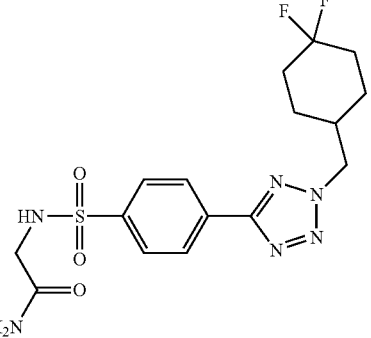<br>2-(4-(2-((4,4-difluorocyclohexyl)methyl)-2H-tetrazol-5-yl)phenylsulfonamido)acetamide<br>(See footnote k) | DIPEA (3 eq, 271 mg, 0.0021 mol)/ Intermediate 25 | 4-(bromomethyl)-1,1-difluorocyclohexane (1.1 eq, 180 mg, 0.0008 mol, Intermediate 3) | Yield: 37%, white solid. $^1$H NMR (400 MHz, DMSO-$d_6$) δ 8.26-8.21 (m, 2H), 7.99-7.895 (m, 2H), 7.40 (br s, 1H), 7.25 (br s, 1H), 7.04 (br s, 1H), 4.77-4.71 (m, 2H), 3.43 (s, 2H), 2.26-2.13 (m, 1H), 2.07-1.95 (m, 2H), 1.91-1.64 (m, 4H), 1.40-1.27 (m, 2H). MS m/z [M + H]$^+$ = 415.05 |
| 40 | 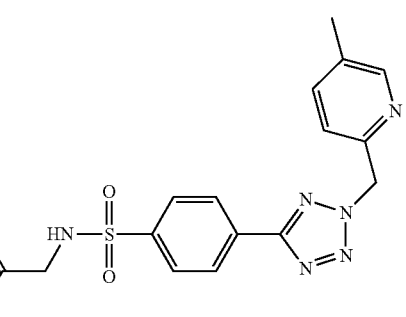<br>2-(4-(2-((5-methylpyridin-2-yl)methyl)-2H-tetrazol-5-yl)phenylsulfonamido)acetamide<br>(See footnote l) | DIPEA (2 eq, 0.23 mL, 1.4 mmol)/ Intermediate 25 | 2-(chloromethyl)-5-methylpyridine (1.1 eq, 110 mg, 0.77 mmol, Intermediate 11) | Yield: 12%, off white solid. $^1$H NMR (400 MHz, DMSO-$d_6$) δ 8.37-8.34 (m, 1H), 8.24-8.19 (m, 2H), 8.01-7.93 (m, 3H), 7.70-7.65 (m, 1H), 7.42-7.37 (m, 1H), 7.24 (br s, 1H), 7.03 (br s, 1H), 6.08 (s, 2H), 3.42 (s, 2H), 2.28 (s, 3H). MS m/z [M + H]$^+$ = 388.11 |

TABLE 3-continued

| Ex. | Structure | Conditions | Alkylating agent & conditions | Yield & Physical data |
|---|---|---|---|---|
| 41 | 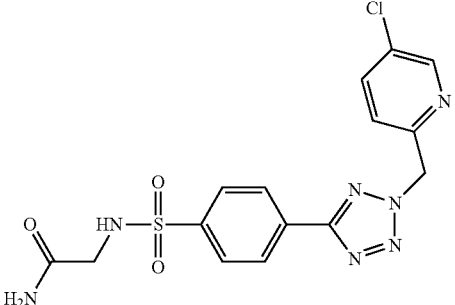<br>2-(4-(2-((5-chloropyridin-2-yl)methyl)-2H-tetrazol-5-yl)phenylsulfonamido)acetamide<br>(See footnote c) | DIPEA (2 eq, 0.24 mL, 0.0014 mol)/ Intermediate 25 | 2-(bromomethyl)-5-chloropyridine (1 eq, 159 mg, 0.0007 mol, Intermediate 8) | Yield: 20.4%, off white solid. $^1$H NMR (400 MHz, DMSO-$d_6$) δ 8.60-8.56 (m, 1H), 8.25-8.19 (m, 2H), 8.05-7.92 (m, 4H), 7.61-7.55 (m, 1H), 7.25 (br s, 1H), 7.04 (br s, 1H), 6.18 (s, 2H), 3.46-3.39 (m, 2H). MS m/z $[M + H]^+$ = 408.14 |
| 42 | 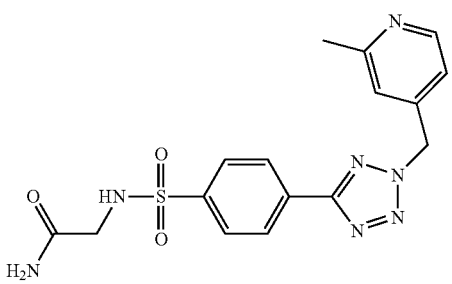<br>2-(4-(2-((2-methylpyridin-4-yl)methyl)-2H-tetrazol-5-yl)phenylsulfonamido)acetamide<br>(See footnote m) | DIPEA (2 eq, 0.23 mL, 1.4 mmol)/ Intermediate 25 | 4-(chloromethyl)-2-methylpyridine (1.1 eq, 110 mg, 0.77 mmol Intermediate 10) | Yield: 19%, off white solid. $^1$H NMR (400 MHz, DMSO-$d_6$) δ 8.47-8.44 (m, 1H), 8.26-8.21 (m, 2H), 8.00-7.94 (m, 2H), 7.86 (br s, 1H), 7.25 (br s, 1H), 7.20-7.18 (m, 1H), 7.14-7.11 (m, 1H), 7.04 (br s, 1H), 6.07 (s, 2H), 3.42 (s, 2H), 2.45 (s, 3H). MS m/z $[M + H]^+$ = 388.11 |
| 43 | 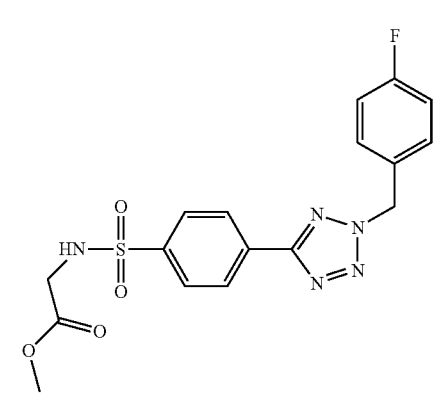<br>Methyl 2-(4-(2-(4-fluorobenzyl)-2H-tetrazol-5-yl)phenylsulfonamido)acetate<br>(See footnotes c and n) | triethylamine (2 eq, 0.36 mL, 0.0026 mol)/ Intermediate 27 | 1-(bromomethyl)-4-fluorobenzene (1.2 eq, 303 mg, 0.0016 mol, commercial source: Combi-Blocks); No work-up | Yield: 46%, white solid. $^1$H NMR (400 MHz, DMSO-$d_6$) δ 8.31 (br s, 1H), 8.27-8.20 (m, 2H), 8.01-7.92 (m, 2H), 7.58-7.47 (m, 2H), 7.30-7.20 (m, 2H), 6.03 (s, 2H), 3.76 (s, 2H), 3.51 (s, 3H). MS m/z $[M + H]^+$ = 406.03 |

TABLE 3-continued

| Ex. | Structure | Conditions | Alkylating agent & conditions | Yield & Physical data |
|---|---|---|---|---|
| 44 | Methyl 2-(4-(2-(pyridin-4-ylmethyl)-2H-tetrazol-5-yl)phenylsulfonamido)acetate (See footnote o) | triethylamine (2 eq, 0.9 mL, 0.0066 mol)/ Intermediate 27 | 4-(chloromethyl) pyridine hydrochloride (1.2 eq, 650 mg, 0.004 mol, commercial source: Combi-Blocks); No work-up | Yield: 37%, off-white solid. $^1$H NMR (400 MHz, DMSO-$d_6$) δ 8.69-8.57 (m, 2H), 8.38 (br s, 1H), 8.25 (d, J = 8.77 Hz, 2H), 7.97 (d, J = 8.55 Hz, 2H), 7.40-7.31 (m, 2H), 6.14 (s, 2H), 3.77 (br s, 2H), 3.52 (s, 3H). MS m/z [M + H]$^+$ = 389.05 | a) Residue was purified by HPLC preparative X-Bridge C18 column (19 × 150 mm, 5μ, Flow: 16 mL/min) Mobile phase: A: H$_2$O (10 mM NH$_4$HCO$_3$) B: ACN; Method (time in min/% of B): 0/10, 10/50, 10.2/100, 12/100, 12.2/100.

b) Residue was purified by HPLC preparative YMC Triart C18 column (25 × 150 mm, 10μ Flow: 25 mL/min) Mobile phase: A: H$_2$O (10 mM NH$_4$HCO$_3$) B: ACN; Method (time in min/% of B): 0/20, 8/55, 9/55, 9.2/98, 13/98, 13.1/20, 16/20.

c) Residue was purified by flash chromatography DCM/MeOH (2%).

d) Residue was purified by HPLC preparative Puritas C18 column (30 × 550 mm, 10μ Flow: 25 mL/min) Mobile phase: A: H$_2$O (10 mM NH$_4$HCO$_3$) B: ACN; Method (time in min/% of B): 0/10, 10/60, 14/100, 14.3/100, 15/10, 18/10.

e) Residue was purified by flash chromatography using 1.5% methanol in dichloromethane.

f) Residue was purified by HPLC preparative Diasogel C18 column (25 × 150 mm, Flow: 25 mL/min) Mobile phase: A: H$_2$O (10 mM NH$_4$HCO$_3$) B: ACN; Method (time in min/% of B): 0/35, 1/40, 8/50, 12/50, 12.2/100.

g) Residue was purified by HPLC preparative Kromasil C18 column (25 × 150 mm, 10μ, Flow: 25 mL/min) Mobile phase: A: H$_2$O (10 mM NH$_4$HCO$_3$) B: ACN; Method (time in min/% of B): 0/10, 1/10, 10/55, 10.5/100, 14/100, 14.5/10.

h) Residue was purified by HPLC preparative X-SELECT C18 column (19 × 150 mm, 5μ, Flow: 20 mL/min) Mobile phase: A: H$_2$O (10 mM NH$_4$HCO$_3$) B: ACN; Method (time in min/% of B): 0/10, 10/60, 10.3/100, 12.7/100, 13/10, 15/10.

i) Residue was purified by HPLC preparative Puritas C18 column (30 × 250 mm, 10μ Flow: 30 mL/min) Mobile phase: A: H$_2$O (10 mM NH$_4$HCO$_3$) B: ACN; Method (time in min/% of B): 0/35, 1/35, 8/75, 10.5/75, 11/100, 15.5/100, 16/35, 20/35.

j) Residue was purified by HPLC preparative X-Terra RP C18 column (19 × 150 mm, 5μ, Flow: 18 mL/min) Mobile phase: A: H$_2$O (10 mM NH$_4$HCO$_3$) B: ACN; Method (time in min/% of B): 0/20, 1/20, 10/45, 11/45, 11.5/100, 14/100.

k) Residue was purified by HPLC preparative X-Bridge C18 column (19 × 150 mm, 5μ, Flow: 15 mL/min) Mobile phase: A: H$_2$O (10 mM NH$_4$HCO$_3$) B: ACN; Method (time in min/% of B): 0/10, 8/45, 8.2/100, 12.5/100, 12.7/10, 15/10.

l) Residue was purified by HPLC preparative Luna C18 column (25 × 150 mm, 10μ Flow: 25 mL/min) Mobile phase: A: H$_2$O (10 mM NH$_4$HCO$_3$) B: ACN; Method (time in min/% of B): 0/20, 8/50, 8.2/100, 9/100.

m) Residue was purified by HPLC preparative YMC Triart C18 column (25 × 150 mm, 10μ Flow: 20 mL/min) Mobile phase: A: H$_2$O (10 mM NH$_4$HCO$_3$) B: ACN; Method (time in min/% of B): 0/20, 1/20, 10/50, 11.5/50, 12/100, 14/100, 14.5/100.

n) Residue was purified by HPLC preparative Kromasil C18 column (25 × 150 mm, 10μ, Flow: 25 mL/min) Mobile phase: A: H$_2$O (10 mM NH$_4$HCO$_3$) B: ACN; Method (time in min/% of B): 0/30, 1/30, 10/70, 10.5/100, 13/100, 13.5/30.

o) Residue was purified by flash chromatography using 2.5% methanol in dichloromethane.

Example 45: 2-(4-(2-(4-fluorobenzyl)-2H-tetrazol-5-yl)phenylsulfonamido)acetamide

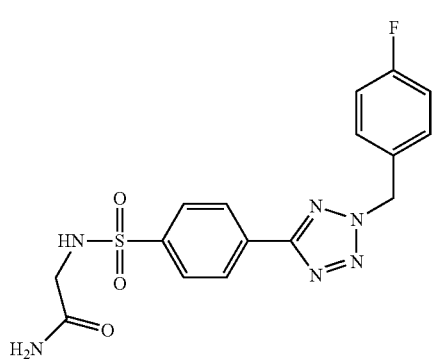

To a solution of 2-(4-(2-(4-fluorobenzyl)-2H-tetrazol-5-yl)phenylsulfonamido)acetic acid (220 mg, 0.00056 mol, Intermediate 28), ammonium chloride (44 mg, 0.00084 mol) in N,N-dimethylformamide (2.2 mL), N,N-diisopropylethylamine (0.24 mL, 0.0014 mol) and HATU (319 mg, 0.00084 mol) were added at 0° C. The reaction mixture was stirred at 28° C. for 16 h. Reaction was monitored by TLC. On completion of the reaction, the reaction mixture was cooled to 0° C. and quenched with ice water (20 mL). The precipitated solid compound was filtered and dried under vacuum. The crude was purified by prep-HPLC to afford 2-(4-(2-(4-fluorobenzyl)-2H-tetrazol-5-yl)phenylsulfonamido)acetamide (62 mg, 28%) as an off-white solid. $^1$H NMR (400 MHz, DMSO-$d_6$) δ 8.24-8.19 (m, 2H), 8.03 (br s, 1H), 7.98-7.93 (m, 2H), 7.53-7.47 (m, 2H), 7.30-7.21 (m, 3H), 7.06 (br s, 1H), 6.03 (s, 2H), 3.41 (s, 2H). MS m/z [M+H]$^+$=391.05

Prep-HPLC Conditions:

Column: Kromasil C18 (150×25) mm, 10μ

Mobile phase: A—10 mM ammonium bicarbonate (aq), B—acetonitrile

Method (time in min/% of B): 0/20, 1/20, 10/20, 10.2/100, 11/100, 11.2/20, 15/20

Flow: 25 mL/min

Temperature: Ambient

Example 46: 2-(4-(2-(pyridin-4-ylmethyl)-2H-tetrazol-5-yl)phenylsulfonamido)acetamide

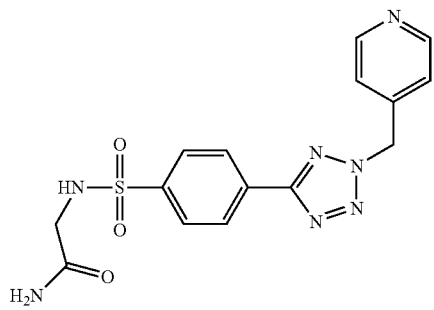

46

To a solution of 2-(4-(2-(pyridin-4-ylmethyl)-2H-tetrazol-5-yl)phenylsulfonamido)acetic acid (200 mg, 0.0005 mol, Intermediate 29), ammonium chloride (42 mg, 0.0008 mol) in N,N-dimethylformamide (2 mL), N,N-diisopropylethylamine (0.209 mL, 0.0012 mol) and HATU (304 mg, 0.0008 mol) were added at 0° C. The reaction mixture temperature was raised to 28° C. and stirred for 16 h at the same temperature. The progress of the reaction was monitored by TLC. On completion of the reaction, the reaction mixture was cooled to 0° C., quenched with ice water (20 mL) and stirred for 15 min. The precipitated solid was filtered and dried under vacuum to afford 2-(4-(2-(pyridin-4-ylmethyl)-2H-tetrazol-5-yl)phenylsulfonamido)acetamide (70 mg, 36%) as an off-white solid. $^1$H NMR (400 MHz, DMSO-$d_6$) δ 8.63-8.56 (m, 2H), 8.28-8.20 (m, 2H), 8.08-8.00 (m, 1H), 8.00-7.92 (m, 2H), 7.38-7.31 (m, 2H), 7.28 (br s, 1H), 7.06 (br s, 1H), 6.14 (s, 2H), 3.46-3.38 (m, 2H). MS m/z [M+H]$^+$=374.06

Example 47: (4-(2-(4-fluorobenzyl)-2H-tetrazol-5-yl)-N-(2-hydroxyethyl)-2-methoxybenzenesulfonamide)

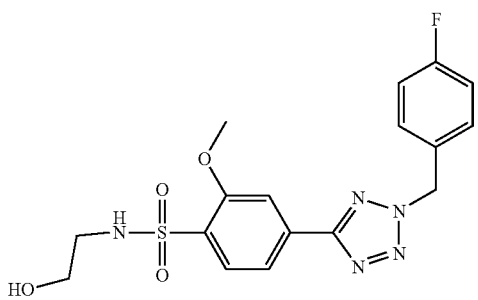

47

To a solution of N-(2-hydroxyethyl)-2-methoxy-4-(2H-tetrazol-5-yl)benzenesulfonamide (200 mg, 0.0006 mol, Intermediate 33), 1-(bromomethyl)-4-fluorobenzene (150 mg, 0.0008 mol, commercial source: Combi-Blocks) in N,N-dimethylformamide (2 mL), potassium carbonate (165 mg, 0.0012 mol) was added at 28° C. The reaction mixture was heated to 100° C. and stirred for 16 h at the same temperature. Reaction was monitored by TLC. On completion of the reaction, the reaction mixture was cooled to 28° C. and concentrated under reduced pressure. The crude was purified by prep-HPLC to afford 4-(2-(4-fluorobenzyl)-2H-tetrazol-5-yl)-N-(2-hydroxyethyl)-2-methoxybenzenesulfonamide (23 mg, 9%) as a white solid. $^1$H NMR (400 MHz, DMSO-$d_6$) δ 7.91-7.87 (m, 1H), 7.77-7.72 (m, 2H), 7.52-7.49 (m, 2H), 7.28-7.21 (m, 2H), 7.18 (br s, 1H), 6.03 (s, 2H), 4.60 (br s, 1H), 3.99 (s, 3H), 3.37-3.30 (m, 2H), 2.87-2.81 (m, 2H). MS m/z [M+H]$^+$=408.04

Prep-HPLC Conditions:

Column: YMC Triart C18 (150×25) mm, 10μ

Mobile phase: A—10 mM ammonium bicarbonate (aq), B—acetonitrile

Method (time in min/% of B): 0/20, 10/60, 12/60, 12.3/100, 15.5/100, 15.8/20, 18/20

Flow: 25 mL/min

Temperature: ambient.

Example 48: (N-(2-hydroxyethyl)-2-methoxy-4-(2-(pyridin-4-ylmethyl)-2H-tetrazol-5-yl)benzenesulfonamide)

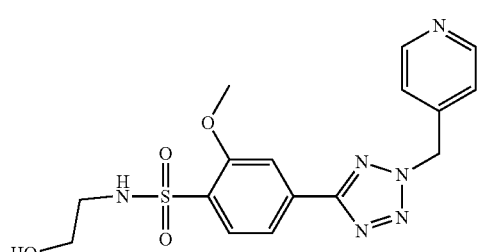

48

To a solution of N-(2-hydroxyethyl)-2-methoxy-4-(2H-tetrazol-5-yl)benzenesulfonamide (200 mg, 0.0006 mol, Intermediate 33) in acetonitrile (4 mL), triethylamine (121 mg, 0.0012 mol) was added at 28° C. and stirred for 15 min at 28° C. Followed by the addition of 4-(chloromethyl)pyridine hydrochloride (131 mg, 0.0008 mol, commercial source: Combi-Blocks) at 28° C. The reaction mixture was heated to 80° C. and stirred for 16 h at the same temperature. Reaction was monitored by TLC. On completion of the reaction, the reaction mixture was cooled to 28° C. and concentrated under reduced pressure. The crude was purified by column chromatography (silica gel 100-200 mesh), eluted with 1.5% methanol in dichloromethane. The pure fractions were collected and concentrated under reduced pressure. The obtained compound was purified by SCX column to afford N-(2-hydroxyethyl)-2-methoxy-4-(2-(pyridin-4-ylmethyl)-2H-tetrazol-5-yl)benzenesulfonamide (21 mg, 8.6%) as an off-white solid. $^1$H NMR (400 MHz, DMSO-$d_6$) δ 8.62-8.58 (m, 2H), 7.93-7.87 (m, 1H), 7.80-7.74 (m, 2H), 7.35-7.30 (m, 2H), 7.23-7.17 (m, 1H), 6.14 (s, 2H), 4.63-4.58 (m, 1H), 4.00 (s, 3H), 3.37-3.30 (m, 2H), 2.88-2.82 (m, 2H). MS m/z [M+H]$^+$=391.23.

143

Example 49: (4-(2-(4-cyanobenzyl)-2H-tetrazol-5-yl)-N-(2-hydroxyethyl)-2-methoxybenzenesulfonamide)

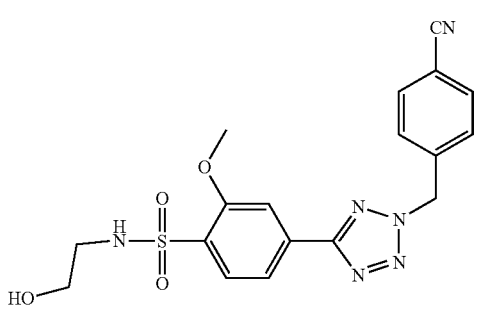

49

To a solution of N-(2-hydroxyethyl)-2-methoxy-4-(2H-tetrazol-5-yl)benzenesulfonamide (200 mg, 0.0006 mol, Intermediate 33) in acetonitrile (2 mL), triethylamine (0.16 mL, 0.0012 mol) was added at 28° C. and stirred at 28° C. for 5 min. Followed by the addition of 4-(bromomethyl)benzonitrile (156 mg, 0.0008 mol, commercial source: AK scientific) at 28° C. The reaction mixture was heated to 80° C. and stirred for 16 h at the same temperature. Reaction was monitored by TLC. On completion of the reaction, the reaction mixture was cooled to 28° C. and concentrated under reduced pressure. The crude was purified by column chromatography (silica gel 100-200 mesh), eluted with 2.5% methanol in dichloromethane. The pure fractions were collected and concentrated under reduced pressure (50 mg, crude). The reaction was repeated two times, each time starting with 200 mg of Intermediate 33, and the obtained crudes were combined and purified by column chromatography (silica gel 100-200 mesh), eluted with 2.5% methanol in dichloromethane. The pure fractions were collected and concentrated under reduced pressure to afford 4-(2-(4-cyanobenzyl)-2H-tetrazol-5-yl)-N-(2-hydroxyethyl)-2-methoxybenzenesulfonamide (28 mg, 11%) as a white solid. $^1$H NMR (400 MHz, DMSO-d$_6$) δ ppm 7.92-7.86 (m, 3H), 7.78-7.73 (m, 2H), 7.60-7.55 (m, 2H), 7.21 (t, J=5.9 Hz, 1H), 6.18 (s, 2H), 4.61 (br s, 1H), 3.99 (s, 3H), 3.37-3.30 (m, 2H), 2.87-2.80 (m, 2H). MS m/z [M+H]$^+$=415.2

Example 50: (4-(2-((5-fluoropyridin-2-yl)methyl)-2H-tetrazol-5-yl)-N-(2-hydroxyethyl)-2-methoxybenzenesulfonamide)

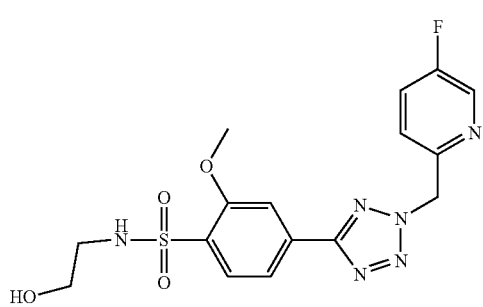

50

144

To a solution of N-(2-hydroxyethyl)-2-methoxy-4-(2H-tetrazol-5-yl)benzenesulfonamide (220 mg, 0.0007 mol, Intermediate 33), 2-(chloromethyl)-5-fluoropyridine (106 mg, 0.0007 mol, Intermediate 9) in acetonitrile (2.2 mL), N,N-diisopropylethylamine (0.24 mL, 0.0014 mol) was added at 26° C. The reaction mixture was heated to 80° C. and stirred for 16 h at the same temperature. Reaction was monitored by TLC. On completion of the reaction, the reaction mixture was cooled to 26° C. and concentrated under reduced pressure. The crude was purified by column chromatography (silica gel 100-200 mesh), eluted with 2.1% methanol in dichloromethane. The pure fractions were collected and concentrated under reduced pressure. The obtained compound was purified by preparative TLC, eluted with 2% methanol in dichloromethane as a mobile phase. The pure fraction was collected and isolated to afford 4-(2-((5-fluoropyridin-2-yl)methyl)-2H-tetrazol-5-yl)-N-(2-hydroxyethyl)-2-methoxybenzenesulfonamide (28 mg, 9.6%) as an off-white solid. $^1$H NMR (400 MHz, DMSO-d$_6$) δ 8.53 (d, J=2.7 Hz, 1H), 7.91-7.87 (m, 1H), 7.84-7.78 (m, 1H), 7.75 (s, 1H), 7.76-7-72 (m, 1H), 7.66-7.61 (m, 1H) 7.21-7.17 (m, 1H), 6.16 (s, 2H), 4.63-4.58 (m, 1H), 3.99 (s, 3H), 3.37-3.30 (m, 2H), 2.84 (q, J=6.4 Hz, 2H). MS m/z [M+H]$^+$=409.13

Example 51: (2-methoxy-N-methyl-4-(2-(pyridin-4-ylmethyl)-2H-tetrazol-5-yl)benzenesulfonamide)

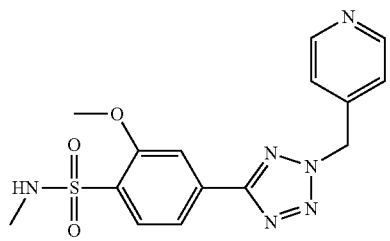

51

To a solution of 2-methoxy-N-methyl-4-(2H-tetrazol-5-yl)benzenesulfonamide (300 mg, 1.114 mmol, Intermediate 35) in N,N-dimethylformamide (10 mL), potassium carbonate (308 mg, 2.229 mmol) and 4-(chloromethyl)pyridine hydrochloride (183 mg, 1.116 mmol, commercial source: Combi-Blocks) were added at 27° C. The reaction mixture was heated to 80° C. and stirred for 3 h at the same temperature. The progress of the reaction was monitored by TLC. On completion of the reaction, the reaction mixture was cooled to 27° C. and concentrated under reduced pressure. The crude was purified by column chromatography (silica gel 100-200 mesh), eluted with 3% methanol in dichloromethane. The pure fractions were collected and concentrated under reduced pressure to afford 2-methoxy-N-methyl-4-(2-(pyridin-4-ylmethyl)-2H-tetrazol-5-yl)benzenesulfonamide (101 mg, 25%) as an off-white solid. $^1$H NMR (400 MHz, DMSO-d$_6$) δ 8.63-8.58 (m, 2H), 7.92-7.87 (m, 1H), 7.80-7.75 (m, 2H), 7.35-7.30 (m, 2H), 7.19-7.14 (m, 1H), 6.14 (s, 2H), 4.00 (s, 3H), 2.43 (d, J=4.8 Hz, 3H). MS m/z [M+H]$^+$=361.0

Example 52: (N-(cyanomethyl)-4-(2-(4-fluorobenzyl)-2H-tetrazol-5-yl)benzenesulfonamide)

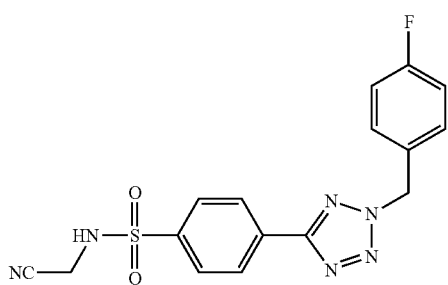

To a solution of 4-(2-(4-fluorobenzyl)-2H-tetrazol-5-yl)benzenesulfonamide (400 mg, 1.2 mmol, Intermediate 44) in ethanol (10 mL), added benzotriazole (144 mg, 1.208 mmol) and formaldehyde (30% aqueous solution) (0.44 mL, 5.867 mmol) were at 27° C. and stirred at 27° C. for 48 h. The precipitated reaction mixture was filtered and the solid was washed with the mixture of ethanol:diethyl ether (1:1, 3×10 mL). The solid was dried under vacuum and treated with potassium cyanide (400 mg, 6.142 mmol) in water (2 mL) for 24 h at 27° C. Reaction was monitored by TLC. On completion of the reaction, the reaction mixture was filtered and washed with the mixture of ethanol: diethyl ether (1:1, 3×10 mL) the filtrate was concentrated. The residue was dissolved in water (10 mL) and extracted with dichloromethane (2×10 mL). The organic layer was dried over anhydrous $Na_2SO_4$, filtered and the filtrate was evaporated under reduced pressure. The crude was purified by prep-HPLC to afford N-(cyanomethyl)-4-(2-(4-fluorobenzyl)-2H-tetrazol-5-yl)benzenesulfonamide (39 mg, 8%) as a white solid. $^1$H NMR (400 MHz, DMSO-$d_6$) δ 8.75 (br s, 1H), 8.28-8.23 (m, 2H), 8.02-7.96 (m, 2H), 7.54-7.47 (m, 2H), 7.28-7.20 (m, 2H), 6.03 (s, 2H), 4.13 (s, 2H). MS m/z [M+H]$^+$=373.00.

Prep-HPLC Conditions:

Column: KROMASIL phenyl (250×25) mm, 10μ

Mobile phase: A—10M ammonium bicarbonate (aq), B—acetonitrile

Method (time in min/% of B): 0/20, 10/65, 10.2/100, 13/100, 13.2/100, 18/20

Flow: 25 mL/min

Temperature: ambient

General Procedure for Boc Deprotection

To a solution of Boc tetrazole derivatives (1 eq) in Dichloromethane (0.2-0.04 M), 2,2,2-trifluoroacetic acid (5 eq) was added at 0° C. under nitrogen. The reaction mixture was stirred at rt for 4-16 h. Then the solution was diluted with water and extracted with DCM twice. The organic layer was dried over anhydrous $Na_2SO_4$, filtered and the filtrate was concentrated under reduced pressure. The crude compound was purified by flash chromatography EtOAc-cyclohexane from 0/100 to 100/0. Alternatively, when the reaction mixture was concentrated under reduced pressure, the crude compound was purified by prep-HPLC. The desired fractions were collected and concentrated in vacuo to yield the final products.

Example 53: 2-(4-(2-(4-fluorobenzyl)-2H-tetrazol-5-yl)-2-methoxyphenylsulfonamido) acetamide

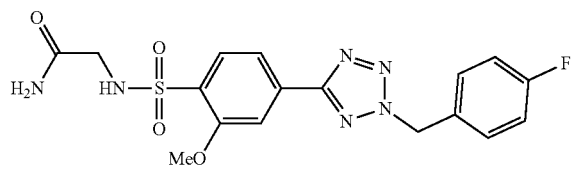

To a solution of tert-butyl (2-amino-2-oxoethyl)((4-(2-(4-fluorobenzyl)-2H-tetrazol-5-yl)-2-methoxyphenyl)sulfonyl)carbamate (240 mg, 0.461 mmol, Intermediate 37) in Dichloromethane (2.3 mL), 2,2,2-trifluoroacetic acid (0.165 mL, 2.305 mmol) was added at 0° C. under nitrogen. The reaction mixture was stirred at rt for 16 h. The solution was diluted with water and extracted with DCM twice. The organic layer was dried over anhydrous $Na_2SO_4$, filtered and the filtrate was concentrated under reduced pressure. The crude compound was purified by flash column chromatography (silica gel; EtOAc-cyclohexane from 0/100 to 100/0). The fractions were collected and concentrated in vacuo to obtain 2-(4-(2-(4-fluorobenzyl)-2H-tetrazol-5-yl)-2-methoxyphenylsulfonamido)acetamide (26 mg, 25%) as a white solid. $^1$H NMR (400 MHz, DMSO-$d_6$) δ 7.91-7.86 (m, 1H), 7.78-7.70 (m, 2H), 7.55-7.46 (m, 2H), 7.40 (br s, 1H), 7.29-7.22 (m, 2H), 7.19 (br s, 1H), 7.05 (br s, 1H), 6.03 (s, 2H), 3.98 (s, 3H), 3.30 (s, 2H). MS m/z [M+H]$^+$=421.2.

Examples 54-61 were prepared by methods analogous to that described for Example 53 replacing the intermediate, solvent and acid conditions with those indicated in Table 4. The method used for purification is indicated as footnotes.

TABLE 4

| Ex. | Structure | Intermediate | DCM/TFA | Yield & Physical data |
|---|---|---|---|---|
| 54 | 2-(4-(2-(4-cyanobenzyl)-2H-tetrazol-5-yl)-2-methoxyphenylsulfonamido) acetamide (See footnote a) | tert-butyl (2-amino-2-oxoethyl)((4-(2-(4-cyanobenzyl)-2H-tetrazol-5-yl)-2-methoxyphenyl)sulfonyl) carbamate (1 eq, 240 mg, 0.364 mmol, Intermediate 39) | 3 mL/ 0.26 mL | Yield: 44.4%, white solid. $^1$H NMR (400 MHz, DMSO-$d_6$) δ 7.96-7.85 (m, 3H), 7.79-7.70 (m, 2H), 7.59 (d, J = 8.3 Hz, 2H), 7.43 (t, J = 5.9 Hz, 1H), 7.21 (br s, 1H), 7.07 (br s, 1H), 6.20 (s, 2H), 4.02-3.95 (m, 3H), 3.48 (d, J = 5.8 Hz, 2H). MS m/z [M − H]$^-$ = 426.11. |

TABLE 4-continued

| Ex. | Structure | Intermediate | DCM/TFA | Yield & Physical data |
|---|---|---|---|---|
| 55 | 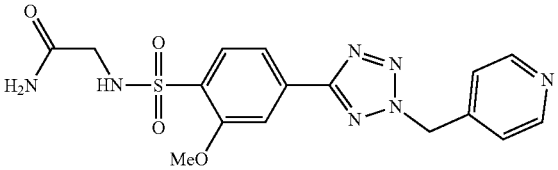<br>2-(2-methoxy-4-(2-(pyridin-4-ylmethyl)-2H-tetrazol-5-yl)phenylsulfonamido) acetamide<br>(See footnote a) | tert-butyl (2-amino-2-oxoethyl)((2-methoxy-4-(2-(pyridin-4-ylmethyl)-2H-tetrazol-5-yl)phenyl)sulfonyl)carbamate (1 eq, 39 mg, 0.077 mmol, Intermediate 41) | 2 mL/ 0.056 | Yield: 38%, white solid. $^1$H NMR (400 MHz, DMSO-d$_6$) δ 8.67-8.57 (m, 2H), 7.95-7.86 (m, 1H), 7.80-7.73 (m, 2H), 7.49-7.40 (m, 1H), 7.38-7.30 (m, 2H), 7.08 (br s, 1H), 6.16 (s, 2H), 4.00 (s, 3H), 3.48 (d, J = 5.3 Hz, 2H). MS m/z [M + H]$^+$ = 404.11. |
| 56 | 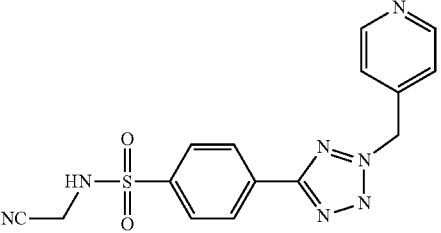<br>(N-(cyanomethyl)-4-(2-(pyridinylmethyl)-2H-tetrazol-5-yl)benzenesulfonamide)<br>(See footnote b) | tert-butyl (cyanomethyl) ((4-(2-(pyridin-4-ylmethyl)-2H-tetrazol-5-yl)phenyl)sulfonyl)carbamate (100 mg, 0.219 mmol, Intermediate 46) | 5 mL/ 0.2 mL | Yield: 18%, off-white solid. $^1$H NMR (400 MHz, DMSO-d$_6$) δ 8.75-8.55 (m, 3H), 8.30 (d, J = 8.8 Hz, 2H), 8.02 (d, J = 8.6 Hz, 2H), 7.35 (d, J = 5.9 Hz, 2H), 6.15 (s, 2H), 4.15 (s, 2H). MS m/z [M + H]$^+$ = 356.00 |
| 57 | 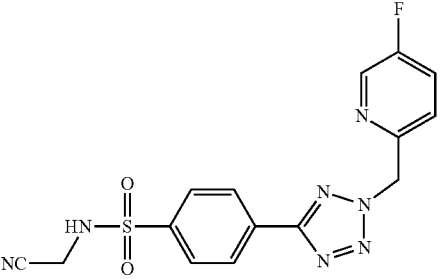<br>(N-(cyanomethyl)-4-(2-((5-fluoropyridin-2-yl)methyl)-2H-tetrazol-5-yl)benzenesulfonamide)<br>(See footnote c) | tert-butyl (cyanomethyl) ((4-(2-((5-fluoropyridin-2-yl)methyl)-2H-tetrazol-5-y))phenyl) sulfonyl) carbamate (600 mg, 1.268 mmol, Intermediate48) | 12 mL/ 9 mL | Yield: 20%, white solid. $^1$H NMR (400 MHz, DMSO-d$_6$) δ 8.70 (br s, 1H), 8.54 (d, J = 3.1 Hz, 1H), 8.32-8.26 (m, 2H), 8.05-7.98 (m, 2H), 7.86-7.81 (m, 1H), 7.68-7.64 (m, 1H), 6.18 (s, 2H), 4.14 (s, 2H). MS m/z [M + H]$^+$ = 374.02. |
| 58 | 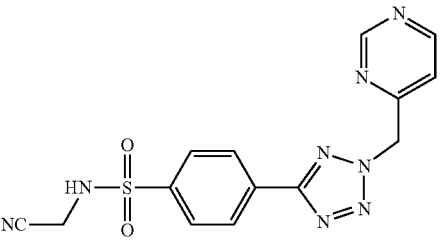<br>(N-(cyanomethyl)-4-(2-(pyrimidin-4-ylmethyl)-2H-tetrazol-5-yl)benzene sulfonamide<br>(See footnote d) | tert-butyl cyanomethyl(4-(2-(pyrimidin-4-ylmethyl)-2H-tetrazol-5-yl)phenylsulfonyl) carbamate (250 mg, 0.548 mmol, Intermediate 50) | 5 mL/ 3.5 mL | Yield: 17%, off white solid. $^1$H NMR (400 MHz, DMSO-d$_6$) δ 9.11 (d, J = 1.1 Hz, 1H), 8.85 (d, J = 5.0 Hz, 1H), 8.25 (d, J = 8.3 Hz, 2H), 7.97 (d, J = 8.3 Hz, 2H), 7.57 (d, J = 5.3 Hz, 1H), 6.25 (s, 2H), 4.09 (s, 2 H). MS m/z [M + H]$^+$ = 357.03. |

TABLE 4-continued

| Ex. | Structure | Intermediate | DCM/TFA | Yield & Physical data |
|---|---|---|---|---|
| 59 | 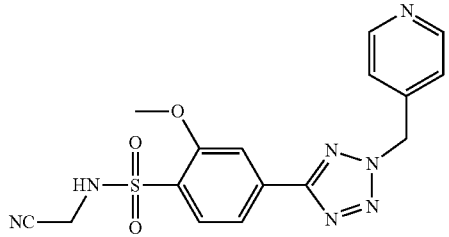<br>(N-(cyanomethyl)-2-methoxy-4-(2-(pyridin-4-ylmethyl)-2H-tetrazol-5-yl)benzenesulfonamide)<br>(See footnote e) | tert-butyl (cyanomethyl) ((2-methoxy-4-(2-(pyridin-4-ylmethyl)-2H-tetrazol-5-yl)phenyl)sulfonyl) carbamate (300 mg, 0.618 mmol, Intermediate 53) | 10 mL/ 1 mL | Yield: 29%, off-white solid. $^1$H NMR (400 MHz, DMSO-$d_6$) δ 8.65-8.56 (m, 2H), 8.31 (br s, 1H), 7.95 (d, J = 8.4 Hz, 1H), 7.84-7.75 (m, 2H), 7.44-7.26 (m, 2H), 6.15 (s, 2H), 4.14 (s, 2H), 4.03 (s, 3H). MS m/z [M + H]$^+$ = 386.16. |
| 60 | 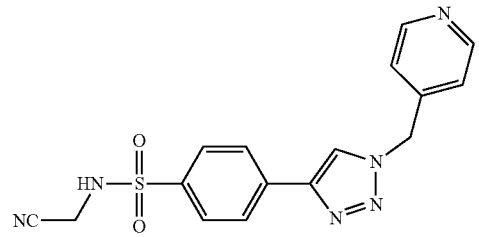<br>(N-(cyanomethyl)-4-(1-(pyridin-4-ylmethyl)-1H-1,2,3-triazol-4-yl)benzenesulfonamide)<br>(See footnote f) | tert-butyl (cyanomethyl) ((4-(1-(pyridin-4-ylmethyl)-1H-1,2,3-triazol-4-yl)phenyl)sulfonyl) carbamate (500 mg, 1.1 mmol, Intermediate 73) | 10 mL/ 2 mL | Yield: 36%, off-white solid. $^1$H NMR (400 MHz, DMSO-$d_6$) δ 8.86 (s, 1H), 8.68-8.50 (m, 3H), 8.10 (d, J = 8.5 Hz, 2H), 7.91 (d, J = 8.5 Hz, 2H), 7.41-7.24 (m, 2H), 5.77 (s, 2H), 4.13 (s, 2H). MS m/z [M + H]$^+$ = 355.14 |
| 61 | 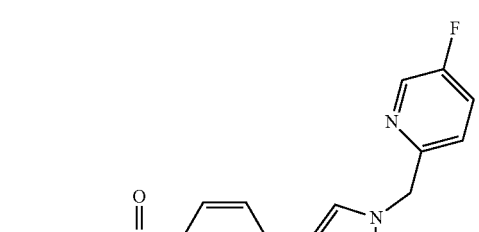<br>(N-(cyanomethyl)-4-(1-((5-fluoropyridin-2-yl)methyl)-1H-1,2,3-triazol-4-yl)benzenesulfonamide)<br>(see footnote g) | tert-butyl (cyanomethyl) ((4-(1-((5-fluoropyridin-2-yl)methyl)-1H-1,2,3-triazol-4-yl)phenyl) sulfonyl) carbamate (2 g, 4.233 mmol, Intermediate 75) | 20 mL/ 10 mL | Yield: 41%, white solid. $^1$H NMR (400 MHz, DMSO-$d_6$) δ 8.81 (s, 1H), 8.55 (d, J = 2.9 Hz, 1H), 8.54 (br s, 1H), 8.12-8.07 (m, 2H), 7.91-7.86 (m, 2H), 7.81-7.76 (m, 1H), 7.54-7.49 (m, 1H), 5.79 (s, 2H), 4.12 (s, 2H). MS m/z [M + H]$^+$ = 373.09 | a) Residue was purified by flash chromatography EtOAc-cyclohexane from 0/100 to 100/0
b) Residue was purified by HPLC preparative Kromasil C18 column (25 × 150 mm, 10μ, Flow: 30 mL/min) Mobile phase: A: H$_2$O (10 mM NH$_4$HCO$_3$) B: ACN; Method (time in min/% of B): 0/10, 1/10, 10/45, 10.5/100, 12.5/100, 13/10, 15/10
c) Residue was purified by HPLC preparative Diasogel C18 column (25 × 150 mm, 8μ, Flow: 20 mL/min) Mobile phase: A: H$_2$O (10 mM NH$_4$HCO$_3$) B: ACN; Method (time in min/% of B): 0/30, 1/30, 10/55, 11.5/55, 11.8/98, 14/98, 14.5/30, 17/30
d) Residue was purified by HPLC preparative Diasogel C18 column (25 × 150 mm, 8μ, Flow: 20 mL/min) Mobile phase: A: H$_2$O (10mM NH$_4$HCO$_3$) B: ACN; Method (time in min/% of B): 0/35, 7.5/35, 8/100, 10/100, 10.2/35, 13/35.
e) Residue was purified by HPLC preparative Phenomenex Luna C18 column (21.2 × 250 mm, 5μ Flow; 30 mL/min) Mobile phase: A: H$_2$O (10 mM NH$_4$HCO$_3$) B: ACN + methanol; Method (time in min/% of B): 0/30, 1/20, 10/60, 11.5/100, 13/100, 13.5/30, 16/30
f) Residue was purified by HPLC preparative Luna C18 column (21.2 × 250 mm, 5μ Flow: 20 mL/min) Mobile phase: A: H$_2$O (10 mM NH$_4$HCO$_3$) B: ACN; Method (time in min/% of B): 0/10, 10/60, 10.3/100, 12.7/100, 13/10, 15/10
g) Residue was purified by HPLC preparative Luna C18 column (25 × 150 mm, 10μ Flow: 25 mL/min) Mobile phase: A: H$_2$O (10 mM NH$_4$HCO$_3$) B: ACN; Method (time in min/% of B): 0/30, 1/30, 7/60, 10/60, 10.2/100

General Procedure for 1,4-Disubstituted 1,2,3-Triazole by a Click Cycloaddition

To a solution of terminal acetylenes (1 eq) and aromatic azides (1 eq) in a 1:1 mixture of ethanol (0.2M) and water (0.2M) were added copper sulphate pentahydrate (0.1 eq) and sodium L-ascorbate (0.3 eq) at rt. The resultant reaction mixture was stirred at rt for 16 h. The progress of the reaction was monitored by TLC. On completion of the reaction, the reaction mixture was concentrated under reduced pressure. The crude compound was purified. The desired fractions were collected and concentrated in vacuo to yield the products.

Example 62: (4-(1-((5-fluoropyridin-2-yl)methyl)-1H-1,2,3-triazol-4-yl)-N-(2-hydroxyethyl)benzene sulfonamide)

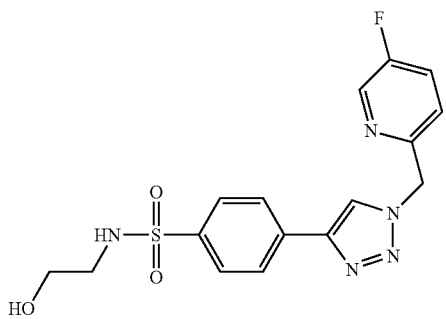

To a solution of 4-ethynyl-N-(2-hydroxyethyl) benzene sulfonamide (200 mg, 0.8888 mmol, Intermediate 62) and 2-(azidomethyl)-5-fluoropyridine (135 mg, 0.8888 mmol, Intermediate 57) in ethanol (5 mL) and water (5 mL), copper sulphate pentahydrate (22 mg, 0.0888 mmol) and sodium L-ascorbate (53 mg, 0.2666 mmol) were added at 27° C. The resultant reaction mixture was stirred at 27° C. for 16 h. The progress of the reaction was monitored by TLC. On completion of the reaction, the reaction mixture was concentrated under reduced pressure. The crude compound was purified by column chromatography (silica gel 100-200 mesh) using 2% methanol in dichloromethane. The pure fractions were collected and concentrated under reduced pressure. The obtained compound was purified by prep-HPLC to afford 4-(1-((5-fluoropyridin-2-yl)methyl)-1H-1,2,3-triazol-4-yl)-N-(2-hydroxyethyl)benzene sulfonamide (52 mg, 15%) as a white solid. $^1$H NMR (400 MHz, DMSO-$d_6$) δ 8.78 (s, 1H), 8.55 (d, J=3.1 Hz, 1H), 8.08-8.03 (m, 2H), 7.88-7.82 (m, 2H), 7.82-7.75 (m, 1H), 7.60 (br s, 1H), 7.54-7.48 (m, 1H), 5.79 (s, 2H), 4.65 (br s, 1H), 3.36 (t, J=6.4 Hz, 2H), 2.81 (t, J=6.4 Hz, 2H). MS m/z [M+H]$^+$=378.40

Prep-HPLC Conditions:

Column: Puritas C18 (250×30) mm, 10μ

Mobile Phase: A—10 mM Ammonium Bicarbonate(Aq), B—Acetonitrile

Method (time in min/% of B)=0/10, 10/60, 10.3/100, 12.7/100, 13/10, 15/10

Flow: 25 mL/min

Temperature: Ambient

Examples 63-69 were prepared by methods analogous to that described for Example 62 replacing the intermediates with those indicated in Table 5. The method used for purification is indicated as footnotes.

TABLE 5

| Ex. | Structure | Terminal acetylenes | Aromatic azides | Yield & Physical data |
| --- | --- | --- | --- | --- |
| 63 | (N-(2-hydroxyethyl)-4-(1-(4-methoxybenzyl)-1H-1,2,3-triazol-4-yl)benzenesulfonamide) (See footnote a) | 4-ethynyl-N-(2-hydroxyethyl)benzenesulfonamide (200 mg, 0.8888 mmol, Intermediate 62) | 1-(azidomethyl)-4-methoxybenzene (145 mg, 0.8888 mmol, commercial source: Alfa Aesar) | Yield: 28%, off white solid. $^1$H NMR (400 MHz, DMSO-$d_6$) δ 8.72 (s, 1H), 8.04 (d, J = 8.5 Hz, 2H), 7.84 (d, J = 8.5 Hz, 2H), 7.59 (t, J = 5.9 Hz, 1H), 7.34 (d, J = 8.7 Hz, 2H), 7.02-6.88 (m, 2H), 5.58 (s, 2H), 4.65 (t, J = 5.6 Hz, 1H), 3.74 (s, 3H), 3.39-3.31 (m, 2H), 2.83-2.77 (m, 2H). MS m/z [M − H]$^-$ = 387.17 |
| 64 | (4-(1-(4-fluorobenzyl)-1H-1,2,3-triazol-4-yl)-N-(2-hydroxyethyl)benzenesulfonamide) (See footnote b) | 4-ethynyl-N-(2-hydroxyethyl)benzenesulfonamide (1 g, 4.439 mmol, Intermediate 62) | 1-(azidomethyl)-4-fluorobenzene (2M in diethylether) (100 mL) (Intermediate 54) | Yield: 30%, off-white solid. $^1$H NMR (400 MHz, DMSO-$d_6$) δ 8.76 (s, 1H) 8.06-8.01 (m, 2H), 7.86-7.82 (m, 2H), 7.62-7.56 (m, 1H), 7.46-7.40 (m, 2H), 7.26-7.19 (m, 2H), 5.66 (s, 2H), 4.64 (t, J = 5.6 Hz, 1H), 3.40-3.31 (m, 2H), 2.83-2.77 (m, 2H). MS m/z [M + H]$^+$ = 377.16 |

TABLE 5-continued

| Ex. | Structure | Terminal acetylenes | Aromatic azides | Yield & Physical data |
|---|---|---|---|---|
| 65 | 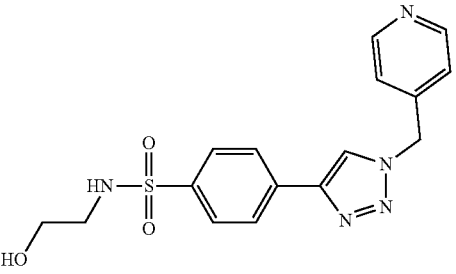<br>(N-(2-hydroxyethyl)-4-(1-(pyridin-4-ylmethyl)-1H-1,2,triazol-4-yl)benzenesulfonamide)<br>(See footnote c) | 4-ethynyl-N-(2-hydroxyethyl)benzenesulfonamide (500 mg, 2.222 mmol, Intermediate 62) | 4-(azidomethyl)pyridine (293 mg, 2.22 mmol, Intermediate 55) | Yield: 32%, off-white solid. $^1$H NMR (400 MHz, DMSO-$d_6$) δ 8.82 (s, 1H), 8.59-8.56 (m, 2H), 8.09-8.04 (m, 2H), 7.91-7.83 (m, 2H), 7.60 (br s, 1H), 7.27-7.24 (m, 2H), 5.76 (s, 2H), 4.65 (t, J = 5.5 Hz, 1H), 3.39-3.33 (m, 2H), 2.84-2.78 (m, 2H). MS m/z [M + H]$^+$ = 360.1. |
| 66 | 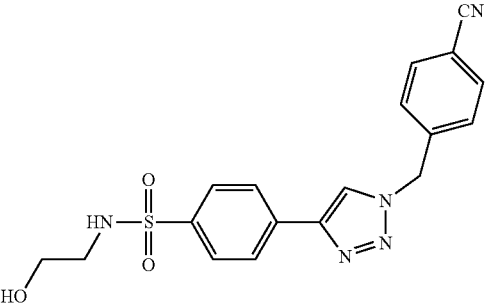<br>(4-(1-(4-cyanobenzyl)-1H-1,2,3-triazol-4-yl)-N-(2-hydroxyethyl)benzenesulfonamide)<br>(See footnote b) | 4-ethynyl-N-(2-hydroxyethyl)benzenesulfonamide (500 mg, 2.222 mmol, Intermediate 62) | 4-(azidomethyl)benzonitrile (351 mg, 2.222 mmol, Intermediate 56) | Yield: 32%, off-white solid. $^1$H NMR (400 MHz, DMSO-$d_6$) δ 8.81 (s, 1H), 8.08-8.01 (m, 2H), 7.90-7.83 (m, 4H), 7.60 (t, J = 5.9 Hz, 1H), 7.54-7.48 (m, 2H), 5.81 (S, 2H), 4.65 (t, J = 5.6 Hz, 1H), 3.36 (q, J = 6.1 Hz, 2H), 2.81 (q, J = 6.1 Hz, 2H). MS m/z [M + H]$^+$ = 384.08. |
| 67 | 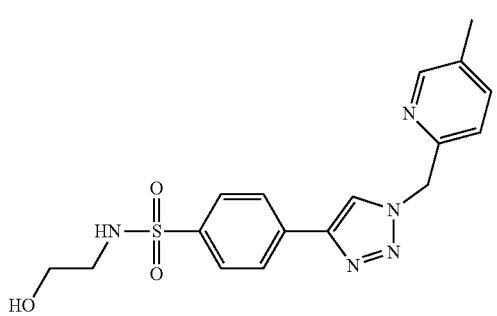<br>(N-(2-hydroxyethyl)-4-(1-((5-methylpyridin-2-yl)methyl)-1,2,3-triazol-4-yl)benzenesulfonamide)<br>(See footnote b) | 4-ethynyl-N-(2-hydroxyethyl)benzenesulfonamide (200 mg, 0.889 mmol, Intermediate 62) | 2-(azidomethyl)-5-methylpyridine (131 mg, 0.885 mmol, Intermediate 58) | Yield: 36%, off-white solid. $^1$H NMR (400 MHz, DMSO-$d_6$) δ 8.77 (s, 1H), 8.38 (m, 1H), 8.06 (d, J = 8.6 Hz, 2H), 7.85 (d, J = 8.5 Hz, 2H), 7.65 (dd, J = 8.0, 1.6 Hz, 1H), 7.59 (t, J = 5.9 Hz, 1H), 7.28 (d, J = 7.9 Hz, 1H), 5.72 (s, 2H), 4.65 (br s, 1H), 3.41-3.31 (m, 2H), 2.81 (q, J = 6.3 Hz, 2H), 2.28 (s, 3H). MS m/z [M + H]$^+$ = 374.08. |

TABLE 5-continued

| Ex. | Structure | Terminal acetylenes | Aromatic azides | Yield & Physical data |
|---|---|---|---|---|
| 68 | (2-(4-(1-(4-fluorobenzyl)-1H-1,2,3-triazol-4-yl)phenylsulfonamido)acetamide) (See footnote d) | 2-(4-ethynylphenyl-sulfonamido)acetamide (500 mg, 0.0021 mol, Intermediate 65) | 1-(azidomethyl)-4-fluorobenzene (317 mg, 0.0021 mol, Intermediate 54) | Yield: 8.5%, white solid. $^1$H NMR (400 MHz, DMSO-$d_6$) δ 8.77 (s, 1H), 8.05-7.99 (m, 2H), 7.88-7.81 (m, 2H), 7.46-7.39 (m, 2H), 7.27-7.18 (m, 3H), 7.05 (brs, 1H), 6.89 (br s, 1H), 5.66 (s, 2H), 3.38 (s, 2H). MS m/z [M − H]$^−$ = 388.12 |
| 69 | (2-(4-(1-((4,4-difluorocyclohexyl)methyl)-1H-1,2,3-triazol-4-yl)phenylsulfonamido)acetamide) (See footnote e) | 2-(4-ethynylphenyl-sulfonamido)acetamide (400 mg, 0.0016 mol, Intermediate 65) | 4-(azidomethyl)-1,1-difluoro-cyclohexane (294 mg, 0.0016 mol, Intermediate 59) | Yield: 2.8%, off-white solid. $^1$H NMR (400 MHz, DMSO-$d_6$) δ 8.70 (s, 1H), 8.02 (d, J = 8.8 Hz, 2H), 7.86 (d, J = 8.8 Hz, 2H) 7, 86 (br s, 1H), 7.24 (br s, 1H), 7.05 (br s, 1H), 4.37 (d, J = 7.0 Hz, 2H), 3.39 (s, 2H), 2.10-1.96 (m, 3H), 1.89-1.61 (m, 4H), 1.36-1.21 (m, 2H). MS m/z [M + H]$^+$ = 414.1. | a) Residue was purified by flash chromatography using 2% methanol in dichloromethane.
b) Residue was purified by flash chromatography using 5% methanol in dichloromethane.
c) Residue was purified by flash chromatography using 10% methanol in dichloromethane. Finally, the residue was purified by HPLC preparative using HPLC preparative Kromasil Phenyl column (25 × 150 mm, 10μ, Flow: 30 mL/min) Mobile phase: A: H₂O (10 mM NH₄HCO₃) B: ACN; Method (time in min/% of B): 0/20, 1/20, 8.5/53.3, 9/100, 11.5/100, 12/20, 14/20
d) Residue was purified by HPLC preparative Kromasil C18 column (25 × 150 mm, 10μ, Flow: 25 mL/min) Mobile phase: A: H₂O (10mM NH₄HCO₃) B: ACN; Method (time in min/% of B): 0/37, 7/37, 7.5/100, 9/100, 9.5/37
e) Residue was purified by flash chromatography using 5% methanol in dichloromethane. Finally, the residue was purified by HPLC preparative using HPLC preparative Kromasil C18 column (25 × 150 mm, 10μ, Flow: 25 mL/min) Mobile phase: A: H₂O (10 mM NH₄HCO₃) B: ACN; Method (time in min/% of B): 0/10, 1/10, 10.5/100, 14/100, 14.5/10

Example 70: (R)-4-(1-(4-fluorobenzyl)-1H-1,2,3-triazol-4-yl)-N-(2-hydroxypropyl) benzenesulfonamide

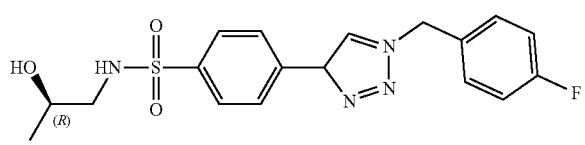

To a solution of 1-(azidomethyl)-4-fluorobenzene (45 mg, 0.420 mmol, Intermediate 54) and (R)-4-ethynyl-N-(2-hydroxypropyl)benzenesulfonamide (50 mg, 0.209 mmol, Intermediate 68) in 1:1 Ethanol (1 mL)/Water (1 mL), CuSO₄ (6 mg, 0.042 mmol) and sodium ascorbate (24 mg, 0.126 mmol) were added each in one portion. The resulting suspension was stirred at room temperature for 16 h. The resulting mixture was partitioned between water (30 mL) and EtOAc (50 mL). The aqueous layer was extracted with additional EtOAc (2×50 mL). The combined organic layers were dried (MgSO₄), filtered and concentrated to give (R)-4-(1-(4-fluorobenzyl)-1H-1,2,3-triazol-4-yl)-N-(2-hydroxypropyl)benzenesulfonamide (54 mg, 0.138 mmol, 66.2%) as a white solid. $^1$H NMR (400 MHz, DMSO-$d_6$) δ 8.78 (s, 1H), 8.06-8.02 (m, 2H), 7.87-7.81 (m, 2H), 7.60 (t, J=6.2 Hz, 1H), 7.47-7.39 (m, 2H), 7.27-7.19 (m, 2H), 5.66 (s, 2H), 4.69 (d, J=4.5 Hz, 1H), 3.61-3.53 (m, 1H), 2.71-2.58 (m, 2H), 0.97 (d, J=6.1 Hz, 3H). MS m/z [M+H]$^+$=391.2.

Example 71: 4-(2-((5-fluoropyridin-2-yl)methyl)-2H-tetrazol-5-yl)-N-(2-hydroxyethyl)-2-methyl Benzenesulfonamide

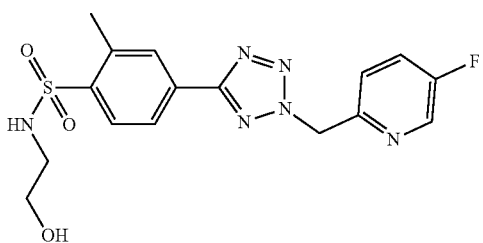

To a solution of N-(2-hydroxyethyl)-2-methyl-4-(2H-tetrazol-5-yl)benzenesulfonamide (250 mg, 0.882 mmol, Intermediate 79) in acetonitrile (5 mL), N,N-diisopropylethylamine (0.46 mL, 2.64 mmol, commercial source: Vinsa) was added, followed by the addition of 2-(chloromethyl)-5-fluoropyridine (192.6 mg, 1.32 mmol, Intermediate 9) at 26° C. The reaction mixture was heated to 85° C. for 16 h. Upon completion, the reaction mixture was cooled to 26° C. and diluted with ethyl acetate (50 mL) and washed with water (20 mL). The organic layer was separated, dried over anhydrous $Na_2SO_4$ and filtered. The filtrate was evaporated under reduced pressure. The crude was purified by column chromatography (silica gel 100-200 mesh), eluted with 1.5% methanol in dichloromethane. The pure fractions were concentrated under reduced pressure to afford 4-(2-((5-fluoropyridin-2-yl)methyl)-2H-tetrazol-5-yl)-N-(2-hydroxyethyl)-2-methylbenzenesulfonamide (89 mg, 25.4%) as a pale yellow solid. $^1$H NMR (400 MHz, DMSO-$d_6$) δ 8.53 (d, J=3.2 Hz, 1H), 8.07-7.97 (m, 3H), 7.84-7.75 (m, 2H), 7.66-7.63 (m, 1H), 6.16 (s, 2H), 4.63 (t, J=5.4 Hz, 1H), 3.33 (q, J=6.4 Hz, 2H), 2.86 (q, J=6.4 Hz, 2H), 2.66 (s, 3H). MS m/z [M+H]$^+$=393.06.

Example 72: N-(2-hydroxyethyl)-2-methyl-4-(2-((tetrahydro-2H-pyran-2-yl)methyl)-2H-tetrazol-5-yl)benzenesulfonamide

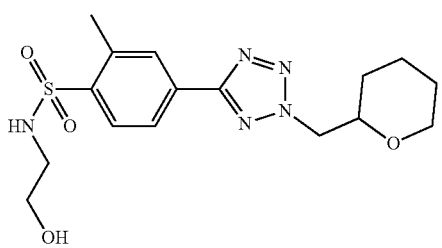

To a solution of N-(2-hydroxyethyl)-2-methyl-4-(2H-tetrazol-5-yl)benzenesulfonamide (350 mg, 1.23 mmol, Intermediate 79) in acetonitrile (7.0 mL), N,N-diisopropylethylamine (1.07 mL, 6.17 mmol, commercial source: Vinsa) was added, followed by the addition of 2-(bromomethyl)tetrahydro-2H-pyran (663 mg, 3.70 mmol, commercial source: Sigma Aldrich) at 26° C. The reaction mixture was heated to 85° C. for 16 h. Upon completion, the reaction mixture was cooled to 26° C. and diluted with ethyl acetate (100 mL) and washed with water (20 mL). The organic layer was separated, dried over anhydrous $Na_2SO_4$ and filtered. The filtrate was evaporated under reduced pressure. The crude was purified by column chromatography (silica gel 100-200 mesh), eluted with 1.5% methanol in dichloromethane. The pure fractions were concentrated under reduced pressure to afford N-(2-hydroxyethyl)-2-methyl-4-(2-((tetrahydro-2H-pyran-2-yl)methyl)-2H-tetrazol-5-yl)benzenesulfonamide which was submitted for chiral SFC separation.

SFC Conditions:
Column/dimensions: Chiralcel OJ-H (21×250 mm), 5μ
% $CO_2$: 90.0%
% Co solvent: 10.0% (100% MeOH)
Total Flow: 60.0 g/min
Back Pressure: 90.0 bar
UV: 254 nm
Stack time: 4.3 min
Load/Inj: 3.7 mg The collected SFC fractions were concentrated under reduced pressure to afford Isomer 1 (21 mg) as a pale yellow gum and another fraction (25 mg).

Isomer 1: $^1$H NMR (400 MHz, DMSO-$d_6$) δ 8.09-7.97 (m, 3H), 7.79 (br s, 1H), 4.79-4.72 (m, 2H), 4.64 (br s, 1H), 3.93-3.88 (m, 1H), 3.83-3.78 (m, 1H), 3.38-3.33 (m, 2H), 3.29-3.27 (m, 1H), 2.89-2.85 (m, 2H), 2.67 (s, 3H), 1.85-1.68 (m, 2H), 1.56-1.31 (m, 4H). MS m/z [M−H]$^-$=380.14. ee %=98.30%.

The other fraction (25 mg) was submitted again for chiral SFC to obtain Isomer 2 (12 mg) as a pale yellow gum.

SFC Conditions:
Column/dimensions: Chiralcel OJ-H (21×250 mm), 5μ
% $CO_2$: 80.0%
% Co solvent: 20.0% (100% MeOH)
Total Flow: 60.0 g/min
Back Pressure: 90.0 bar
UV: 254 nm
Stack time: 2.0 min
Load/Inj: 0.78 mg Isomer 2: $^1$H NMR (400 MHz, DMSO-$d_6$) δ 8.16-7.98 (m, 3H), 7.82 (br s, 1H), 4.82-4.76 (m, 2H), 4.68 (t, J=5.5 Hz, 1H), 3.95-3.88 (m, 1H), 3.83-3.77 (m, 1H), 3.37-3.34 (m, 2H), 3.28-3.23 (m, 1H), 2.86 (t, J=6.4 Hz, 2H), 2.67 (s, 3H), 1.87-1.77 (m, 1H), 1.75-1.69 (m, 1H), 1.55-1.38 (m, 4H), 1.28-1.23 (m, 1H). MS m/z [M−H]$^-$=380.05. ee %=97.41%.

The absolute configuration has not been determined.

Example 73: 4-(2-((5-fluoropyridin-2-yl)methyl)-2H-tetrazol-5-yl)-N-(2-hydroxyethyl)-3-methylbenzenesulfonamide

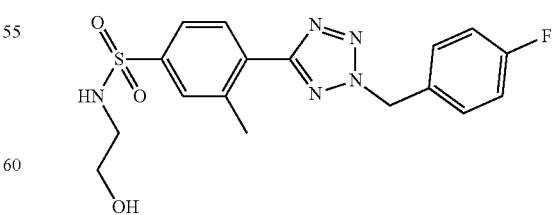

To a solution of N-(2-hydroxyethyl)-3-methyl-4-(2H-tetrazol-5-yl)benzenesulfonamide (0.6 g, 2.11 mmol, Intermediate 83) in acetonitrile (10 mL), N,N-diisopropylethylamine (0.9 mL, 5.27 mmol, commercial source: Vinsa) was added followed by the addition of 2-(chloromethyl)-5-fluoropyridine (0.43 g, 1.56 mmol, Intermediate 9) at 26° C. The reaction mixture was heated to 85° C. for 16 h. Upon completion, the reaction mixture was diluted with ethyl acetate (250 mL), washed with water (2×100 mL) and brine solution (100 mL). The organic layer was dried over anhydrous $Na_2SO_4$, filtered and the filtrate was evaporated under reduced pressure. The crude was purified by prep-HPLC (Prep HPLC conditions: XBridge C18 Column (250×19) mm, 5 u; Mobile Phase A: 10 mM Ammonium Bicarbonate (aq), Mobile Phase B: Acetonitrile; Method (time in min/% of B): 0/10, 1/10, 10/30, 12.8/100, 17.8/100, 18/30, 21/30; Flow: 16 mL/Min, Temp: ambient). The pure fractions were collected, lyophilized and triturated with pentane to afford 4-(2-((5-fluoropyridin-2-yl)methyl)-2H-tetrazol-5-yl)-N-(2-hydroxyethyl)-3-methylbenzenesulfonamide (145 mg, 34.7%) as a white solid. $^1$H NMR (400 MHz, DMSO-$d_6$) δ 8.56-8.53 (m, 1H), 8.14-8.10 (m, 1H), 7.86-7.75 (m, 3H), 7.66-7.60 (m, 1H), 7.0 (br s, 1H), 6.17 (s, 2H), 4.69-4.63 (m, 1H), 3.38 (q, J=5.9 Hz, 2H), 2.84 (t, J=6.2 Hz, 2H), 2.62 (s, 3H). MS m/z [M+H]$^+$=391.17.

Example 74: N-(2-hydroxyethyl)-3-methyl-4-(2-((tetrahydro-2H-pyran-2-yl)methyl)-2H-tetrazol-5-yl)benzenesulfonamide

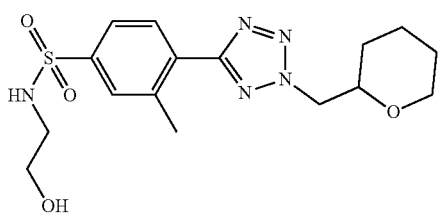

74

To a solution of N-(2-hydroxyethyl)-3-methyl-4-(2H-tetrazol-5-yl)benzenesulfonamide (1.0 g, 3.32 mmol, Intermediate 83) in N,N-dimethylformamide (10.0 mL), potassium carbonate (0.97 g, 7.04 mmol, commercial source: RCP) was added, followed by the addition of 2-(bromomethyl)tetrahydro-2H-pyran (0.75 g, 4.22 mmol, commercial source: Sigma Aldrich) at 26° C. The reaction mixture was heated to 100° C. for 12 h. Upon completion, the reaction mixture was cooled to 26° C. and quenched with ice cold water (100 mL). The mixture was washed with water (3×100 mL) and brine solution (50 mL). The organic extract was dried over anhydrous $Na_2SO_4$, filtered and the filtrate was evaporated under reduced pressure. The crude was purified by column chromatography, eluted with 2% methanol in DCM. The pure fractions were concentrated under reduced pressure to obtain a product which was further purified by prep-HPLC (YMC Triart C18 column (25×150 mm, 10μ Flow: 25 mL/min), Mobile phase: A: $H_2O$ (10 mM $NH_4HCO_3$) B: ACN; Method (time in min/% of B): 0/25, 1/25, 10/65, 105/100, 12/100, 12.5/25, 15/25; temperature: ambient). The pure fractions were collected and lypholized to afford N-(2-hydroxyethyl)-3-methyl-4-(2-((tetrahydro-2H-pyran-2-yl)methyl)-2H-tetrazol-5-yl)benzenesulfonamide which was submitted for chiral SFC separation.

SFC Conditions:
Column/dimensions: Lux Cellulose-2 (30×250 mm), 5μ
% $CO_2$: 60.0%
% Co solvent: 40.0% (100% MeOH)
Total Flow: 60.0 g/min Back Pressure: 100.0 bar
UV: 214 nm
Stack time: 3.5 min
Load/Inj: 10.0 mg The collected SFC fractions were concentrated under reduced pressure to afford:

Isomer 1: (33 mg) as an off-white solid. $^1$H NMR (400 MHz, DMSO-$d_6$) δ 8.14 (d, J=8.1 Hz, 1H), 7.81 (d, J=1.4 Hz, 1H), 7.81-7.76 (m, 1H), 7.73 (s, 1H), 4.83-4.79 (m, 2H), 4.71 (t, J=5.5 Hz, 1H), 3.96-3.90 (m, 1H), 3.84-3.79 (m, 1H), 3.41-3.36 (m, 2H), 3.30-3.27 (m, 1H), 2.84 (t, J=6.2 Hz, 2H), 2.66 (s, 3H), 1.86-1.79 (m, 1H), 1.76-1.70 (m, 1H), 1.56-1.35 (m, 4H). MS m/z [M–H]$^-$=380.21. ee %=99.80%

Isomer 2: (33 mg) as an off-white solid. $^1$H NMR (400 MHz, DMSO-$d_6$) δ 8.16-8.12 (m, 1H), 7.84-7.77 (m, 2H), 7.70-7.65 (m, 1H), 4.81-4.78 (m, 2H), 4.68-4.64 (m, 1H), 3.97-3.90 (m, 1H), 3.84-3.78 (m, 1H), 3.41-3.35 (m, 2H), 3.28-3.24 (m, 1H), 2.88-2.81 (m, 2H), 2.66 (s, 3H), 1.85-1.71 (m, 2H), 1.60-1.37 (m, 4H). MS m/z [M–H]$^-$=380.14. ee %=94.23%

Their absolute configuration has not been determined.

Example 75: 2-fluoro-4-(2-((5-fluoropyridin-2-yl)methyl)-2H-tetrazol-5-yl)-N-(2-hydroxyethyl) benzenesulfonamide

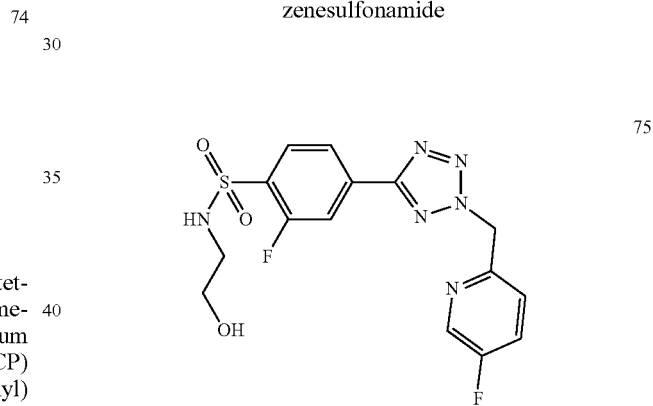

75

To a solution of 2-fluoro-N-(2-hydroxyethyl)-4-(2H-tetrazol-5-yl)benzenesulfonamide (300 mg, 1.044 mmol, Intermediate 87) in acetonitrile, N,N-diisopropylethylamine (0.54 mL, 3.13 mmol, commercial source: Vinsa) was added followed by the addition of 2-(chloromethyl)-5-fluoropyridine (228 mg, 1.56 mmol, Intermediate 9) at 26° C. The reaction mixture was heated to 85° C. for 16 h. Upon completion, the reaction mixture was cooled to 26° C. and partitioned between ethyl acetate (100 mL) and water (20 mL). The organic layer was separated, dried over anhydrous $Na_2SO_4$, filtered and the filtrate was evaporated under reduced pressure. The crude was purified by column chromatography (silicagel 100-200 mesh), eluted with 1.3% methanol in dichloromethane. The pure fractions were concentrated under reduced pressure to afford 2-fluoro-4-(2-((5-fluoropyridin-2-yl)methyl)-2H-tetrazol-5-yl)-N-(2-hydroxyethyl)benzenesulfonamide (145 mg, 34.7%) as a white solid. $^1$H NMR (400 MHz, DMSO-$d_6$) δ 8.53 (d, J=2.8 Hz, 1H), 8.06-7.97 (m, 4H), 7.85-7.80 (m, 1H), 7.69-7.62 (m, 1H), 6.18 (s, 2H), 4.65 (t, J=5.5 Hz, 1H), 3.41-3.36 (m, 2H), 2.99-2.94 (m, 2H). MS m/z [M+H]$^+$=397.06.

Example 76: 2-fluoro-N-(2-hydroxyethyl)-4-(2-((tetrahydro-2H-pyran-2-yl)methyl)-2H-tetrazol-5-yl)benzenesulfonamide

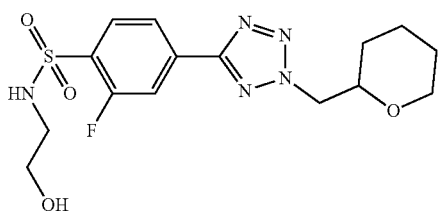

Example 77: 2-fluoro-4-(2-(4-fluorobenzyl)-2H-tetrazol-5-yl)-N-(2-hydroxyethyl)benzenesulfonamide

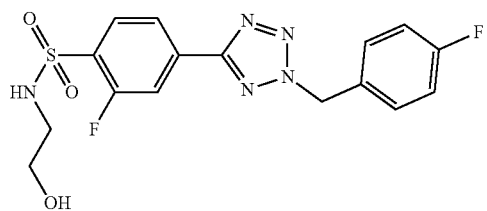

To a solution of 2-fluoro-N-(2-hydroxyethyl)-4-(2H-tetrazol-5-yl)benzenesulfonamide (400 mg, 1.392 mmol, Intermediate 87) in acetonitrile (8.0 mL), N,N-diisopropylethylamine (1.21 mL, 6.96 mmol, commercial source: Vinsa) was added, followed by the addition of 2-(bromomethyl)tetrahydro-2H-pyran (747 mg, 4.17 mmol, commercial source: Sigma Aldrich) at 26° C. The reaction mixture was heated to 85° C. for 16 h. Upon completion, the reaction mixture was cooled to 25° C. and diluted with ethyl acetate (100 mL) and washed with water (20 mL). The organic phase was separated, dried over anhydrous $Na_2SO_4$, filtered and the filtrate was evaporated under reduced pressure. The crude was purified by column chromatography (silica gel 100-200 mesh), eluted with 1.5% methanol in dichloromethane. The pure fractions were concentrated under reduced pressure to afford 2-fluoro-N-(2-hydroxyethyl)-4-(2-((tetrahydro-2H-pyran-2-yl)methyl)-2H-tetrazol-5-yl)benzenesulfonamide which was submitted for chiral SFC separation.

SFC Conditions: Column/Dimensions

Lux Cellulose-2 (30×250 mm), 5µ

% $CO_2$: 65.0%

% Co solvent: 35.0% (100% MeOH)

Total Flow: 60.0 g/min

Back Pressure: 90.0 bar

UV: 254 nm

Stack time: 3.5 min

Load/Inj: 13.0 mg

The collected SFC fractions were concentrated under reduced pressure to afford:

Isomer 1: (32 mg) as an off white solid. $^1$H NMR (400 MHz, DMSO-$d_6$) δ 8.07-7.97 (m, 4H), 4.83-4.78 (m, 2H), 4.65 (t, J=6.4 Hz, 1H), 3.95-3.88 (m, 1H), 3.83-3.77 (m, 1H), 3.39 (q, J=6.1 Hz, 2H), 3.29-3.25 (m, 1H), 2.97 (t, J=6.4 Hz, 2H), 1.85-1.70 (m, 2H), 1.53-1.31 (m, 4H). MS m/z [M−H]$^−$=384.24. ee %=99.45%

Isomer 2: (50 mg) as an off-white solid. $^1$H NMR (400 MHz, DMSO-$d_6$) δ 8.08-7.96 (m, 4H), 4.84-4.78 (m, 2H), 4.66 (t, J=5.5 Hz, 1H), 3.96-3.89 (m, 1H), 3.84-3.78 (m, 1H), 3.42-3.36 (m, 2H), 3.29-3.25 (m, 1H), 2.97 (t, J=6.4 Hz, 2H), 1.88-1.67 (m, 2H), 1.56-1.33 (m, 4H). MS m/z [M−H]$^−$=384.17. ee %=96.16%

Their absolute configuration has not been determined.

To a solution of 2-fluoro-N-(2-hydroxyethyl)-4-(2H-tetrazol-5-yl)benzenesulfonamide (250 mg, 0.871 mmol, Intermediate 87) in acetonitrile (5 mL), N,N-diisopropylethylamine (0.3 mL, 1.742 mmol, commercial source: Finar) was added followed by the addition of 1-(bromomethyl)-4-fluorobenzene (0.16 g, 0.871 mmol, commercial source: Alfa) at 26° C. The reaction mixture was heated to 85° C. for 16 h. Upon completion, the reaction mixture was cooled to 26° C. and partitioned between ethyl acetate (80 mL) and water (20 mL). Aqueous layer was extracted with ethyl acetate (2×30 mL). The combined organic layers were washed with brine (50 mL), dried over anhydrous $Na_2SO_4$ and filtered. The filtrate was evaporated under reduced pressure. The crude was purified by column chromatography (silicagel 100-200 mesh), eluted with 1.5% methanol in dichloromethane. The pure fractions were concentrated under reduced pressure to afford 2-fluoro-4-(2-(4-fluorobenzyl)-2H-tetrazol-5-yl)-N-(2-hydroxyethyl)benzenesulfonamide (137 mg, 38%) as an off white solid. $^1$H NMR (400 MHz, DMSO-$d_6$) δ 8.02-7.97 (m, 4H), 7.52-7.50 (m, 2H), 7.27-7.23 (m, 2H), 6.04 (s, 2H), 4.66-4.64 (m, 1H), 3.40-3.34 (m, 2H), 2.98-2.94 (m, 2H). MS m/z [M+H]$^+$=396.04

Example 78: 2-fluoro-N-(2-hydroxyethyl)-4-(2-((tetrahydro-2H-pyran-4-yl)methyl)-2H-tetrazol-5-yl)benzenesulfonamide

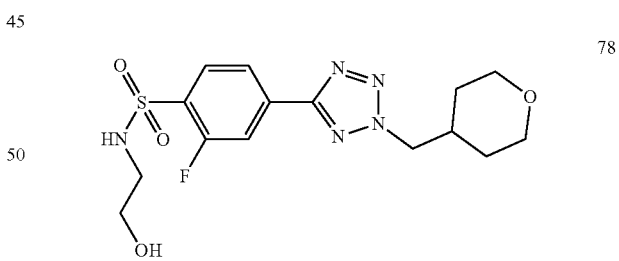

To a solution of 2-fluoro-N-(2-hydroxyethyl)-4-(2H-tetrazol-5-yl)benzenesulfonamide (250 mg, 0.871 mmol, Intermediate 87) in acetonitrile (5 mL), N,N-diisopropylethylamine (0.3 mL, 1.742 mmol, commercial source: Finar) was added followed by the addition of 4-(bromomethyl)tetrahydro-2H-pyran (0.15 g, 0.871 mmol, commercial source: Apollo Scientific) at 26° C. The reaction mixture was heated to 85° C. for 16 h. Upon completion, the reaction mixture was cooled to 26° C. and partitioned between ethyl acetate (100 mL) and water (30 mL). Aqueous layer was extracted with ethyl acetate (2×40 mL). The combined organic layers were dried over anhydrous $Na_2SO_4$ and filtered. The filtrate was evaporated under reduced pressure. The crude was purified by column chromatography (silicagel 100-200 mesh), eluted with 1.5% methanol in dichloromethane. The pure fractions were concentrated under reduced pressure to afford 2-fluoro-N-(2-hydroxyethyl)-4-(2-((tetrahydro-2H-pyran-4-yl)methyl)-2H-tetrazol-5-yl)benzenesulfonamide (71 mg, 21%) as an off white solid. $^1$H NMR (400 MHz, DMSO-d$_6$) δ 8.06-7.97 (m, 4H), 4.72-4.70 (m, 2H), 4.67-4.64 (m, 1H), 3.86-3.83 (m, 2H), 3.41-3.36 (m, 2H), 3.00-2.94 (m, 2H), 2.33-2.21 (m, 1H), 1.52-1.45 (m, 2H), 1.40-1.29 (m, 2H). MS m/z [M+H]$^+$=386.10

Example 79: 4-(2-(cyclohexylmethyl)-2H-tetrazol-5-yl)-2-fluoro-N-(2-hydroxyethyl)benzenesulfonamide

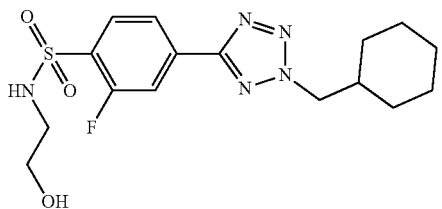

To a solution of 2-fluoro-N-(2-hydroxyethyl)-4-(2H-tetrazol-5-yl)benzenesulfonamide (250 mg, 0.871 mmol, Intermediate 87) in acetonitrile (5 mL), N,N-diisopropylethylamine (0.3 mL, 1.742 mmol, commercial source: Finar) was added followed by the addition of (bromomethyl)cyclohexane (0.153 g, 0.871 mmol, commercial source: Apollo Scientific) at 26° C. The reaction mixture was heated to 85° C. for 16 h. Upon completion, the reaction mixture was cooled to 26° C. and partitioned between ethyl acetate (100 mL) and water (30 mL). Aqueous layer was extracted with ethyl acetate (2×30 mL). The combined organic layers were washed with brine (50 mL), dried over anhydrous Na$_2$SO$_4$ and filtered. The filtrate was evaporated under reduced pressure. The crude was purified by column chromatography (silicagel 100-200 mesh), eluted with 1.5% methanol in dichloromethane. The pure fractions were concentrated under reduced pressure to afford 4-(2-(cyclohexylmethyl)-2H-tetrazol-5-yl)-2-fluoro-N-(2-hydroxyethyl)benzenesulfonamide (38 mg, 11%) as an off white solid. $^1$H NMR (400 MHz, DMSO-d$_6$) δ 8.07-7.97 (m, 4H), 4.68-4.62 (m, 3H), 3.41-3.37 (m, 2H), 3.01-2.94 (m, 2H), 2.07-1.06 (m, 1H), 1.72-1.54 (m, 5H), 1.28-1.00 (m, 5H). MS m/z [M+H]$^+$= 384.10

Example 80: 2-chloro-4-(2-((5-fluoropyridin-2-yl)methyl)-2H-tetrazol-5-yl)-N-(2-hydroxyethyl)benzenesulfonamide

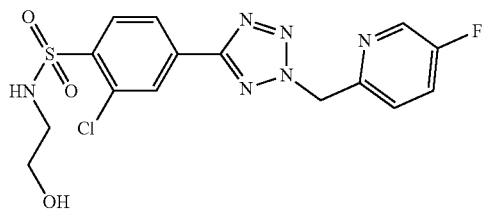

To a solution of 2-chloro-N-(2-hydroxyethyl)-4-(2H-tetrazol-5-yl)benzenesulfonamide (300 mg, 0.990 mmol, Intermediate 91) in acetonitrile (6 mL), N,N-diisopropylethylamine (0.34 mL, 1.98 mmol, commercial source: Finar) was added followed by the addition of 2-(chloromethyl)-5-fluoropyridine (0.172 g, 1.188 mmol, Intermediate 9) at 26° C. The reaction mixture was heated to 85° C. for 16 h. Upon completion, the reaction mixture was cooled to 26° C. and acetonitrile was evaporated. The crude was diluted with ethyl acetate (100 mL) and washed with water (3×50 mL) and then with brine (50 mL). The organic layer was dried over anhydrous Na$_2$SO$_4$ and filtered. The filtrate was evaporated under reduced pressure. The crude was purified by column chromatography (silicagel 100-200 mesh), eluted with 1.5% methanol in dichloromethane. The pure fractions were concentrated under reduced pressure to afford 2-chloro-4-(2-((5-fluoropyridin-2-yl)methyl)-2H-tetrazol-5-yl)-N-(2-hydroxyethyl)benzenesulfonamide (208 mg, 50.8%) as an off white solid. $^1$H NMR (400 MHz, DMSO-d$_6$) δ 8.54-8.53 (m, 1H), 8.20-8.18 (m, 1H), 8.16-8.13 (m, 2H), 7.97-7.94 (m, 1H), 7.85-7.80 (m, 1H), 7.67-7.64 (m, 1H), 6.18 (s, 2H), 4.66-4.63 (t, 1H), 3.39-3.35 (m, 2H), 2.96-2.92 (m, 2H). MS m/z [M+H]$^+$=412.98

Example 81: 3-chloro-4-(2-((5-fluoropyridin-2-yl)methyl)-2H-tetrazol-5-yl)-N-(2-hydroxyethyl)benzenesulfonamide

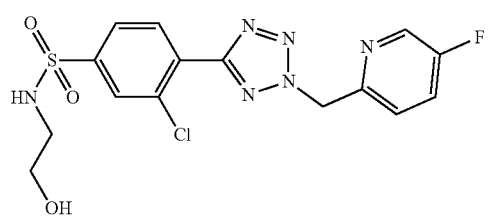

To a solution of 3-chloro-N-(2-hydroxyethyl)-4-(2H-tetrazol-5-yl)benzenesulfonamide (800 mg (crude, purity 37%), 0.977 mmol, Intermediate 95) in acetonitrile (5.9 mL), N,N-diisopropylethylamine (0.34 mL, 1.95 mmol, commercial source: Finar) was added followed by the addition of 2-(chloromethyl)-5-fluoropyridine (0.169 g, 1.172 mmol, Intermediate 9) at 26° C. The reaction mixture was heated to 85° C. for 16 h. Upon completion, the reaction mixture was cooled to 28° C. and diluted with ethyl acetate (80 mL). the crude was washed with water (2×40 mL) and then with brine (40 mL). The organic layer was dried over anhydrous Na$_2$SO$_4$ and filtered. The filtrate was evaporated under reduced pressure. The crude was purified by column chromatography (silicagel 100-200 mesh), eluted with 1% methanol in dichloromethane. The pure fractions were collected and concentrated under reduced pressure. The obtained solid compound was further purified by prep-HPLC to afford, after lyophilisation, 3-chloro-4-(2-((5-fluoropyridin-2-yl)methyl)-2H-tetrazol-5-yl)-N-(2-hydroxyethyl)benzenesulfonamide (22 mg, 5.4%) as an off white solid. $^1$H NMR (400 MHz, DMSO-d$_6$) δ 8.55 (d, 1H), 8.16 (d, 1H), 8.02 (d, 1H), 7.92-7.81 (m, 3H), 7.66-7.63 (m, 1H), 6.20 (s, 2H), 4.71-4.68 (m, 1H), 3.41-3.37 (m, 2H), 2.90-2.87 (m, 2H). MS m/z [M+H]$^+$=412.98

Prep-HPLC Conditions:
Column: Kromasil C18 column (25×150 mm, 10μ)
Mobile phase: A: H$_2$O (10 mM NH$_4$HCO$_3$) B: ACN Method (time in min/% of B): 0/20, 1/20, 10/50, 10.5/100, 13/100, 13.1/20

Flow: 25 mL/min

Temperature: ambient

Example 82: 2-(2-chloro-4-(2-(4-fluorobenzyl)-2H-tetrazol-5-yl)phenylsulfonamido)acetamide

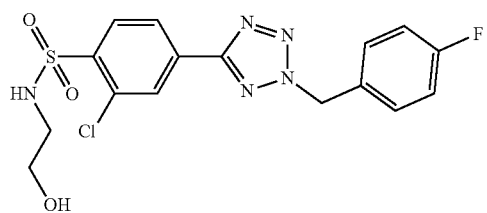

To a solution of tert-butyl (2-amino-2-oxoethyl)((2-chloro-4-(2-(4-fluorobenzyl)-2H-tetrazol-5-yl)phenyl)sulfonyl)carbamate (440 mg, 0.838 mmol, Intermediate 99) in 1,4-dioxane (4.4 mL), 4M HCl IN 1,4-dioxane (4.4 mL) was added at 26° C. The resultant reaction mixture was stirred at 26° C. for 3 h. Upon completion, the reaction was concentrated under reduced pression to afford the crude that was dissolved with water (30 mL). Then, it was basified with sat. NaHCO₃ solution (20 mL) and extracted with EtOAc (3×30 mL). The organic layers were dried over Na₂SO₄ and filtered off. Solvent was evaporated under reduced pressure. The crude was purified by column chromatography (silica-gel 100-200 mesh), eluted with 2% methanol in dichloromethane. The pure fractions were collected and concentrated under reduced pressure to afford 2-(2-chloro-4-(2-(4-fluorobenzyl)-2H-tetrazol-5-yl)phenylsulfonamido) acetamide (140 mg, 37%) as an off white solid. MS m/z [M−H]⁻=422.91.

Example 83: 3-fluoro-4-(2-((5-fluoropyridin-2-yl)methyl)-2H-tetrazol-5-yl)-N-(2-hydroxyethyl)benzenesulfonamide

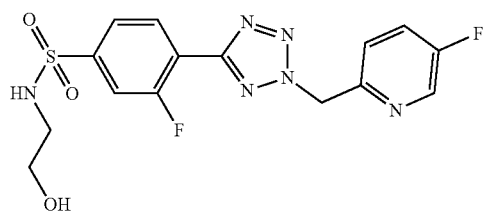

To a solution of 3-fluoro-N-(2-hydroxyethyl)-4-(2H-tetrazol-5-yl)benzenesulfonamide (250 mg, 0.87 mmol, Intermediate 103) in acetonitrile (5.0 mL), N,N-diisopropylethylamine (0.53 mL, 3.04 mmol, commercial source: Vinsa) was added, followed by the addition of 2-(chloromethyl)-5-fluoropyridine (190 mg, 1.30 mmol, Intermediate 9) at 26° C. The reaction mixture was heated to 85° C. for 16 h. Upon completion, the reaction mixture was cooled to 26° C. and diluted with ethyl acetate (40 mL) and washed with water (40 mL). The organic phase was separated, dried over anhydrous Na₂SO₄, filtered and the filtrate was evaporated under reduced pressure. The crude was purified by column chromatography (silicagel 100-200 mesh), eluted with 1.5% methanol in dichloromethane. The pure fractions were collected and concentrated under reduced pressure to afford 3-fluoro-4-(2-((5-fluoropyridin-2-yl)methyl)-2H-tetrazol-5-yl)-N-(2-hydroxyethyl) benzenesulfonamide (160 mg, 45.7%) as an off-white solid. ¹H NMR (400 MHz, DMSO-d₆) δ 8.55-8.53 (m, 1H), 8.32-8.28 (m, 1H), 7.91-7.80 (m, 4H), 7.67-7.62 (m, 1H), 6.20-6.18 (m, 2H), 4.69-4.65 (m, 1H), 3.38 (q, J=6.0 Hz, 2H), 2.91-2.84 (m, 2H). MS m/z [M+H]⁺=397.12.

Example 84: 3-fluoro-N-(2-hydroxyethyl)-4-(2-((tetrahydro-2H-pyran-2-yl)methyl)-2H-tetrazol-5-yl)benzenesulfonamide

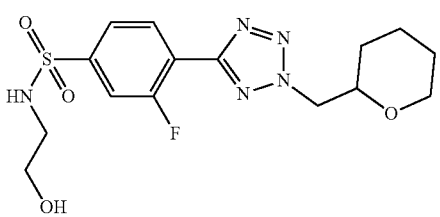

To a solution of 3-fluoro-N-(2-hydroxyethyl)-4-(2H-tetrazol-5-yl)benzenesulfonamide (200 mg, 0.696 mmol, Intermediate 103) in acetonitrile (4.0 mL), N,N-diisopropylethylamine (0.6 mL, 3.48 mmol, commercial source: Vinsa) was added, followed by the addition of 2-(bromomethyl) tetrahydro-2H-pyran (373 mg, 2.08 mmol, commercial source: Sigma Aldrich) at 26° C. The reaction mixture was heated to 85° C. for 16 h. Upon completion, the reaction mixture was cooled to 26° C. and diluted with ethyl acetate (50 mL) and washed with water (15 mL). The organic phases were combined, dried over anhydrous Na₂SO₄, filtered and the filtrate was evaporated under reduced pressure. The crude was purified by column chromatography (silica gel 100-200 mesh), eluted with 1.5% methanol in dichloromethane. The pure fractions were concentrated under reduced pressure to afford 3-fluoro-N-(2-hydroxyethyl)-4-(2-((tetrahydro-2H-pyran-2-yl)methyl)-2H-tetrazol-5-yl)benzenesulfonamide which was submitted for chiral SFC separation.

SFC Conditions: Column/Dimensions

Lux Cellulose-2 (4.6*250 mm), 5μ

% CO₂: 60.0%

% Co solvent: 40.0% (100% MeOH)

Total Flow: 60.0 g/min

Back Pressure: 100.0 bar

The collected SFC fractions were concentrated under reduced pressure to afford:

Isomer 1: (22 mg) as an off-white solid. ¹H NMR (400 MHz, DMSO-d₆) δ 8.30 (t, J=7.4 Hz, 1H), 7.88 (br s, 1H), 7.81 (d, J=8.8 Hz, 2H), 4.84-4.78 (m, 2H), 4.71-4.67 (m, 1H), 3.94-3.89 (m, 1H), 3.83-3.78 (m, 1H), 3.41-3.36 (m, 2H), 3.28-3.24 (m, 1H), 2.89 (t, J=6.1 Hz, 2H), 1.86-1.80 (m, 1H), 1.76-1.70 (m, 1H), 1.53-1.29 (m, 4H). MS m/z [M−H]⁻=384.17. ee %=99.11%

Isomer 2: (16 mg) as an off-white solid. ¹H NMR (400 MHz, DMSO-d₆) δ 8.29 (t, J=6.1 Hz, 1H), 7.96 (br s, 1H), 7.80 (d, J=8.8 Hz, 2H), 4.85-4.79 (m, 2H), 4.75-4.69 (m, 1H), 3.97-3.89 (m, 1H), 3.84-3.78 (m, 1H), 3.38 (t, J=6.1 Hz, 2H), 3.27-3.23 (m, 1H), 2.88 (t, J=6.1 Hz, 2H), 1.85-1.71 (m, 2H), 1.55-1.30 (m, 4H). MS m/z [M−H]⁻=384.17. ee %=97.35%

Their absolute configuration has not been determined.

Example 85: 2,3-difluoro-4-(2-((5-fluoropyridin-2-yl)methyl)-2H-tetrazol-5-yl)-N-(2-hydroxyethyl)benzenesulfonamide

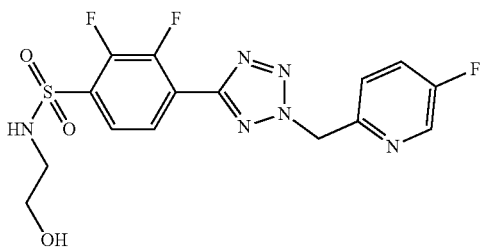

To a solution of 2,3-difluoro-N-(2-hydroxyethyl)-4-(2H-tetrazol-5-yl)benzenesulfonamide (250 mg, 0.819 mmol, Intermediate 107) in acetonitrile (5 mL), N,N-diisopropylethylamine (0.42 mL, 2.458 mmol, commercial source: Vinsa) was added, followed by the addition of 2-(chloromethyl)-5-fluoropyridine (154 mg, 1.06 mmol, Intermediate 9) at 26° C. The reaction mixture was heated to 85° C. for 16 h. Upon completion, the reaction mixture was cooled to 26° C. and diluted with ethyl acetate (60 mL) and water (10 mL). The organic phase was washed with water (2×30 mL), brine (2×30 mL), dried over anhydrous $Na_2SO_4$, filtered and the filtrate was evaporated under reduced pressure. The crude was purified by prep HPLC. The pure fractions were lypholized to afford 2,3-difluoro-4-(2-((5-fluoropyridin-2-yl)methyl)-2H-tetrazol-5-yl)-N-(2-hydroxyethyl)benzenesulfonamide (196 mg, 57%) as a white solid. $^1$H NMR (400 MHz, DMSO-$d_6$) δ 8.52-8.49 (m, 1H), 8.22-8.18 (m, 1H), 8.06-8.00 (m, 1H), 7.84-7.79 (m, 1H), 7.76-7.72 (m, 1H), 7.66-7.63 (m, 1H), 6.19 (s, 2H), 4.64-4.60 (m, 1H), 3.39-3.34 (m, 2H), 3.01-2.96 (m, 2H). MS m/z [M–H]$^-$=412.94.

Prep-HPLC Conditions:
Column: YMC C8 (150×19) mm, 10 u
Mobile phase: A—10 mM ammonium bicarbonate (aq), B—acetonitrile
Method (time in min/% of B): 0/10, 1/20, 8/55
Flow: 30 ml/min
Temperature: Ambient

Example 86: 2,3-difluoro-N-(2-hydroxyethyl)-4-(2-((tetrahydro-2H-pyran-2-yl)methyl)-2H-tetrazol-5-yl)benzenesulfonamide

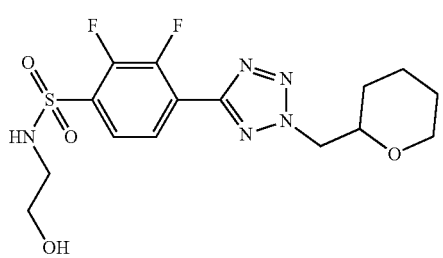

To a solution of 2,3-difluoro-N-(2-hydroxyethyl)-4-(2H-tetrazol-5-yl)benzenesulfonamide (450 mg, 1.47 mmol, Intermediate 107) in acetonitrile (9.0 mL), N,N-diisopropylethylamine (1.28 mL, 7.37 mmol, commercial source: Vinsa) was added, followed by the addition of 2-(bromomethyl)tetrahydro-2H-pyran (525 mg, 2.95 mmol, commercial source: Sigma Aldrich) at 26° C. The reaction mixture was heated to 85° C. for 16 h. Upon completion, the reaction mixture was cooled to 26° C. and diluted with ethyl acetate (100 mL) and washed with water (20 mL). The organic phase were separated, dried over anhydrous $Na_2SO_4$, filtered and the filtrate was evaporated under reduced pressure. The crude was purified by column chromatography (silica gel 100-200 mesh), eluted with 1.5% methanol in dichloromethane. The pure fractions were concentrated under reduced pressure to afford 2,3-difluoro-N-(2-hydroxyethyl)-4-(2-((tetrahydro-2H-pyran-2-yl) methyl)-2H-tetrazol-5-yl) benzene sulfonamide which was submitted for chiral SFC separation.

SFC Conditions: Column/Dimensions
Lux Cellulose-2 (30×250 mm), 5µ
% $CO_2$: 60.0%
% Co solvent: 40.0% (100% MeOH)
Total Flow: 90.0 g/min
Back Pressure: 90.0 bar
UV: 254 nm
Stack time: 4.0 min
Load/Inj: 3.0 mg Collected SFC fractions were concentrated under reduced pressure to afford:

Isomer 1: (26 mg) as an off-white solid. $^1$H NMR (400 MHz, DMSO-$d_6$) δ 8.23 (br s, 1H), 8.04 (t, J=6.7 Hz, 1H), 7.76 (t, J=6.7 Hz, 1H), 4.88-4.80 (m, 2H), 4.64 (br s, 1H), 3.94-3.89 (m, 1H), 3.82-3.77 (m, 1H), 3.42-3.35 (m, 2H), 3.03-2.94 (m, 2H), 1.87-1.71 (m, 2H), 1.57-1.37 (m, 4H), 1.25-1.20 (m, 1H). MS m/z [M+H]$^+$=404.18. ee %=99.48%.

Isomer 2: (22 mg) as an off-white solid. $^1$H NMR (400 MHz, DMSO-$d_6$) δ 8.25 (br s, 1H), 8.05 (t, J=6.8 Hz, 1H), 7.76 (t, J=7.1 Hz, 1H), 4.88-4.79 (m, 2H), 4.65 (br s, 1H), 3.96-3.88 (m, 1H), 3.85-3.75 (m, 1H), 3.45-3.39 (m, 2H), 3.04-2.95 (m, 2H), 1.87-1.70 (m, 2H), 1.56-1.32 (m, 4H), 1.27-1.21 (m, 1H). MS m/z [M+H]$^+$=404.18. ee %=97.96%.

Their absolute configuration has not been determined.

Example 87: 2,6-difluoro-4-(2-((5-fluoropyridin-2-yl)methyl)-2H-tetrazol-5-yl)-N-(2-hydroxyethyl)benzenesulfonamide

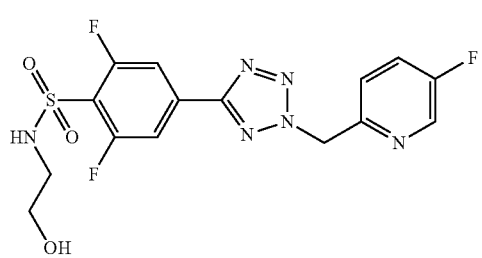

To a solution of 2,6-difluoro-N-(2-hydroxyethyl)-4-(2H-tetrazol-5-yl)benzenesulfonamide (300 mg, 0.983 mmol, Intermediate 111) in acetonitrile (6.0 mL), N,N-diisopropylethylamine (0.51 mL, 2.95 mmol, commercial source: Vinsa) was added, followed by the addition of 2-(chloromethyl)-5-fluoropyridine (185 mg, 1.27 mmol, Intermediate 9) at 26° C. The reaction mixture was heated to 85° C. for 16 h. Upon completion, the reaction mixture was cooled to 26° C. and diluted with ethyl acetate (100 mL) and water (20 mL). The organic phase was separated, dried over anhydrous Na₂SO₄, filtered and the filtrate was evaporated under reduced pressure. The crude was purified by column chromatography, eluted with 15% ethyl acetate in petroleum ether. The pure fractions were collected and concentrated under reduced pressure. The obtained solid compound was further purified by prep HPLC (Kromasil phenyl column (25×150 mm, 10p Flow: 25 mL/min), Mobile phase: A: H2O (10 mM NH₄HCO₃) B: ACN; Method (time in min/% of B): 0/30, 1/30, 8/50, 10/50, 10.2/100, 12/100, 12.1/30, 14/30; temperature: ambient). The pure fractions were lyophilized to afford 2,6-difluoro-4-(2-((5-fluoropyridin-2-yl)methyl)-2H-tetrazol-5-yl)-N-(2-hydroxyethyl)benzenesulfonamide (45 mg, 10%) as an off white solid. $^1$H NMR (400 MHz, DMSO-d₆) δ 8.52 (d, J=2.8 Hz, 1H), 7.85-7.81 (m, 3H), 7.69-7.63 (m, 2H), 6.18 (s, 2H), 4.61 (br s, 1H), 3.41-3.39 (m, 2H), 3.03 (t, J=6.3 Hz, 2H). MS m/z [M−H]⁻=413.01.

Example 88: (R)-2,6-difluoro-N-(2-hydroxyethyl)-4-(2-((tetrahydro-2H-pyran-2-yl)methyl)-2H-tetrazol-5-yl)benzenesulfonamide

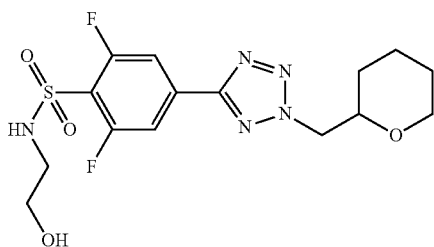

To a solution of 2,6-difluoro-N-(2-hydroxyethyl)-4-(2H-tetrazol-5-yl)benzenesulfonamide (700 mg, 2.295 mmol, Intermediate 111) in acetonitrile (14.0 mL), N,N-diisopropylethylamine (2 mL, 11.475 mmol, commercial source: Vinsa) was added, followed by the addition of 2-(bromomethyl)tetrahydro-2H-pyran (817 mg, 4.59 mmol, commercial source: Aldrich) at 26° C. The reaction mixture was heated to 85° C. for 16 h. Upon completion, the reaction mixture was cooled to 26° C. and diluted with ethyl acetate (50 mL) and water (10 mL). The organic phase was separated, dried over anhydrous Na₂SO₄, filtered and the filtrate was evaporated under reduced pressure. The crude was purified by column chromatography, eluted with 1.5% methanol in dichloromethane. The pure fractions were collected and concentrated under reduced pressure. The obtained solid compound was further purified by prep HPLC (Lux chiral Cellulose column (30×250 mm, 5μ),% CO₂: 60. % of co-solvent: 40% (100% Methanol); Total Flow: 90 g/min, Back Pressure: 90.0 bar, UV: 254 nm, Stack time: 4.2 min, Load/Inj: 13 mg). The pure fractions were evaporated to afford a single known enantiomer 2,6-difluoro-N-(2-hydroxyethyl)-4-(2-((tetrahydro-2H-pyran-2-yl)methyl)-2H-tetrazol-5-yl)benzenesulfonamide (5 mg) as an off white solid. $^1$H NMR (400 MHz, DMSO-d₆) δ 7.86-7.84 (m, 2H), 4.82-4.79 (m, 2H), 4.66 (t, J=5.5 Hz, 1H), 3.82-3.77 (m, 1H), 3.44-3.39 (m, 2H), 3.10-2.99 (m, 2H), 1.83-1.24 (m, 8H). MS m/z [M−H]⁻=402.05, Chiral purity ee=99.4%.

Example 89: N-(cyanomethyl)-4-(2-((tetrahydro-2H-pyran-4-yl)methyl)-2H-tetrazol-5-yl)benzenesulfonamide

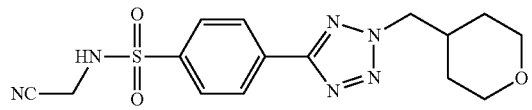

To a solution of tert-butyl (cyanomethyl)((4-(2-((tetrahydro-2H-pyran-4-yl)methyl)-2H-tetrazol-5-yl)phenyl)sulfonyl)carbamate (400 mg, 0.865 mmol, Intermediate 113) in DCM (10 mL), trifluoroacetic acid (4.0 mL, commercial source: Avra) was added at 0° C. Then the reaction was allowed to reached 26° C. and it was stirred at 26° C. for 4 h. Upon completion, the reaction mixture was concentrated under reduced pressure. The crude was purified prep HPLC.
Prep-HPLC Condition:
Column: —YMC Trait C18 (150×25) mm, 10 u
Mobile Phase A: 10 mM Ammonium Bicarbonate (Aq),
Mobile phase B: —Acetonitrile
Flow: 25 ml/min,
Method (time in min/% of B): 0/10, 1/10, 10/60, 11/100
Temperature: Ambient
The pure fractions were lyophilized to afford N-(cyanomethyl)-4-(2-((tetrahydro-2H-pyran-4-yl)methyl)-2H-tetrazol-5-yl)benzenesulfonamide (46 mg, 15%) as an off-white solid. $^1$H NMR (400 MHz, DMSO-d₆) δ 8.53 (br s, 1H), 8.29 (d, J=8.6 Hz, 2H), 8.02 (d, J=8.6 Hz, 2H), 4.71 (d, J=7.2 Hz, 2H), 4.15 (s, 2H), 3.88-3.78 (m, 2H), 3.35-3.30 (m, 1H), 3.28-3.21 (m, 1H), 2.35-2.23 (m, 1H), 1.52-1.46 (m, 2H), 1.41-1.29 (m, 2H). MS m/z [M+H]⁺=363.10.

Example 90: N-(cyanomethyl)-4-(2-(pyrazin-2-ylmethyl)-2H-tetrazol-5-yl)benzenesulfonamide

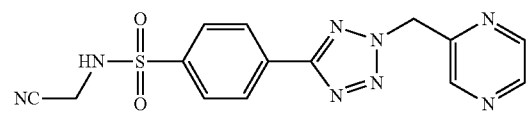

The solution of 2-(4-(2-(pyrazin-2-ylmethyl)-2H-tetrazol-5-yl)phenylsulfonamido)acetamide (200 mg, 0.0005 mol, Intermediate 118) in phosphoryl chloride (2 mL, commercial source: Avra) was heated to 100° C. and stirred for 2 h at the same temperature. Upon completion, the reaction mixture was cooled to 26° C., poured into cooled saturated sodium bicarbonate solution (0° C.) (100 mL) dropwise and extracted with ethyl acetate (4×30 mL). The organic layer was dried over anhydrous Na₂SO₄, filtered and the filtrate was concentrated under reduced pressure. The crude was purified by column chromatography (silicagel 100-200 mesh), eluted with 2% methanol in dichloromethane. The pure fractions were concentrated under reduced pressure to afford N-(cyanomethyl)-4-(2-(pyrazin-2-ylmethyl)-2H-tetrazol-5-yl)benzenesulfonamide (32 mg, 17%) as an off-white solid. $^1$H NMR (400 MHz, DMSO-d₆) δ 8.89 (d, J=1.5 Hz, 1H), 8.74-8.66 (m, 2H), 8.64-8.61 (m, 1H), 8.31-8.25 (m, 2H), 8.04-7.98 (m, 2H), 6.28 (s, 2H), 4.15 (s, 2H). MS m/z [M−H]⁻=355.12.

Example 91: N-(cyanomethyl)-4-(2-((5-methylpyrazin-2-yl)methyl)-2H-tetrazol-5-yl)benzenesulfonamide

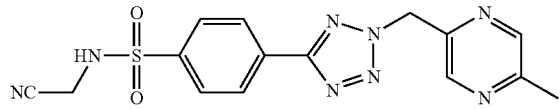

91

The solution of 2-(4-(2-((5-methylpyrazin-2-yl)methyl)-2H-tetrazol-5-yl)phenylsulfonamido)acetamide (220 mg, 0.0005 mol, Intermediate 121) in phosphoryl chloride (2.2 mL, commercial source: Avra) was heated to 100° C. and stirred for 2 h at the same temperature. Upon completion, the reaction mixture was cooled to 26° C., poured into ice cold aqueous saturated sodium bicarbonate solution (0° C.) (100 mL) dropwise and extracted with ethyl acetate (4×30 mL). The combined organic solution was dried over anhydrous Na$_2$SO$_4$, filtered and the filtrate was concentrated under reduced pressure. The crude was purified by column chromatography (silica gel 100-200 mesh), eluted with 1.5% methanol in dichloromethane. The pure fractions were concentrated under reduced pressure to afford N-(cyanomethyl)-4-(2-((5-methylpyrazin-2-yl)methyl)-2H-tetrazol-5-yl)benzenesulfonamide (52 mg, 27.5%) as an off-white solid. $^1$H NMR (400 MHz, DMSO-d$_6$) δ 8.74 (s, 1H), 8.70 (s, 1H), 8.51 (s, 1H), 8.27 (d, J=6.6 Hz, 2H), 8.0 (d, J=6.6 Hz, 2H), 6.21 (s, 2H), 4.15 (s, 2H), 2.49 (s, 3H). MS m/z [M+H]$^+$=371.12.

Example 92: N-(cyanomethyl)-4-(2-((5-methoxypyrazin-2-yl)methyl)-2H-tetrazol-5-yl)benzenesulfonamide

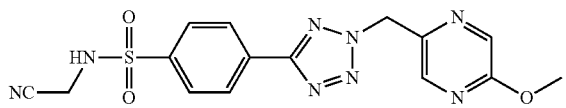

92

The solution of 2-(4-(2-((5-methoxypyrazin-2-yl)methyl)-2H-tetrazol-5-yl)phenylsulfonamido)acetamide (250 mg, 0.0006 mol, Intermediate 123) in phosphoryl chloride (2.5 mL, commercial source: Avra) was heated to 100° C. and stirred for 2 h at the same temperature. Upon completion, the reaction mixture was cooled to 26° C. and poured into saturated sodium bicarbonate solution (100 mL) slowly at 0° C. The resultant reaction mixture was extracted with ethyl acetate (3×50 mL), dried over anhydrous Na$_2$SO$_4$, filtered and the filtrate was evaporated under reduced pressure. The crude was purified by column chromatography (silicagel 100-200 mesh), eluted with 1.5% methanol in dichloromethane. The pure fractions were concentrated under reduced pressure to afford N-(cyanomethyl)-4-(2-((5-methoxypyrazin-2-yl)methyl)-2H-tetrazol-5-yl)benzenesulfonamide (35 mg, 14%) as an off white solid. $^1$H NMR (400 MHz, DMSO-d$_6$) δ 8.71 (br s, 1H), 8.49 (d, J=1.3 Hz, 1H), 8.31-8.24 (m, 3H), 8.04-7.98 (m, 2H), 6.13 (s, 2H), 4.15 (d, J=4.6 Hz, 2H), 3.93 (s, 3H). MS m/z [M+H]$^+$=387.06.

Example 93: N-(cyanomethyl)-4-(2-((6-methoxypyridin-3-yl)methyl)-2H-tetrazol-5-yl)benzenesulfonamide

93

To a solution of tert-butyl (cyanomethyl)((4-(2-((tetrahydro-2H-pyran-4-yl)methyl)-2H-tetrazol-5-yl)phenyl)sulfonyl)carbamate (100 mg, 0.206 mmol, Intermediate 125) in DCM (10 mL), trifluoroacetic acid (1.0 mL, commercial source: Advent) was added and stirred at 26° C. for 4 h. Upon completion, the reaction mixture was concentrated under reduced pressure. The crude was purified prep HPLC (Prep-HPLC conditions: Column: XBridge C18 (150×19) mm, 5 u; Mobile Phase A: 10 mM Ammonium Bicarbonate (Aq), Mobile phase B: Acetonitrile, Flow: 16 ml/min, Method (time in min/% of B): 0/10, 1/10, 13/50, 16.8/50, 17/100, 21.8/100, 22/10, 25/10; Temperature: Ambient). The pure fractions were collected and lyophilized to afford N-(cyanomethyl)-4-(2-((6-methoxypyridin-3-yl)methyl)-2H-tetrazol-5-yl)benzenesulfonamide (15 mg, 19%) as an off-white solid. $^1$H NMR (400 MHz, DMSO-d$_6$) δ 8.46 (br s, 1H), 8.35-8.38 (m, 1H), 8.25-8.28 (m, 2H), 7.99-8.02 (m, 2H), 7.79-7.83 (m, 1H), 6.85-6.88 (m, 1H), 6.00 (s, 2H), 4.14 (s, 2H), 3.86 (s, 3H). MS m/z [M–H]$^-$=384.1

Example 94: N-(cyanomethyl)-4-(2-((tetrahydro-2H-pyran-2-yl)methyl)-2H-tetrazol-5-yl)benzenesulfonamide

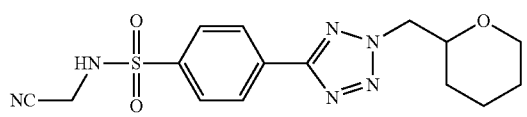

94

To a solution of tert-butyl (cyanomethyl)((4-(2-((tetrahydro-2H-pyran-2-yl)methyl)-2H-tetrazol-5-yl)phenyl)sulfonyl)carbamate (1.0 g, 2.162 mmol, Intermediate 127) in DCM (20 mL), trifluoroacetic acid (10.0 mL, Commercial source: Advent) was added, and the reaction mixture was stirred at 26° C. for 4 h. Upon completion, the reaction mixture was concentrated under reduced pressure to obtain N-(cyanomethyl)-4-(2-((tetrahydro-2H-pyran-2-yl)methyl)-2H-tetrazol-5-yl)benzenesulfonamide (1.1 g, crude). Two crude batches (1.4 g and 300 mg) were mixed and dried under vacuum to obtain a combined crude (1.4 g) which was purified by prep-HPLC (Prep-HPLC conditions: Kromasil C18 column (150×25) mm 10 u; Mobile phase A: 10 mM Ammonium Bicarbonate (Aq) Mobile phase B: Acetonitrile; Method (time in min/% of B): 0/30, 1/30, 10/70, 10.5/100, 12/100, 12.5/30, 15/30; Flow: 25 mL/min, temperature: ambient). The pure fractions were collected and lyophilized for 16 h to afford N-(cyanomethyl)-4-(2-((tetrahydro-2H-pyran-2-yl)methyl)-2H-tetrazol-5-yl)benzenesulfonamide (250 mg) that was submitted to prep-SFC.

SFC Conditions:
Column/dimensions: Chiralpak AD-H (4.6×250 mm), 5µ
% CO$_2$: 60.0%
% Co solvent: 40.0% (100% MeOH)
Total Flow: 4.0 g/min
Back Pressure: 90.0 bar
UV: 254 nm
Stack time: 10.0 min
Load/Inj: 8.5 mg The collected SFC fractions were concentrated under reduced pressure to afford isomer 1 (90 mg) as an off white solid and isomer 2 (24 mg) as an off-white solid.

Isomer 1: $^1$H NMR (400 MHz, DMSO-d$_6$) δ=ppm 8.76 (br s, 1H), 8.32-8.25 (m, 2H), 8.04-8.00 (m, 2H), 4.85-4.76 (m, 2H), 4.1 (s, 2H), 3.95-3.90 (m, 1H), 3.83-3.77 (m, 1H), 3.30-3.26 (m, 1H), 1.87-1.71 (m, 2H), 1.54-1.38 (m, 4H). MS m/z [M−H]$^-$=361.11, Chiral purity ee=99.82%.

Isomer 2 $^1$H NMR (400 MHz, DMSO-d$_6$) δ=ppm 8.81 (br s, 1H), 8.25 (d, J=8.55 Hz, 2H), 7.98 (d, J=8.55 Hz, 2H), 4.83-4.77 (m, 2H), 4.08 (s, 2H), 3.94-3.88 (m, 1H), 3.84-3.77 (m, 1H), 3.30-3.25 (m, 1H), 1.87-1.71 (m, 2H), 1.57-1.36 (m, 4H). MS m/z [M−H]$^-$=361.03, Chiral purity ee=99.82%.

Their absolute configuration has not been determined.

Example 95: 2-((4-(2-((4,4-difluorocyclohexyl)methyl)-2H-tetrazol-5-yl)-2-methoxyphenyl)sulfonamido)acetamide

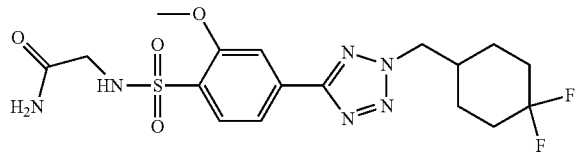

95

To a solution of tert-butyl (2-amino-2-oxoethyl)((4-(2-((4,4-difluorocyclohexyl)methyl)-2H-tetrazol-5-yl)-2-methoxyphenyl)sulfonyl)carbamate (210 mg, 0.270 mmol, Intermediate 129) in Dichloromethane (5 mL), 2,2,2-trifluoroacetic acid (97 μL, 1.350 mmol) was added dropwise at 0° C. under nitrogen. The reaction mixture was stirred at rt overnight. More 2,2,2-trifluoroacetic acid (97 μL, 1.350 mmol) was added dropwise at 0° C. under nitrogen and the mixture was stirred at rt overnight. The crude was diluted with water and extracted with DCM twice. The organic layer was dried over anhydrous Na$_2$SO$_4$, filtered and the filtrate was concentrated under reduced pressure. The crude was purified by flash column chromatography (silica gel; MeOH/CH$_2$Cl$_2$ from 0/100 to 20/80). The fractions were collected and concentrated in vacuo to obtain 2-((4-(2-((4,4-difluorocyclohexyl)methyl)-2H-tetrazol-5-yl)-2-methoxyphenyl)sulfonamido)acetamide (20 mg, 16.7%) as a white solid. $^1$H NMR (400 MHz, DMSO-d$_6$) δ 7.90 (m, 1H), 7.75 (m, 2H), 7.42 (br s, 1H), 7.21 (br s, 1H), 7.08 (br s, 1H), 4.75 (m, 2H), 4.00 (s, 3H), 3.48 (s, 2H), 2.26-1.65 (m, 7H), 1.34 (m, 2H). MS m/z [M+H]$^+$=445.3.

Example 96: 2-((4-(2-((tetrahydro-2H-pyran-2-yl)methyl)-2H-tetrazol-5-yl)phenyl)sulfonamido)acetamide

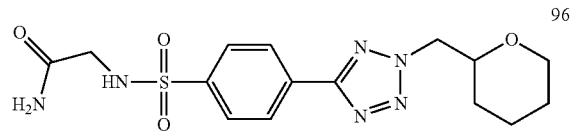 [SMILES: NC(=O)CNS(=O)(=O)c1ccc(-c2nnn(CC3CCCCO3)n2)cc1]

96

N-ethyl-N-isopropylpropan-2-amine (371 μL, 2.126 mmol, commercial source: Aldrich) was added to a stirred solution of 2-((4-(2H-tetrazol-5-yl)phenyl)sulfonamido)acetamide (200 mg, 0.709 mmol, Intermediate 25') in N,N-Dimethylformamide (4 mL). The mixture was heated at 70° C., and then 2-(bromomethyl)tetrahydro-2H-pyran (91 μL, 0.709 mmol, commercial source: Aldrich) was added and the reaction mixture was stirred at 70° C. over the weekend. The reaction mixture was concentrated under reduced pressure and the crude was purified by flash column chromatography (silica; MeOH/CH$_2$Cl$_2$ from 0/100 to 10/90). The fractions were concentrated in vacuo to obtain 2-((4-(2-((tetrahydro-2H-pyran-2-yl)methyl)-2H-tetrazol-5-yl)phenyl)sulfonamido)acetamide). To remove minimal impurities, the solid was triturated in Et$_2$O and filtered. Then, it was dissolved in DCM and washed with water (twice). The organic layer was dried over Na$_2$SO$_4$ and concentrated under reduced pressure to obtain 2-((4-(2-((tetrahydro-2H-pyran-2-yl)methyl)-2H-tetrazol-5-yl)phenyl)sulfonamido)acetamide (26 mg, 9.6%) as a yellowish solid. $^1$H NMR (400 MHz, DMSO-d$_6$) δ 8.24 (m, 2H), 8.04 (m, 1H), 7.98 (m, 2H), 7.29 (br s, 1H), 7.08 (br s, 1H), 4.83-4.75 (m, 2H), 3.95-3.89 (m, 1H), 3.82-3.76 (m, 1H), 3.43 (m, 2H), 3.30-3.25 (m, 1H), 1.83-1.72 (m, 2H), 1.54-1.31 (m, 4H). MS m/z [M+H]$^+$=381.2.

Examples 97-100 were prepared by methods analogous to that described for Example 18 replacing the alkylating reagents and base conditions with those indicated in Table 6. The method used for purification is indicated as footnotes.

TABLE 6

| Ex. | Structure | Conditions | Alkylating agent & conditions | Yield & Physical data |
|---|---|---|---|---|
| 97 | N-(2-hydroxyethyl)-4-(2-(4-(trifluoromethoxy)benzyl)-2H-tetrazol-5-yl)benzenesulfonamide (See footnote a, then b) | DIPEA (3 eq, 389 μL, 2.233 mmol)/ Intermediate 17' | 1-(bromomethyl)-4-(trifluoromethoxy)benzene (2 eq, 238 μL, 1.486 mmol, commercial source: Aldrich); stirred at rt for 16 h, then at 50° C. for 2 h | Yield: 53.7%, white solid. 1H NMR (400 MHz, DMSO-d$_6$) δ 8.25 (m, 2H), 7.97 (m, 2H), 7.78 (br s, 1H), 7.58 (m, 2H), 7.42 (m, 2H), 6.10 (s, 2H), 4.69 (m, 1H), 3.39-3.34 (m, 2H), 2.85-2.80 (m, 2H). MS m/z [M − H]$^-$ = 442.1. |

TABLE 6-continued

| Ex. | Structure | Conditions | Alkylating agent & conditions | Yield & Physical data |
|---|---|---|---|---|
| 98 | 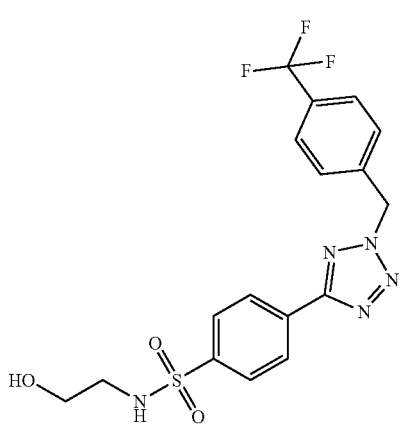<br>N-(2-hydroxyethyl)-4-(2-(4-(trifluoromethyl)benzyl)-2H-tetrazol-5-yl)benzenesulfonamide<br>(See footnote a) | DIPEA (3 eq, 389 µL, 2.233mmol)/ Intermediate 17' | 1-(chloromethyl)-4-(trifluoromethyl)benzene (2 eq, 220 µL, 1.486 mmol, commercial source: Aldrich); stirred at rt overnight, then at 50° C. for 2 h. | Yield: 42 %, white solid. $^1$H NMR (400 MHz, DMSO-$d_6$) δ 8.25 (m, 2H), 7.97 (m, 2H), 7.79 (m, 2H), 7.78 (s, 1H), 7.63 (m, 2H), 6.19 (s, 2H), 4.69 (m, 1H), 3.39-3.34 (m, 2H), 2.85-2.80 (m, 2H). MS m/z [M − H]$^−$ = 426.1 |
| 99 | 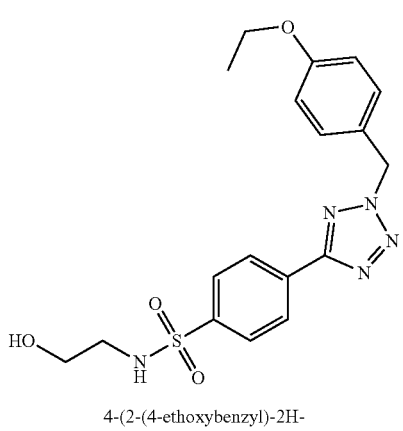<br>4-(2-(4-ethoxybenzyl)-2H-tetrazol-5-yl)-N-(2-hydroxyethyl)benzenesulfonamide<br>(See footnote b,d) | DIPEA (2.8 eq, 363 µL, 2.079 mmol)/ Intermediate 17' | 4-ethoxybenzyl methanesulfonate (1.5 eq, 257 mg, 1.114 mmol, Intermediate 130); stirred at rt overnight | Yield: 13%, white solid. 1H NMR (400 MHz, DMSO-$d_6$) δ 8.24 (m, 2H), 7.96 (m, 2H), 7.77 (m, 2H), 7.38 (m, 2H), 6.94 (m, 2H), 5.94 (s, 2H), 4.68 (m, 1H), 4.01 (q, J = 7 Hz, 2H), 3.36 (q, J = 6.1 Hz, 2H), 2.83 (q, J = 6.2 Hz, 2H), 1.30 (t, J = 6.9 Hz, 3H). MS m/z [M + H]$^+$ = 404.2 | h) Residue was purified by flash chromatography EtOAc-cyclohexane from 0/100 to 100/0.
i) Residue was purified by flash chromatography EtOAc-cyclohexane from 0/100 to 50/50
j) The obtained solid was washed in Et$_2$O and filtered to afford the final product.
k) Finally, the residue was purified by HPLC preparative using X-Bridge column (19 × 150 mm) linear gradient 50-100% ACN/H2O (10 mM NH$_4$HCO$_3$)

Example 100: 4-(2-(cyclohexylmethyl)-2H-tetrazol-5-yl)-N-(2-hydroxyethyl)benzenesulfonamide

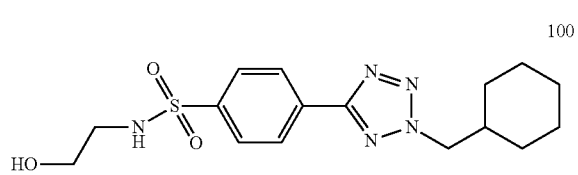 [SMILES: O=S(=O)(NCCO)c1ccc(-c2nnn(CC3CCCCC3)n2)cc1]

To a solution of N-(2-hydroxyethyl)-4-(2H-tetrazol-5-yl)benzenesulfonamide (200 mg, 0.743 mmol, Intermediate 17) in N,N-Dimethylformamide (DMF) (10.0 mL), potassium carbonate (205 mg, 1.48 mmol, commercial source: RCP) was added, followed by the addition of (bromomethyl)cyclohexane (158 mg, 0.89 mmol, commercial source: Sigma Aldrich) at 26° C. The reaction mixture was heated to 100° C. for 16 h. Upon completion, the reaction mixture was cooled to 26° C. and evaporated under reduced pressure. The crude was purified by column chromatography (silicagel 100-200 mesh), eluted with 3% methanol in dichloromethane. The pure fractions were collected and concentrated under reduced pressure to afford 4-(2-(cyclohexylmethyl)-2H-tetrazol-5-yl)-N-(2-hydroxyethyl)benzenesulfonamide (50 mg, 18%). $^1$H NMR (400 MHz, DMSO-$d_6$) δ 8.28-8.24 (m, 2H), 8.00-7.96 (m, 2H), 7.74 (br s, 1H), 4.69-4.61 (m, 3H), 3.37 (q, J=6.4 Hz, 2H), 2.84 (t, J=6.4 Hz, 2H), 2.07-1.97 (m, 1H), 1.72-1.56 (m, 5H), 1.27-1.05 (m, 5H). MS m/z [M+H]$^+$=366.18.

Example 101: N-(2-hydroxyethyl)-4-(2-((6-methylpyridin-3-yl)methyl)-2H-tetrazol-5-yl)benzenesulfonamide

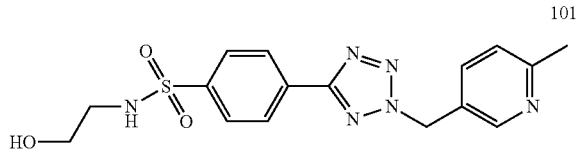 [SMILES: Cc1ccc(Cn2nnc(-c3ccc(S(=O)(=O)NCCO)cc3)n2)cn1]

101

To a solution of N-(2-hydroxyethyl)-4-(2H-tetrazol-5-yl)benzenesulfonamide (200 mg, 0.743 mmol, Intermediate 17) in N,N-Dimethylformamide (DMF) (10.0 mL), potassium carbonate (205 mg, 1.48 mmol, commercial source: RCP) was added, followed by the addition of 5-(chloromethyl)-2-methylpyridine (126 mg, 0.89 mmol, commercial source: AstaTech) at 26° C. The reaction mixture was heated to 80° C. for 4 h. Upon completion, the reaction mixture was cooled to 26° C. and evaporated under reduced pressure. The crude was purified by column chromatography (silicagel 100-200 mesh), eluted with 5% methanol in dichloromethane. The pure fractions were collected and concentrated under reduced pressure to afford a batch, which was purified by prep-HPLC.

Prep-HPLC Conditions:
Column: Kromasil C18 (150×25) mm, 10µ
Mobile phase: A—10 mM ammonium bicarbonate (aq), B—acetonitrile
Method (time in min/% of B): 0/10, 1/10, 10/40, 10.5/100, 13/100, 13.5/10
Flow: 25 mL/min
Temperature: Ambient The pure fractions were lyophilized to afford N-(2-hydroxyethyl)-4-(2-((6-methylpyridin-3-yl)methyl)-2H-tetrazol-5-yl)benzenesulfonamide (100 mg, 36%) as a white solid. $^1$H NMR (400 MHz, DMSO-d$_6$) δ 8.59 (d, J=2.0 Hz, 1H), 8.25-8.23 (m, 2H), 7.97-7.94 (m, 2H), 7.75-7.72 (m, 1H), 7.29 (d, J=7.9 Hz, 1H), 6.05 (s, 2H), 4.66 (br s, 1H), 3.36 (t, J=6.4 Hz, 2H), 2.83 (t, J=6.3 Hz, 2H), 2.47 (s, 3H). MS m/z [M+H]$^+$=375.12.

Example 102: N-(2-hydroxyethyl)-4-(2-(pyridin-3-ylmethyl)-2H-tetrazol-5-yl)benzenesulfonamide

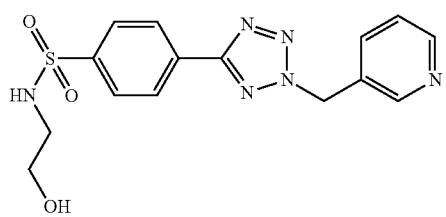

102

To a solution of N-(2-hydroxyethyl)-4-(2H-tetrazol-5-yl)benzenesulfonamide (200 mg, 0.743 mmol, Intermediate 17) in acetonitrile (10.0 mL), was added N,N-diisopropylethylamine (191 mg, 1.478 mmol, commercial source: Avra) followed by the addition of 3-(chloromethyl)pyridine hydrochloride (146 mg, 0.89 mmol, commercial source: Combi-Blocks) at 26° C. The reaction mixture was heated to 80° C. for 16 h. Upon completion, the reaction mixture was cooled to 26° C. was evaporated under reduced pressure. The crude was purified by column chromatography (silicagel 100-200 mesh), eluted with 5% methanol in dichloromethane. The pure fractions were collected and concentrated under reduced pressure to afford N-(2-hydroxyethyl)-4-(2-(pyridin-3-ylmethyl)-2H-tetrazol-5-yl)benzenesulfonamide (65 mg, 24%). $^1$H NMR (400 MHz, DMSO-d$_6$) δ=8.73 (d, J=2.0 Hz, 1H), 8.59 (dd, J=1.6 Hz, 4.7 Hz, 1H), 8.27-8.23 (m, 2H), 7.99-7.96 (m, 2H), 7.88-7.86 (m, 1H), 7.78 (d, J=6.1 Hz, 1H), 7.49-7.42 (m, 4.8, 7.9 Hz, 1H), 6.12 (s, 2H), 4.69 (t, J=5.6 Hz, 1H), 3.40-3.34 (m, 2H), 2.83 (d, J=6.1 Hz, 1H). MS m/z [M+H]$^+$=361.12.

Example 103: (N-(2-hydroxyethyl)-4-(2-((5-methoxypyridin-2-yl)methyl)-2H-tetrazol-5-yl)benzenesulfonamide)

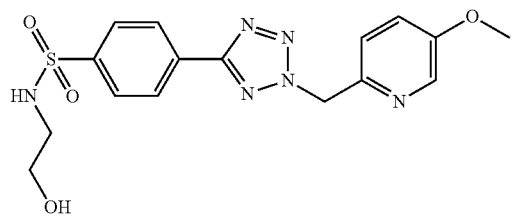

103

To a solution of N-(2-hydroxyethyl)-4-(2H-tetrazol-5-yl)benzenesulfonamide (1) (200 mg, 0.743 mmol, Intermediate 17) in acetonitrile (10.0 mL), potassium carbonate (205 mg, 0.88 mmol, commercial source: RCP) was added, followed by the addition of 2-(chloromethyl)-5-methoxypyridine (140 mg, 0.89 mmol, commercial source: Enamine) at 26° C. The reaction mixture was heated to 80° C. for 16 h. Upon completion, the reaction mixture was cooled to 26° C. was evaporated under reduced pressure. The crude was purified by column chromatography (silicagel 100-200 mesh), eluted with 3% methanol in dichloromethane. The pure fractions were collected and concentrated under reduced pressure to afford a batch (100 mg, 63%), which was submitted for prep HPLC purification.

Prep HPLC Conditions:
Mobile Phase A: —10 mM Ammonium Bicarbonate (Aq), Mobile phase B: —Acetonitrile Column: —XBridge C18 (150*19) mm, 5 u Flow: —16 ml/min, Method (t/% of B): —0/10. 1/10, 10/55, 22/100, 22.2/35.5, 25/35.5. Solubility: —ACN+THF+WATER Temperature: —Ambient.

The pure fractions were lyophilized to afford N-(2-hydroxyethyl)-4-(2-((5-methoxypyridin-2-yl)methyl)-2H-tetrazol-5-yl)benzenesulfonamide (28 mg, 10%). $^1$H NMR (400 MHz, DMSO-d$_6$) δ 8.36 (d, J=2.4 Hz, 1H), 8.26-8.23 (m, 2H), 7.98-7.96 (m, 2H), 7.83-7.79 (m, 2H), 6.86 (d, J=8.6 Hz, 1H), 5.99 (s, 2H), 4.65 (br s, 1H), 3.85 (s, 3H), 3.38-3.36 (m, 2H), 2.86-2.83 (m, 2H). MS m/z [M+H]$^+$=391.12.

Example 104: N-(2-hydroxyethyl)-4-(2-((tetrahydro-2H-pyran-3-yl)methyl)-2H-tetrazol-5-yl)benzenesulfonamide

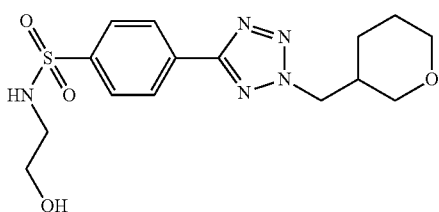

To a solution of N-(2-hydroxyethyl)-4-(2H-tetrazol-5-yl)benzenesulfonamide (200 mg, 0.743 mmol, Intermediate 17) in N,N-Dimethylformamide (10 mL), potassium carbonate (205 mg, 1.478 mmol, commercial source: RCP) was added followed by the addition of 3-(chloromethyl)tetrahydro-2H-pyran (120 mg, 0.89 mmol, Intermediate 131) at 26° C. The reaction mixture was heated to 100° C. for 16 h. Upon completion, the reaction mixture was cooled to 26° C. and evaporated under reduced pressure. The crude was purified by column chromatography (silicagel 100-200 mesh), eluted with 2% methanol in dichloromethane. The pure fractions were concentrated under reduced pressure to afford the compound with a purity by LCMS of 80%, which was further purified by Prep-HPLC.

PrepHPLC Condition:
Column: YMC-Triart C8 (150×25) mm, 10 u
Mobile Phase A: 10 mM Ammonium Bicarbonate(Aq) B: Acetonitrile
Method (time in min/% of B): 0/20, 1/20, 10/40, 10.5/100, 15/100, 15.5/20
Flow: 25 ml/min
Temp: ambient The pure fractions were collected and lyophilized to afford N-(2-hydroxyethyl)-4-(2-((tetrahydro-2H-pyran-3-yl)methyl)-2H-tetrazol-5-yl)benzenesulfonamide (28 mg, 24%). $^1$H NMR (400 MHz, DMSO-$d_6$) δ 8.26 (d, J=8.3 Hz, 2H), 7.98 (d, J=8.3 Hz, 2H), 7.75 (br s, 1H), 4.80-4.63 (m, 3H), 3.77-3.66 (m, 2H), 3.43-3.35 (m, 3H), 3.26 (s, 1H), 2.90-2.80 (m, 2H), 2.26 (br s, 1H), 1.79-1.60 (m, 2H), 1.52-1.43 (m, 1H), 1.39-1.28 (m, 1H). MS m/z [M+H]$^+$=368.18.

Example 105: N-(2-hydroxyethyl)-4-(2-((tetrahydro-2H-pyran-4-yl)methyl)-2H-tetrazol-5-yl)benzenesulfonamide

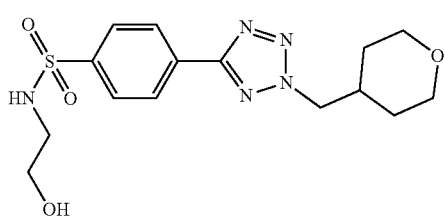

To a solution of N-(2-hydroxyethyl)-4-(2H-tetrazol-5-yl)benzenesulfonamide (200 mg, 0.743 mmol, Intermediate 17) in N,N-dimethylformamide (10 mL), potassium carbonate (205 mg, 1.485 mmol, commercial source: RCP) was added followed by the addition of 4-(bromomethyl)tetrahydro-2H-pyran (159 mg, 0.88 mmol, commercial source: Aldrich) at 26° C. The reaction mixture was heated to 80° C. for 8 h. Upon completion, the reaction mixture was cooled to 26° C. and evaporated under reduced pressure. The crude was purified by column chromatography (silicagel 100-200 mesh), eluted with 5% methanol in dichloromethane. The pure fractions were concentrated under reduced pressure to afford N-(2-hydroxyethyl)-4-(2-((tetrahydro-2H-pyran-4-yl)methyl)-2H-tetrazol-5-yl)benzenesulfonamide (80 mg, 18%). $^1$H NMR (400 MHz, DMSO-$d_6$) δ 8.28-8.24 (m, 2H), 7.98 (d, J=8.6 Hz, 2H), 7.79-7.72 (m, 1H), 4.73-4.65 (m, 3H), 3.88-3.80 (m, 2H), 3.38 (q, J=6.1 Hz, 2H), 3.29-3.27 (m, 2H), 2.85 (q, J=5.3 Hz, 2H), 2.35-2.23 (m, 1H), 1.52-1.46 (m, 2H), 1.40-1.31 (m, 2H). MS m/z [M+H]$^+$=368.12.

Example 106: N-(2-hydroxyethyl)-4-(2-(pyridazin-4-ylmethyl)-2H-tetrazol-5-yl)benzenesulfonamide

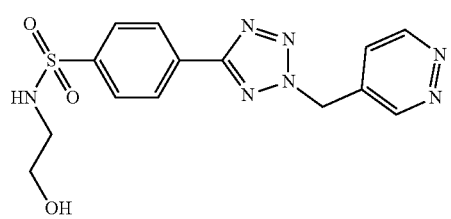

To a solution of N-(2-hydroxyethyl)-4-(2H-tetrazol-5-yl)benzenesulfonamide (200 mg, 0.743 mmol, Intermediate 17) in N,N-Dimethylformamide (10 mL), potassium carbonate (205 mg, 1.485 mmol, commercial source: RCP) was added followed by the addition of 4-(chloromethyl)pyridazine (115 mg, 0.89 mmol, Intermediate 132) at 26° C. The reaction mixture was stirred at 26° C. for 16 h. Upon completion, the reaction mixture was evaporated under reduced pressure. The crude was purified by column chromatography (silicagel 100-200 mesh), eluted with 4% methanol in dichloromethane. The pure fractions were concentrated under reduced pressure to afford N-(2-hydroxyethyl)-4-(2-(pyridazin-4-ylmethyl)-2H-tetrazol-5-yl)benzenesulfonamide (10 mg, 3.7%). $^1$H NMR (400 MHz, DMSO-$d_6$) δ 9.35-9.32 (m, 1H), 9.28-9.26 (m, 1H), 8.28-8.25 (m, 2H), 7.98 (d, J=8.6 Hz, 2H), 7.80-7.72 (m, 1H), 7.65-7.63 (m, 1H), 6.23-6.21 (m, 2H), 4.68-4.65 (m, 1H), 3.40-3.35 (m, 2H), 2.88-2.81 (m, 2H). MS m/z [M+H]$^+$=362.12.

Example 107: N-(2-hydroxyethyl)-4-(2-(pyridazin-3-ylmethyl)-2H-tetrazol-5-yl)benzenesulfonamide

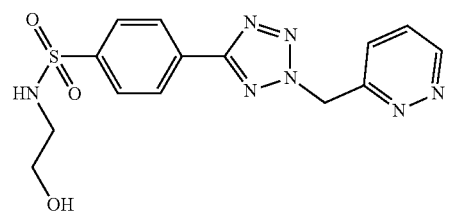

To a solution of N-(2-hydroxyethyl)-4-(2H-tetrazol-5-yl)benzenesulfonamide (200 mg, 0.743 mmol, Intermediate 17) in N,N-Dimethylformamide (10 mL), potassium carbonate (205 mg, 1.485 mmol, commercial source: RCP) was added followed by the addition of 3-(chloromethyl)pyridazine (115 mg, 0.89 mmol, Intermediate 133) at 26° C. The reaction mixture was stirred at 26° C. for 16 h. Upon completion, the reaction mixture was evaporated under reduced pressure. The crude was purified by column chromatography (silica-gel 100-200 mesh), eluted with 5% methanol in dichloromethane. The pure fractions were concentrated under reduced pressure to afford the compound with a purity by LCMS of 77%. The compound was further purified by Prep-HPLC.

PrepHPLC Condition:
Column: Kromasil C18 (150×25) mm, 10 u
Mobile Phase: A—10 mM Ammonium Bicarbonate (Aq), B—Acetonitrile
Method (time in min/% of B): 0/40, 1/40, 10/75, 13/75, 13.2/100, 17/100, 17.2/40, 20/40
Flow: 25 ml/min,
Temperature: ambient The pure fractions were collected and lyophilized to afford N-(2-hydroxyethyl)-4-(2-(pyridazin-3-ylmethyl)-2H-tetrazol-5-yl)benzenesulfonamide (66 mg, 24.6%). $^1$H NMR (400 MHz, DMSO-d$_6$) δ 9.28-9.23 (m, 1H), 8.29-8.24 (m, 2H), 7.97 (d, J=8.3 Hz, 2H), 7.85-7.73 (m, 3H), 6.40 (m, 2H), 4.66 (d, J=5.4 Hz, 1H), 3.40-3.36 (m, 2H), 2.84 (d, J=6.3 Hz, 2H). MS m/z [M−H]$^−$=360.12.

Example 108: 4-(2-(4-cyanobenzyl)-2H-tetrazol-5-yl)-N-methylbenzenesulfonamide

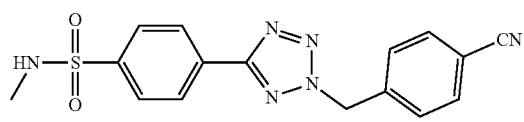

108

To a solution of N-methyl-4-(2H-tetrazol-5-yl)benzenesulfonamide (500 mg, 2.092 mmol, Intermediate 21) in N,N-Dimethylformamide (7 mL), potassium carbonate (577 mg, 4.184 mmol, commercial source: Avra) was added, followed by the addition of 4-(bromomethyl)benzonitrile (410 mg, 2.092 mmol, commercial source: Alfa Aesar) at 26° C. and stirred for 24 h. Upon completion, the reaction mixture was evaporated under reduced pressure. The crude was purified by column chromatography (silicagel 100-200 mesh), eluted with 2% methanol in dichloromethane and the product obtained was further purified by Prep-HPLC.

Prep-HPLC Conditions:
Column: Xselect CSH Phenyl-Hexyl (150×19) mm, 5μ
Mobile Phase: A—10 mM ammonium bicarbonate (Aq) B—acetonitrile
Method (time in min/% of B): 0/25, 10/55, 10.3/100, 12.7/100, 13/25, 15/25.
Flow: 20 mL/min
Temp: Ambient The pure fractions were concentrated under reduced pressure to afford 4-(2-(4-cyanobenzyl)-2H-tetrazol-5-yl)-N-methylbenzenesulfonamide (170 mg, 22%). $^1$H NMR (400 MHz, DMSO-d$_6$) δ 8.27 (d, J=8.6 Hz, 2H), 7.95 (d, J=8.6 Hz, 2H), 7.89 (d, J=8.3 Hz, 2H), 7.60 (d, J=8.3 Hz, 3H), 6.18 (s, 2H), 2.45 (s, 3H). MS m/z [M+H]$^+$=355.10.

Example 109: N-(2-hydroxyethyl)-2-methoxy-4-(2-((5-methoxypyridin-2-yl)methyl)-2H-tetrazol-5-yl)benzenesulfonamide

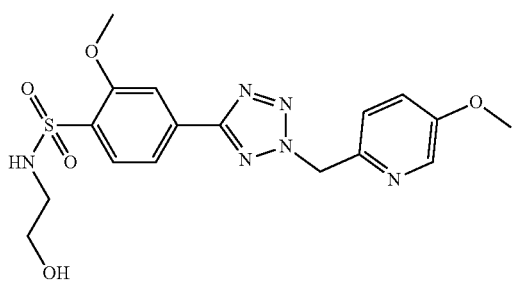

109

To a solution of N-(2-hydroxyethyl)-2-methoxy-4-(2H-tetrazol-5-yl)benzenesulfonamide-(380 mg, 0.0012 mol, Intermediate 33) in acetonitrile (7.6 mL), N,N-diisopropylethylamine (0.79 mL, 0.0048 mol, commercial source: Finar) was added, followed by the addition of 2-(chloromethyl)-5-methoxypyridine (239 mg, 0.0015 mol, Intermediate 134) at 26° C. The reaction mixture was heated to 80° C. for 16 h. Upon completion, the reaction mixture was cooled to 26° C. and diluted with ethyl acetate (50 mL) and water (10 mL). The aqueous layer was extracted with ethyl acetate (2×20 mL), dried over anhydrous Na$_2$SO$_4$, filtered and the filtrate was evaporated under reduced pressure. The crude was purified by column chromatography, eluted with 2% methanol in dichloromethane. The pure fractions were collected and concentrated under reduced pressure to afford N-(2-hydroxyethyl)-2-methoxy-4-(2-((5-methoxypyridin-2-yl)methyl)-2H-tetrazol-5-yl)benzenesulfonamide (7 mg) as an off-white solid. $^1$H NMR (400 MHz, DMSO-d$_6$) δ 8.23 (d, J=2.9 Hz, 1H), 7.89 (d, J=7.9 Hz, 1H), 7.76-7.73 (m, 2H), 7.52-7.46 (m, 2H), 7.18 (t, J=5.9 Hz, 1H), 6.06 (s, 2H), 4.60 (t, J=5.9 Hz, 1H), 4.00 (s, 3H), 3.82 (s, 3H), 3.38-3.33 (m, 2H), 2.88-2.83 (m, 2H). MS m/z [M+H]$^+$=421.13.

Example 110: 2-fluoro-4-(2-((5-fluoropyridin-2-yl)methyl)-2H-tetrazol-5-yl)-N-(2-hydroxyethyl)-5-methylbenzenesulfonamide

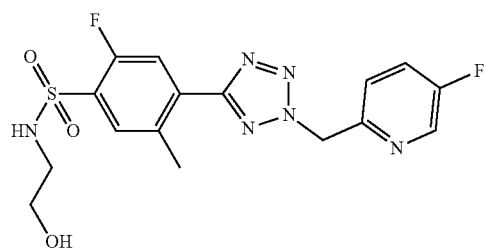

110

To a solution of 2-fluoro-N-(2-hydroxyethyl)-5-methyl-4-(2H-tetrazol-5-yl)benzenesulfonamide (1 g, 3.32 mmol, Intermediate 138) in acetonitrile (10 mL), 2-(bromomethyl)-5-fluoropyridine hydrobromide (1.07 g, 3.98 mmol, Intermediate 5) and N,N-diisopropylethylamine (1.71 mL, 9.96 mmol, commercial source: Avra) were added at room temperature. The reaction mixture was stirred at 90° C. overnight. Upon completion, the reaction mixture was poured into ice-cold water (200 mL) and extract with ethyl acetate (2×500 mL). The combined organic layers were dried over anhydrous $Na_2SO_4$, filtered and the filtrate was evaporated under reduced pressure. The crude was purified by column chromatography, eluted with 30% ethyl acetate in pet. ether. The pure fractions were collected and concentrated under reduced pressure and then it was purified by prep-HPLC (Prep HPLC conditions: XBridge C18 Column (150×19) mm, 5 u; Mobile Phase A: 10 mM Ammonium Bicarbonate (aq), Mobile Phase B: Acetonitrile; Method (time in min/% of B): 0/10, 15/10; Flow: 16 mL/Min, Temp: ambient). The pure fractions were collected, and concentrated under reduced pression to afford 2-fluoro-4-(2-((5-fluoropyridin-2-yl)methyl)-2H-tetrazol-5-yl)-N-(2-hydroxyethyl)-5-methylbenzenesulfonamide (157 mg, 11.4%) as an off-white solid. $^1$H NMR (400 MHz, DMSO-$d_6$) δ 8.55-8.54 (m, 1H), 8.01-7.88 (m, 2H), 7.85-7.80 (m, 2H), 7.66-7.63 (m, 1H), 6.18 (s, 2H), 4.65 (bs, 1H), 3.38 (t, J=6.5 Hz, 2H), 2.96 (t, J=6.3 Hz, 2H), 2.58 (s, 3H). MS m/z $[M+H]^+$=411.10

Example 111: (4-(2-(1-(5-fluoropyridin-2-yl)ethyl)-2H-tetrazol-5-yl)-N-(2-hydroxyethyl)benzenesulfonamide

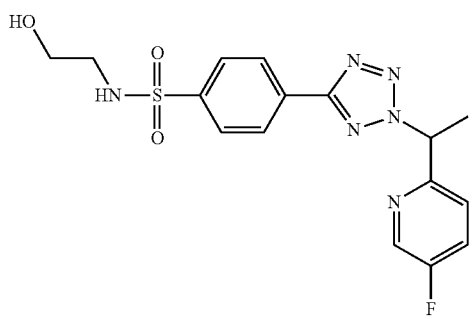

111

To a solution of N-(2-hydroxyethyl)-4-(2H-tetrazol-5-yl) benzenesulfonamide (400 mg, 0.0014 mol, intermediate 17), 2-(1-bromoethyl)-5-fluoropyridine (301 mg, 0.0014 mol, Intermediate 141) in acetonitrile (4 mL), N,N-diisopropylethylamine (0.46 mL, 0.0028 mol, commercial source: Finar) was added at 26° C. The reaction mixture was heated to 80° C. and stirred for 16 h at the same temperature. Upon completion, the reaction mixture was dissolved in ethyl acetate (100 mL) and washed with water (2×30 mL). The organic layer was concentrated under reduced pressure. The crude was purified by prep-HPLC and the pure fraction was dried under lyophilization to afford 4-(2-(1-(5-fluoropyridin-2-yl) ethyl)-2H-tetrazol-5-yl)-N-(2-hydroxyethyl) benzene sulfonamide (200 mg, 36%) as an off white solid.

Prep-HPLC Conditions:
Column: YMC Triart C8 (150×25) mm, 10μ
Mobile phase: $H_2O$ (10 mM $NH_4HCO_3$) B: ACN
Method (time in min/% of B): 0/30, 1/30, 10/65, 11/65, 11.5/100, 13.5/100, 14/30, 16/30
Flow: 20 mL/min
Temperature: Ambient The obtained racemic compound was submitted to chiral prep-SFC for the separation of isomers.

SFC Prep Conditions:
Column: Chiralpak AD-H (30×250 mm), 5μ
% $CO_2$: 70%: % co-solvent: 30% (100% ethanol)
Flow: 70 g/mm, Back pressure: 100 bar, UV: 253 nm, Stack time: 3.5 mn
Loading: 4 mg, Solubility: MeOH, No. of inj: 55
Instrument model: Make/model: SFC-80

The two pure fractions were dried under lyophilization to afford:

(S)-4-(2-(1-(5-fluoropyridin-2-yl)ethyl)-2H-tetrazol-5-yl)-N-(2-hydroxyethyl)benzenesulfonamide

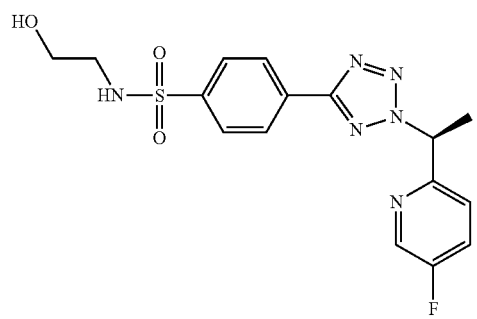

111-Isomer 1

(78 mg, 14%) as an off-white solid. $^1$H NMR (400 MHz, DMSO-$d_6$) δ 8.54 (d, J=2.9 Hz, 1H), 8.24 (d, J=8.6 Hz, 2H), 7.96 (d, J=8.6 Hz, 2H), 7.85-7.75 (m, 1H), 7.74 (br s, 1H), 7.66-7.58 (m, 1H), 6.48 (q, J=6.9 Hz, 1H), 4.66 (t, J=5.5 Hz, 1H), 3.36 (q, J=6.1 Hz, 2H), 2.83 (q, J=5.8 Hz, 2H), 2.06 (d, J=7.0 Hz, 3H). MS m/z $[M+H]^+$=393.14, chiral purity: ee %=99.86%. The absolute configuration was determined by ab initio vibrational circular dichroism (VCD).

(R)-4-(2-(1-(5-fluoropyridin-2-yl)ethyl)-2H-tetrazol-5-yl)-N-(2-hydroxyethyl)benzenesulfonamide

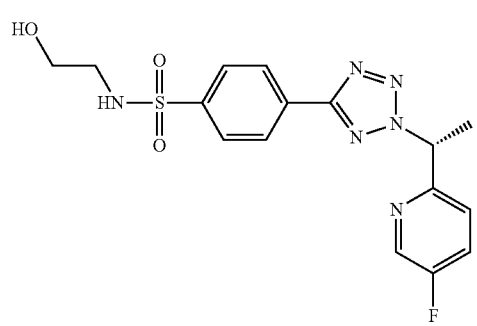

111-Isomer 2

(69 mg, 13%) as a pale yellow gum. $^1$H NMR (400 MHz, DMSO-$d_6$) δ 8.54 (d, J=2.9 Hz, 1H), 8.24 (d, J=8.6 Hz, 2H), 7.96 (d, J=8.3 Hz, 2H), 7.85-7.77 (m, 1H), 7.74 (t, J=5.8 Hz, 1H), 7.65-7.58 (m, 1H), 6.48 (q, J=6.9 Hz, 1H), 4.66 (t, J=5.6 Hz, 1H), 3.36 (q, J=6.1 Hz, 2H), 2.83 (q, J=6.1 Hz, 2H), 2.06 (d, J=7.0 Hz, 3H). MS m/z $[M+H]^+$=393.14, chiral purity: ee %=97.5%. The absolute configuration was determined by ab initio vibrational circular dichroism (VCD).

Example 112: 4-(2-(1-(5-fluoropyridin-2-yl)ethyl)-2H-tetrazol-5-yl)-N-(2-hydroxyethyl)benzenesulfonamide

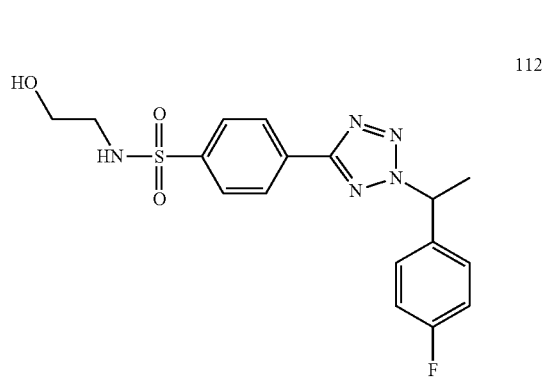 [SMILES: CC(c1ccc(F)cc1)n1nnc(-c2ccc(S(=O)(=O)NCCO)cc2)n1]

Example 113: 4-(1-(1-(4-fluorophenyl)ethyl)-1H-1,2,3-triazol-4-yl)-N-(2-hydroxyethyl)benzenesulfonamide

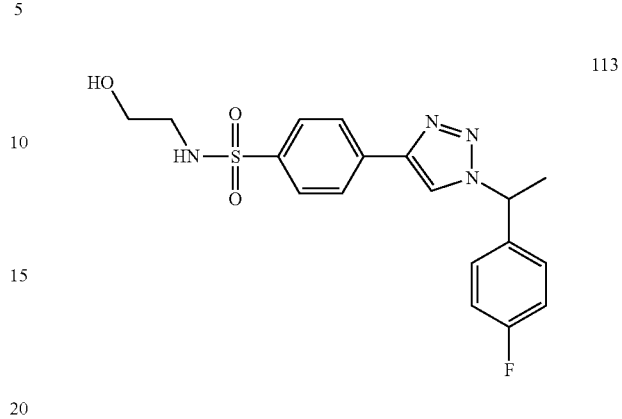

To a solution of N-(2-hydroxyethyl)-4-(2H-tetrazol-5-yl)benzenesulfonamide (300 mg, 0.0011 mol, intermediate 17) and N,N-diisopropylethylamine (0.38 mL, 0.0022 mol, commercial source: Finar) in acetonitrile (6 mL), 1-(1-bromoethyl)-4-fluorobenzene (271 mg, 0.0013 mol, Intermediate 142) was added at 26° C. The reaction mixture was heated to 85° C. and stirred for 16 h at the same temperature. Upon completion, the reaction mixture was cooled to 26° C., dissolved in ethyl acetate (10 mL) and washed with water (30 mL) and brine (40 mL). The organic layer was dried over $Na_2SO_4$, filtered and concentrated under reduced pressure. The crude was purified by column chromatography (silicagel 100-200 mesh), eluted with 1.5% methanol in dichloromethane. The pure fractions were collected and concentrated under reduced pressure to afford (4-(2-(1-(5-fluoropyridin-2-yl)ethyl)-2H-tetrazol-5-yl)-N-(2-hydroxyethyl)benzenesulfonamide (110 mg, 26%) as an off white solid.

The obtained racemic compound was submitted to chiral prep-SFC for the separation of isomers.

SFC Prep Conditions:

Column: Chiralpak IG (30×250 mm), 5µ

% $CO_2$: 55%: % co-solvent: 45% (100% methanol)

Flow: 90 g/mm, Back pressure: 90 bar, UV: 254 nm, Stack time: 5.5 mn

Loading: 8.6 mg, Solubility: MeOH, No. of inj: 20

Instrument model: Make/model: SFC-200-002

The two pure fractions were dried under lyophilization to afford:

Isomer 1: (43 mg, 10%) as a brown gummy solid and as a single unknown enantiomer. $^1$H NMR (400 MHz, DMSO-$d_6$) δ 8.24 (d, J=8.1 Hz, 2H), 7.96 (d, J=8.3 Hz, 2H), 7.52-7.49 (m, 2H), 7.26-7.21 (m, 2H), 6.44-6.39 (m, 1H), 3.38-3.35 (m, 2H), 2.85-2.82 (m, 2H), 2.02 (d, J=7 Hz, 3H). MS m/z [M+H]$^+$=392.05, chiral purity: ee %=99.53%.

Isomer 2: (49 mg, 11%) as a brown gummy solid and as a single unknown enantiomer. $^1$H NMR (400 MHz, DMSO-$d_6$) δ 8.25 (d, J=8.3 Hz, 2H), 7.97 (d, J=8.3 Hz, 2H), 7.76-7.73 (m, 1H), 7.52-7.49 (m, 2H), 7.26-7.21 (m, 2H), 6.44-6.39 (m, 1H), 4.67-4.64 (m, 2H), 3.39-3.34 (m, 2H), 2.86-2.81 (m, 2H), 2.03-2.01 (m, 3H). MS m/z [M+H]$^+$= 392.02, chiral purity: ee %=99.80%.

To a solution of 4-ethynyl-N-(2-hydroxyethyl)benzenesulfonamide (310 mg, 0.0014 mol, intermediate 62), and 1-(1-azidoethyl)-4-fluorobenzene (227 mg, 0.0014 mol, Intermediate 144) in ethanol (6.2 mL) and water (6.2 mL), sodium-L-ascarbate (81.8 mg, 0.00041 mol, commercial source: Aldrich) and $CuSO_4.5H_2O$ (34.3 mg, 0.00014 mol, commercial source: Finar) were added and the reaction mixture stirred for 16 h at 26° C. Upon completion, ethanol was removed under vacuum. The reaction mixture was dissolved in ethyl acetate (100 mL), washed with brine (2×30 mL), dried over $Na_2SO_4$, filtered and concentrated under reduced pressure. The crude was purified by column chromatography (silicagel 100-200 mesh), eluted with 1.8% methanol in dichloromethane. The pure fractions were collected and concentrated under reduced pressure to afford 4-(1-(1-(4-fluorophenyl)ethyl)-1H-1,2,3-triazol-4-yl)-N-(2-hydroxyethyl)benzenesulfonamide (170 mg, 32%).

The obtained racemic compound was submitted to chiral prep-SFC for the separation of isomers.

SFC Prep Conditions:

Column: (R,R) Whelk-01 (30×250 mm), 5µ

% $CO_2$: 70%: % co-solvent: 30% (100% isopropanol)

Flow: 90 g/mm, Back pressure: 90 bar, UV: 261 nm, Stack time: 6.4 mn

Loading: 6 mg, Solubility: MeOH, No. of inj: 30

Instrument model: Make/model: SFC-200-003

The two pure fractions were dried under lyophilization to afford:

Isomer 1: (68 mg, 12%) as an off white solid and as a single unknown enantiomer. $^1$H NMR (400 MHz, DMSO-$d_6$) δ 8.88 (s, 1H), 8.05 (d, J=8.1 Hz, 2H), 7.85 (d, J=8.3 Hz, 2H), 7.59 (br s, 1H), 7.45-7.42 (m, 2H), 7.24-7-20 (m, 2H), 6.07-6.01 (m, 1H), 4.66-4.64 (m, 1H), 3.39-3.34 (m, 2H), 2.83-2.80 (m, 2H), 1.93 (d, J=7.2 Hz, 3H). MS m/z [M+H]$^+$= 391.04, chiral purity: ee %=99.38%.

Isomer 2: (43 mg, 8%) as an off white solid and as a single unknown enantiomer. $^1$H NMR (400 MHz, DMSO-$d_6$) δ 8.89 (s, 1H), 8.05 (d, J=8.6 Hz, 2H), 7.85 (d, J=8.3 Hz, 2H), 7.61-7.58 (m, 1H), 7.45-7.42 (m, 2H), 7.24-7-20 (m, 2H), 6.07-6.01 (m, 1H), 4.67-4.64 (m, 1H), 3.38-3.34 (m, 2H), 2.84-2.79 (m, 2H), 1.93 (d, J=7 Hz, 3H). MS m/z [M+H]$^+$=391.10, chiral purity: ee %=97.59%.

Example 114: 2-(4-(2-(1-(4-fluorophenyl)ethyl)-2H-tetrazol-5-yl)phenylsulfonamido)acetamide

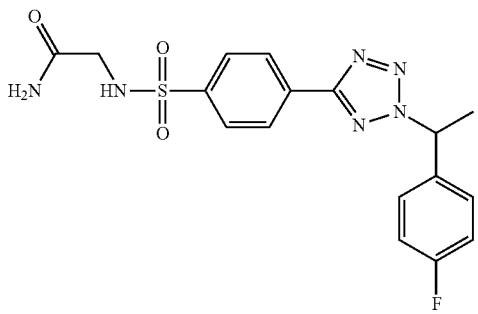

114

To a solution of 2-(4-(2-(1-(4-fluorophenyl)ethyl)-2H-tetrazol-5-yl)phenylsulfonamido)acetic acid (140 mg, 0.00035 mol, intermediate 146) in DMF (1.4 mL), N,N-diisopropylethylamine (0.12 mL, 0.00069 mol, commercial source: Finar), NH$_4$Cl (27 mg, 0.00052 mol, commercial source: Finar) and HATU (144 mg, 0.00038 mol, commercial source: Aldrich) were added and the mixture stirred at 26° C. for 16 h. Upon completion, the reaction mixture was dissolved in ethyl acetate (100 mL) and washed with cold water (4×50 mL) and brine (50 mL). The organic layer was dried over Na$_2$SO$_4$, filtered and concentrated under reduced pressure. The crude was purified by column chromatography (silicagel 100-200 mesh), eluted with 2% methanol in dichloromethane. The pure fractions were collected and concentrated under reduced pressure to afford 2-(4-(2-(1-(4-fluorophenyl)ethyl)-2H-tetrazol-5-yl)phenylsulfonamido)acetamide (130 mg, 92%).

The obtained racemic compound was submitted to chiral prep-SFC for the separation of isomers.

SFC Prep Conditions:
Column: Chiralpak AD-H (30×250 mm), 5µ
% CO$_2$: 70%: % co-solvent: 30% (100% methanol)
Flow: 70 g/mm, Back pressure: 90 bar, UV: 254 nm, Stack time: 11.0 mn
Loading: 4.5 mg, Solubility: MeOH+MeCN, No. of inj: 30
Instrument model: Make/model: SFC-80

The two pure fractions were dried under lyophilization to afford:

Isomer 1: (23 mg, 16%) as an off white solid and a single unknown enantiomer. $^1$H NMR (400 MHz, DMSO-d$_6$) δ 8.23 (d, J=8.3 Hz, 2H), 8.01 (br s, 1H), 7.97 (d, J=8.3 Hz, 2H), 7.52-7.49 (m, 2H), 7.26-7.21 (m, 3H), 7.04 (br s, 1H), 6.44-6.39 (m, 1H), 3.43 (s, 2H), 2.02 (d, J=6.8 Hz, 3H). MS m/z [M+H]$^+$=405.05, chiral purity: ee %=99.34%.

Isomer 2: (30 mg, 21%) as an off white solid and as a single unknown enantiomer. Chiral purity: ee %=90.09%. It was repurified again by chiral-SFC (Column: Chiralpak AD-H (30×250 mm), 5µ; % CO$_2$: 70%: % co-solvent: 30% (100% methanol); Flow: 70 g/mm, Back pressure: 90 bar, UV: 254 nm, Stack time: 12.0 mn; Loading: 2.3 mg, Solubility: MeOH+MeCN, No. of inj: 10; Instrument model: Make/model: SFC-80). The pure compound was dried under lyophilization to afford 2-(4-(2-(1-(4-fluorophenyl)ethyl)-2H-tetrazol-5-yl)phenylsulfonamido)acetamide (14 mg, 10%) as an off white solid and as a single unknown enantiomer. $^1$H NMR (400 MHz, DMSO-d$_6$) δ 8.22 (d, J=8.3 Hz, 2H), 7.96 (d, J=8.3 Hz, 2H), 7.52-7.49 (m, 2H), 7.26-7.21 (m, 3H), 7.03 (br s, 1H), 6.44-6.39 (m, 1H), 3.43 (s, 2H), 2.02 (d, J=7 Hz, 3H). MS m/z [M+H]$^+$=405.05, chiral purity: ee %=99.26%.

Example 115: 2-(4-(2-(1-(4-fluorophenyl)ethyl)-2H-tetrazol-5-yl)-2-methoxyphenylsulfonamido)acetamide

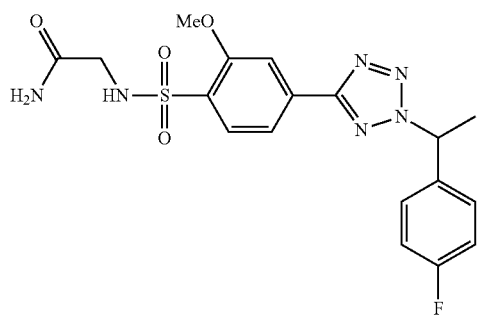

115

To a solution of tert-butyl (2-amino-2-oxoethyl)((4-(2-(1-(4-fluorophenyl)ethyl)-2H-tetrazol-5-yl)-2-methoxyphenyl)sulfonyl)carbamate (300 mg, 0.00056 mol, intermediate 148) in 1,4-dioxane (3 mL), 4M HCl (1.5 mL, commercial source: Hychem) was slowly added at 0° C. and the mixture stirred at 26° C. for 5 h. Upon completion, the reaction mixture was concentrated and dissolved in ethyl acetate (100 mL) and saturated NaHCO$_3$ solution. The organic layer was separated and the aqueous extracted with ethil acetate (2×30 mL). Combined organics were concentrated under reduced pressure. The crude was purified by column chromatography (silicagel 100-200 mesh), eluted with 1.5% methanol in dichloromethane. The pure fractions were collected and concentrated under reduced pressure to afford 2-(4-(2-(1-(4-fluorophenyl)ethyl)-2H-tetrazol-5-yl)-2-methoxyphenylsulfonamido)acetamide (220 mg, 90%).

The obtained racemic compound was submitted to chiral prep-SFC for the separation of isomers.

SFC Prep Conditions:
Column: Chiralpak OJ-H (21×250 mm), 5µ
% CO$_2$: 90%: % co-solvent: 10% (100% ethanol)
Flow: 70 g/mm, Back pressure: 90 bar, UV: 214 nm, Stack time: 6.5 mn
Loading: 5.1 mg, Solubility: MeOH+MeCN, No. of inj: 40
Instrument model: Make/model: SFC-80

The two pure fractions were dried under lyophilization to afford:

Isomer 1: (58 mg, 24%) as an off white solid and as a single unknown enantiomer. $^1$H NMR (400 MHz, DMSO-d$_6$) δ 7.90-7.88 (m, 1H), 7.74-7.73 (m, 2H), 7.51-7.48 (m, 2H), 7.38 (br s, 1H), 7.26-7.21 (m, 2H), 7.18 (br s, 1H), 7.04 (br s, 1H), 6.44-6.39 (m, 1H), 4.00 (s, 3H), 3.47 (s, 2H), 2.02 (d, J=7 Hz, 3H). MS m/z [M+H]$^+$=435.05, chiral purity: ee %=99.61%.

Isomer 2: (58 mg, 24%) as a white solid and as a single unknown enantiomer. $^1$H NMR (400 MHz, DMSO-d$_6$) δ 7.90-7.88 (m, 1H), 7.74-7.73 (m, 2H), 7.51-7.48 (m, 2H), 7.38 (br s, 1H), 7.26-7.21 (m, 2H), 7.18 (br s, 1H), 7.04 (br s, 1H), 6.44-6.39 (m, 1H), 4.00 (s, 3H), 3.47 (s, 2H), 2.02 (d, J=7 Hz, 3H). MS m/z [M+H]$^+$=435.11, chiral purity: ee %=98.69%.

Biological Activity

*Mycobacterium tuberculosis* H37Rv Inhibition Assay (Whole Cell Assay)

The measurement of the Minimum Inhibitory Concentration (MIC) against *M. tuberculosis* H37Rv for each tested compound was performed in 96-well flat-bottom, polystyrene microtiter plates in a final volume of 200 µL. Ten two-fold drug dilutions in neat DMSO starting at 80 µM were performed from column 1 to 10. Isoniazid (INH) (Sigma Aldrich) was used as a positive control as a dose response compound control with 2-fold dilutions starting at 4 µg/mL in column 11. In G-12 and H-12 Rifampicin were dispensed at 1 µg/mL as non-growing control. From A12 to F12 we dispense DMSO as growth control.

The inoculum was standardized to approximately 1×107 cfu/mL and diluted 1 in 200 in Middlebrook 7H9 broth complemented with ADC (Difco). This inoculum (200 µL and 10e4 CFUs/well) was added to the entire plate.

All plates were placed in a sealed box to prevent drying out of the peripheral wells and incubated at 37° C. without shaking for six days.

A Resazurin solution was prepared by dissolving one tablet of Resazurin (Resazurin Tablets for Milk Testing; Ref 330884Y' VWR International Ltd) in 30 mL of sterile PBS (phosphate buffered saline). Of this solution, 25 µL were added to each well.

Fluorescence was measured (Spectramax M5 Molecular Devices, Excitation

Results of the *Mycobacterium tuberculosis* H37Rv Inhibition Assay (Whole Cell Assay)

All Examples were tested essentially in accordance with the above described whole cell assay.

| Example | Structure | MIC_H37Rv (µM) |
|---|---|---|
| 1 | 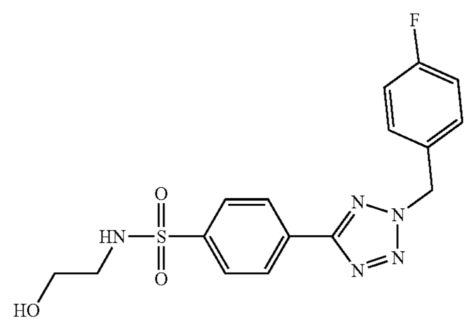 [SMILES: O=S(=O)(NCCO)c1ccc(-c2nnn(Cc3ccc(F)cc3)n2)cc1] | +++++ |
| 2 | 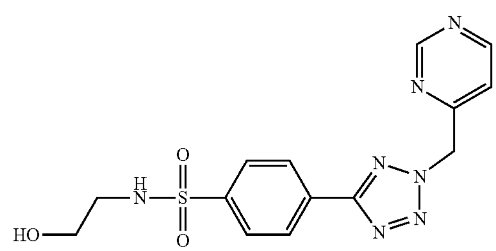 [SMILES: O=S(=O)(NCCO)c1ccc(-c2nnn(Cc3ccncn3)n2)cc1] | +++ |
| 3 | 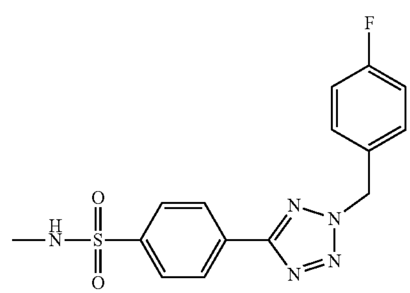 [SMILES: CNS(=O)(=O)c1ccc(-c2nnn(Cc3ccc(F)cc3)n2)cc1] | +++ |
| 4 | 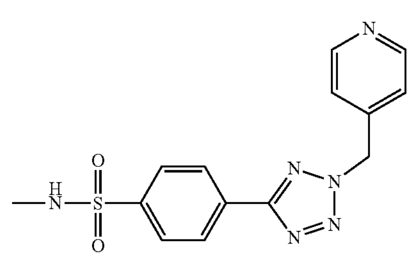 [SMILES: CNS(=O)(=O)c1ccc(-c2nnn(Cc3ccncc3)n2)cc1] | +++ |

-continued
| Example | Structure | MIC_H37Rv (μM) |
|---------|-----------|----------------|
| 5 | 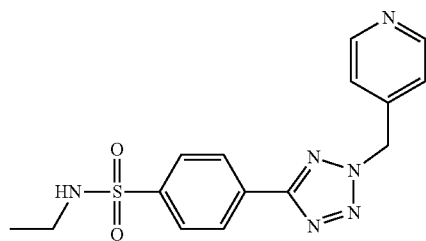 [SMILES: CCNS(=O)(=O)c1ccc(-c2nnn(Cc3ccncc3)n2)cc1] | + |
| 6 | 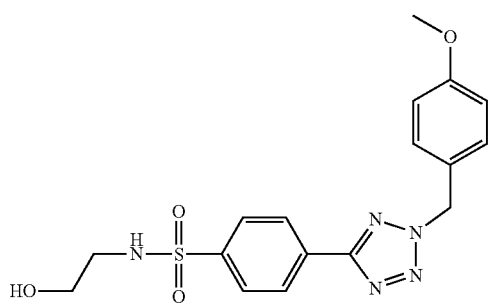 [SMILES: COc1ccc(Cn2nnc(-c3ccc(S(=O)(=O)NCCO)cc3)n2)cc1] | ++++ |
| 7 | 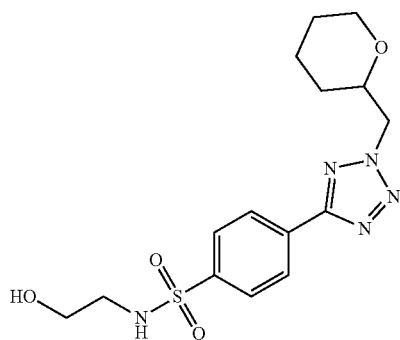 [SMILES: O=S(=O)(NCCO)c1ccc(-c2nnn(CC3CCCCO3)n2)cc1] | ++++ |
| 8 | 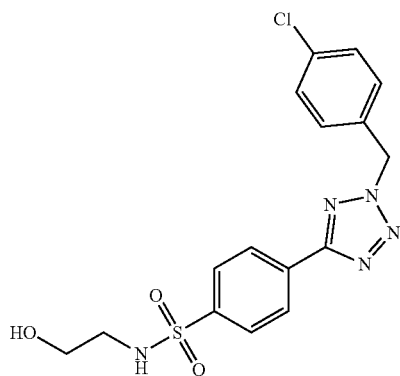 [SMILES: O=S(=O)(NCCO)c1ccc(-c2nnn(Cc3ccc(Cl)cc3)n2)cc1] | +++++ |

-continued

| Example | Structure | MIC_H37Rv (μM) |
|---|---|---|
| 9 | 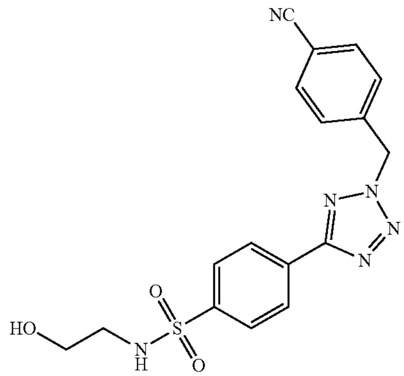 [SMILES: N#Cc1ccc(Cn2nnc(-c3ccc(S(=O)(=O)NCCO)cc3)n2)cc1] | +++++ |
| 10 | 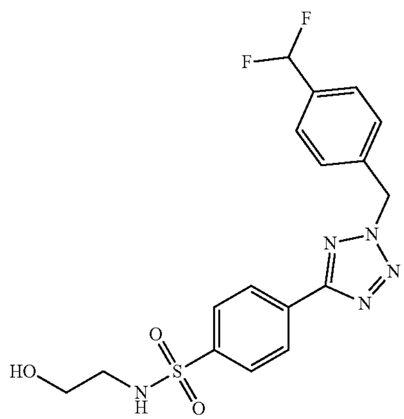 [SMILES: O=S(=O)(NCCO)c1ccc(-c2nnn(Cc3ccc(C(F)F)cc3)n2)cc1] | ++++ |
| 11 | 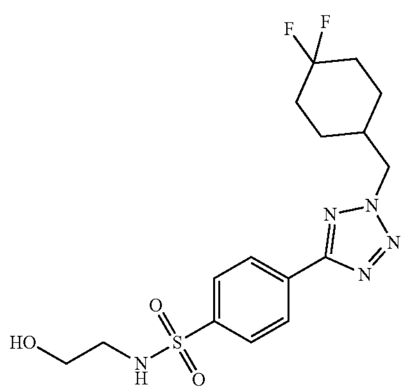 [SMILES: O=S(=O)(NCCO)c1ccc(-c2nnn(CC3CCC(F)(F)CC3)n2)cc1] | ++++ |
| 12 | 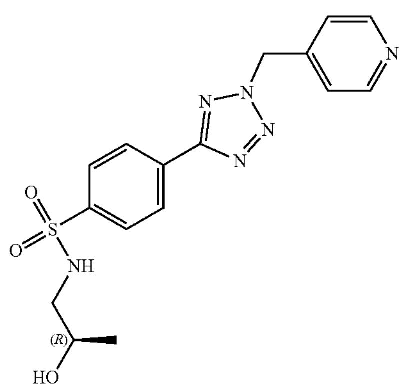 | ++++ |

-continued
| Example | Structure | MIC_H37Rv (μM) |
|---|---|---|
| 13 | 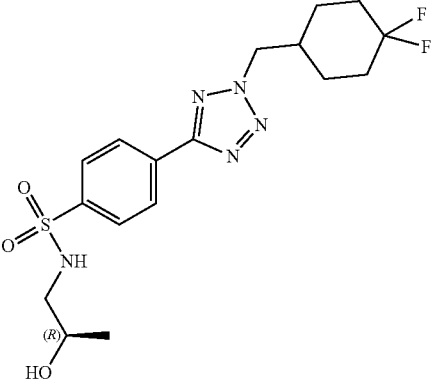 | + |
| 14 | 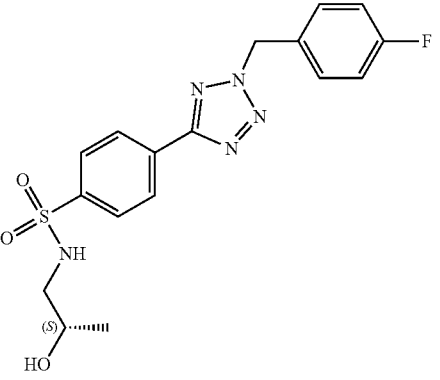 | +++ |
| 15 | 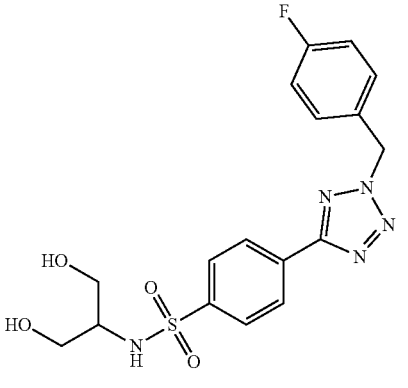 [SMILES: O=S(=O)(NC(CO)CO)c1ccc(-c2nnn(Cc3ccc(F)cc3)n2)cc1] | ++ |
| 16 | 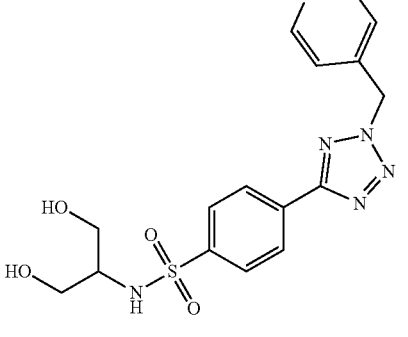 | ++ |

-continued
| Example | Structure | MIC_H37Rv (μM) |
|---|---|---|
| 17 | 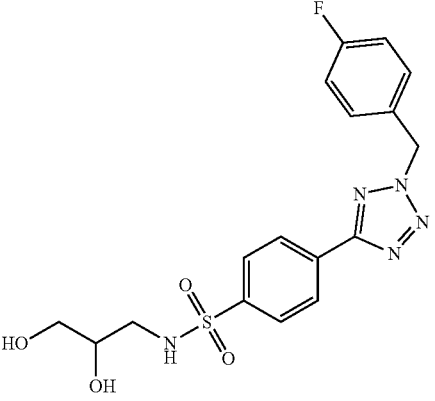 [SMILES: O=S(=O)(NCC(O)CO)c1ccc(-c2nnn(Cc3ccc(F)cc3)n2)cc1] | ++ |
| 18 | 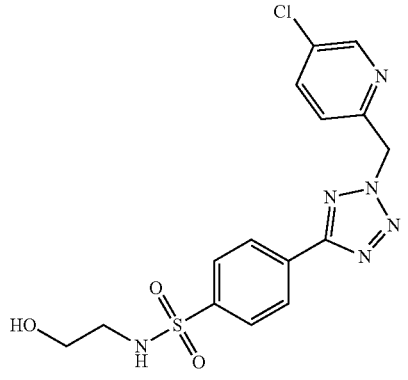 [SMILES: O=S(=O)(NCCO)c1ccc(-c2nnn(Cc3ccc(Cl)cn3)n2)cc1] | ++++ |
| 19 | 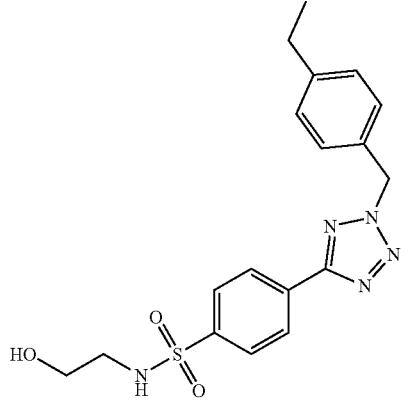 [SMILES: CCc1ccc(Cn2nnc(-c3ccc(S(=O)(=O)NCCO)cc3)n2)cc1] | +++ |
| 20 | 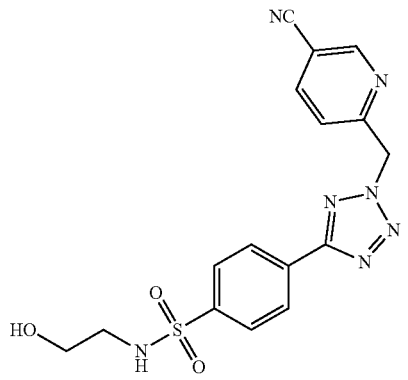 [SMILES: N#Cc1ccc(Cn2nnc(-c3ccc(S(=O)(=O)NCCO)cc3)n2)nc1] | ++++ |

-continued

| Example | Structure | MIC_H37Rv (µM) |
|---|---|---|
| 21 | 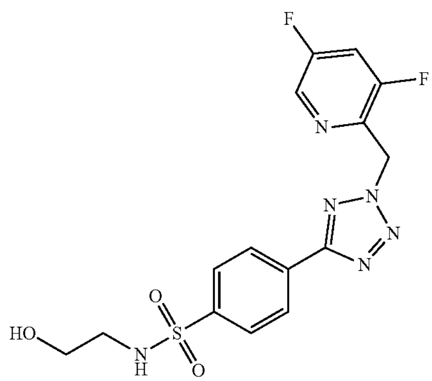 [SMILES: O=S(=O)(NCCO)c1ccc(-c2nnn(Cc3ncc(F)cc3F)n2)cc1] | +++ |
| 22 | 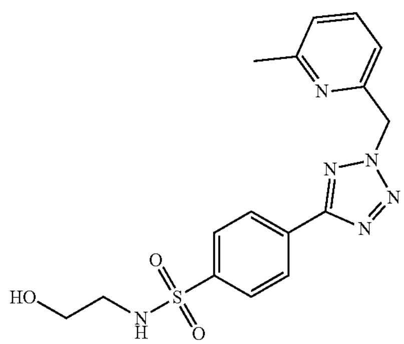 [SMILES: Cc1cccc(Cn2nnc(-c3ccc(S(=O)(=O)NCCO)cc3)n2)n1] | + |
| 23 | 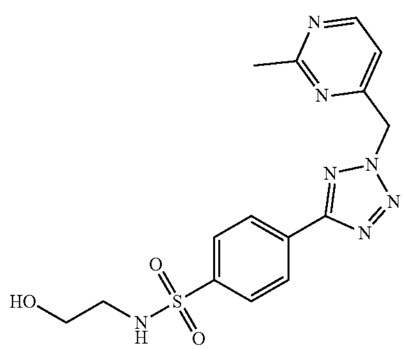 [SMILES: Cc1nccc(Cn2nnc(-c3ccc(S(=O)(=O)NCCO)cc3)n2)n1] | ++ |
| 24 | 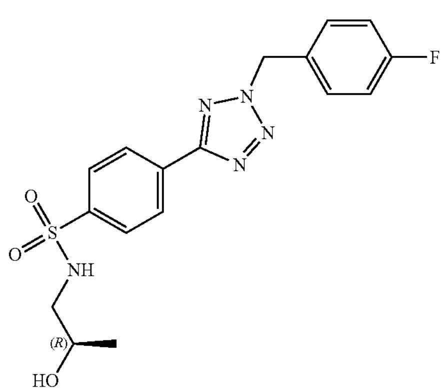 | ++++ |

-continued

| Example | Structure | MIC_H37Rv (μM) |
|---------|-----------|----------------|
| 25 | 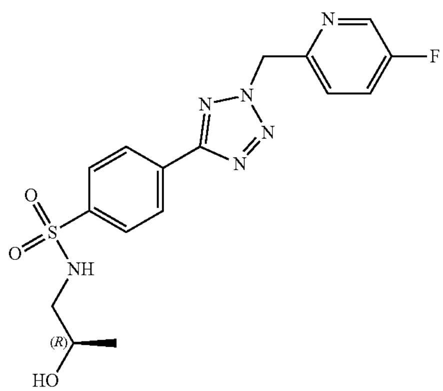 | ++++ |
| 26 | 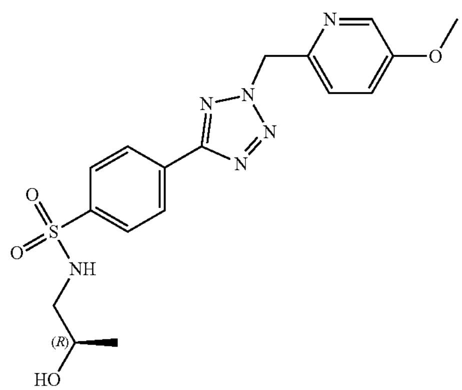 | + |
| 27 | 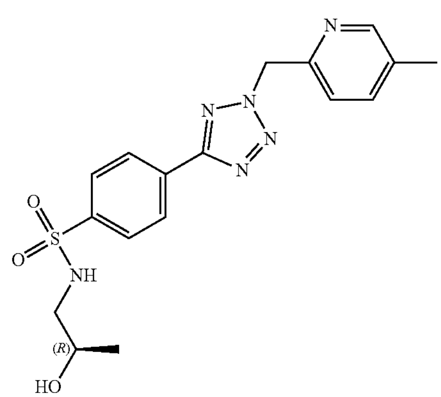 | + |
| 28 | 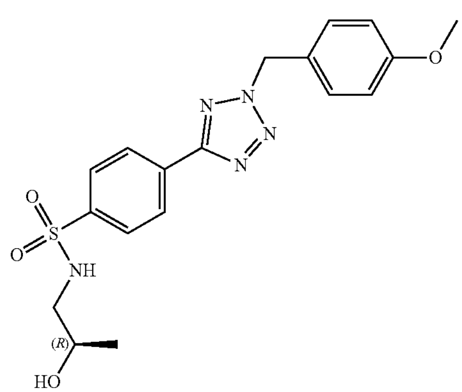 | +++ |

-continued

| Example | Structure | MIC_H37Rv (μM) |
|---|---|---|
| 29 | 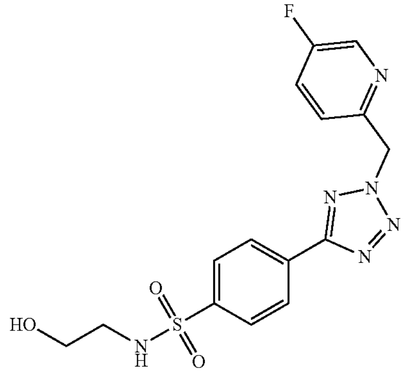 [SMILES: O=S(=O)(NCCO)c1ccc(-c2nnn(Cc3ccc(F)cn3)n2)cc1] | ++++ |
| 30 | 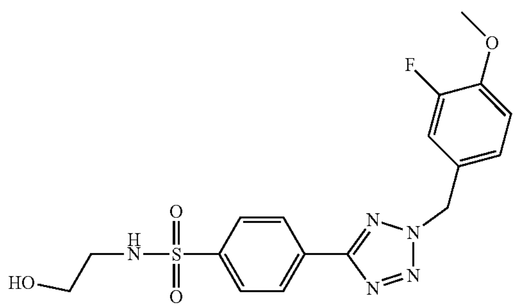 [SMILES: COc1ccc(Cn2nnc(-c3ccc(S(=O)(=O)NCCO)cc3)n2)cc1F] | ++++ |
| 31 | 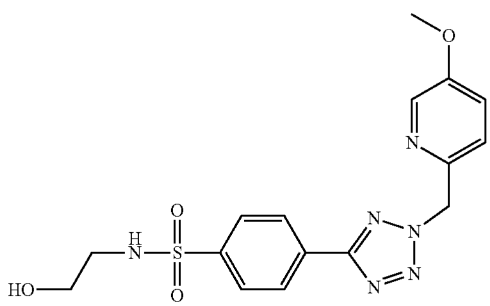 | +++ |
| 32 | 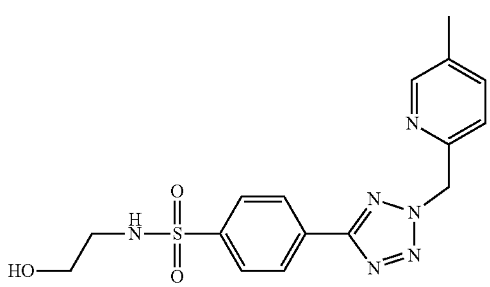 [SMILES: Cc1ccc(Cn2nnc(-c3ccc(S(=O)(=O)NCCO)cc3)n2)nc1] | +++ |
| 33 | 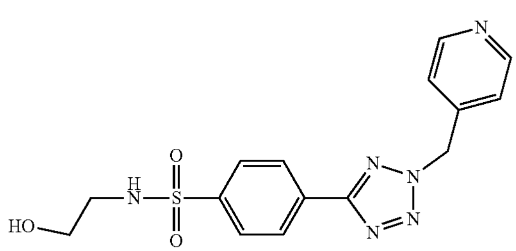 [SMILES: O=S(=O)(NCCO)c1ccc(-c2nnn(Cc3ccncc3)n2)cc1] | ++++ |

-continued

| Example | Structure | MIC_H37Rv (μM) |
|---|---|---|
| 34 | 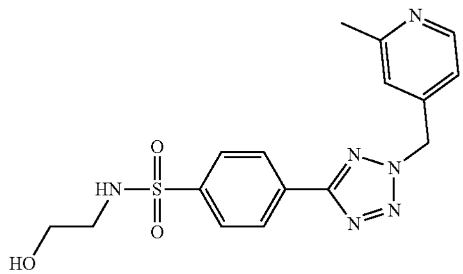 [SMILES: Cc1cc(Cn2nnc(-c3ccc(S(=O)(=O)NCCO)cc3)n2)ccn1] | +++ |
| 35 | 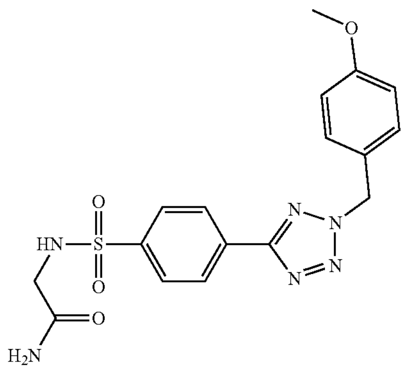 [SMILES: COc1ccc(Cn2nnc(-c3ccc(S(=O)(=O)NCC(N)=O)cc3)n2)cc1] | +++++ |
| 36 | 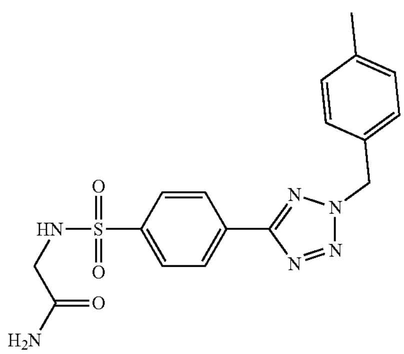 [SMILES: Cc1ccc(Cn2nnc(-c3ccc(S(=O)(=O)NCC(N)=O)cc3)n2)cc1] | +++++ |
| 37 | 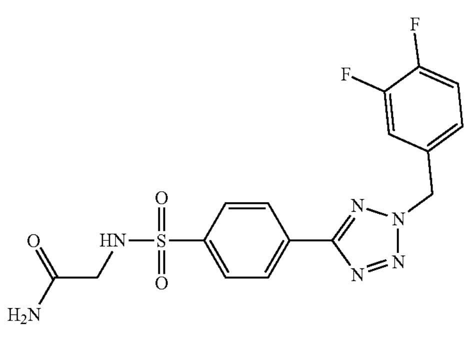 [SMILES: NC(=O)CNS(=O)(=O)c1ccc(-c2nnn(Cc3ccc(F)c(F)c3)n2)cc1] | +++++ |

| Example | Structure | MIC_H37Rv (μM) |
|---|---|---|
| 38 | 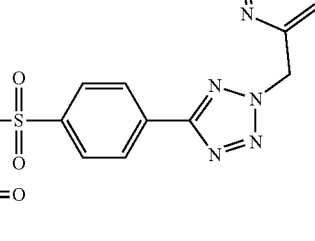 | ++++ |
| 39 | 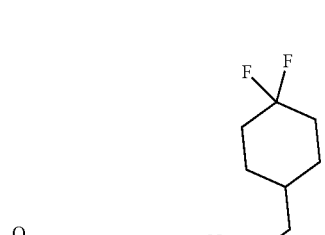 | ++++ |
| 40 | 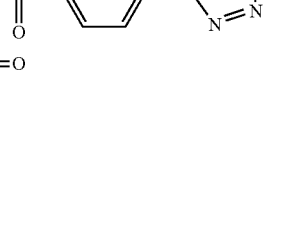 | ++++ |
| 41 | 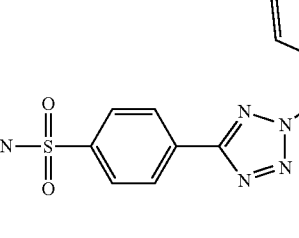 | +++++ |

-continued

| Example | Structure | MIC_H37Rv (μM) |
|---|---|---|
| 42 | 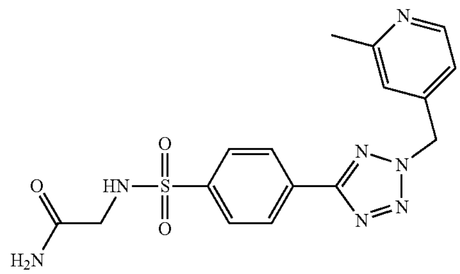 [SMILES: Cc1cc(Cn2nnc(-c3ccc(S(=O)(=O)NCC(N)=O)cc3)n2)ccn1] | ++++ |
| 43 | 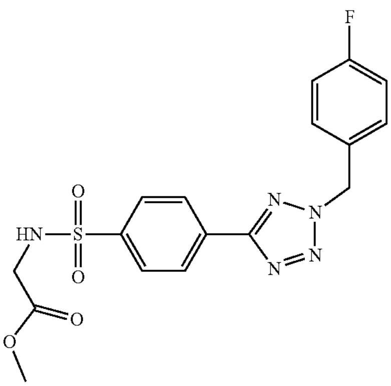 [SMILES: COC(=O)CNS(=O)(=O)c1ccc(-c2nnn(Cc3ccc(F)cc3)n2)cc1] | +++ |
| 44 | 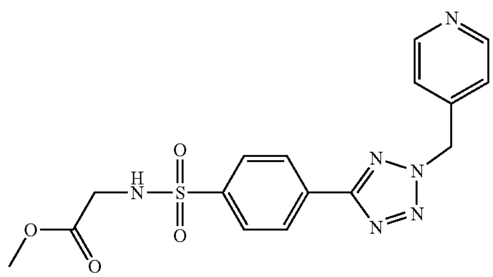 [SMILES: COC(=O)CNS(=O)(=O)c1ccc(-c2nnn(Cc3ccncc3)n2)cc1] | ++ |
| 45 | 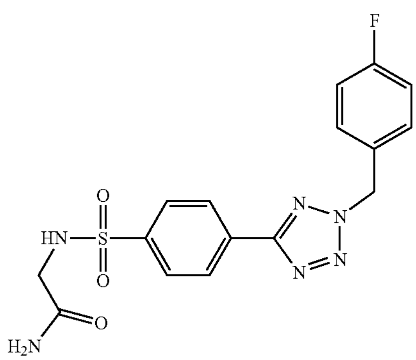 [SMILES: NC(=O)CNS(=O)(=O)c1ccc(-c2nnn(Cc3ccc(F)cc3)n2)cc1] | +++++ |
| 46 | 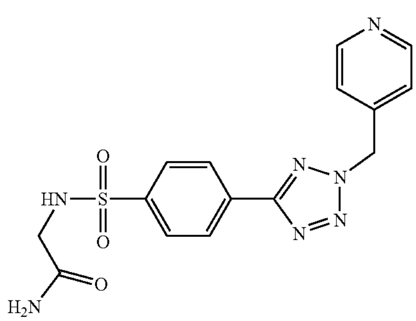 [SMILES: NC(=O)CNS(=O)(=O)c1ccc(-c2nnn(Cc3ccncc3)n2)cc1] | ++++ |

-continued

| Example | Structure | MIC_H37Rv (μM) |
|---------|-----------|----------------|
| 47 | 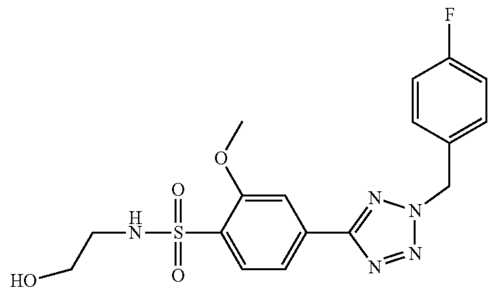 [SMILES: COc1cc(-c2nnn(Cc3ccc(F)cc3)n2)ccc1S(=O)(=O)NCCO] | ++++ |
| 48 | 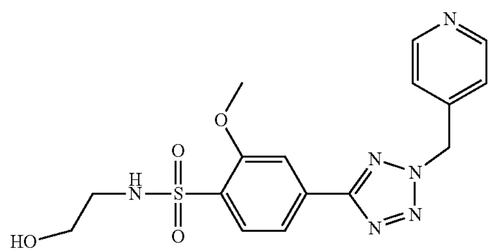 [SMILES: COc1cc(-c2nnn(Cc3ccncc3)n2)ccc1S(=O)(=O)NCCO] | +++ |
| 49 | 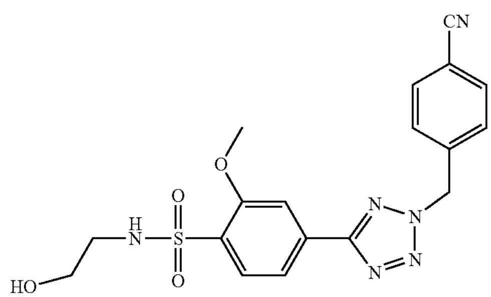 [SMILES: COc1cc(-c2nnn(Cc3ccc(C#N)cc3)n2)ccc1S(=O)(=O)NCCO] | ++++ |
| 50 | 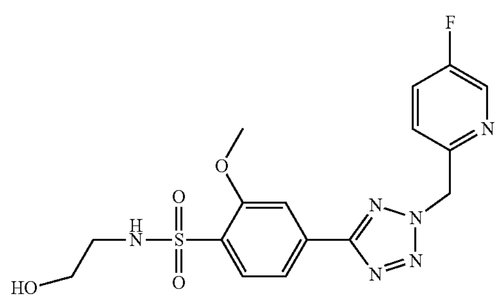 [SMILES: COc1cc(-c2nnn(Cc3ccc(F)cn3)n2)ccc1S(=O)(=O)NCCO] | +++ |
| 51 | 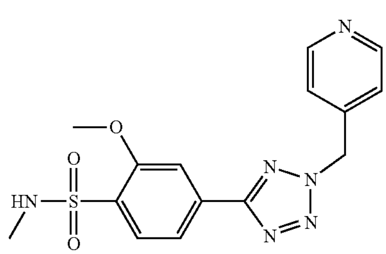 [SMILES: CNS(=O)(=O)c1ccc(-c2nnn(Cc3ccncc3)n2)cc1OC] | +++ |

-continued

| Example | Structure | MIC_H37Rv (μM) |
|---|---|---|
| 52 | 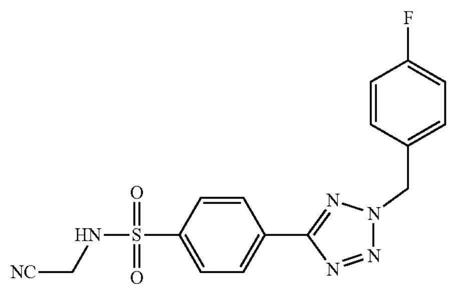 [SMILES: N#CCNS(=O)(=O)c1ccc(-c2nnn(Cc3ccc(F)cc3)n2)cc1] | +++++ |
| 53 | 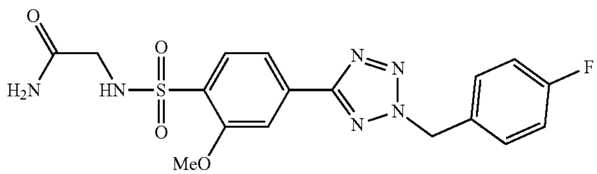 [SMILES: COc1cc(-c2nnn(Cc3ccc(F)cc3)n2)ccc1S(=O)(=O)NCC(N)=O] | +++++ |
| 54 | 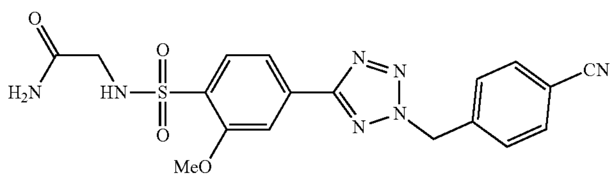 [SMILES: COc1cc(-c2nnn(Cc3ccc(C#N)cc3)n2)ccc1S(=O)(=O)NCC(N)=O] | +++++ |
| 55 | 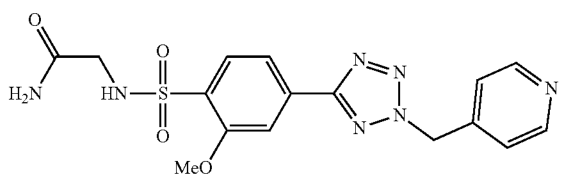 [SMILES: COc1cc(-c2nnn(Cc3ccncc3)n2)ccc1S(=O)(=O)NCC(N)=O] | ++++ |
| 56 | 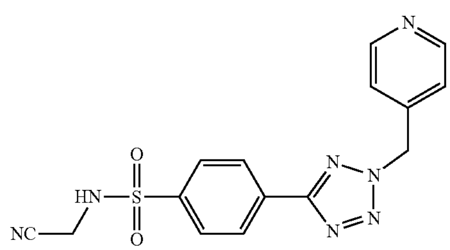 [SMILES: N#CCNS(=O)(=O)c1ccc(-c2nnn(Cc3ccncc3)n2)cc1] | ++++ |
| 57 | 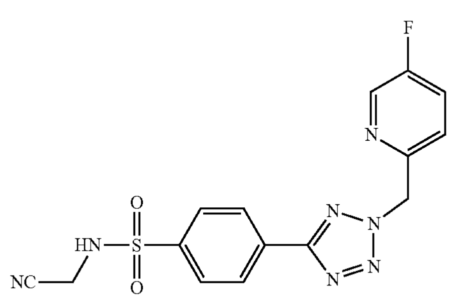 [SMILES: N#CCNS(=O)(=O)c1ccc(-c2nnn(Cc3ccc(F)cn3)n2)cc1] | +++++ |

-continued
| Example | Structure | MIC_H37Rv (μM) |
|---|---|---|
| 58 | 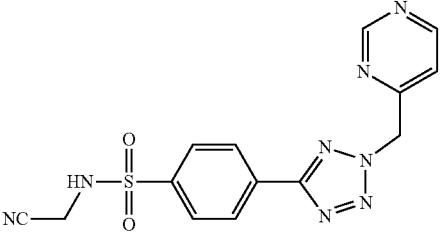 [SMILES: N#CCNS(=O)(=O)c1ccc(-c2nnn(Cc3ccncn3)n2)cc1] | ++++ |
| 59 | 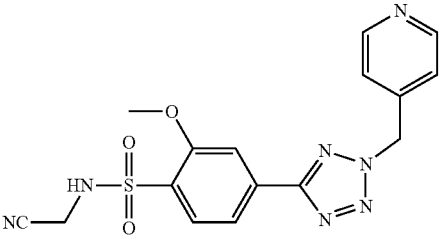 [SMILES: COc1cc(-c2nnn(Cc3ccncc3)n2)ccc1S(=O)(=O)NCC#N] | +++++ |
| 60 | 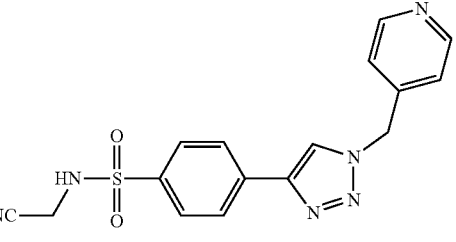 | ++++ |
| 61 | 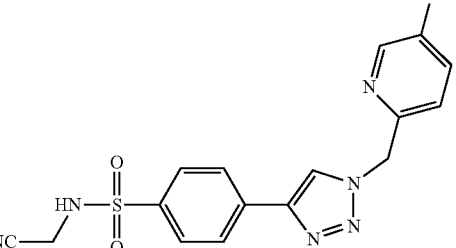 | ++++ |
| 62 | 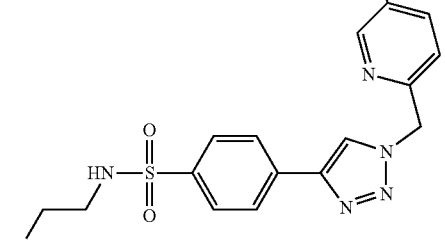 | +++ |

-continued

| Example | Structure | MIC_H37Rv (μM) |
|---|---|---|
| 63 | 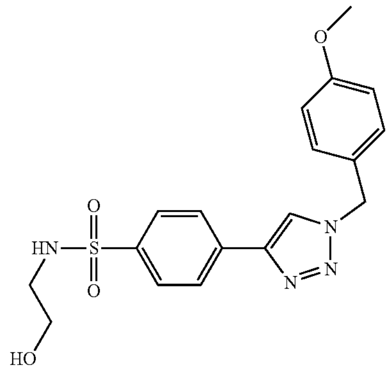 [SMILES: COc1ccc(Cn2cc(-c3ccc(S(=O)(=O)NCCO)cc3)nn2)cc1] | ++++ |
| 64 | 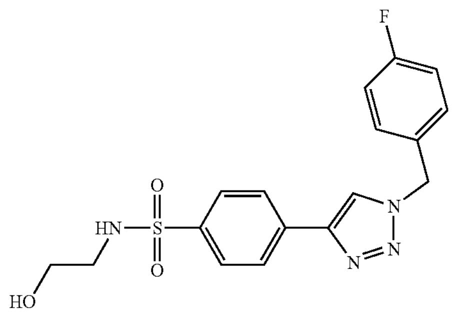 [SMILES: O=S(=O)(NCCO)c1ccc(-c2cn(Cc3ccc(F)cc3)nn2)cc1] | +++++ |
| 65 | 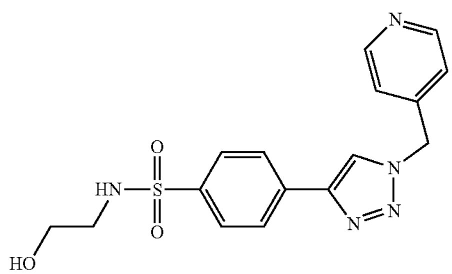 [SMILES: O=S(=O)(NCCO)c1ccc(-c2cn(Cc3ccncc3)nn2)cc1] | ++++ |
| 66 | 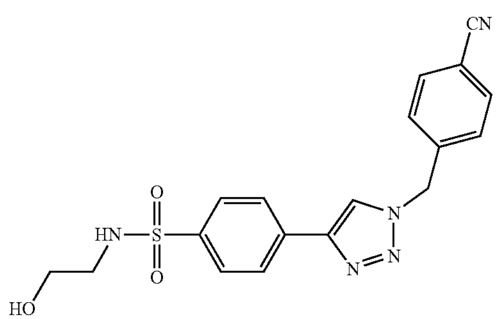 [SMILES: N#Cc1ccc(Cn2cc(-c3ccc(S(=O)(=O)NCCO)cc3)nn2)cc1] | ++++ |
| 67 | 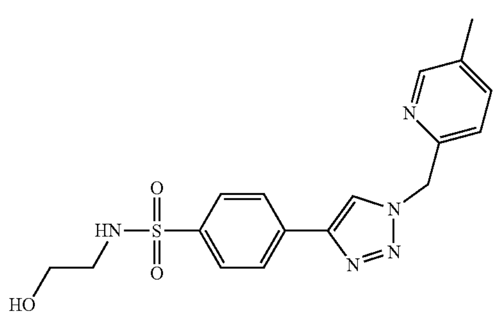 [SMILES: Cc1ccc(Cn2cc(-c3ccc(S(=O)(=O)NCCO)cc3)nn2)nc1] | + |

-continued

| Example | Structure | MIC_H37Rv (μM) |
|---|---|---|
| 68 | 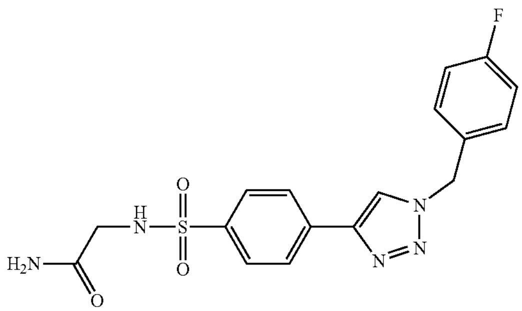 [SMILES: NC(=O)CNS(=O)(=O)c1ccc(-c2cn(Cc3ccc(F)cc3)nn2)cc1] | +++++ |
| 69 | 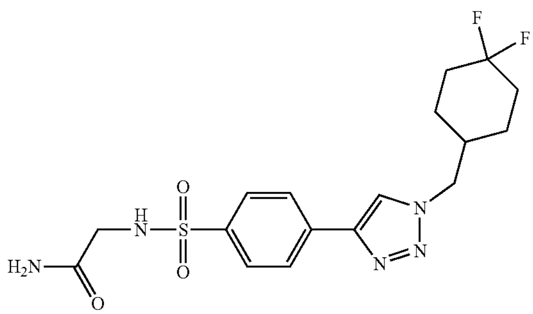 [SMILES: NC(=O)CNS(=O)(=O)c1ccc(-c2cn(CC3CCC(F)(F)CC3)nn2)cc1] | +++ |
| 70 | 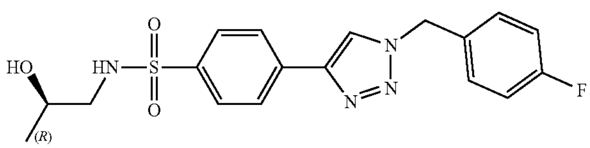 | ++++ |
| 71 | 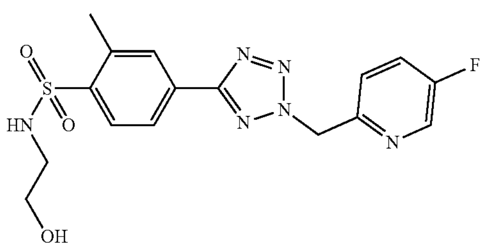 [SMILES: Cc1cc(-c2nnn(Cc3ccc(F)cn3)n2)ccc1S(=O)(=O)NCCO] | ++++ |
| 72 | 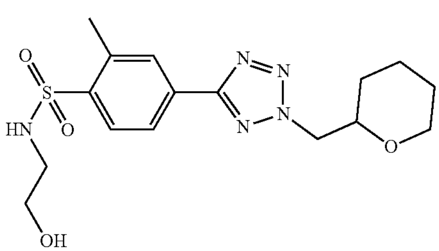 [SMILES: Cc1cc(-c2nnn(CC3CCCCO3)n2)ccc1S(=O)(=O)NCCO] | +++ (Isomer 1)<br>+ (Isomer 2) |
| 73 | 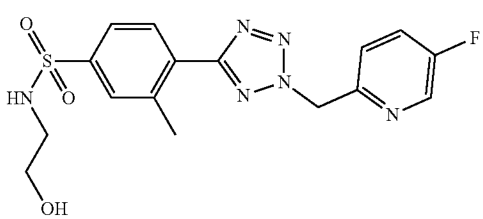 [SMILES: Cc1cc(S(=O)(=O)NCCO)ccc1-c1nnn(Cc2ccc(F)cn2)n1] | ++++ |

-continued

| Example | Structure | MIC_H37Rv (μM) |
|---------|-----------|----------------|
| 74 | 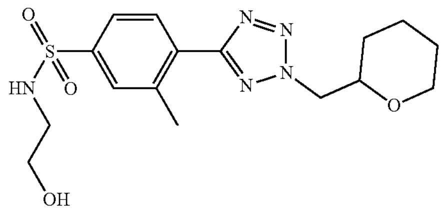 [SMILES: Cc1cc(S(=O)(=O)NCCO)ccc1-c1nnn(CC2CCCCO2)n1] | ++ (Isomer 1)<br>+ (Isomer 2) |
| 75 | 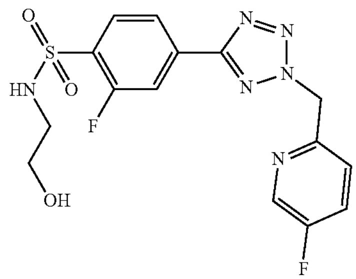 [SMILES: O=S(=O)(NCCO)c1ccc(-c2nnn(Cc3ccc(F)cn3)n2)cc1F] | ++++ |
| 76 | 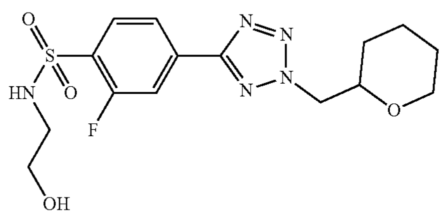 [SMILES: O=S(=O)(NCCO)c1ccc(-c2nnn(CC3CCCCO3)n2)cc1F] | ++++ (Isomer 1)<br>++ (Isomer 2) |
| 77 | 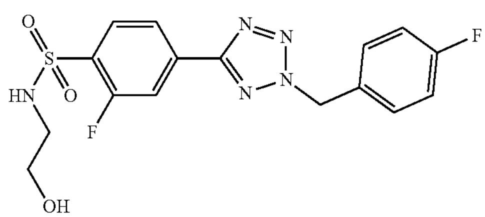 [SMILES: O=S(=O)(NCCO)c1ccc(-c2nnn(Cc3ccc(F)cc3)n2)cc1F] | +++++ |
| 78 | 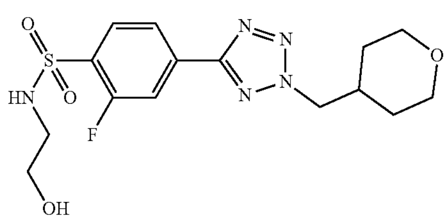 [SMILES: O=S(=O)(NCCO)c1ccc(-c2nnn(CC3CCOCC3)n2)cc1F] | ++++ |
| 79 | 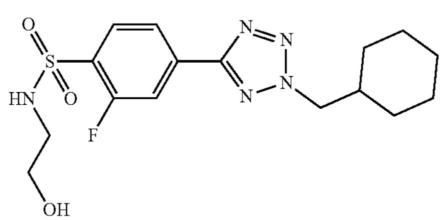 [SMILES: O=S(=O)(NCCO)c1ccc(-c2nnn(CC3CCCCC3)n2)cc1F] | ++++ |
| 80 | 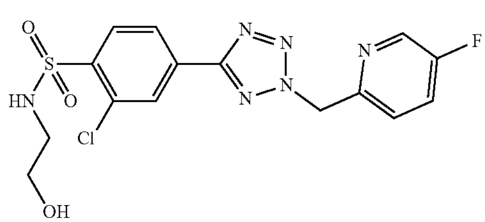 [SMILES: O=S(=O)(NCCO)c1ccc(-c2nnn(Cc3ccc(F)cn3)n2)cc1Cl] | +++++ |

-continued

| Example | Structure | MIC_H37Rv (µM) |
|---|---|---|
| 81 | 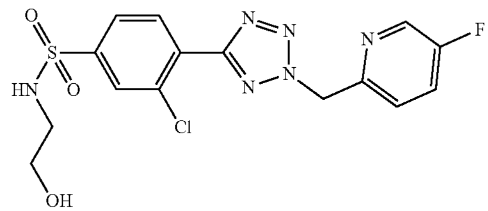 [SMILES: O=S(=O)(NCCO)c1ccc(-c2nnn(Cc3ccc(F)cn3)n2)c(Cl)c1] | ++++ |
| 82 | 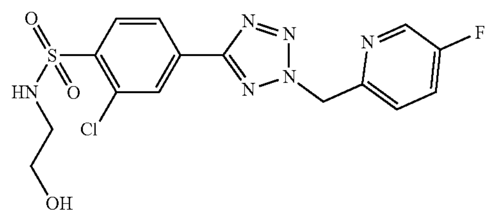 [SMILES: O=S(=O)(NCCO)c1ccc(-c2nnn(Cc3ccc(F)cn3)n2)cc1Cl] | +++++ |
| 83 | 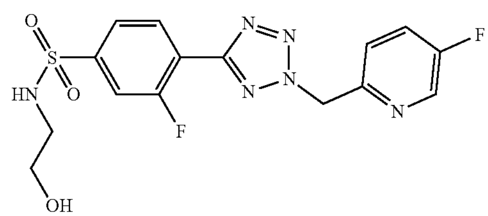 [SMILES: O=S(=O)(NCCO)c1ccc(-c2nnn(Cc3ccc(F)cn3)n2)c(F)c1] | +++++ |
| 84 | 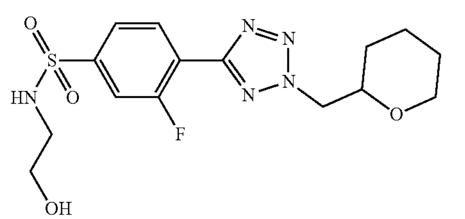 | ++++ (Isomer 1)<br>+++ (Isomer 2) |
| 85 | 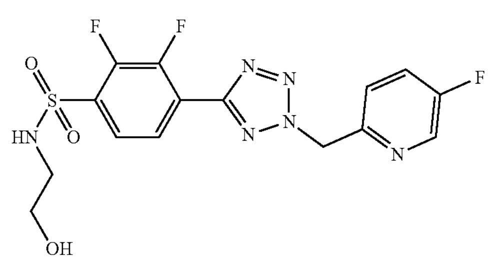 [SMILES: O=S(=O)(NCCO)c1ccc(-c2nnn(Cc3ccc(F)cn3)n2)c(F)c1F] | +++++ |
| 86 | 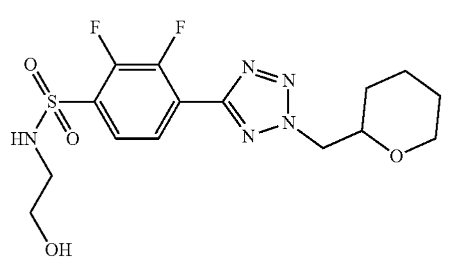 [SMILES: O=S(=O)(NCCO)c1ccc(-c2nnn(CC3CCCCO3)n2)c(F)c1F] | ++++ (Isomer 1)<br>++ (Isomer 2) |

-continued

| Example | Structure | MIC_H37Rv (μM) |
|---|---|---|
| 87 | 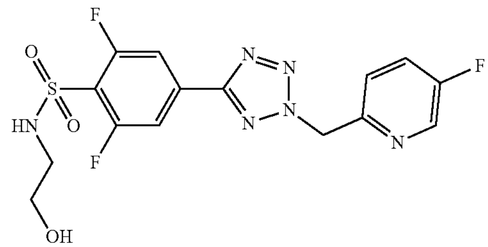 [SMILES: O=S(=O)(NCCO)c1c(F)cc(-c2nnn(Cc3ccc(F)cn3)n2)cc1F] | +++++ |
| 88 | 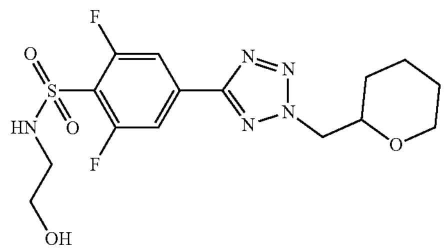 [SMILES: O=S(=O)(NCCO)c1c(F)cc(-c2nnn(CC3CCCCO3)n2)cc1F] | ++++ (Isomer 1) +++ (Isomer 2) |
| 89 | 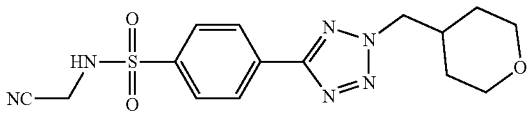 [SMILES: N#CCNS(=O)(=O)c1ccc(-c2nnn(CC3CCOCC3)n2)cc1] | ++++ |
| 90 | 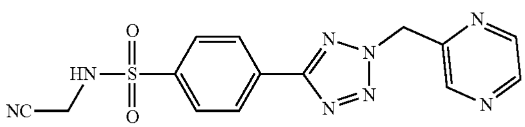 [SMILES: N#CCNS(=O)(=O)c1ccc(-c2nnn(Cc3cnccn3)n2)cc1] | ++++ |
| 91 | 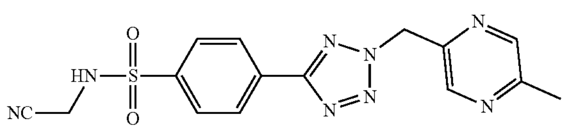 [SMILES: Cc1cnc(Cn2nnc(-c3ccc(S(=O)(=O)NCC#N)cc3)n2)cn1] | ++++ |
| 92 | 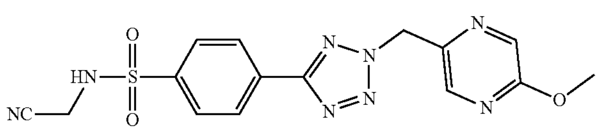 [SMILES: COc1cnc(Cn2nnc(-c3ccc(S(=O)(=O)NCC#N)cc3)n2)cn1] | +++ |
| 93 | 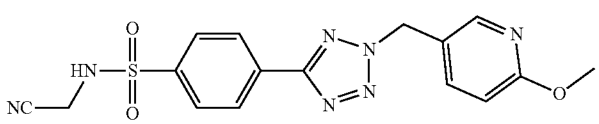 [SMILES: COc1ccc(Cn2nnc(-c3ccc(S(=O)(=O)NCC#N)cc3)n2)cn1] | ++++ |
| 94 | 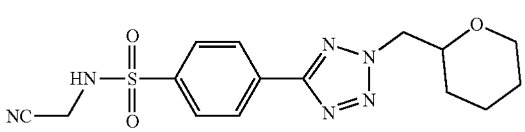 [SMILES: N#CCNS(=O)(=O)c1ccc(-c2nnn(CC3CCCCO3)n2)cc1] | ++++ (Isomer 1) +++ (Isomer 2) |
| 95 | 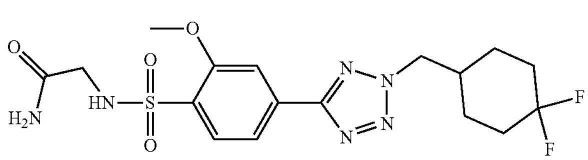 [SMILES: COc1cc(-c2nnn(CC3CCC(F)(F)CC3)n2)ccc1S(=O)(=O)NCC(N)=O] | +++ |
| 96 | 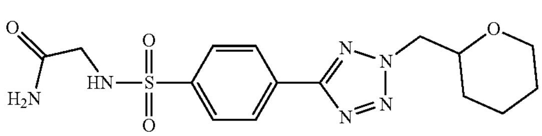 [SMILES: NC(=O)CNS(=O)(=O)c1ccc(-c2nnn(CC3CCCCO3)n2)cc1] | ++++ |

| Example | Structure | MIC_H37Rv (μM) |
|---|---|---|
| 97 | 4-[2-[[4-(trifluoromethoxy)phenyl]methyl]tetrazol-5-yl]-N-(2-hydroxyethyl)benzenesulfonamide | +++ |
| 98 | 4-[2-[[4-(trifluoromethyl)phenyl]methyl]tetrazol-5-yl]-N-(2-hydroxyethyl)benzenesulfonamide | ++ |
| 99 | 4-[2-[(4-ethoxyphenyl)methyl]tetrazol-5-yl]-N-(2-hydroxyethyl)benzenesulfonamide | ++++ |
| 100 | 4-[2-(cyclohexylmethyl)tetrazol-5-yl]-N-(2-hydroxyethyl)benzenesulfonamide | ++++ |
| 101 | 4-[2-[(6-methylpyridin-3-yl)methyl]tetrazol-5-yl]-N-(2-hydroxyethyl)benzenesulfonamide | ++++ |

| Example | Structure | MIC_H37Rv (μM) |
|---|---|---|
| 102 | 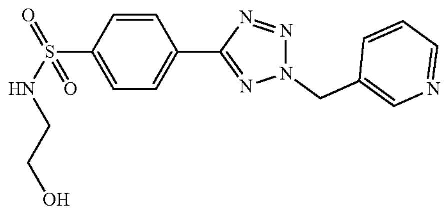 [SMILES: O=S(=O)(NCCO)c1ccc(-c2nnn(Cc3cccnc3)n2)cc1] | ++++ |
| 100 | 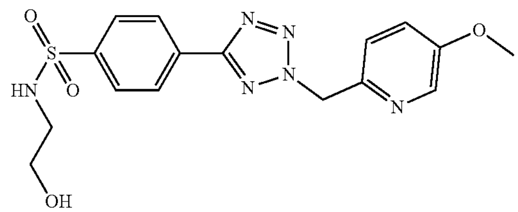 [SMILES: COc1ccc(Cn2nnc(-c3ccc(S(=O)(=O)NCCO)cc3)n2)nc1] | ++++ |
| 104 | 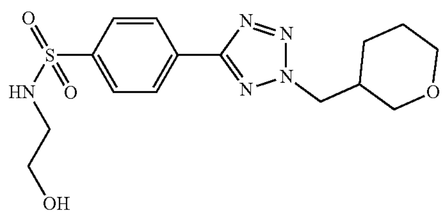 [SMILES: O=S(=O)(NCCO)c1ccc(-c2nnn(CC3CCCOC3)n2)cc1] | ++ |
| 105 | 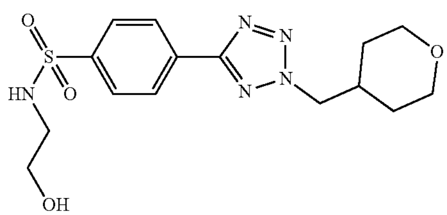 [SMILES: O=S(=O)(NCCO)c1ccc(-c2nnn(CC3CCOCC3)n2)cc1] | +++ |
| 106 | 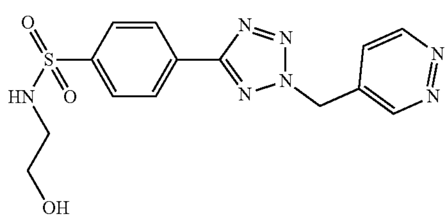 [SMILES: O=S(=O)(NCCO)c1ccc(-c2nnn(Cc3ccnnc3)n2)cc1] | ++++ |
| 107 | 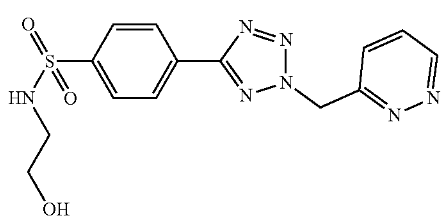 [SMILES: O=S(=O)(NCCO)c1ccc(-c2nnn(Cc3cccnn3)n2)cc1] | * |
| 108 | 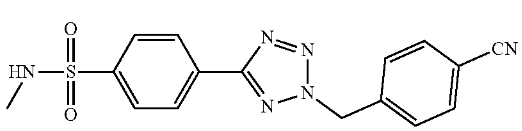 [SMILES: CNS(=O)(=O)c1ccc(-c2nnn(Cc3ccc(C#N)cc3)n2)cc1] | +++ |

-continued

| Example | Structure | MIC_H37Rv (μM) |
|---|---|---|
| 109 | 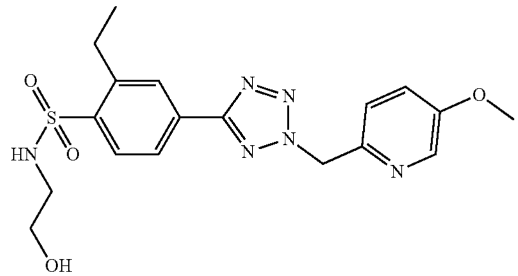 [SMILES: CCc1cc(-c2nnn(Cc3ccc(OC)cn3)n2)ccc1S(=O)(=O)NCCO] | +++ |
| 110 | 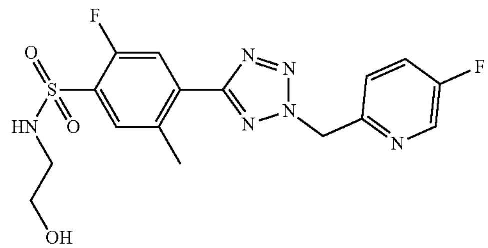 [SMILES: Cc1cc(S(=O)(=O)NCCO)c(F)cc1-c1nnn(Cc2ccc(F)cn2)n1] | ++++ |
| 111 | 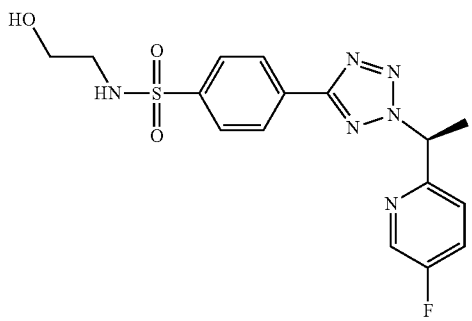 [SMILES: C[C@@H](c1ccc(F)cn1)n1nnc(-c2ccc(S(=O)(=O)NCCO)cc2)n1] | +++ |
| 112 | 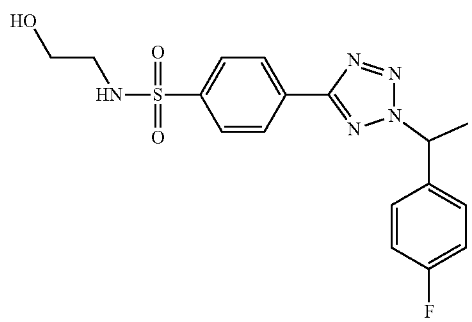 [SMILES: CC(c1ccc(F)cc1)n1nnc(-c2ccc(S(=O)(=O)NCCO)cc2)n1] | ++++ (Isomer 1)<br>+ (Isomer 2) |
| 113 | 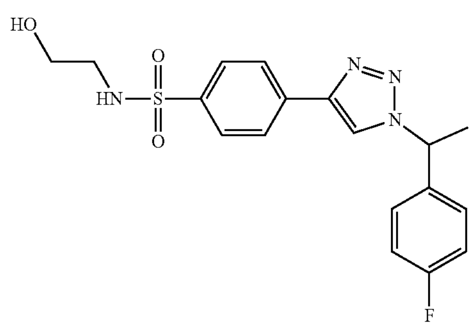 [SMILES: CC(c1ccc(F)cc1)n1cc(-c2ccc(S(=O)(=O)NCCO)cc2)nn1] | +++ (Isomer 1)<br>+ (Isomer 2) |

-continued

| Example | Structure | MIC_H37Rv (μM) |
|---|---|---|
| 114 | 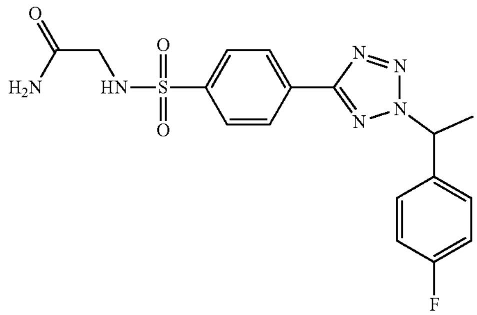 [SMILES: CC(c1ccc(F)cc1)n1nnc(-c2ccc(S(=O)(=O)NCC(N)=O)cc2)n1] | +++ (Isomer 1)<br>++++ (Isomer 2) |
| 115 | 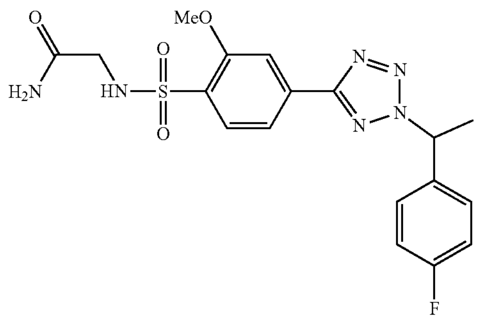 [SMILES: COc1cc(-c2nnn(C(C)c3ccc(F)cc3)n2)ccc1S(=O)(=O)NCC(N)=O] | + (Isomer 1)<br>++++ (Isomer 2) |

<0.1 μM = ++++
≥0.1 μM to <1 μM = ++++
≥1 μM to <5 μM = +++
≥5 μM to <10 μM = ++
≥10 μM to ≤25 μM = +

In particular, Example 25 was found to have an MIC of 0.6 μM (as determined by testing of the compound two times).

Example 29 was found to have an MIC value in the range of 0.07 to 0.16 μM (as determined by testing of the compound twelve times).

Example 53 was found to have an MIC value of 0.04 μM (as determined by testing of the compound six times).

Example 75 was found to have an MIC value of 0.16 μM (as determined by testing of the compound two times).

Example 87 was found to have an MIC value of ≤0.04 μM (as determined by testing of the compound four times giving ≤0.16 μM and one ≤0.04 μM)

Example 111 (S-isomer) was found to have an MIC value in the range of 0.6 to 1.875 μM (as determined by testing of the compound three times).

Example 115 Isomer 2 was found to have an MIC value in the range of 0.45 to 1.25 μM (as determined by testing of the compound two times).

The invention claimed is:

1. A compound of Formula (I) or a pharmaceutically acceptable salt thereof:

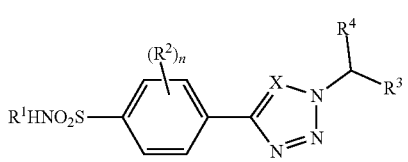

wherein
X is CH or N;
n is 0, 1 or 2;
$R^1$ is methyl, ethyl, cyanomethyl, C-linked acetamido, methyl acetate, 2-hydroxyethyl, 2-hydroxy-1-propyl, 1,3-dihydroxy-2-propyl or 1,2-dihydroxy-3-propyl;
$R^2$ is independently selected from halo, amino, hydroxymethyl, $C_{1-2}$ alkyl optionally substituted by up to three fluoro or $C_{1-2}$ alkoxy optionally substituted by up to three fluoro;
$R^3$ is phenyl, pyridyl, pyrimidinyl, pyrazinyl or pyridazinyl wherein each of these groups may be optionally substituted by one or two substituents selected from halo, cyano, $C_{1-2}$ alkyl optionally substituted by up to three fluoro and $C_{1-2}$ alkoxy optionally substituted by up to three fluoro, wherein the substituents may be the same or different; or
$R^3$ is cyclohexyl which may be optionally substituted by one or two fluoro or chloro wherein each substituent may be attached to the same carbon atom and each substituent may be the same or different; or
$R^3$ is tetrahydropyran; and
$R^4$ is H or methyl.

2. The compound or pharmaceutically acceptable salt thereof according to claim 1, wherein X is N.

3. The compound or pharmaceutically acceptable salt thereof according to claim 1, wherein $R^4$ is H.

4. The compound or pharmaceutically acceptable salt thereof according to claim 1, wherein n is 0.

5. The compound or pharmaceutically acceptable salt thereof according to claim 1, wherein $R^1$ is methyl, cyanomethyl, C-linked acetamido, 2-hydroxyethyl, (R)-2-hydroxy-1-propyl or (S)-2-hydroxy-1-propyl.

6. The compound or pharmaceutically acceptable salt thereof according to claim 1, wherein $R^3$ is phenyl, pyridyl or pyrimidinyl, wherein each of these groups may be optionally substituted by one substituent selected from fluoro, chloro, cyano, methyl, difluoromethyl (—$CHF_2$), trifluoromethyl, methoxy and trifluoromethoxy (—$OCF_3$).

7. The compound or pharmaceutically acceptable salt thereof according to claim 1, wherein $R^3$ is phenyl or pyridyl, wherein each of these groups may be optionally substituted by one substituent selected from halo, cyano, $C_{1-2}$ alkyl optionally substituted by up to three fluoro and $C_{1-2}$ alkoxy optionally substituted by up to three fluoro.

8. The compound or pharmaceutically acceptable salt thereof according to claim 1, wherein $R^3$ is pyridyl optionally substituted by fluoro or chloro.

9. The compound or pharmaceutically acceptable salt thereof according to claim 1, wherein $R^3$ is 2-pyridyl optionally substituted by fluoro.

10. The compound or pharmaceutically acceptable salt thereof according to claim 1 selected from:
- (4-(2-(4-fluorobenzyl)-2H-tetrazol-5-yl)-N-(2-hydroxyethyl)benzenesulfonamide);
- N-(2-hydroxyethyl)-4-(2-(pyrimidin-4-ylmethyl)-2H-tetrazol-5-yl)benzenesulfonamide;
- 4-(2-(4-fluorobenzyl)-2H-tetrazol-5-yl)-N-methylbenzenesulfonamide;
- N-methyl-4-(2-(pyridin-4-ylmethyl)-2H-tetrazol-5-yl)benzenesulfonamide;
- N-ethyl-4-(2-(pyridin-4-ylmethyl)-2H-tetrazol-5-yl)benzenesulfonamide;
- N-(2-hydroxyethyl)-4-(2-(4-methoxybenzyl)-2H-tetrazol-5-yl)benzenesulfonamide;
- N-(2-hydroxyethyl)-4-(2-((tetrahydro-2H-pyran-2-yl)methyl)-2H-tetrazol-5-yl)benzenesulfonamide;
- 4-(2-(4-chlorobenzyl)-2H-tetrazol-5-yl)-N-(2-hydroxyethyl)benzenesulfonamide;
- 4-(2-(4-cyanobenzyl)-2H-tetrazol-5-yl)-N-(2-hydroxyethyl)benzenesulfonamide;
- 4-(2-(4-(difluoromethyl)benzyl)-2H-tetrazol-5-yl)-N-(2-hydroxyethyl)benzenesulfonamide;
- 4-(2-((4,4-difluorocyclohexyl)methyl)-2H-tetrazol-5-yl)-N-(2-hydroxyethyl)benzenesulfonamide;
- (R)-N-(2-hydroxypropyl)-4-(2-(pyridin-4-ylmethyl)-2H-tetrazol-5-yl)benzenesulfonamide
- (R)-4-(2-((4,4-difluorocyclohexyl)methyl)-2H-tetrazol-5-yl)-N-(2-hydroxypropyl)benzenesulfonamide;
- (S)-4-(2-(4-fluorobenzyl)-2H-tetrazol-5-yl)-N-(2-hydroxypropyl)benzenesulfonamide;
- N-(1,3-dihydroxypropan-2-yl)-4-(2-(4-fluorobenzyl)-2H-tetrazol-5-yl)benzenesulfonamide;
- N-(1,3-dihydroxypropan-2-yl)-4-(2-(pyridin-4-ylmethyl)-2H-tetrazol-5-yl)benzenesulfonamide;
- N-(2,3-dihydroxypropyl)-4-(2-(4-fluorobenzyl)-2H-tetrazol-5-yl)benzenesulfonamide;
- 4-(2-((5-chloropyridin-2-yl)methyl)-2H-tetrazol-5-yl)-N-(2-hydroxyethyl)benzenesulfonamide;
- 4-(2-(4-ethylbenzyl)-2H-tetrazol-5-yl)-N-(2-hydroxyethyl)benzenesulfonamide;
- 4-(2-((5-cyanopyridin-2-yl)methyl)-2H-tetrazol-5-yl)-N-(2-hydroxyethyl)benzenesulfonamide;
- 4-(2-((3,5-difluoropyridin-2-yl)methyl)-2H-tetrazol-5-yl)-N-(2-hydroxyethyl)benzenesulfonamide;
- N-(2-hydroxyethyl)-4-(2-((6-methylpyridin-2-yl)methyl)-2H-tetrazol-5-yl)benzenesulfonamide;
- N-(2-hydroxyethyl)-4-(2-((2-methylpyrimidin-4-yl)methyl)-2H-tetrazol-5-yl)benzenesulfonamide;
- (R)-4-(2-(4-fluorobenzyl)-2H-tetrazol-5-yl)-N-(2-hydroxypropyl)benzenesulfonamide;
- (R)-4-(2-((5-fluoropyridin-2-yl)methyl)-2H-tetrazol-5-yl)-N-(2-hydroxypropyl)benzenesulfonamide;
- (R)-N-(2-hydroxypropyl)-4-(2-((5-methoxypyridin-2-yl)methyl)-2H-tetrazol-5-yl)benzenesulfonamide;
- (R)-N-(2-hydroxypropyl)-4-(2-((5-methylpyridin-2-yl)methyl)-2H-tetrazol-5-yl)benzenesulfonamide;
- (R)-N-(2-hydroxypropyl)-4-(2-(4-methoxybenzyl)-2H-tetrazol-5-yl)benzenesulfonamide;
- 4-(2-((5-fluoropyridin-2-yl)methyl)-2H-tetrazol-5-yl)-N-(2-hydroxyethyl)benzenesulfonamide;
- 4-(2-(3-fluoro-4-methoxybenzyl)-2H-tetrazol-5-yl)-N-(2-hydroxyethyl)benzenesulfonamide;
- N-(2-hydroxyethyl)-4-(2-((5-methoxypyridin-2-yl)methyl)-2H-tetrazol-5-yl)benzenesulfonamide;
- (N-(2-hydroxyethyl)-4-(2-((5-methylpyridin-2-yl)methyl)-2H-tetrazol-5-yl)benzenesulfonamide);
- N-(2-hydroxyethyl)-4-(2-(pyridin-4-ylmethyl)-2H-tetrazol-5-yl)benzenesulfonamide;
- N-(2-hydroxyethyl)-4-(2-((2-methylpyridin-4-yl)methyl)-2H-tetrazol-5-yl)benzenesulfonamide;
- 2-(4-(2-(4-methoxybenzyl)-2H-tetrazol-5-yl) phenyl sulfonamido)acetamide;
- 2-(4-(2-(4-methylbenzyl)-2H-tetrazol-5-yl)phenylsulfonamido)acetamide;
- 2-(4-(2-(3,4-difluorobenzyl)-2H-tetrazol-5-yl)phenylsulfonamido)acetamide;
- 2-(4-(2-((5-fluoropyridin-2-yl)methyl)-2H-tetrazol-5-yl)phenylsulfonamido)acetamide;
- 2-(4-(2-((4,4-difluorocyclohexyl)methyl)-2H-tetrazol-5-yl)phenylsulfonamido)acetamide;
- 2-(4-(2-((5-methylpyridin-2-yl)methyl)-2H-tetrazol-5-yl)phenylsulfonamido)acetamide;
- 2-(4-(2-((5-chloropyridin-2-yl)methyl)-2H-tetrazol-5-yl)phenylsulfonamido)acetamide;
- 2-(4-(2-((2-methylpyridin-4-yl)methyl)-2H-tetrazol-5-yl)phenylsulfonamido)acetamide;
- Methyl 2-(4-(2-(4-fluorobenzyl)-2H-tetrazol-5-yl)phenylsulfonamido)acetate;
- Methyl 2-(4-(2-(pyridin-4-ylmethyl)-2H-tetrazol-5-yl)phenylsulfonamido)acetate;
- 2-(4-(2-(4-fluorobenzyl)-2H-tetrazol-5-yl)phenylsulfonamido)acetamide;
- 2-(4-(2-(pyridin-4-ylmethyl)-2H-tetrazol-5-yl)phenylsulfonamido)acetamide;
- (4-(2-(4-fluorobenzyl)-2H-tetrazol-5-yl)-N-(2-hydroxyethyl)-2-methoxybenzenesulfonamide);
- (N-(2-hydroxyethyl)-2-methoxy-4-(2-(pyridin-4-ylmethyl)-2H-tetrazol-5-yl)benzenesulfonamide);
- (4-(2-(4-cyanobenzyl)-2H-tetrazol-5-yl)-N-(2-hydroxyethyl)-2-methoxybenzenesulfonamide);
- (4-(2-((5-fluoropyridin-2-yl)methyl)-2H-tetrazol-5-yl)-N-(2-hydroxyethyl)-2-methoxybenzenesulfonamide);
- (2-methoxy-N-methyl-4-(2-(pyridin-4-ylmethyl)-2H-tetrazol-5-yl)benzenesulfonamide);
- (N-(cyanomethyl)-4-(2-(4-fluorobenzyl)-2H-tetrazol-5-yl)benzenesulfonamide);
- 2-(4-(2-(4-fluorobenzyl)-2H-tetrazol-5-yl)-2-methoxyphenylsulfonamido) acetamide;
- 2-(4-(2-(4-cyanobenzyl)-2H-tetrazol-5-yl)-2-methoxyphenylsulfonamido)acetamide;
- 2-(2-methoxy-4-(2-(pyridin-4-ylmethyl)-2H-tetrazol-5-yl)phenylsulfonamido)acetamide;
- (N-(cyanomethyl)-4-(2-(pyridin-4-ylmethyl)-2H-tetrazol-5-yl)benzenesulfonamide);

(N-(cyanomethyl)-4-(2-((5-fluoropyridin-2-yl)methyl)-2H-tetrazol-5-yl)benzenesulfonamide);
(N-(cyanomethyl)-4-(2-(pyrimidin-4-ylmethyl)-2H-tetrazol-5-yl)benzenesulfonamide;
(N-(cyanomethyl)-2-methoxy-4-(2-(pyridin-4-ylmethyl)-2H-tetrazol-5-yl)benzenesulfonamide);
(N-(cyanomethyl)-4-(1-(pyridin-4-ylmethyl)-1H-1,2,3-triazol-4-yl)benzenesulfonamide);
(N-(cyanomethyl)-4-(1-((5-fluoropyridin-2-yl)methyl)-1H-1,2,3-triazol-4-yl)benzenesulfonamide);
(4-(1-((5-fluoropyridin-2-yl)methyl)-1H-1,2,3-triazol-4-yl)-N-(2-hydroxyethyl)benzene sulfonamide);
(N-(2-hydroxyethyl)-4-(1-(4-methoxybenzyl)-1H-1,2,3-triazol-4-yl)benzenesulfonamide);
(4-(1-(4-fluorobenzyl)-1H-1,2,3-triazol-4-yl)-N-(2-hydroxyethyl)benzenesulfonamide);
(N-(2-hydroxyethyl)-4-(1-(pyridin-4-ylmethyl)-1H-1,2,3-triazol-4-yl)benzenesulfonamide);
(4-(1-(4-cyanobenzyl)-1H-1,2,3-triazol-4-yl)-N-(2-hydroxyethyl)benzenesulfonamide);
(N-(2-hydroxyethyl)-4-(1-((5-methylpyridin-2-yl)methyl)-1H-1,2,3-triazol-4-yl)benzenesulfonamide);
(2-(4-(1-(4-fluorobenzyl)-1H-1,2,3-triazol-4-yl)phenylsulfonamido)acetamide);
(2-(4-(1-((4,4-difluorocyclohexyl)methyl)-1H-1,2,3-triazol-4-yl)phenylsulfonamido)acetamide);
(R)-4-(1-(4-fluorobenzyl)-1H-1,2,3-triazol-4-yl)-N-(2-hydroxypropyl)benzenesulfonamide;
4-(2-((5-fluoropyridin-2-yl)methyl)-2H-tetrazol-5-yl)-N-(2-hydroxyethyl)-2-methylbenzenesulfonamide;
N-(2-hydroxyethyl)-2-methyl-4-(2-((tetrahydro-2H-pyran-2-yl)methyl)-2H-tetrazol-5-yl)benzenesulfonamide;
4-(2-((5-fluoropyridin-2-yl)methyl)-2H-tetrazol-5-yl)-N-(2-hydroxyethyl)-3-methylbenzenesulfonamide;
N-(2-hydroxyethyl)-3-methyl-4-(2-((tetrahydro-2H-pyran-2-yl)methyl)-2H-tetrazol-5-yl)benzenesulfonamide;
2-fluoro-4-(2-((5-fluoropyridin-2-yl)methyl)-2H-tetrazol-5-yl)-N-(2-hydroxyethyl) benzenesulfonamide;
2-fluoro-N-(2-hydroxyethyl)-4-(2-((tetrahydro-2H-pyran-2-yl)methyl)-2H-tetrazol-5-yl)benzenesulfonamide;
2-fluoro-4-(2-(4-fluorobenzyl)-2H-tetrazol-5-yl)-N-(2-hydroxyethyl)benzenesulfonamide;
2-fluoro-N-(2-hydroxyethyl)-4-(2-((tetrahydro-2H-pyran-4-yl)methyl)-2H-tetrazol-5-yl)benzenesulfonamide;
4-(2-(cyclohexylmethyl)-2H-tetrazol-5-yl)-2-fluoro-N-(2-hydroxyethyl)benzenesulfonamide;
2-chloro-4-(2-((5-fluoropyridin-2-yl)methyl)-2H-tetrazol-5-yl)-N-(2-hydroxyethyl)benzenesulfonamide;
3-chloro-4-(2-((5-fluoropyridin-2-yl)methyl)-2H-tetrazol-5-yl)-N-(2-hydroxyethyl)benzenesulfonamide;
2-(2-chloro-4-(2-(4-fluorobenzyl)-2H-tetrazol-5-yl)phenylsulfonamido)acetamide;
3-fluoro-4-(2-((5-fluoropyridin-2-yl)methyl)-2H-tetrazol-5-yl)-N-(2-hydroxyethyl)benzenesulfonamide;
3-fluoro-N-(2-hydroxyethyl)-4-(2-((tetrahydro-2H-pyran-2-yl)methyl)-2H-tetrazol-5-yl)benzenesulfonamide;
2,3-difluoro-4-(2-((5-fluoropyridin-2-yl)methyl)-2H-tetrazol-5-yl)-N-(2-hydroxyethyl)benzenesulfonamide;
2,3-difluoro-N-(2-hydroxyethyl)-4-(2-((tetrahydro-2H-pyran-2-yl)methyl)-2H-tetrazol-5-yl)benzenesulfonamide;
2,6-difluoro-4-(2-((5-fluoropyridin-2-yl)methyl)-2H-tetrazol-5-yl)-N-(2-hydroxyethyl)benzenesulfonamide;
(R)-2,6-difluoro-N-(2-hydroxyethyl)-4-(2-((tetrahydro-2H-pyran-2-yl)methyl)-2H-tetrazol-5-yl)benzenesulfonamide
N-(cyanomethyl)-4-(2-((tetrahydro-2H-pyran-4-yl)methyl)-2H-tetrazol-5-yl)benzenesulfonamide;
N-(cyanomethyl)-4-(2-(pyrazin-2-ylmethyl)-2H-tetrazol-5-yl)benzenesulfonamide;
N-(cyanomethyl)-4-(2-((5-methylpyrazin-2-yl)methyl)-2H-tetrazol-5-yl)benzenesulfonamide;
N-(cyanomethyl)-4-(2-((5-methoxypyrazin-2-yl)methyl)-2H-tetrazol-5-yl)benzenesulfonamide;
N-(cyanomethyl)-4-(2-(6-methoxypyridin-3-yl)methyl)-2H-tetrazol-5-yl)benzenesulfonamide;
N-(cyanomethyl)-4-(2-((tetrahydro-2H-pyran-2-yl)methyl)-2H-tetrazol-5-yl)benzenesulfonamide;
2-((4-(2-((4,4-difluorocyclohexyl)methyl)-2H-tetrazol-5-yl)-2-methoxyphenyl)sulfonamido)acetamide;
2-((4-(2-((tetrahydro-2H-pyran-2-yl)methyl)-2H-tetrazol-5-yl)phenyl)sulfonamido)acetamide;
N-(2-hydroxyethyl)-4-(2-(4-(trifluoromethoxy)benzyl)-2H-tetrazol-5-yl)benzenesulfonamide;
N-(2-hydroxyethyl)-4-(2-(4-(trifluoromethyl)benzyl)-2H-tetrazol-5-yl)benzenesulfonamide;
4-(2-(4-ethoxybenzyl)-2H-tetrazol-5-yl)-N-(2-hydroxyethyl)benzenesulfonamide;
4-(2-(cyclohexylmethyl)-2H-tetrazol-5-yl)-N-(2-hydroxyethyl)benzenesulfonamide;
N-(2-hydroxyethyl)-4-(2-((6-methylpyridin-3-yl)methyl)-2H-tetrazol-5-yl)benzenesulfonamide;
N-(2-hydroxyethyl)-4-(2-(pyridin-3-ylmethyl)-2H-tetrazol-5-yl)benzenesulfonamide;
(N-(2-hydroxyethyl)-4-(2-((5-methoxypyridin-2-yl)methyl)-2H-tetrazol-5-yl)benzenesulfonamide);
N-(2-hydroxyethyl)-4-(2-((tetrahydro-2H-pyran-3-yl)methyl)-2H-tetrazol-5-yl)benzenesulfonamide;
N-(2-hydroxyethyl)-4-(2-((tetrahydro-2H-pyran-4-yl)methyl)-2H-tetrazol-5-yl)benzenesulfonamide;
N-(2-hydroxyethyl)-4-(2-(pyridazin-4-ylmethyl)-2H-tetrazol-5-yl)benzenesulfonamide;
N-(2-hydroxyethyl)-4-(2-(pyridazin-3-ylmethyl)-2H-tetrazol-5-yl)benzenesulfonamide;
4-(2-(4-cyanobenzyl)-2H-tetrazol-5-yl)-N-methylbenzenesulfonamide;
N-(2-hydroxyethyl)-2-methoxy-4-(2-((5-methoxypyridin-2-yl)methyl)-2H-tetrazol-5-yl)benzenesulfonamide;
2-fluoro-4-(2-((5-fluoropyridin-2-yl)methyl)-2H-tetrazol-5-yl)-N-(2-hydroxyethyl)-5-methylbenzenesulfonamide;
(4-(2-(1-(5-fluoropyridin-2-yl)ethyl)-2H-tetrazol-5-yl)-N-(2-hydroxyethyl)benzenesulfonamide;
4-(2-(1-(5-fluoropyridin-2-yl)ethyl)-2H-tetrazol-5-yl)-N-(2-hydroxyethyl)benzenesulfonamide;
4-(1-(1-(4-fluorophenyl)ethyl)-1H-1,2,3-triazol-4-yl)-N-(2-hydroxyethyl)benzenesulfonamide;
2-(4-(2-(1-(4-fluorophenyl)ethyl)-2H-tetrazol-5-yl)phenylsulfonamido)acetamide; and
2-(4-(2-(1-(4-fluorophenyl)ethyl)-2H-tetrazol-5-yl)-2-methoxyphenylsulfonamido)acetamide.

11. The compound or pharmaceutically acceptable salt thereof according to claim 10, wherein the compound is 4-(2-((5-fluoropyridin-2-yl)methyl)-2H-tetrazol-5-yl)-N-(2-hydroxyethyl)benzenesulfonamide having the following structure:

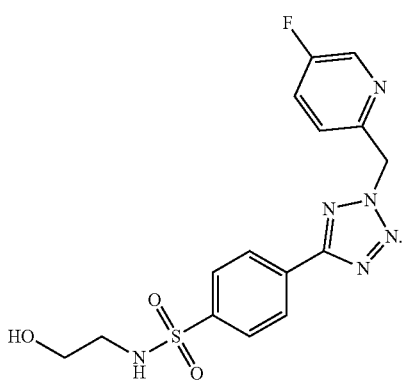

12. A method for the treatment of a mycobacterial infection in a human in need thereof, comprising administering to said human a therapeutically effective amount of the compound or a pharmaceutically acceptable salt thereof, according to claim 1.

13. A method for the treatment of a disease caused by infection with a *mycobacterium* in a human in need thereof, comprising administering to said human a therapeutically effective amount of the compound, or a pharmaceutically acceptable salt thereof, according to claim 1.

14. A pharmaceutical composition comprising (a) the compound or pharmaceutically acceptable salt thereof according to claim 1; and (b) a pharmaceutically acceptable excipient.

15. A combination of (a) the compound or pharmaceutically acceptable salt thereof according to claim 1; and (b) at least one other anti-mycobacterial agent.

16. The combination according to claim 15, wherein the at least one other anti-mycobacterial agent is an anti-tuberculosis agent.

17. The combination according to claim 16, wherein the anti-tuberculosis agent is selected from isoniazid, rifampin, pyrazinamide, ethambutol, moxifloxacin, rifapentine, clofazimine, ethionamide, prothionamide, isoxyl, thiacetazone, a diarylquinoline such as bedaquiline (TMC207) or TBAJ-587, nitroimidazo-oxazine PA-824 (pretomanid), delamanid (OPC-67683), an oxazolidinone such as linezolid, tedizolid, radezolid, sutezolid (PNU-100480), posizolid (AZD-5847) or TBI-223, EMB analogue SQ109, OPC-167832, GSK3036656A (also known as GSK070), GSK2556286, GSK3211830, a benzothiazinone such as BTZ043 or PBTZ169, an azaindole such as TBA-7371, a dinitrobenzamide, and a beta-lactam such as sanfetrinem, meropenem, faropenem, ertapenem, tebipenemor beta-lactam combinations such as AUGMENTIN (amoxicillin-clavulanate).

18. The combination according to claim 15, further comprising an antiviral agent, including an antiretroviral agent.

19. The combination according to claim 18, wherein the antiretroviral agent is selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

20. A method for the treatment of tuberculosis in a human in need thereof, comprising administering to said human a therapeutically effective amount the compound, or pharmaceutically acceptable salt thereof according to claim 1.

21. The method according to claim 12, wherein the mycobacterial infection is a *Mycobacterium tuberculosis* infection.

22. The method according to claim 13, wherein the disease is tuberculosis.

23. A method for the treatment of a mycobacterial infection in a human in need thereof, comprising administering to said human (a) the compound or pharmaceutically acceptable salt thereof according to claim 1; and (b) at least one other anti-mycobacterial agent.

24. The method according to claim 23, wherein the at least one other anti-mycobacterial agent is an anti-tuberculosis agent.

25. The method according to claim 24, wherein the anti-tuberculosis agent is selected from isoniazid, rifampin, pyrazinamide, ethambutol, moxifloxacin, rifapentine, clofazimine, ethionamide, prothionamide, isoxyl, thiacetazone, a diarylquinoline such as bedaquiline (TMC207) or TBAJ-587, nitroimidazo-oxazine PA-824 (pretomanid), delamanid (OPC-67683), an oxazolidinone such as linezolid, tedizolid, radezolid, sutezolid (PNU-100480), posizolid (AZD-5847) or TBI-223, EMB analogue SQ109, OPC-167832, GSK3036656A (also known as GSK070), GSK2556286, GSK3211830, a benzothiazinone such as BTZ043 or PBTZ169, an azaindole such as TBA-7371, a dinitrobenzamide, and a beta-lactam such as sanfetrinem, meropenem, faropenem, ertapenem, tebipenem, or beta-lactam combinations such as AUGMENTIN (amoxicillin-clavulanate).

26. The method according to claim 23, further comprising an antiviral agent, including an antiretroviral agent.

27. The method according to claim 26, wherein the antiretroviral agent is selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

* * * * *